(12) United States Patent
Campbell et al.

(10) Patent No.: US 6,867,185 B2
(45) Date of Patent: Mar. 15, 2005

(54) INHIBITORS OF HEPATITIS C VIRUS

(75) Inventors: Jeffrey Allen Campbell, Cheshire, CT (US); Andrew Charles Good, Wallingford, CT (US)

(73) Assignee: Bristol-Myers Squibb Company, Princeton, NJ (US)

(*) Notice: Subject to any disclaimer, the term of this patent is extended or adjusted under 35 U.S.C. 154(b) by 258 days.

(21) Appl. No.: 10/317,451

(22) Filed: Dec. 12, 2002

(65) Prior Publication Data

US 2004/0038872 A1 Feb. 26, 2004

Related U.S. Application Data

(60) Provisional application No. 60/382,103, filed on May 20, 2002, and provisional application No. 60/344,080, filed on Dec. 20, 2001.

(51) Int. Cl.⁷ .............................................. A61K 38/00
(52) U.S. Cl. ......................................................... 514/9
(58) Field of Search ............................................. 514/9

(56) References Cited

U.S. PATENT DOCUMENTS 6,323,180 B1  11/2001  Llinas-Brunet et al.

FOREIGN PATENT DOCUMENTS

| WO | WO 00/59929 | * 10/2000 | .......... A61K/38/50 |
|---|---|---|---|
| WO | WO 02/060926 | 8/2002 | |
| WO | WO 03/064416 A1 | 8/2003 | |
| WO | WO 03/064455 A2 | 8/2003 | |
| WO | WO 03/064456 A1 | 8/2003 | |
| WO | WO 03/066103 A1 | 8/2003 | |

* cited by examiner

*Primary Examiner*—Patricia Leith
*Assistant Examiner*—Maury Audet

(57) ABSTRACT

The present invention relates to macrocyclic compounds, methods for making these compounds, pharmaceutical compositions and the therapeutic or prophylactic use of these compounds by administering said compounds to mammals or treat hepatitis C virus (HCV) infection.

14 Claims, No Drawings

INHIBITORS OF HEPATITIS C VIRUS

REFERENCE TO RELATED APPLICATIONS

This application claims the benefit of U.S. Provisional Application Ser. No. 60/382,103 filed May 20, 2002 and No. 60/344,080 filed Dec. 20, 2001.

BACKGROUND OF THE INVENTION

Hepatitis C virus (HCV) is the major etiological agent of 90% of all cases of non-A, non-B hepatitis (Choo et al., 1989, Kuo et al., 1989). The incidence of HCV infection is becoming an increasingly severe public health concern with 2–15% individuals infected worldwide. While primary infection with HCV is often asymptomatic, most HCV infections progress to a chronic state that can persist for decades. Of those with chronic HCV infections, it is believed that about 20–50% will eventually develop chronic liver disease (e.g. cirrhosis) and 20–30% of these cases will lead to liver failure or liver cancer. As the current HCV-infected population ages, the morbidity and mortality associated with HCV are expected to triple.

An approved treatment for HCV infection uses interferon (IFN) which indirectly effects HCV infection by stimulating the host antiviral response. IFN treatment is suboptimal, however, as a sustained antiviral response is produced in less than 30% of treated patients. Further, IFN treatment induces an array of side effects of varying severity in upwards of 90% of patients (eg: acute pancreatitis, depression, retinopathy, thyroiditis). Therapy with a combination of IFN and ribavirin has provided a slightly higher sustained response rate, but not alleviated the IFN-induced side effects.

The use of protease inhibitors, particularly those selectively targeting HCV serine protease, has great potential to be useful in treating HCV infections in patients by inhibiting HCV replication.

Amongst the compounds that have demonstrated efficacy in inhibiting HCV replication, as selective HCV serine protease inhibitors, are the macrocyclic peptide compounds disclosed in International Application PCT/CA00/00353 (Publication No. WO 00/59929). The present invention describes selective inhibitors of the HCV NS3/NS4A serine protease complex of improved chemical design relative to the previously described invention, that have the potential to demonstrate suitable whole cell permeability for the treatment of HCV-infected patients.

SUMMARY OF THE INVENTION

The present invention relates to compounds of Formula I, including pharmaceutically acceptable salts thereof,

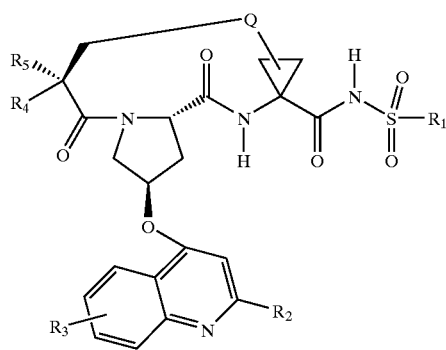

I wherein:
(a) $R_1$ is $C_{1-6}$ alkyl or unsubstituted $C_{3-7}$ cycloalkyl;
(b) $R_2$ is H, halo, $C_{1-6}$ alkyl, $C_{1-6}$ alkoxy, $C_{3-6}$ cycloalkoxy, $C_6$ or 10 aryl or heterocycle; wherein heterocyle is a five-, six-, or seven-membered saturated or unsaturated heterocycle containing from one to four heteroatoms selected from nitrogen, oxygen and sulfur; said aryl or heterocycle being substituted with $R_{24}$; wherein $R_{24}$ is H, halo, $C_{1-6}$ alkyl, —N($R_a$) ($R_b$), —N($R_a$)C(O)(O$R_d$), —N($R_a$)C(O)($R_b$), —NHC(O)($R_a$)($R_c$) or —N($R_c$)SO$_2R_b$; wherein $R_a$ and $R_b$ are independently H, $C_{1-6}$ alkyl or $C_{3-6}$ cycloalkyl; $R_c$ is H, $C_{1-6}$ alkyl, $C_{3-6}$ cycloalkyl or $C_{1-6}$ alkoxy; $R_d$ is $C_{1-6}$ alkyl or $C_{3-6}$ cycloalkyl;
(c) $R_3$ is H, halo, $CF_3$, $C_{1-6}$ alkoxy or $C_{3-6}$ cycloalkoxy;
(d) $R_4$ is $NH_2$, or —NH—$R_{31}$; wherein $R_{31}$ is —C(O)—$R_{32}$, C(O)—$NHR_{32}$ or C(O)—$OR_{32}$; wherein $R_{32}$ is $C_1$–$C_6$ alkyl optionally substituted with halo, —(CH$_2$)$_p$—$C_{3-7}$ cycloalkyl or a tetrahydrofuran ring linked through the C3 or C4 position of the ring; wherein p is 0–6;
(e) $R_5$ is H; and
(f) Q is a three to nine atom saturated or unsaturated alkylene chain optionally containing one to three heteroatoms independently selected from O or S(O)$_m$; wherein m is 0, 1 or 2.

The present invention also relates to a pharmaceutical composition, useful for inhibiting HCV NS3 protease, or for treating patients infected with the hepatitis C virus, comprising a therapeutically effective amount of a compound of the present invention and a pharmaceutically acceptable carrier.

The present invention further relates to a method of treating mammals infected with hepatitis C virus, comprising administering to said mammal an effective amount of a compound of the present invention.

Additionally, the present invention relates to a method of inhibiting HCV NS3 protease by administering to a patient an effective amount of a compound of the present invention.

DETAILED DESCRIPTION OF THE INVENTION

As used herein, the following definitions apply unless otherwise noted. With reference to the instances where (R) or (S) is used to designate the configuration of a substituent in context to the whole compound and not in context to the substituent alone.

The term "halo" as used herein means a halogen substituent selected from bromo, chloro, fluoro or iodo.

The term "$C_{1-6}$ alkyl" as used herein means acyclic, straight or branched chain alkyl substituents containing from 1 to six carbon atoms and includes, for example, methyl, ethyl, propyl, butyl, tert-butyl, hexyl, 1-methylethyl, 1-methylpropyl, 2-methypropyl, 1,1-dimethylethyl.

The term "$C_{1-6}$ alkoxy" as used herein means the radical —O($C_{1-6}$ alkyl) wherein alkyl is as defined above containing up to six carbon atoms. Alkoxy includes, for example, methoxy, ethoxy, propoxy, 1-methylethoxy, butoxy and 1,1-dimethylethoxy. The latter radical is known commonly as tert-butoxy.

The term "$C_{3-7}$ cycloalkyl" as used herein means a cycloalkyl substituent containing from three to seven carbon atoms and includes, for example, cyclopropyl, cyclobutyl, cyclopentyl, cyclohexyl and cycloheptyl.

The term "$C_{3-7}$ cycloalkoxy" as used herein means a $C_{3-7}$ cycloalkyl group linked to an oxygen atom, such as, for example, butyloxy or cyclopropyloxy.

The term "$C_{6\ or\ 10}$ aryl" as used herein means either an aromatic monocyclic group containing 6 carbon atoms or an aromatic bicyclic group containing 10 carbon atoms, for example, aryl includes phenyl, 1-naphthyl or 2-naphthyl.

The term "carboxy($C_{1-6}$ alkyl)" as used herein means a carboxyl group (COOH) linked through a $C_{1-6}$ alkyl group as defined above and includes, for example, butyric acid.

The term "heterocycle", as used herein means a monovalent radical derived by removal of a hydrogen from a five-, six-, or seven-membered saturated or unsaturated (including aromatic) heterocycle containing from one to four heteroatoms selected from nitrogen, oxygen and sulfur. Furthermore, the term heterocycle includes heterocycles, as defined above, that are fused to one or more other ring structure. Examples of suitable heterocycles include, but are not limited to, pyrrolidine, tetrahydrofuran, thiazolidine, pyrrole, thiophene, diazepine, 1H-imidazole, isoxazole, thiazole, tetrazole, piperidine, 1,4-dioxane, 4-morpholine, pyridine, pyrimidine, thiazolo[4,5-b]-pyridine, quinoline, or indole, or the following heterocycles:

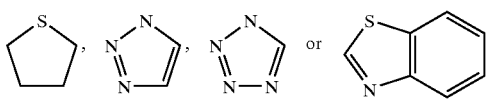

The term "$C_{1-6}$ alkyl-heterocycle" as used herein, means a heterocyclic radical as defined above linked through a chain or branched alkyl group, wherein alkyl as defined above containing from 1 to 6 carbon atoms. Examples of $C_{1-6}$ alkyl-Het include:

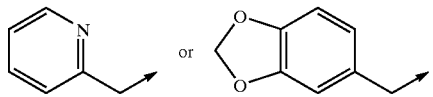

In a preferred embodiment, the compounds of the present invention have the structure of Formula II Formula II

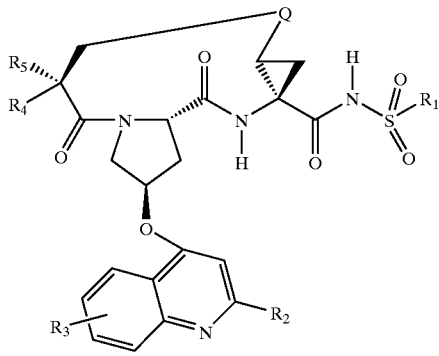

wherein $R_1$, $R_2$, $R_3$, $R_4$, $R_5$ and Q are as defined for Formula I.

For compounds of Formula II, it is preferred that $R_1$ is cyclopropyl. In addition, it is preferred that $R_2$ is phenyl. It is further preferred that $R_3$ is methoxy. Furthermore, it is further preferred that $R_4$ is $NH_2$ or tert-butoxycarbonylNH—. It is also preferred that Q is —$(CH_2)_n$ CH=C— wherein n is 1–5. It is more preferred that n is 3 or 4.

In a more preferred embodiment, the compounds of the present invention have the structure of Formula III

III

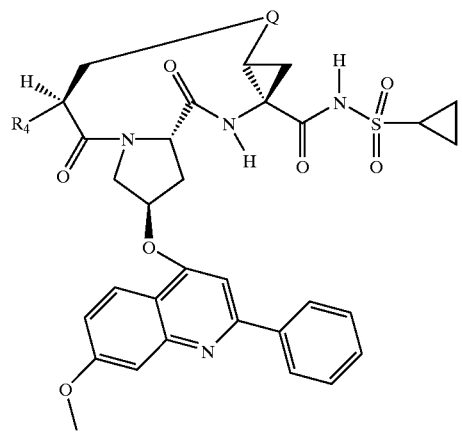

wherein $R_4$ is $NH_2$ or tert-butoxycarbonylNH—, Q is $(CH_2)_n$ CH=C—, and n is 1–5. For the compounds of Formula III, it is more preferred that n is 3 or 4.

In another preferred embodiment for compounds of Formula II, wherein:

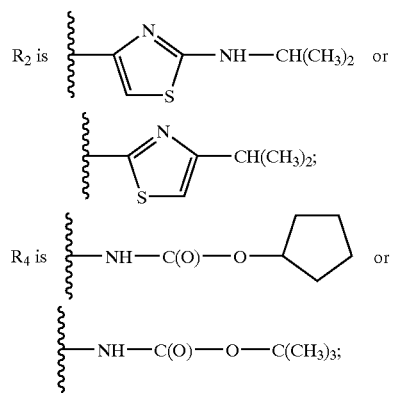

and $R_1$ is cyclopropyl.

Compounds of the present invention, by virtue of their basic moiety, can form salts by the addition of a pharmaceutically acceptable acid. The acid addition salts are formed from a compound of Formula I and a pharmaceutically acceptable inorganic acid, including but not limited to hydrochloric, hydrobromic, hydroiodic, sulfuric, phosphoric, or organic acid such as p-toluenesulfonic, methanesulfonic, acetic, benzoic, citric, malonic, fumaric, maleic, oxalic, succinic, sulfamic, or tartaric. Thus, examples of such pharmaceutically acceptable salts include chloride, bromide, iodide, sulfate, phosphate, methanesulfonate, citrate, acetate, malonate, fumarate, sulfamate, and tartrate.

Salts of an amine group may also comprise quaternary ammonium salts in which the amino nitrogen carries a suitable organic group such as an alkyl, alkenyl, alkynyl or aralkyl moiety.

Compounds of the present invention, which are substituted with a acidic group, may exist as salts formed through base addition. Such base addition salts include those derived from inorganic bases which include, for example, alkali metal salts (e.g. sodium and potassium), alkaline earth metal salts (e.g. calcium and magnesium), aluminum salts and ammonium salts. In addition, suitable base addition salts include salts of physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bishydroabietylamine, glucamine, N-methylglucamine, collidine, quinine, quinoline, ethylenediamine, ornithine, choline, N,N'-benzylphenethylamine, chloroprocaine, diethanolamine, diethylamine, piperazine, tris(hydroxymethyl) aminomethane and tetramethylammonium hydroxide and basic amino acids such as lysine, arginine and N-methylglutamine. These salts may be prepared by methods known to those skilled in the art.

In addition, compounds of the present invention, or a salt thereof, may exhibit polymorphism. The present invention also encompasses any such polymorphic form.

Compounds of the present invention (Formula I, II or III) also contain two or more chiral centers and exist in different optically active forms. For example, compounds of Formula I may include a cyclopropyl of formula

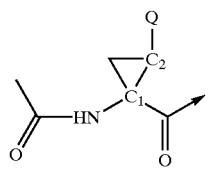

wherein $C_1$ and $C_2$ each represent an asymmetric carbon atom at positions 1 and 2 of the cyclopropyl ring. Not withstanding other possible asymmetric centers at other segments of the compounds of formula I, the presence of these two asymetric centers means that the compounds of formula I can exist as mixtures of diastereomers, such as the diastereomers of compounds of Formula II wherein Q is configured either syn to the amide or syn to the carbonyl as shown below.

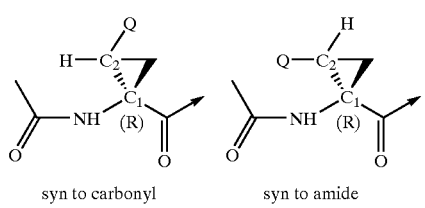

syn to carbonyl      syn to amide

Alternatively, the structures can be viewed as:

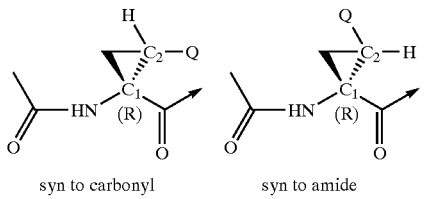

syn to carbonyl      syn to amide

The present invention includes both enantiomers and mixtures of enantiomers such as racemic mixtures.

As illustrated in the examples, the racemic mixtures can be prepared and thereafter separated into individual optical isomers, or these optical isomers can be prepared by chiral synthesis.

The enantiomers may be resolved by methods known to those skilled in the art, for example, by formation of diastereoisomeric salts which may be separated by crystallization, gas-liquid or liquid chromatography, selective reaction of one enantiomer with an enantiomer-specific reagent. It will be appreciated that where the desired enantiomer is converted into another chemical entity by a separation technique, then an additional step is required to form the desired enantiomeric form. Alternatively, specific enantiomers may be synthesized by asymmetric synthesis using optically active reagents, substrates, catalysts or solvents, or by converting one enantiomer into the other by asymmetric transformation.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

Certain compounds of the present invention may exist in zwitterionic form and the present invention includes each zwitterionic form of these compounds and mixtures thereof.

The compounds of the present invention are useful in the inhibition of HCV NS3 protease, as well as, the prevention or treatment of infection by the hepatitis C virus and the treatment of consequent pathological conditions. The treatment involves administering to a patient, in need of such treatment, a compound of the present invention, or a pharmaceutically acceptable salt thereof, or a pharmaceutical composition comprising a pharmaceutical carrier and a therapeutically effective amount of a compound of the present invention, or a pharmaceutically acceptable salt thereof.

It will be appreciated by those skilled in the art that reference herein to treatment extends to prophylaxis as well as the treatment of established infections or symptoms. This includes initiating treatment pre- and post-exposure to the virus. In addition, the present invention can be administered in conjunction with immunomodulators, such as α-, β-, or γ-interferons; other antiviral agents such as ribavirin, amantadine; other inhibitors of HCV NS3 protease; inhibitors of other targets in the HCV life cycle, which include but not limited to, helicase, polymerase, metalloprotease, or internal ribosome entry site (IRES); or combinations thereof. The additional agents may be combined with the compounds of this invention to create a single dosage form. Alternatively these additional agents may be separately administered to a mammal as part of a multiple dosage form.

These methods are useful in decreasing HCV NS3 protease activity in a mammal. These methods are useful for inhibiting viral replication in a mammal. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle such as helicase, polymerase, or metalloprotease or IRES. Such additional agent may be administered to the mammal prior to, concurrently with, or following the administration of the compositions of this invention.

The compounds of the present invention are also useful in the preparation and execution of screening or replication assays for antiviral compounds. Furthermore, the compounds of the present invention are useful in establishing or determining the binding site of other antiviral compounds to HCV NS3 protease, for example, by competitive inhibition.

The compounds of the present invention may be administered orally, parenterally (including subcutaneous injections, intravenous, intramuscular, intrasternal injection or infusion techniques), by inhalation spray or rectally, in dosage unit formulations containing conventional non-toxic pharmaceutically acceptable carriers, adjuvants and vehicles.

This invention also provides a pharmaceutical composition for use in the above-described therapeutic method. A pharmaceutical composition of the present invention comprises an effective amount of a compound of Formula I in association with a pharmaceutically acceptable carrier, excipient or diluent.

The active ingredient in such formulations comprises from 0.1 percent to 99.9 percent by weight of the formulation. By "pharmaceutically acceptable" it is meant that the carrier, diluent or excipient must be compatible with the other ingredients of the formulation and not deleterious to the recipient thereof.

The present pharmaceutical compositions are prepared by known procedures using well-known and readily available ingredients. The compositions of this invention may be formulated so as to provide quick, sustained or delayed release of the active ingredient after administration to the patient by employing procedures well known in the art. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, beadlets, lozenges, sachets, elixirs, suspensions, emulsions, solutions, syrups, aerosols, (as a solid or in a liquid medium), soft and hard gelatin capsules, suppositories, sterile injectable solutions, sterile packaged powders and the like.

The compounds can be administered by a variety of routes including oral, intranasally, rectal, transdermal, subcutaneous, intravenous, intramuscular and intranasal.

When administered orally, these compositions are prepared according to techniques well-known in the art of pharmaceutical formulation. For oral administration, the compound is typically formulated with excipients such as binders, fillers, lubricants, extenders, diluents, disintegration agents and the like as are known in the art.

For parenteral administration, the compound is formulated in pharmaceutically acceptable non-toxic, parenterally-acceptable diluents or solvents, such as mannitol, 1,3-butanediol, water, 5 percent dextrose, Ringer's solution or isotonic sodium chloride solution, or suitable dispersing or wetting and suspending agents, such as sterile, bland, fixed oils, including synthetic mono- or diglycerides, and fatty acids, including oleic acid.

A compound of the present invention, or a salt or solvate thereof, can be formulated in unit dosage formulations comprising a dose between about 0.1 mg and about 1000 mg, or more, according to the particular treatment involved. An example of a unit dosage formulation comprises 5 mg of a compound of the present invention in a 10 mL sterile glass ampoule. Another example of a unit dosage formulation comprises about 10 mg of a compound of the present invention as a pharmaceutically acceptable salt in 20 mL of isotonic saline contained in a sterile ampoule.

The compounds of the present invention can also be administered to humans in a dosage range of 1 to 100 mg/kg body weight in divided doses. One preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the route of administration, the age, body weight, general health, sex, diet, mode and time of administration, rate of excretion, drug combination, the severity of the particular condition, and the host undergoing therapy.

General methods useful for the synthesis of compounds embodied in this invention are shown below. The preparations shown below are disclosed for the purpose of illustration and are not meant to be interpreted as limiting the processes to make the compounds by any other methods.

It will be appreciated by those skilled in the art that a number of methods are available for the preparation of the compounds of the present invention. These compounds may be prepared by processes which include processes known in the chemical art for the production of structurally analogous compounds or by a novel process described herein. A process for the preparation of these compounds (or a pharmaceutically acceptable salt thereof) and novel intermediates for the manufacture of these compounds provide further features of the invention and are illustrated by the following procedures in which the meanings of the generic radicals are as defined above, unless otherwise specified. It will be recognized that it may be preferred or necessary to prepare such a compound in which a functional group is protected using a conventional protecting group then to remove the protecting group to provide a compound of the present invention.

For example, compounds of the present invention, having the structure of Formula I, II or III, such as those compounds of Formula IIIA and IIIB, shown below, were synthesized, as shown in the following scheme, indirectly from compounds of formula IV, and directly from compounds of formula VIIA or VIIB.

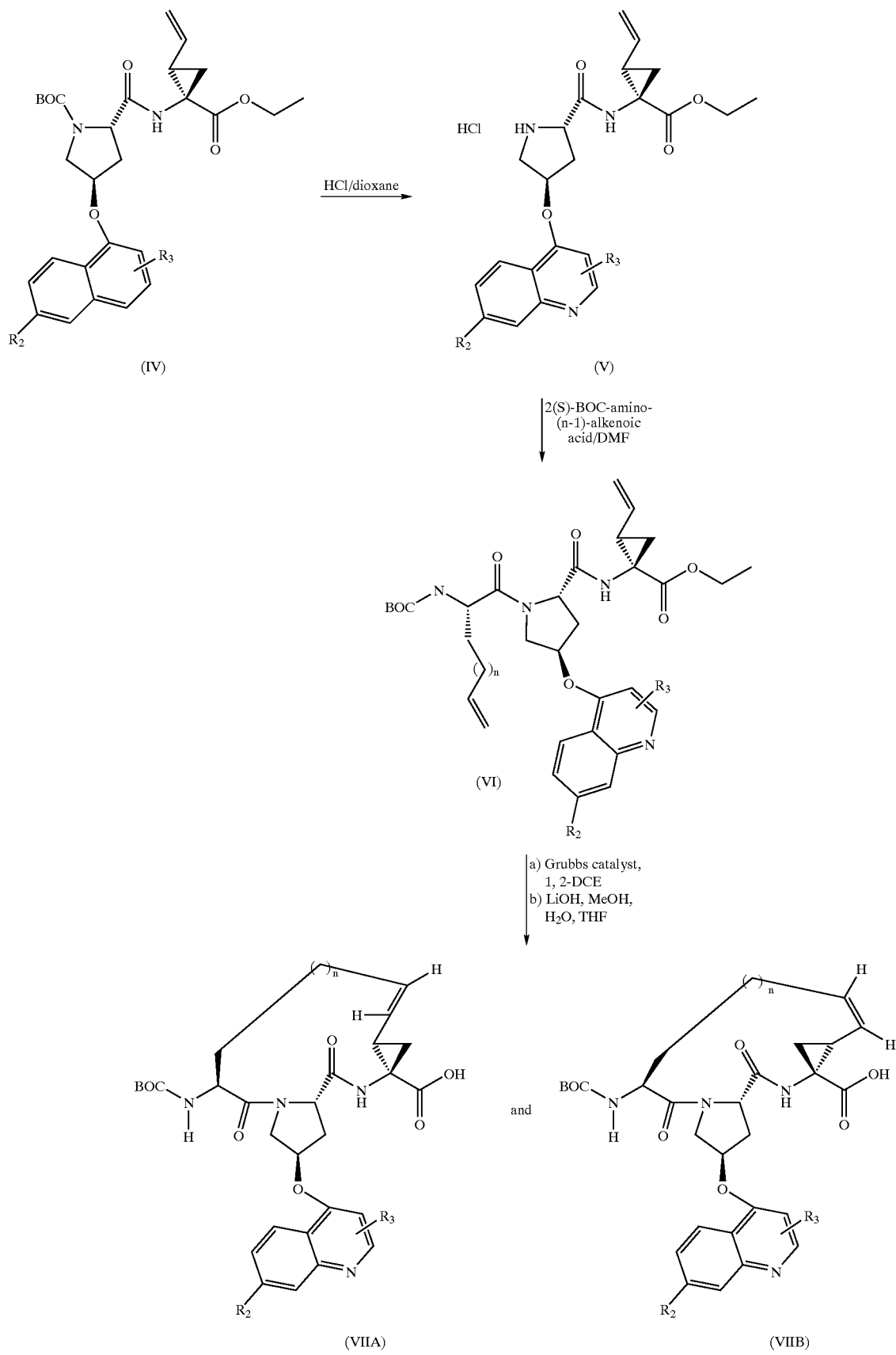

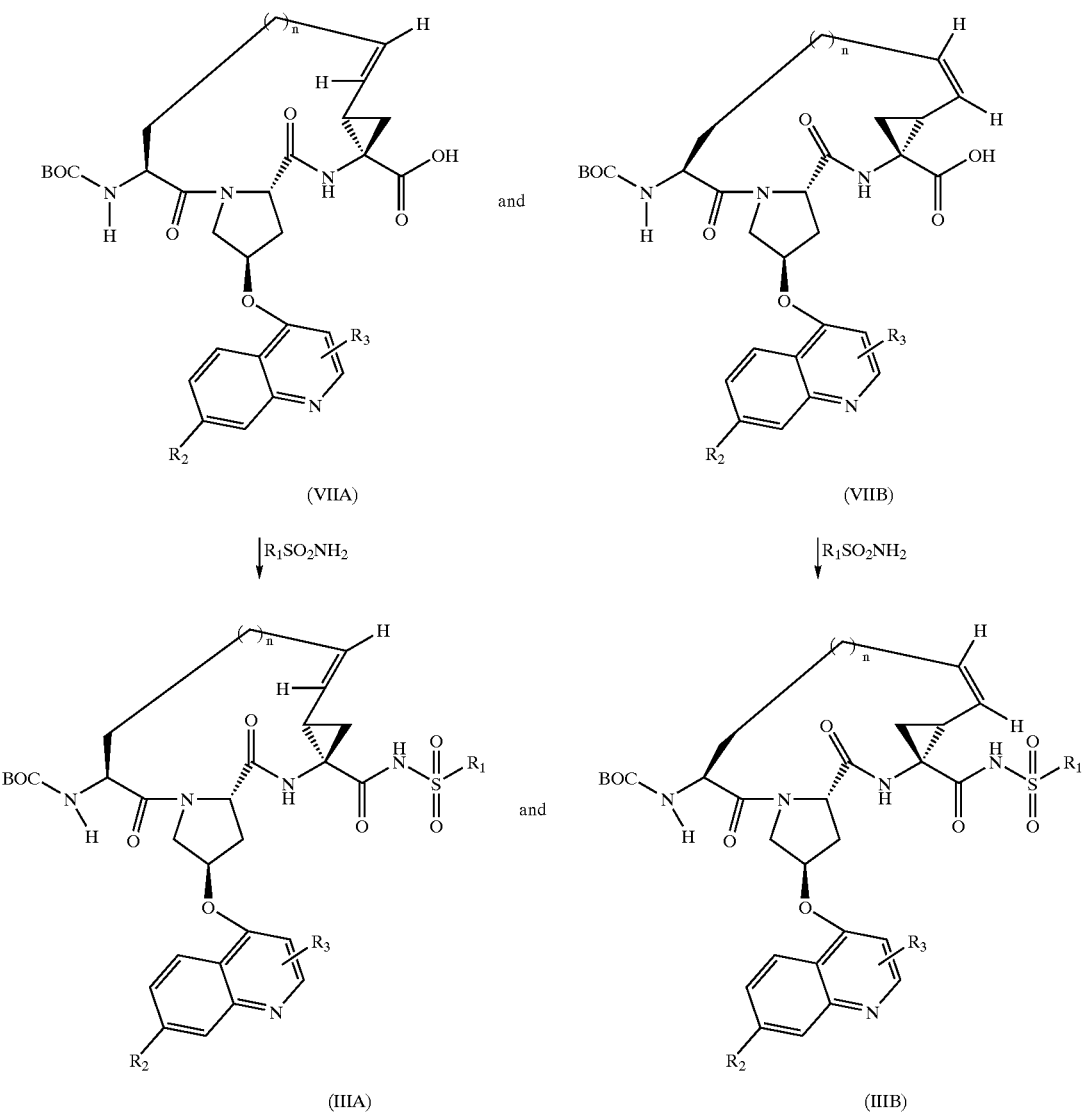

(VIIA) and (VIIB)

↓ R₁SO₂NH₂     ↓ R₁SO₂NH₂

(IIIA) and (IIIB)

The α-carboxylic acid of a compound of Formula VIIA or VIIB is coupled with $R_1SO_2NH_2$, which was prepared by treatment of $R_1SO_2Cl$ in ammonia saturated tetrahydrofuran solution, in the presence of peptide coupling agent, such as CDI or EDAC, and in the presence of a base, such as 4-dimethylaminopyridine (4-DMAP) and/or 1,8-diazabicyclo [5.4.0]undec-7-ene (DBU), to form a compound of Formula I, II or III.

Compounds having the structure of Formula IV, VI, VITA or VIIB can be prepared as described herein, and in non-provisional application U.S. Ser. No. 10/001,850 filed Nov. 20, 2001; International Application Number PCT/CA00/00353, Publication No. WO 00/59929, published Oct. 12, 2000 titled "Macrocyclic Peptides Active Against the Hepatitis C Virus"; and U.S. Pat. No. 6,323,180 granted Nov. 27, 2001 (corresponding to International Application Number PCT/CA99/00736, Publication No. WO 00/09543), titled "Hepatitis C Inhibitor TriPeptides". The disclosure of U.S. Pat. No. 6,323,180 is incorporated, in its entirety, herein by reference.

Compounds having the structure of Formula IV can also be prepared by coupling chemical precursor A with chemical precursor B as shown below.

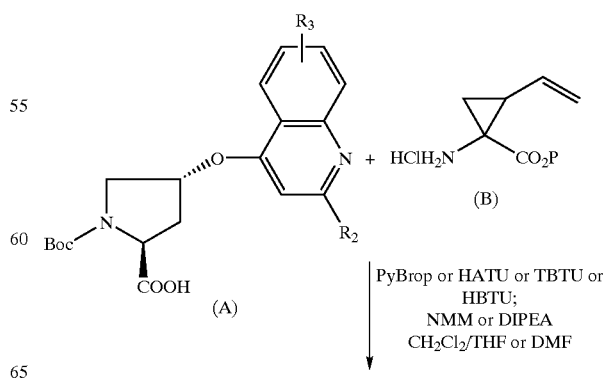

PyBrop or HATU or TBTU or HBTU;
NMM or DIPEA
CH₂Cl₂/THF or DMF

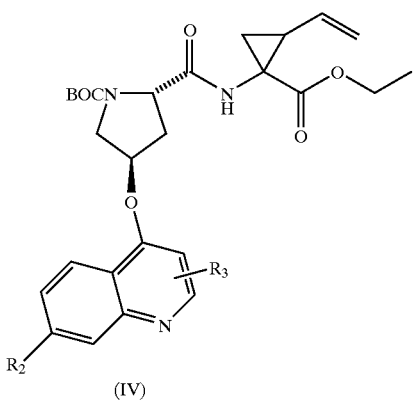

(IV)

Chemical precursor A, which is shown above, may be synthesized as described in the following.

butoxide, to form an alkoxide of A5 which is then reacted with the 4-chloroquinoline (A4) to give chemical precursor A.

Alternate means of forming the chemical precursor A, and of forming fragments or precursors of chemical precursor (A), are described in International Application Number PCT/CA00/00353, Publication No. WO 00/59929, titled "Macrocyclic Peptides Active Against the Hepatitis C Virus", and U.S. Pat. No. 6,323,180 granted Nov. 27, 2001 (corresponding to International Application Number PCT/CA99/00736, Publication No. WO 00/09543), titled "Hepatitis C Inhibitor Tri-Peptides". The disclosure of U.S. Pat. No. 6,323,180 is incorporated, in its entirety, herein by reference.

Chemical precursor B, which is also shown above, may be synthesized as described in the following scheme with slight modifications depicted in the experimental herein.

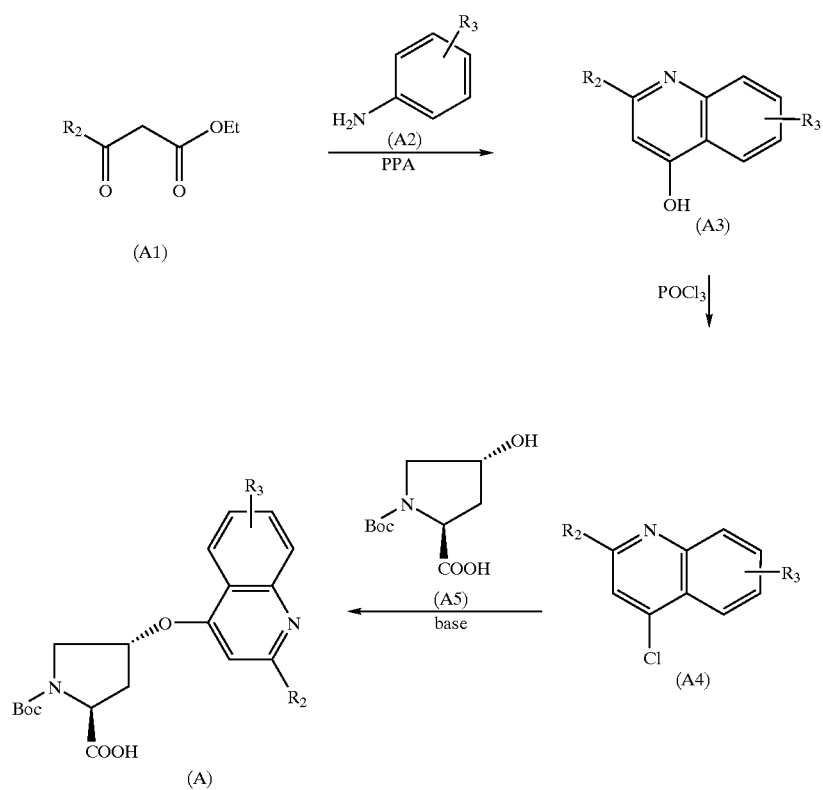

In this scheme, the ethyl ester (A1) is condensed with the appropriate aniline (A2), in the presence of acid, to form an imine. The imine is then cyclized by heating at about 260–280° C. to give the corresponding 4-hydroxyquinoline (A3). The 4-hydroxyquinoline (A3) is subsequently refluxed with phosphorous oxychloride to form a 4-chloroquinoline (A4).

Commercially available Boc-4(R)-hydroxyproline (A5), in a suitable solvent such as DMSO, is then treated with a base, for example, sodium hydride or potassium tert-

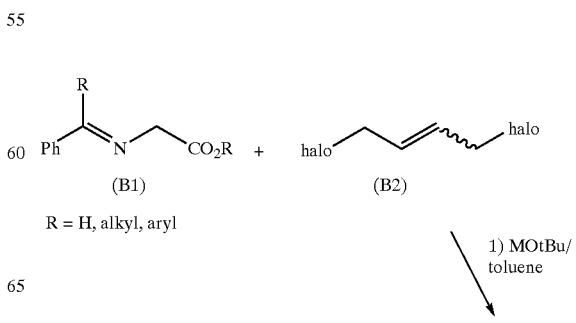

R = H, alkyl, aryl

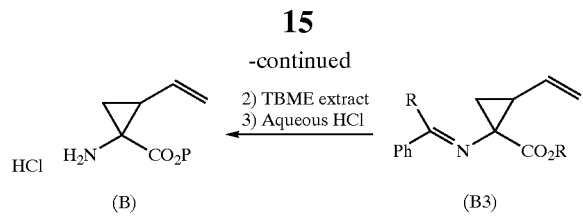

Treatment of commercially available or easily obtainable imine (B1) with 1,4-dihalobutene (B2) in presence of a base produces, provides the resulting imine (B3). Acid hydrolysis of B3 then provides B, which has an allyl substituent syn to the carboxyl group. It is preferred that for compounds B3 and B that the vinyl group is syn to the ester.

Exemplification

The specific examples that follow illustrate the syntheses of the compounds of the instant invention, and are not to be construed as limiting the invention in sphere or scope. The methods may be adapted to variations in order to produce compounds embraced by this invention but not specifically disclosed. Further, variations of the methods to produce the same compounds in somewhat different manner will also be evident to one skilled in the art.

Chemical abbreviations commonly used to identify chemical compounds in the literature include Bn: benzyl; Boc: tert-butyloxycarbonyl {Me₃COC(O)}; BSA: bovine serum albumin; CDI: carbonyldiimidazole; DBU: 1,8-diazabicy-clo[5.4.0]-undec-7-ene; CH₂Cl₂=DCM: methylene chloride; DEAD: diethylazodicarboxylate; DIAD: diisopropylazodicarboxylate; DIEA: diisopropylethylamine; DIPEA: diisopropylethylamine; 4-DMAP: 4-dimethylaminopyridine; DCC: 1,3-dicyclohexylcarbodiimide; DMF: dimethylformamide; DMSO: dimethylsulfoxide; DPPA: diphenylphosphoryl azide; EDAC: ethyldimethylaminopropylcarbodimide hydrochloride; EDTA: ethylenediaminetetraacetic acid; Et: ethyl; EtOH: ethanol; EtOAc: ethyl acetate; Et₂O: diethyl ether; Grubb's Catalyst: bis(tricyclohexylphosphine)benzylidene ruthenium (IV) dichloride; HATU: [O-7-azabenzotriazol-1-yl)-1, HBTU: [O-(1H-benzotriazol-1-yl)-N,N,N',N'-tetramethyluronium hexafluorophosphate; PYBROP: Bromo-tris-pyrrolidino-phosphonium hexafluorophosphate; HOAT, 1-hydroxy-7-azabenzotriazole; HPLC: high performance liquid chromatography; MS: mass spectrometry; Me: methyl; MeOH: methanol; NMM: N-methylmorpholine; NMP: N-methylpyrrol-idine; Pr: propyl; Succ: 3-carboxypropanoyl; PPA: polyphosphoric acid; TBAF: tetra-n-butylammonium fluoride; 1,2-DCE or DCE: 1,2-dichloroethane; TBTU:2-(1H-benzotriazole-1-yl)-1,1,3,3-tetramethyluronium tetrafluoroborate; TFA: trifluoroacetic acid; THF: tetrahydrofuran Solution percentages express a weight to volume relationship, and solution ratios express a volume to volume relationship, unless stated otherwise. Nuclear magnetic resonance (NMR) spectra were recorded either on a Bruker 300, 400 or 500 MHz spectrometer; the chemical shifts (δ) are reported in parts per million. Flash chromatography was carried out on silica gel (SiO₂) evident to one skilled in the art. All Liquid Chromatography (LC) data were recorded on a Shimadzu LC-10AS liquid chromatograph using a SPD-11AV UV-Vis detector and Mass Spectrometry (MS) data were determined with a Micromass Platform for LC in electrospray mode (ES+).

Unless otherwise noted, each compound was analyzed, by LC/MS, using one of five methodologies, having the following conditions.

Columns:
  (Method A)—YMC ODS S7 C18 3.0×50 mm
  (Method B)—YMC ODS-A S7 C18 3.0×50 mm
  (Method C)—YMC S7 C18 3.0×50 mm
  (Method D)—YMC Xterra ODS S7 3.0×50 mm
  (Method E)—YMC Xterra ODS S7 3.0×50 mm
  (Method F)—YMC ODS-A S7 C18 3.0×50 mm
  (Method G)—YMC C18 S5 4.6×50 mm]
  (Method H)—Xterra S7 3.0×50 mm
  (Method I)—Xterra S7 C18 3.0×50 mm
Gradient:
  100% Solvent A/0% Solvent B to
  0% Solvent A/100% Solvent B
Gradient time: 2 min. (A, B, D, F, G, H, I); 8 min. (C, E)
Hold time: 1 min. (A, B, D, F, G, H, I); 2 min. (C, E)
Flow rate: 5 mL/min
Detector Wavelength: 220 nm
Solvent A: 10% MeOH/90% H₂O/0.1% TFA
Solvent B: 10% H₂O/90% MeOH/0.1% TFA.
  (Method J)—YMC Xterra ODS S7 3.0×50 mm
Gradient:
  100% Solvent A/0% Solvent B to
  0% Solvent A/100% Solvent B
Gradient time: 4 min (A)
Hold time: 1 min (A); 2 min
Flow rate: 4 mL/min
Detector Wavelength: 220 nm
Solvent A: 10% MeOH/90% H₂O/0.1% TFA
Solvent B: 10% H₂O/90% MeOH/0.1% TFA.

The compounds and chemical intermediates of the present invention, described in the following examples, were prepared according to the following methods. For the description of the examples, in a synthetic step such as 1a, the numeral refers to the example number and the letter refers to the relative sequential step in the sequence.

EXAMPLE 1

Step 1a: Preparation of 4-hydroxy-2-phenyl-7-methoxy-quinoline

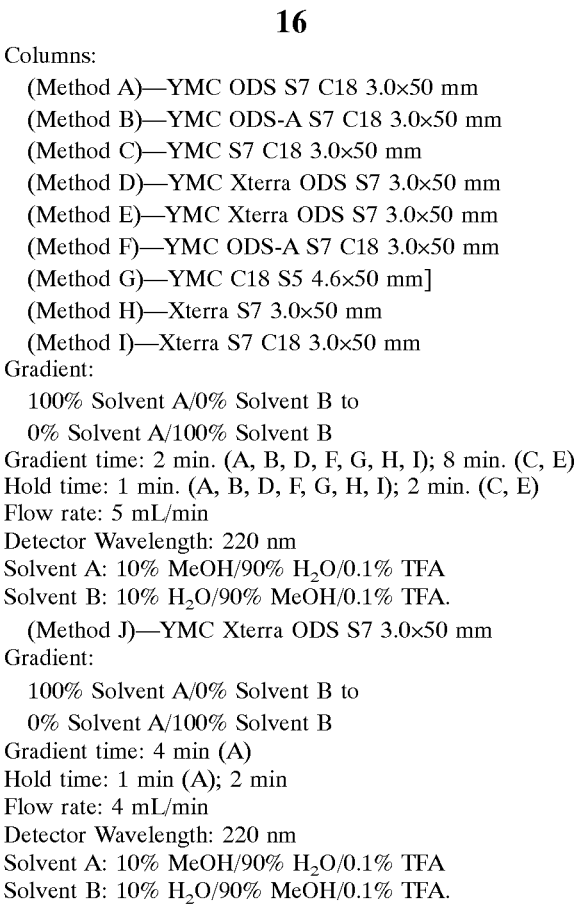

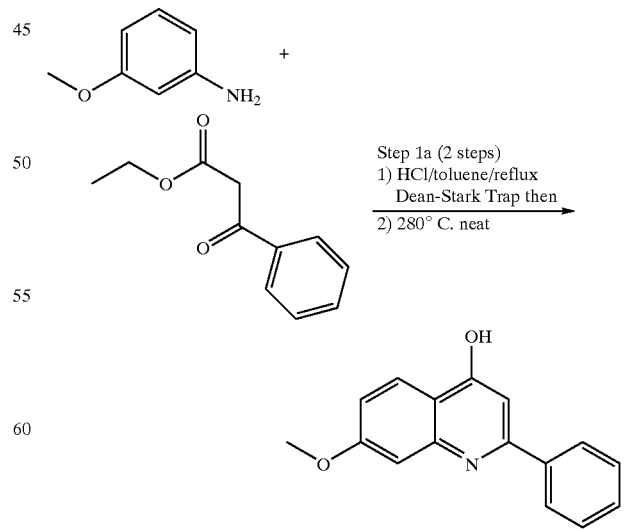

To a solution of m-anisidine (300 g, 2.44 mole) and ethyl benzoylacetate (234.2 g, 1.22 mole) in toluene (2.0 L) was added HCl (4.0 N in dioxane, 12.2 mL, 48.8 mmole). The resulting solution was refluxed for 6.5 hr using a Dean-Stark apparatus (about 56 ml of aqueous solution was collected). The mixture was cooled to rt, partitioned multiple times with aqueous HCl (10%, 3×500 mL), aqueous NaOH (1.0 N, 2×200 mL), water (3×200 mL), and the organic layer dried (MgSO₄) and concentrated in vacuo to supply an oily residue (329.5 g). The crude product was heated in an oil bath (280° C.) for 80 min using a Dean-Stark apparatus (about 85 mL liquid was collected). The reaction mixture was cooled down to rt, the solid residue triturated with CH₂Cl₂ (400 mL), the resulting suspension filtered, and the filter cake washed with more CH₂Cl₂ (2×150 mL). The resulting solid was dried in vacuo (50° C.; 1 torr; 1 day) affording analytically pure 4-hydroxy-7-methoxy-2-phenylquinoline as a light brown solid (60.7 g, 20% overall): $^1$H NMR δ (DMSO) 3.86 (s, 3H), 6.26 (s, 1H), 6.94 (dd, J=9.0, 2.4 Hz, 1H), 7.21 (d, J=2.4 Hz, 1H), 7.56–7.61 (m, 3H), 7.80–7.84 (m, 2H), 8.00 (d, J=9.0 Hz, 1H), 11.54 (s, 1H); $^{13}$C NMR (DMSO-d₆) δ 55.38, 99.69, 107.07, 113.18, 119.22, 126.52, 127.17, 128.97, 130.34, 134.17, 142.27, 149.53, 161.92, 176.48.

Step 1b: Preparation of 4-Chloro-7-methoxy-2-phenyl-quinoline

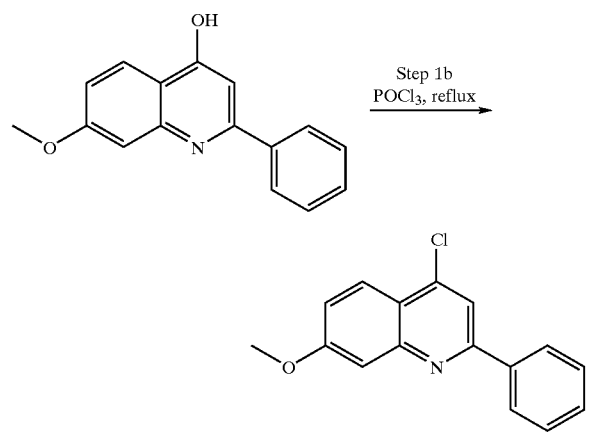

The 4-hydroxy-2-phenyl-7-methoxyquinoline (21.7 g, 86.4 mmole) was suspended in POCl₃ (240 mL). The suspension was refluxed for 2 hours. After removal of the POCl₃ in vacuo, the residue was partitioned between EtOAc (1L), and cold aqueous NaOH (generated from 1.0N 200 mL NaOH and 20 mL 10.0 N NaOH) and stirred for 15 min. The organic layer was washed with water (2×200 mL), brine (200 mL), dried (MgSO₄), and concentrated in vacuo to supply 4-chloro-2-phenyl-7-methoxyquinoline (21.0 g, 90%) as a light brown solid. $^1$H NMR (DMSO-d₆) δ 3.97 (s, 3H), 7.36 (dd, J=9.2, 2.6 Hz, 1H), 7.49–7.59 (m, 4H), 8.08 (d, J=9.2 Hz, 1H), 8.19 (s, 1H), 8.26–8.30 (m, 2H); $^{13}$C NMR (DMSO-d₆) δ 55.72, 108.00, 116.51, 119.52, 120.48, 124.74, 127.26, 128.81, 130.00, 137.58, 141.98, 150.20, 156.65, 161.30. LC-MS (Method D: retention time: 1.547), MS m/z 270 (M⁺+1)

Step 1c: Preparation of N-Boc (2S,4R)-(2-phenyl-7-methoxy quinoline-4-oxo)proline

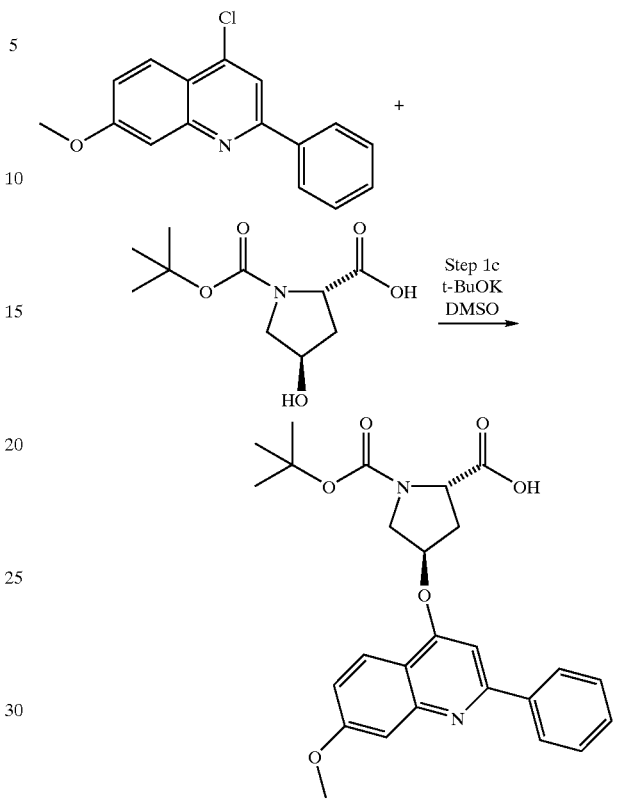

To a suspension of N-Boc (2S,4R)-hydroxyproline (16.44 g, 71.1 mmol) (Fluka) in DMSO (250 mL) was added t-BuOK (19.93 g, 177.6 mmol) at 0° C. The generated mixture was stirred for 1.5 hour and then 4-chloro-7-methoxy-2-phenylquinoline (21.02 g, 77.9 mmol) added in three portions over 1 h. The reaction was stirred for one day, the reaction mixture was poured into cold water (1.5L) and washed with Et₂O (4×200 mL). The aqueous solution was acidified to pH 4.6, filtered to obtain a white solid, and dried in vacuo to supply the product, N-Boc (2S,4R)-(2-phenyl-7-methoxyquinoline-4-oxo)proline (32.5 g, 98%): $^1$H NMR (DMSO) δ 1.30, 1.32 (2s, 9H), 2.27–2.31 (m, 1H), 2.58–2.69 (m, 1H), 3.73 (s, 2H), 3.88 (s, 3H), 4.30–4.35 (m, 1H), 5.72 (s, 1H), 7.11–7.17 (m, 1H), 7.35–7.57 (m, 5H), 7.92–7.97 (m, 1H), 8.24 (d, J=9.0 Hz, 2H), 12.76 (bs, 1H); LC-MS (Method D: retention time: 2.01; MS m/z 465 (M⁺+H).

Step 1d: Preparation of Racemic (1R,2S)/(1S,2R)-1-amino-2-vinylcyclopropane carboxylic acid ethyl ester hydrochloride (Method A and Method B) and chiral resolution of this racemate for the preparation of N-(1R, 2S)-1-amino-2-vinylcyclopropane carboxylic acid ethyl ester hydrochloride (Method C)

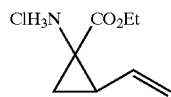

The named compound was made (Step d) racemic by each of the following methods A and B. This racemate could also be resolved to afford chiral Boc-(1R, 2S)-1-amino-2-vinylcyclopropyl carboxylic acid ester which was deprotected under acid conditions to afford (1R, 2S)-1-amino-2-vinylcyclopropane carboxylic acid ester hydrochloride (Method C).

Method A
A.1 Preparation of N-Benzyl Imine of Glycine Ethyl Ester

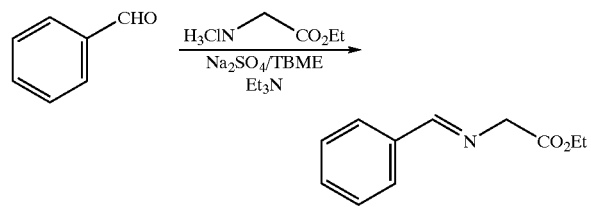

Glycine ethyl ester hydrochloride (303.8 g, 2.16 mole) was suspended in tert-butylmethyl ether (1.6 L). Benzaldehyde (231 g, 2.16 mole) and anhydrous sodium sulfate (154.6 g, 1.09 mole) were added and the mixture cooled to 0° C. using an ice-water bath. Triethylamine (455 mL, 3.26 mole) was added dropwise over 30 min and the mixture stirred for 48 h at rt. The reaction was then quenched by addition of ice-cold water (1 L) and the organic layer was separated. The aqueous phase was extracted with tert-butylmethyl ether (0.5 L) and the combined organic phases washed with a mixture of saturated aqueous NaHCO$_3$ (1 L) and brine (1 L). The solution was dried over MgSO$_4$, concentrated in vacuo to afford 392.4 g of the N-benzyl imine product as a thick yellow oil that was used directly in the next step. $^1$H NMR (CDCl$_3$, 300 MHz) δ 1.32 (t, J=7.1 Hz, 3H), 4.24 (q, J=7.1 Hz, 2H), 4.41 (d, J=1.1 Hz, 2H), 7.39–7.47 (m, 3H), 7.78–7.81 (m, 2H), 8.31 (s, 1H).

A.2 Preparation of racemic N-Boc-(1R,2S)/(1S,2R)-1-amino-2-vinylcyclopropane carboxylic acid ethyl ester

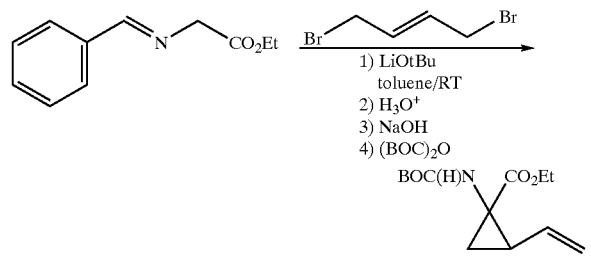

To a suspension of lithium tert-butoxide (84.06 g, 1.05 mol) in dry toluene (1.2 L), was added dropwise a mixture of the N-benzyl imine of glycine ethyl ester (100.4 g, 0.526 mol) and trans-1,4-dibromo-2-butene (107.0 g, 0.500 mol) in dry toluene (0.6 L) over 60 min. After completion of the addition, the deep red mixture was quenched by addition of water (1 L) and tert-butylmethyl ether (TBME, 1 L). The aqueous phase was separated and extracted a second time with TBME (1 L). The organic phases were combined, 1 N HCl (1 L) was added and the mixture stirred at room temperature for 2 h. The organic phase was separated and extracted with water (0.8 L). The aqueous phases were then combined, saturated with salt (700 g), TBME (1 L) was added and the mixture cooled to 0° C. The stirred mixture was then basified to pH 14 by the dropwise addition of 10 N NaOH, the organic layer separated, and the aqueous phase extracted with TBME (2×500 mL). The combined organic extracts were dried (MgSO$_4$) and concentrated to a volume of 1L. To this solution of free amine, was added BOC$_2$O or di-tert-butyldicarbonate (131.0 g, 0.6 mol) and the mixture stirred 4 days at rt. Additional di-tert-butyldicarbonate (50 g, 0.23 mol) was added to the reaction, the mixture refluxed for 3 h, and was then allowed cool to room temperature overnight. The reaction mixture was dried over MgSO$_4$ and concentrated in vacuo to afford 80 g of crude material. This residue was purified by flash chromatography (2.5 Kg of SiO$_2$, eluted with 1% to 2% MeOH/CH$_2$Cl$_2$) to afford 57 g (53%) of racemic N-Boc-(1R,2S)/(1S,2R)-1-amino-2-vinylcyclopropane carboxylic acid ethyl ester as a yellow oil which solidified while sitting in the refrigerator: $^1$H NMR (CDCl$_3$, 300 MHz) δ 1.26 (t, J=7.1 Hz, 3H), 1.46 (s, 9H), 1.43–1.49 (m, 1H), 1.76–1.82 (br m, 1H), 2.14 (q, J=8.6 Hz, 1H), 4.18 (q, J=7.2 Hz, 2H), 5.12 (dd J=10.3, 1.7 Hz, 1H), 5.25 (br s, 1H), 5.29 (dd, J=17.6, 1.7 Hz, 1H), 5.77 (ddd, J=17.6, 10.3, 8.9 Hz, 1H); MS m/z 254.16 (M-1)

A.3 Preparation of Racemic (1R,2S)/(1S,2R) 1-amino-2-vinylcyclopropane carboxylic acid ethyl ester hydrochloride

N-Boc-(1R,2S)/(1S,2R)-1-amino-2-vinylcyclopropane carboxylic acid ethyl ester (9.39 g, 36.8 mmol) was dissolved in 4 N HCl/dioxane (90 ml, 360 mmol) and was stirred for 2 h at rt. The reaction mixture was concentrated to supply (1R,2S)/(1S,2R)-1-amino-2-vinylcyclopropane carboxylic acid ethyl ester hydrochloride in quanitative yield (7 g, 100%). $^1$H NMR (methanol-d$_4$) δ 1.32 (t, J=7.1, 3H), 1.72 (dd, J=10.2, 6.6 Hz, 1H), 1.81 (dd, J=8.3, 6.6 Hz, 1H), 2.38 (q, J=8.3 Hz, 1H), 4.26–4.34 (m, 2H), 5.24 (dd, 10.3, 1.3 Hz, 1H) 5.40 (d, J=17.2, 1H), 5.69–5.81 (m, 1H).

Method B

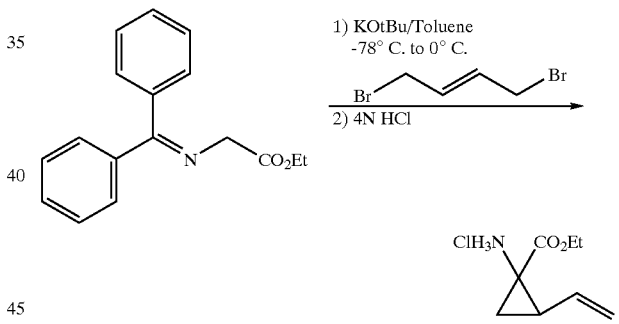

To a solution of potassium tert-butoxide (11.55 g, 102.9 mmol) in THF (450 mL) at −78° C. was added the commercially available N,N-dibenzyl imine of glycine ethyl ester (25.0 g, 93.53 mmol) in THF (112 mL). The reaction mixture was warmed to 0° C., stirred for 40 min, and was then cooled back to −78° C. To this solution was added trans-1,4-dibromo-2-butene (20.0 g, 93.50 mmol), the mixture stirred for 1 h at 0° C. and was cooled back to −78° C. Potassium tert-butoxide (11.55 g, 102.9 mmol) was added, the mixture immediately warmed to 0° C., and was stirred one more hour before concentrating in vacuo. The crude product was taken up in Et$_2$O (530 mL), 1N aq. HCl solution (106 mL, 106 mmol) added and the resulting biphasic mixture stirred for 3.5 h at rt. The layers were separated and the aqueous layer was washed with Et$_2$O (2×) and basified with a saturated aq. NaHCO$_3$ solution. The desired amine was extracted with Et$_2$O (3×) and the combined organic extract was washed with brine, dried (MgSO$_4$), and concentrated in vacuo to obtain the free amine. This material was treated with a 4N HCl solution in dioxane (100 mL, 400 mmol) and concentrated to afford (1R,2S)/(1S,2R)-1-amino-2-vinylcyclopropane carboxylic acid ethyl ester hydrochloride as a brown semisolid (5.3 g, 34% yield) identical to the material obtained from procedure A, except for the presence of a small unidentified aromatic impurity (8%).

Method C

C.1 Resolution of N-Boc-(1R,2S)/(1S,2R)-1-amino-2-vinylcyclopropane Carboxylic Acid Ethyl Ester Hydrochloride

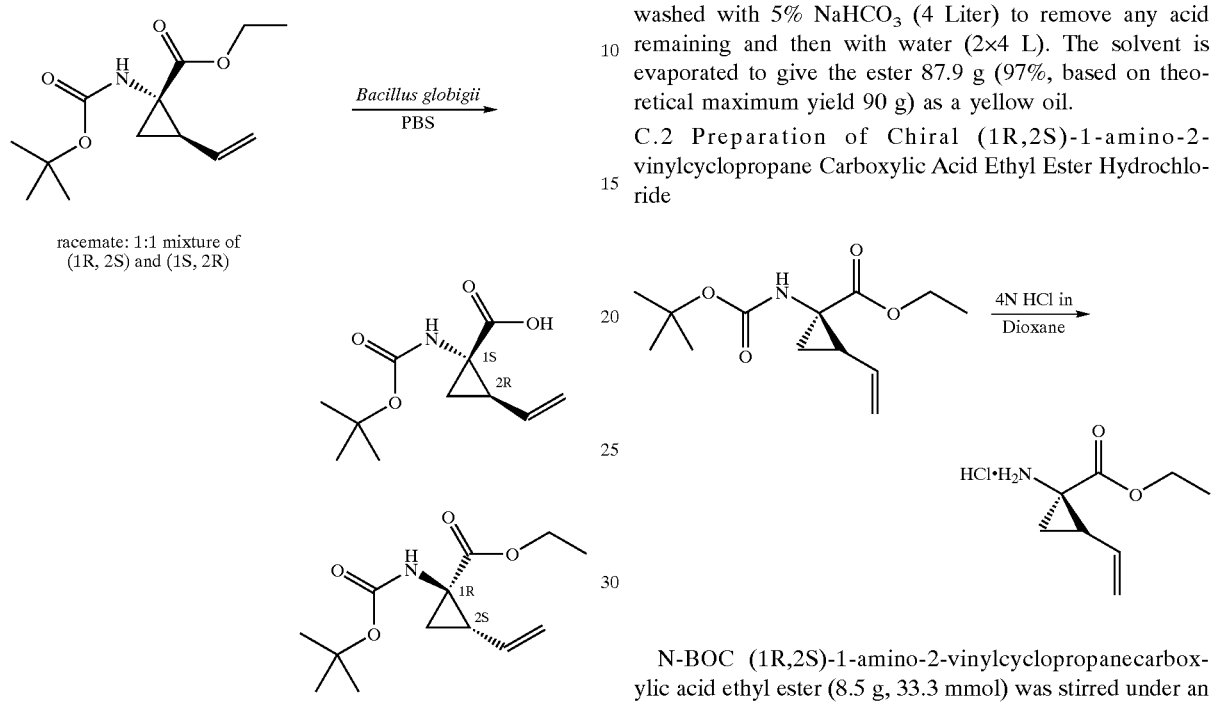

racemate: 1:1 mixture of (1R, 2S) and (1S, 2R)

A solution of phosphate buffer (pH 8.0, 6.12 g, KH$_2$PO$_4$, 121.41 g, Na$_2$PO$_4$, in 9 L of water) was warmed to 40° C. in a jacketed reactor with a mechanical stirrer. If needed, the pH was adjusted to 8.0 with the addition of phosphoric acid. A solution (1.8 kg) of protease enzyme from Bacillus globigii (Sigma) was added and the pH of the resulting mixture was adjusted to 8.0 by the addition of 50% NaOH. To this mixture was then added the racemic ester (180 g, 0.75 mmol) as a DMSO solution (1.8 L) over a period of 2 hours. A few ml of 50% NaOH was added in the first 4 hours to keep the pH at 8.0. Aliquots (1 ml) were taken from the reaction mixture at various tires and analyzed by the following procedure: 1) Acidification to pH 4 by addition of 6 (N) sulfuric acid. 2) The aliquot (1 ml) was extracted with MTBE (2 ml) and the MTBE extract divided into two portions and evaporated. 3) One portion was redissolved in acetonitrile and analyzed by HPLC to determine the conversion: HPLC Column: YMC Propack C-18, 150×4.6 mm, S-3 μm. 40° C. Solvent: Gradient 0.2% H$_3$PO$_4$—CH$_3$CN 70:30 to 10:90 in 15 minutes, Re-equilibration back to original at 16 minutes and continue till 20 min before next injection. Flow Rate: 1 ml/min, Detection: UV 210 nm. Elution Time: Acid 4.7 min, Ester 8 min 4) The second portion portion was redissolved in the mobile phase and analyzed by HPLC to determine the enantiomeric excess: Column: Chiralpak AD, Room Temperature, Solvent: Heptane:Ethanol (Absolute, 200 proof): Trifluoroacetic acid (97.4:2.5:0.1) Flow rate: 1 ml/min, Detection: UV 210 nm Elution: Desired (1R,2S) enantiomer 9.2 min, Undesired (1S,2R) enantiomer 9.7 min Note: The reaction was terminated when the analysis showed that the enantiomeric-excess of the ester has reached the desired level (usually ee>95% in 16–24 hrs). After 22 hours, the reaction was cooled to room temperature. The pH was 7.75. Analyses of an aliquot (as above) showed acid to ester ratio of 55:45. Sodium hydroxide (10%) was added to the reaction mixture to bring the pH to 8.5. The aqueous layer was extracted with MTBE (2×6 Liter) until no ester remained in the aqueous layer. The MTBE extracts were washed with 5% NaHCO$_3$ (4 Liter) to remove any acid remaining and then with water (2×4 L). The solvent is evaporated to give the ester 87.9 g (97%, based on theoretical maximum yield 90 g) as a yellow oil.

C.2 Preparation of Chiral (1R,2S)-1-amino-2-vinylcyclopropane Carboxylic Acid Ethyl Ester Hydrochloride N-BOC (1R,2S)-1-amino-2-vinylcyclopropanecarboxylic acid ethyl ester (8.5 g, 33.3 mmol) was stirred under an N$_2$ atmosphere with 200 mL of 4N HCl/dioxane (Aldrich) at rt for 3 h. The solvent was removed under reduced pressure keeping the temperature below 40 C. This gave 6.57 g (~100%) of (1R,2S)-1-amino-2-vinylcyclopropanecarboxylic acid ethyl ester hydrochloride as a light tan solid. $^1$H NMR (300 MHz, CD$_3$OD) δ 1.31 (t, J=7.0 Hz, 3H), 1.69–1.82 (m, 2H), 2.38 (q, J=8.8 Hz, 1H), 4.29 (q, J=7.0 Hz, 2H), 5.22 (d, J=10.3 Hz, 1H), 5.40 (d, J=17.2 Hz, 1H), 5.69–5.81 (m, 1H). LC-MS (Method J, retention time: 0.58 min), MS m/z 156 (M$^+$+1)

Step 1e: Preparation of 2(S)-(1(R)-ethoxycarbonyl-2(S)-vinylcyclopropylcarbamoyl)-4(R)-(7-methoxy-2-phenyl-quinolin-4-yloxy)pyrrolidine-1-carboxylic acid tert-butyl ester (High Rf Diastereomer) and 2(S)-(1(S)-ethoxycarbonyl-2(R)-vinylcyclopropylcarbamoyl)-4(R)-(7-methoxy-2-phenylquinolin-4-yloxy)-pyrrolidine-1-carboxylic acid tert-butyl ester (Low Rf Diastereomer)

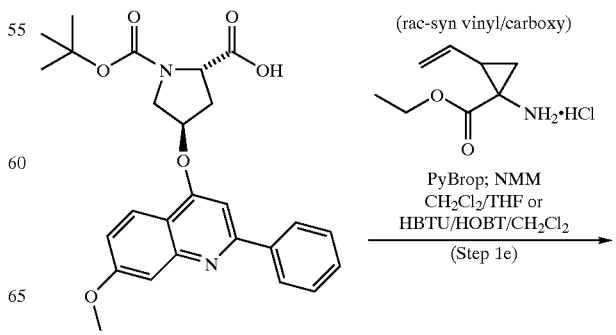

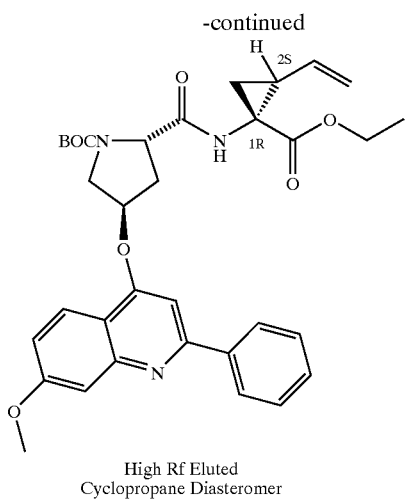

High Rf Eluted
Cyclopropane Diasteromer

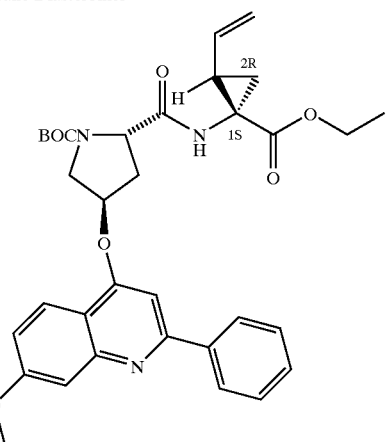

Low Rf Eluted
Cyclopropane Diasteromer

Method A: To a solution of Boc-(2S,4R)-(2-phenyl-7-methoxyquinoline-4-oxo)proline (11.0 g, 23.7 mmole), (1R,2S)/(1S,2R)-1-amino-2-vinylcyclopropane carboxylic acid ethyl ester hydrochloride where carboxy group is syn to vinyl moiety (5.40 g, 28.2 mmole), NMM (20.8 mL; 18.9 mmole) in 500 mL of 50% CH$_2$Cl$_2$/THF was added the coupling reagent PyBrop or Bromotrispyrrolidinophosphonium hexafluorophosphate (16.0 g, 34.3 mmole) in three portions in 10 min at 0° C. The solution was stirred at rt for one day and then was washed with pH 4.0 buffer (4×50 mL). The organic layer was washed with saturated aqueous NaHCO$_3$ (100 mL), the aqueous washing extracted with ethyl acetate (150 mL), and the organic layer backwashed with pH 4.0 buffer (50 mL), and saturated aqueous NaHCO$_3$ (50 mL). The organic solution was dried (MgSO$_4$), concentrated and purified using a Biotage 65M column (eluted with 50% EtOAc/Hexanes) to provide over 7.5 g of a 1:1 mixture of (1R,2S) and (1S,2R) cyclopropane diastereomers (50% overall) or alternatively elution using a slow to 15% to 60% EtOAc in hexanes gradient to supply 3.54 g, 25% overall of the high Rf eluted (1R,2S) cyclopropane diastereomer and 3.54 g, 25% overall of the low Rf eluted (1S,2R) cyclopropane diastereomer.

Method B: To a solution of (1R,2S)/(1S,2R)-1-amino-2-vinylcyclopropane carboxylic acid ethyl ester hydrochloride (7.5 g, 39.1 mmol) was combined with diisopropylethylamine (32.5 mL, 186 mmol) in dichloromethane (150 mL). To the resulting mixture was added HOBT hydrate (6.85 g, 44.7 mmol) and N-Boc (2S,4R)-(2-phenyl-7-methoxyquinoline-4-oxo)proline (17.3 g, 37.3 mmol) followed by addition of HBTU (16.96 g, 44.7 mmol). A slight exotherm occurred immediately, and the mixture was stirred at room temperature overnight. The mixture was then concentrated in vacuo and redissolved in ethyl acetate (600 mL).

The solution was washed with water (2×200 mL), then with 10% aqueous sodium bicarbonate (2×200 mL), then with water (150 mL) and finally with brine (150 mL). The organic was dried over anhydrous magnesium sulfate and filtered, and the filtrate was concentrated in vacuo to a beige glassy solid. Purification was performed in multiple batches (7 g each) by flash chromatography on a Biotage Flash 75M cartridge (66% hexanes/ethyl acetate) to provide the high Rf eluted (1R,2S) cyclopropane diastereomer (9.86 g total, 44.0% yield), followed by the low Rf eluted cyclopropane diastereomer (10.43 g total, 46.5% yield). A total of 1.97 g of mixed fractions were recovered to give an overall conversion of 99.3% to the two diastereomers.

Data for 2(S)-(1(R)-ethoxycarbonyl-2(S)-vinylcyclopropylcarbamoyl)-4(R)-(7-methoxy-2-phenylquinolin-4-yloxy)pyrrolidine-1-carboxylic acid tert-butyl ester (High Rf Cyclopropane Diastereomer): $^1$H NMR (CDCl$_3$) δ 1.22 (t, J=7.1 Hz, 3H), 1.44 (s, 9H), 1.48–1.58 (m, 1H), 1.89 (bs, 1H), 2.05–2.20 (m, 1H), 2.4 (bs, 1H), 2.90 (bs, 1H), 3.80, 3.87 (2bs, 2H), 3.94 (s, 3H), 4.07–4.22 (m, 2H), 4.56 (bs, 1H), 5.13 (d, J=10.2 Hz, 1H), 5.30 (d, J=17.1 Hz, 1H), 5.70–5.82 (m, 1H), 7.03 (bs, 1H), 7.09 (dd, J=9.1, 2 Hz, 1H), 7.42–7.53 (m, 4H), 7.61 (bs, 1H), 7.96 (d, J=9.1 Hz, 1H), 8.05 (d, J=7.2 Hz, 2H); $^1$H NMR (methanol-d$_4$) δ 1.23 (t, J=7.2 Hz, 3H), 1.4 (s, 4H), 1.45 (s, 6H), 1.73 (dd, J=7.9, 1.5 Hz, 0.4H), 1.79 (dd, J=7.8, 2.4 Hz, 0.6H), 2.21 (q, J=8.2 Hz, 1H), 2.44–2.49 (m, 1H), 2.66–2.72 (m, 0.4H), 2.73–2.78 (m, 0.6H), 3.93–3.95 (m, 2H), 3.96 (s, 3H), 4.10–4.17 (m, 2H), 4.44 (q, J=7.8 Hz, 1H), 5.13 (d, J=10.7 Hz, 1H), 5.31 (d, J=17.7 Hz, 0.4H), 5.32 (d, J=17.4 Hz, 0.6H), 5.49 (bs, 1H), 5.66–5.82 (m, 1H), 7.16 (dd, J=9.2, 2.5 Hz, 1H), 7.26 (s, 1H), 7.42 (d, J=2.4 Hz, 1H), 7.48–7.55 (m, 3H), 8.02–8.05 (m, 3H); $^{13}$C NMR (CDCl$_3$) δ 14.22; 22.83, 28.25, 33.14, 33.58, 39.92, 51.84, 55.47, 58.32, 61.30, 75.86, 81.27, 98.14, 107.42, 115.00, 117.84, 118.27, 122.63, 123.03, 127.50, 128.72, 129.26, 133.39, 140.06, 151.23, 159.16, 160.34, 161.35, 169.78, 171.68. LC-MS (Method D: retention time: 1.62), MS m/z 602 (M$^+$+1).

Data for 2(S)-(1(S)-ethoxycarbonyl-2(R)-vinylcyclopropylcarbamoyl)-4(R)-(7-methoxy-2-phenylquinolin-4-yloxy)pyrrolidine-1-carboxylic acid tert-butyl ester (Low Rf Cyclopropane Diastereomer): $^1$H NMR (CDCl$_3$) δ 1.25 (t, J=7.2 Hz, 3H), 1.45 (s, 9H), 1.35–1.52 (m, 1H), 1.85 (bs, 1H), 2.13–2.22 (m, 1H), 2.4 (bs, 1H), 2.95 (bs, 1H), 3.83 (bs, 2H), 3.99 (s, 3H), 4.13 (q, J=7.2 Hz, 2H), 4.59 (s, 1H), 5.16 (d, J=10.8 Hz, 1H), 5.33 (d, J=17.2 Hz, 1H), 5.40 (bs, 1H), 5.74–5.86 (m, 1H), 7.06 (s, 1H), 7.14 (dd, J=9.2, 2.3 Hz, 1H), 7.46–7.6 (m, 3H), 8.00 (d, J=9.2 Hz, 1H), 8.08, 8.10 (2s, 2H) LC-MS (Method D: retention time: 1.66), MS m/z 602 (M$^+$+1).

Step 1f: Preparation of 1-{[4-(7-Methoxy-2-phenylquinolin-4(R)-yloxy)pyrrolidine-2(S)-carbonyl]-1(R)-amino}-2(S)-vinylcyclopropanecarboxylic acid ethyl ester, dihydrochloride

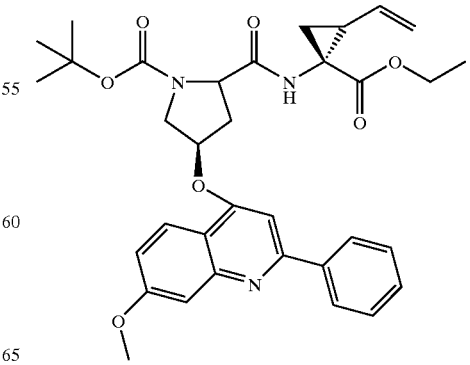

Step 1f
HCl/dioxane

-continued

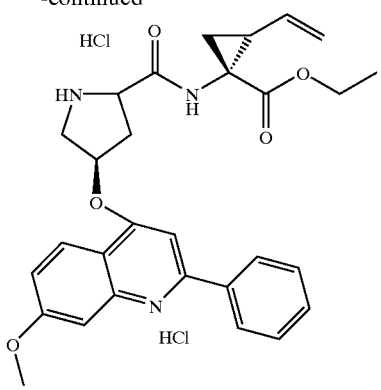

5.88 g (9.77 mmol) of 2(S)-(1(R)-ethoxycarbonyl-2(S)-vinylcyclopropylcarbamoyl)-4(R)-(7-methoxy-2-phenylquinolin-4-yloxy)pyrrolidine-1-carboxylic acid tert-butyl ester (High Rf Cyclopropane Diastereomer) was dissolved in HCl/dioxane (4.0M; 200 ml) and was stirred for 2.5 h at rt. The reaction mixture was concentrated to supply the titled compound which was directly used in the next step. $^1$H NMR (methanol-$d_4$) δ 1.25 (t, J=7.1 Hz, 3H), 1.51 (dd, J=9.6, 5.4 Hz, 1H), 1.78 (dd, J=8.1, 5.5 Hz, 1H), 2.30 (dd, J=17.7, 8.7 Hz, 1H), 2.27–2.67 (m, 1H), 3.06 (dd, J=14.6, 7.4 Hz, 1H), 3.56–3.76 (m, 3H), 3.99 (s, 2H), 4.07 (s, 3H), 4.16 (q, 2H), 4.77 (dd, J=10.4, 7.4 Hz, 1H), 5.13 (dd, J=10.3, 1.7 Hz), 5.33 (dd, J=17.1, 1.7 Hz), 5.71–5.81 (m, 1H), 6.06 (bs, 1H), 7.49 (dd, J=9.4, 2.3 Hz, 1H), 7.66–7.77 (m, 4H), 8.12–816 (m, 2H), 8.55 (d, J=9.4 Hz, 1H). $^{13}$C NMR (methanol-$d_4$) δ 14.77, 23.23, 34.86, 37.25, 41.19, 43.90, 52.66, 60.35, 62.32, 62.83, 68.27, 72.58, 73.70, 81.21, 100.70, 102.44, 116.13, 118.67, 122.25, 126.93, 130.27, 130.94, 133.19, 134.14, 134.89, 143.79, 158.39, 166.84, 167.44, 169.57, 171.33. LC-MS (Method D: retention time: 1.55), MS m/z 502 (M$^+$+1)

EXAMPLES 1,2

Preparation of Compounds 1 and 2

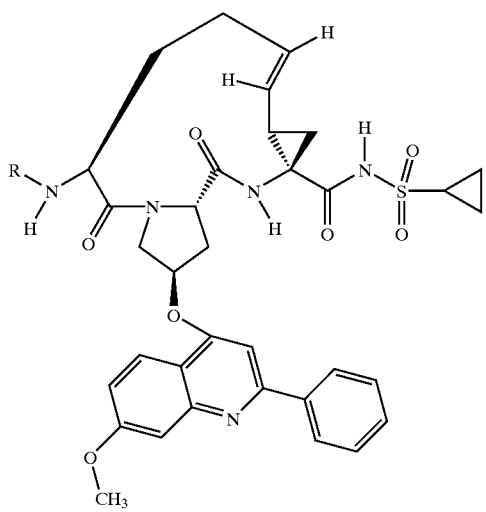

Compound 1-R is Boc
Compound 2-R is H

Step 1g: Preparation of 1-{[1-(2(S)-tert-butoxycarbonyl-amino-hex-5-enoyl)-4-(7-methoxy-2-phenyl-quinolin-4(R)-yloxy)pyrrolidine-2(S)-carbonyl]-1(R)-amino]-2(S)-vinylcyclopropanecarboxylic acid ethyl ester

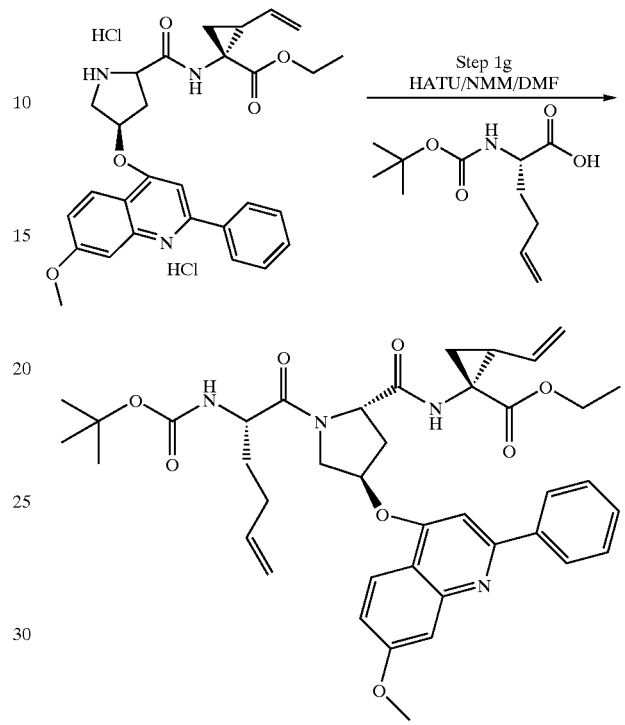

To suspension of (0.600 g; 1.04 mmol) of 1-{[4-(7-Methoxy-2-phenylquinolin-4(R)-yloxy) pyrrolidine-2(S)-carbonyl]-1(R)-amino}-2(S)-vinylcyclopropanecarboxylic acid ethyl ester, dihydrochloride, 2(S)-tert-butoxycarbonyl-amino-5-hexenoic acid purchased from RSP Amino Acids (0.34 g, 1.46 mmol), NMM (0.57 ml, 5.22 mmol) in DMF (5 mL) was added HATU (0.56 g, 1.46 mmol) at 0° C. After being stirred for 2 days, the reaction mixture was diluted with EtOAc (200 mL), washed with pH 4.0 buffer (2×30 mL), saturated aqueous NaHCO$_3$ (30 mL), brine (30 mL), dried (MgSO$_4$), purified by a Biotage 40 M column (eluted with 30% to 60% EtOAc in Hexanes) to supply the titled compound, 1-{[1-(2(S)-tert-butoxycarbonylamino-hex-5-enoyl)-4-(7-methoxy-2-phenyl-quinolin-4(R)-yloxy)-pyrrolidine-2(S)-carbonyl]-11(R)-amino}-2(S)-vinylcyclopropanecarboxylic acid ethyl ester, as a yellow oil (0.56 g, 76%): $^1$H NMR (300 MHz, CDCl$_3$) δ 1.20 (t, J=7 Hz, 3H), 1.39 (s, 9H), 1.43–1.48 (m, 1H), 1.64–1.92 (m, 4H), 2.10–2.20 (m, 2H), 2.36–2.44 (m, 1H), 2.91–2.99 (m, 1H), 3.94 (s, 3H), 4.04–4.22 (m, 2H), 4.29 (d, J=11 Hz, 1H), 4.46–4.51 (m, 1H), 4.81 (dd, J=8.1, 5.5 Hz, 1H),4.98–5.15 (m, 4H), 5.29 (dd, J=17.2, 1.5 Hz, 1H), 5.41 (brs, 1H), 5.67–5.86 (m, 2H), 7.04 (s, 1H), 7.08 (dd, J=9.2, 2.6 Hz, 1H), 7.42–7.64 (m, 4H), 7.97–8.06 (m,-3H). LC-MS (Method E-retention time: 1.59), MS m/z 713 (M$^+$+1).

Step 1h: Preparation of (1S,4R,6S,11S)-7-trans-11-tert-butoxycarbonylamino-15-(7-methoxy-2-phenylquinolin-4-yloxy)-2,12-dioxo-3,13-diazatricyclo[11.3.0.04,6]hexadec-7-ene-4-carboxylic acid ethyl ester

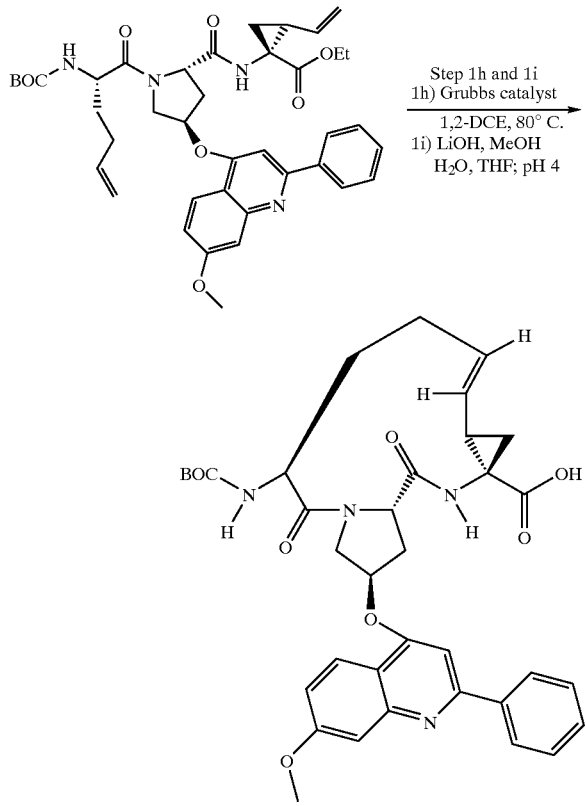

To a solution of 1-{[1-(2(S)-tert-butoxycarbonylamino-hex-5-enoyl)-4-(7-methoxy-2-phenyl-quinolin-4(R)-yloxy)-pyrroiidine-2(S)-carbonyl]-1(R)-amino}-2(S)-vinyl-cyclopropanecarboxylic acid ethyl ester (360 mg, 0.505 mmol) in 0.25L of Argon degassed 1,2-DCE, was added 70 mg of Grubbs catalyst, the mixture degassed under Ar and heated to reflux for 3 h. The reaction mixture was cooled to rt, the mixture degassed once more, a final 70 mg portion of Grubbs catalyst added, and the mixture heated to reflux for 12 h. The dark brown solution was concentrated in vacuo, purified by a Biotage 40 M column (eluted with 30% to 65% EtOAc in Hexanes) to supply the intermediate (1S,4R,6S,11S, 15R)-7-trans-11-tert-butoxycarbonylamino-15-(7-methoxy-2-phenylquinolin-4-yloxy)-2,12-dioxo-3,13-diazatricyclo-[11.3.0.0$^{4,6}$]hexadec-7-ene-4-carboxylic acid ethyl ester (165 mg, 46%) as a pale yellow oil: $^1$H NMR (500 MHz, CD$_3$OD) δ 1.12 (s, 9H), 1.23 (t, J=7 Hz, 3H), 1.41 (dd, J=7.5, 5.8 Hz, 1H), 1.64–1.71 (m, 2H), 2.04–2.18 (m, 2H), 2.32 (m, 2H), 2.60–2.70 (m, 2H), 3.95 (s, 3H), 4.11–4.23 (m, 4H), 4.34 (m, 1H), 4.64 (m, 1H), 5.25 (m, 1H), 5.54 (d, J=15.3 Hz, 1H), 5.65 (s, 1H), 7.18 (dd, J=9.2, 2.4 Hz, 1H), 7.29 (s, 1H), 7.40 (d, J=2.4 Hz, 1H), 7.56–7.59 (m, 3H), 8.02–8.04 (m, 2H), 8.09 (d, J=9.2 Hz, 1H). LC-MS (Method E-retention time: 1.66), MS m/z 685 (M$^+$+1).

Step 1i: Preparation of (1S,4R,6S,11S,15R)-7-trans-11-tert-butoxycarbonylamino-15-(7-methoxy-2-phenyl-quinolin-4-yloxy)-2,12-dioxo-3,13-diazatricyclo[11.3.0.0$^{4,6}$]hexadec-7-ene-4-carboxylic acid To a solution of (1S,4R,6S,11S,15R)-7-trans-11-tert-butoxycarbonylamino-15-(7-methoxy-2-phenylquinolin-4-yloxy)-2,12-dioxo-3,13-diazatricyclo[11.3.0.04,6]hexadec-7-ene-4-carboxylic acid ethyl ester (80 mg, 0.12 mmol) in 7 mL of 4:2:1 THF/H$_2$O/MeOH was added 28 mg of LiOH (0.70 mmol), the mixture stirred 24 h, the solution adjusted to pH 7, and the mixture concentrated until only the water layer remained. The solution was adjusted to pH 4, the acidic aqueous solution extracted with EtOAc (3×100 mL portions) and the organic extracts combined, dried (MgSO$_4$) and concentrated to afford (1S,4R,6S,11S,15R)-7-trans-11-tert-butoxycarbonyl-amino-15-(7-methoxy-2-phenylquinolin-4-yloxy)-2,12-dioxo-3,13-diazatricyclo[11.3.0.0$^{4,6}$]hexa-dec-7-ene-4-carboxylic acid (62.2 mg, 80%): $^1$H NMR (300 MHz, CD$_3$OD) δ 1.12 (s, 9H) 1.18–2.48 (m, 8H), 2.65–2.69 (m, 1H), 3.94 (s, 3H), 4.18–4.34 (m, 3H), 4.83 (t, J=8 Hz, 1H), 5.30–5.38 (m, 2H), 5.53–5.61 (m, 2H), 7.14 (dd, J=9.2, 2.4 Hz, 1H), 7.24 (s, 1H), 7.39 (d, J=2.4 Hz, 1H), 7.48–7.64 (m, 3H), 8.02–8.07 (m, 3H). LC-MS (Method E-retention time: 1.45), MS m/z 657 (M$^+$+1). HRMS m/z (M+H)+calcd for C$_{36}$H$_{41}$N$_4$O$_8$: 657.2924, found 657.2924.

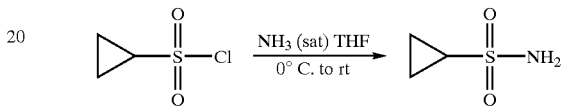

Preparation of Cyclopropylsulfonamide from Cyclopropyl Sulfonyl Chloride.

To a solution of 100 mL of THF cooled to 0° C. was bubbled in gaseous ammonia until saturation was reached. To this solution was added a solution of 5 g (28.45 mmol) of cyclopropylsulfonyl chloride (purchased from Array Biopharma) in 50 mL of THF, the solution warmed to rt overnite and stirred one additional day. The mixture was concentrated until 1–2 mL of solvent remained, applied on to 30 g plug of SiO$_2$ (eluted with 30% to 60% EtOAc/Hexanes) to afford 3.45 g (100%) of cyclopropyl sulfonamide as a white solid. $^1$H NMR (Methanol-d$_4$) δ 0.94–1.07 (m, 4H), 2.52–2.60 (m, 1H); $^{13}$C NMR (methanol-d$_4$) δ 5.92, 33.01.

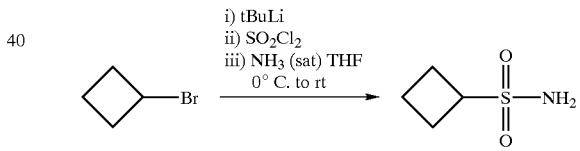

Preparation of Cyclobutylsulfonamide from Cylobutylbromide

To a solution of 5.0 g (37.0 mmol) of cyclobutyl bromide in 30 mL of anhydrous diethyl ether (Et$_2$O) cooled to −78° C. was added 44 mL (74.8 mmol) of 1.7M tert-butyl lithium in pentanes and the solution slowly warmed to −35° C. over 1.5 h. This mixture was cannulated slowly into a solution of 5.0 g (37.0 mmol) freshly distilled sulfuryl chloride in 100 mL of hexanes cooled to −40° C., warmed to 0° C. over 1 h and carefully concentrated in vacuo. This mixture was redissolved in Et$_2$O, washed once with some ice-cold water, dried (MgSO$_4$) and concentrated carefully. This mixture was redissolved in 20 mL of THF, added dropwise to 500 mL of saturated NH$_3$ in THF and was allowed to stir overnite. The mixture was concentrated in vacuo to a crude yellow solid and was recrystallized from the minimum amount of CH$_2$Cl$_2$ in hexanes with 1–2 drops of MeOH to afford 1.90 g (38%) of cyclobutylsulfonamide as a white solid. $^1$H NMR (CDCl$_3$) δ 1.95–2.06 (m, 2H), 2.30–2.54 (m, 4H), 3.86 (p, J=8 Hz, 1H), 4.75 (brs, 2H); $^{13}$C NMR (CDCl$_3$) δ 16.43, 23.93, 56.29. HRMS m/z (M−H)$^-$ calcd for C$_4$H$_8$NSO$_2$: 134.0276, found 134.0282.

Step 1j: Preparation of Compound 1, Example 1 (1S,4R,6S,11S,15R)-7-trans-[4-Cyclopropanesulfonyl-aminocarbonyl-15-(7-methoxy-2-phenylquinolin-4-yloxy)-2,12-dioxo-3,13-diazatricyclo[11.3.0.0⁴,⁶]hexa-dec-7-en-11-yl]carbamic acid tert-butyl ester

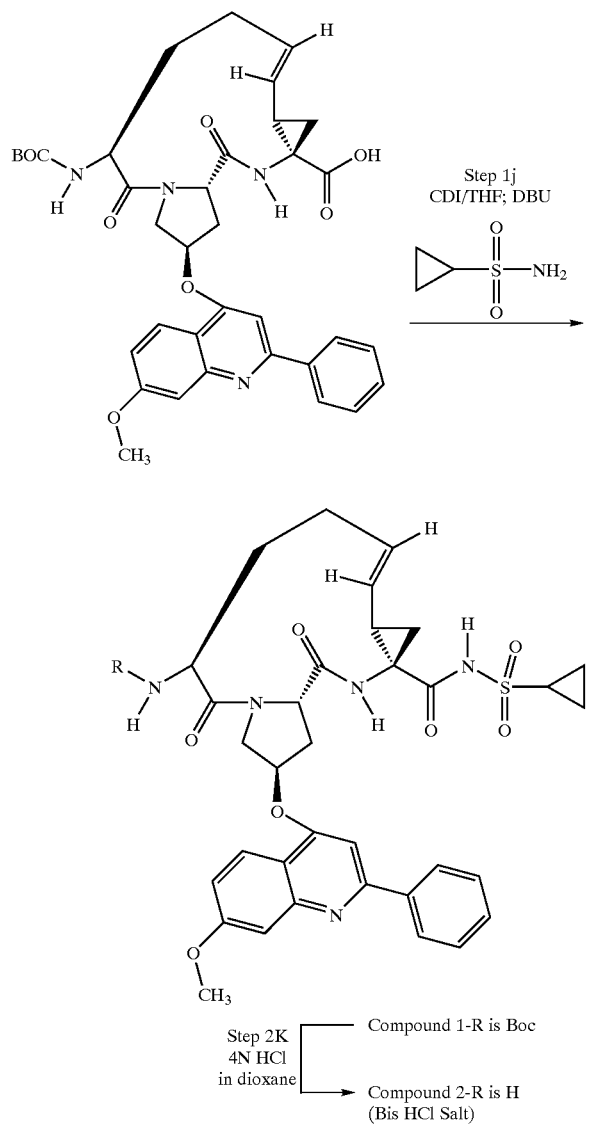

To a solution of (1S,4R,6S,11S,15R)-7-trans-11-tert-Butoxycarbonylamino-15-(7-methoxy-2-phenylquin-olin-4-yloxy)-2,12-dioxo-3,13-diazatricyclo[11.3.0.0⁴,⁶]hexadec-7-ene-4-carboxylic acid (47.7 mg, 0.0726 mmol) in THF (2 mL) was added was added CDI (16.5 mg, 0.102 mmol) in one portion under argon. The resulting solution was stirred for 30 min, refluxed for 30 min and allowed to cool down to rt. Cyclopropylsulfonamide (12.3 mg, 0.102 mmol was added in one portion before the addition of a neat solution of DBU (0.016 mL, 0.102 mmol). The reaction was stirred for 24 h, diluted with EtOAc (100 mL) and washed pH 4.0 buffer (3×20 mL), brine (20 mL), dried (MgSO₄) and purified using one preparative TLC plate (Analtech 20×40 cm 1000 uM thickness) to supply (1S,4R,6S,11S,15R)-7-trans-[4-cyclopropanesulfonyl-aminocarbonyl-15-(7-methoxy-2-phenylquinolin-4-yloxy)-2,12-dioxo-3,13-diazatricyclo[11.3.0.0⁴,⁶]hexadec-7-en-11-yl]carbamic acid tert-butyl ester, Compound 1, Example 1, as a foam (31.8 mg, 58%): $^1$H NMR (300 MHz, CD₃OD) δ 0.86–1.43 (m, 5H), 1.15 (s, 9H), 1.63–1.73 (m, 2H), 2.03–2.20 (m, 2H), 2.27–2.41 (m, 2H), 2.56–2.80 (m, 3H), 3.92 (s, 3H), 4.16–4.37 (m, 3H), 4.83 (t, J=8 Hz, 1H), 5.28–5.36 (m, 1H), 5.52–5.56 (m, 2H), 7.09 (dd, J=9.2, 2.2 Hz, 1H), 7.22 (s, 1H), 7.37 (d, J=2.2 Hz, 1H), 7.44–7.54 (m, 3H), 8.00–8.04 (m, 3H). LC-MS (Method D-retention time: 1.43), MS m/z 760 (M⁺+1). HRMS m/z (M+H)⁺ calcd for C₃₉H₄₆SN₅O₉: 760.3016, found 760.3002.

Step 2k: Preparation of Compound 2, Example 2 (1S 4R,6S, 11S,15R)-7-trans-Cyclopropanesulfonic acid [11-amino-15-(7-methoxy-2-phenylquinolin-4-yloxy)-2,12-dioxo-3,13-diazatricyclo-[11.3.0.0⁴,⁶]hexadec-7-ene-4-carbonyl]amide dihydrochloride

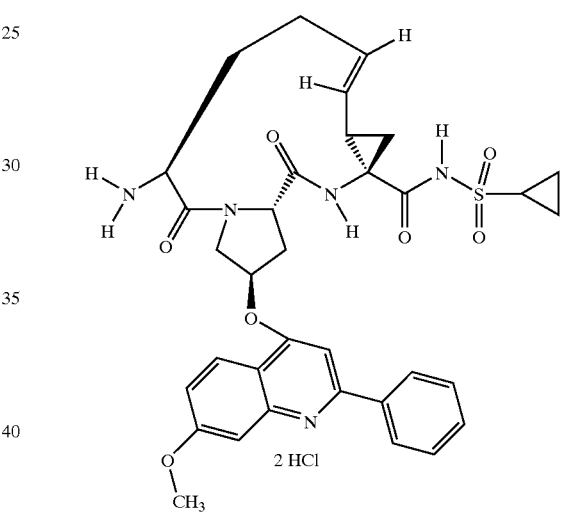

A solution of 2 mL (8 mmol) of 4N HCl/dioxane was added to 11 mg (0.014 mmol) of (1S,4R,6S,11S,15R)-7-trans-[4-cyclopropanesulfonylaminocarbonyl-15-(7-methoxy-2-phenylquinolin-4-yloxy)-2,12-dioxo-3,13-diazatricyclo-[11.3.0.0⁴,⁶]hexadec-7-en-11-yl]carbamic acid tert-butyl ester, the mixture stirred 2 h, concentrated and dried (50° C.; 20 torr; 12 h) to afford 10.5 mg (~100%) of (1S,4R,6S,11S,15R)-7-trans-cyclopropanesulfonic acid [11-amino-15-(7-methoxy-2-phenylquinolin-4-yloxy)-2,12-dioxo-3,13-diazatricyclo-[11.3.0.0⁴,⁶]hexadec-7-ene-4-carbonyl]amide dihydrochloride as a white solid: $^1$H NMR (300 MHz, CD₃OD) δ 0.87–1.41 (m, 8H), 1.70 (m, 1H), 2.16 (s, 1H), 2.30 (m, 1H), 2.45 (m, 1H), 2.65 (m, 1H), 2.96 (m, 1H), 4.05 (s, 3H), 4.33 (s, 3H), 4.48 (m, 1H), 5.46–5.67 (m, 2H), 5.99 (s, 1H), 7.45 (m, 1H), 7.58–7.85 (m, 5H), 8.12 (brs, 2H), 8.35 (m, 1H). LC-MS (Method E-retention time: 1.09), MS m/z 660 (M⁺+1). HRMS m/z (M+H)⁺ calcd for C₃₄H₃₈SN₅O₇: 660.2492, found 660.2492.

EXAMPLES 3,4

Preparation of Compounds 3 and 4

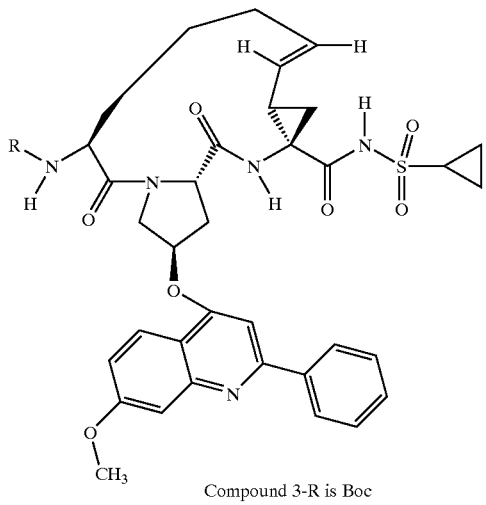

Compound 3-R is Boc
Compound 4-R is H
(Bis HCl Salt)

Step 3g: Preparation of 1-{[1-(2(S)-tert-butoxycarbonylamino-hept-6-enoyl)-4-(7-methoxy-2-phenylquinolin-4(R)-yloxy)pyrrolidine-2(S)-carbonyl]-1(R)-amino]-2(S)-vinylcyclopropanecarboxylic acid ethyl ester

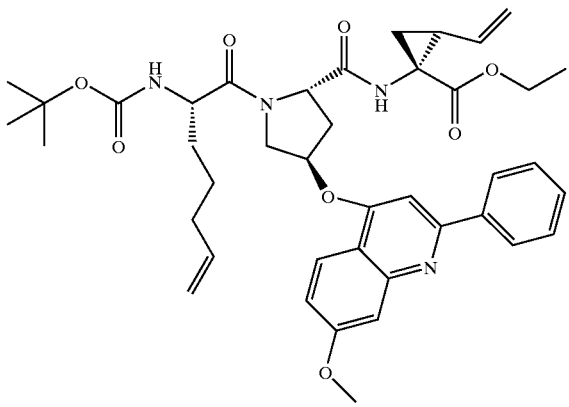

Following the procedure of Step 1 g, except that (0.356 g, 1.46 mmol) of 2(S)-tert-butoxycarbonylamino-6-heptenoic acid purchased from RSP Amino Acids, was coupled in place of 2(S)-tert-butoxycarbonylamino-5-hexenoic acid, to give the titled compound, 1-{[1-(2(S)-tert-butoxycarbonylamino-hept-6-enoyl)-4-(7-methoxy-2-phenylquinolin-4(R)-yloxy)pyrrolidine-2(S)-carbonyl]-1(R)-amino]-2(S)-vinylcyclopropanecarboxylic acid ethyl ester as a yellow oil (0.600 g, 79%): $^1$H NMR (CDCl$_3$) δ (300 MHz, CDCl$_3$); 1.21 (t, J=7 Hz, 3H), 1.40 (s, 9H), 1.42–2.18 (m, 9H), 2.36–2.45 (m, 1H), 2.91–2.99 (m, 1H), 3.94 (s, 3H), 4.05–4.22 (m, 2H), 4.26–4.30 (m, 1H), 4.39–4.49 (m, 1H), 4.83 (dd, J=8.2, 5.6 Hz, 1H),4.92–5.14 (m, 4H), 5.29 (dd, J=17.2, 1.4 Hz, 1H), 5.41 (brs, 1H), 5.63–5.80 (m, 2H), 7.04 (s, 1H), 7.09 (dd, J=9, 2 Hz, 1H), 7.42–7.54 (m, 4H), 8.00–8.05 (m, 3H). LC-MS (Method E-retention time: 1.53), MS m/z 727 (M$^+$+1).

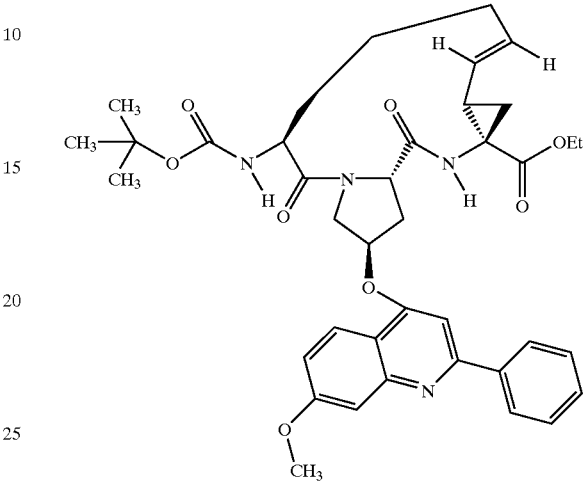

Step 3h: Preparation of (1S,4R,6S,12S, 16R)-7-trans-12-tert-butoxycarbonylamino-16-(7-methoxy-2-phenylquinolin-4-yloxy)-2,13-dioxo-3,14-diazatricyclo[12.3.0.0$^{4,6}$]-heptadec-7-ene-4-carboxylic acid ethyl ester Following the experimental and purification procedure of Step 1h, 1-{[1-(2(S)-tert-butoxycarbonylamino-hept-6-enoyl)-4-(7-methoxy-2-phenylquinolin-4(R)-yloxy)-pyrrolidine-2(S)-carbonyl]-1(R)-amino]-2(S)-vinyl-cyclopropanecarboxylic acid ethyl ester (404 mg, 0.555 mmol) was reacted with two 75 mg portions of Grubbs catalyst to afford (1S,4R,6S,12S,16R)-7-trans-12-tert-butoxycarbonylamino-16-(7-methoxy-2-phenylquinolin-4-yloxy)-2,13-dioxo-3,14-diazatricyclo[12.3.0.0$^{4,6}$]hepta-dec-7-ene-4-carboxylic acid ethyl ester (190 mg, 49%): $^1$H NMR (500 MHz, CD$_3$OD) δ 1.22 (t, J=7 Hz, 3H), 1.26 (s, 9H), 1.32–1.43 (m, 3H), 1.59–1.64 (m, 1H), 1.77–1.90 (m, 3H), 2.11 (brs, 1H), 2.29–2.34 (m, 1H), 2.60–2.65 (m, 1H), 2.70–2.74 (m, 1H), 3.93 (s, 3H), 4.07–4.18 (m, 3H), 4.30 (d, J=7.6 Hz, 1H), 4.52 (d, J=11.3 Hz, 1H), 4.67 (t, J=8.2 Hz, 1H), 5.35 (dd, J=15.7, 6.0 Hz, 1H), 5.50–5.56 (m, 1H), 5.60 (brs, 1H), 7.10 (dd, J=9.2, 2 Hz, 1H), 7.26 (s, 1H), 7.37 (d, J=2 Hz, 1H), 7.53–7.57 (m, 3H), 8.00, 8.01 (2s, 2H), 8.17 (d, J=9.2 Hz, 1H). LC-MS (Method E-retention time: 1.58), MS m/z 699 (M$^+$+1)

Step 3i: Preparation of (1S,4R,6S,12S,16R)-7-trans-12-tert-butoxycarbonylamino-16-(7-methoxy-2-phenyl-quinolin-4-yloxy)-2,13-dioxo-3,14-diazatricyclo-[12.3.0.0$^{4,6}$]heptadec-7-ene-4-carboxylic acid

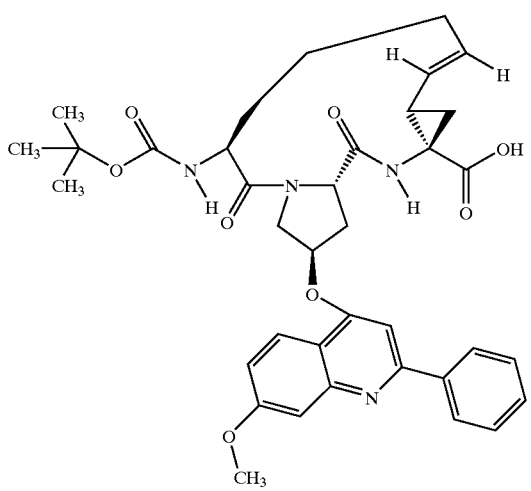

Following the experimental and purification procedure of Step 1i, (1S,4R,6S,12S,16R)-7-trans-12-tert-butoxycarbonyl-amino-16-(7-methoxy-2-phenylquinolin-4-yloxy)-2,13-dioxo-3,14-diazatricyclo-[12.3.0.0$^{4,6}$]heptadec-7-ene-4-carboxylic acid ethyl ester (185 mg, 0.265 mmol) was reacted with 64 mg (1.6 mmol) of LiOH in 15.5 mL of 9:5:1.5 of THF/H$_2$O/MeOH to afford (1S,4R,6S,12S,16R)-7-trans-12-tert-butoxycar-bonyiamino-16-(7-methoxy-2-phenylquinolin-4-yloxy)-2,13-dioxo-3,14-diazatricyclo [12.3.0.0$^{4,6}$]heptadec-7-ene-4-carboxylic acid (180 mg, 100%): $^1$H NMR (300 MHz, CD$_3$OD) δ 1.24 (s, 9H), 1.33–1.43 (m, 1H), 1.61–1.97 (m, 6H), 2.10 (brs, 1H), 2.28–2.36 (m, 1H), 2.70 (m, 2H), 3.94 (s, 3H), 4.17 (d, J=10.6 Hz, 1H), 4.28 (d, J=4.8 Hz, 1H), 4.65–4.70 (m, 1H), 5.34 (dd, J=15.7, 5.9 Hz, 2H), 5.53–5.62 (m, 2H), 7.14 (d, J=9 Hz, 1H), 7.32 (s, 1H), 7.39 (s, 1H), 7.56 (m, 3H), 8.01–8.02 (m, 2H), 8.22 (d, J=9.2 Hz, 1H). LC-MS (Method E-retention time: 1.49), MS m/z 671 (M$^+$+1). HRMS m/z (M+H)$^+$ calcd for C$_{37}$H$_{43}$N$_4$O$_8$: 671.3081, found 671.3080.

Step 3j: Preparation of Compound 3, Example 3 (1S,4R,6S,12S,16R)-7-trans-[4-Cyclopanesulfonyl-aminocarbonyl-16-(7-methoxy-2-phenylquinolin-4-yloxy)-2,13-dioxo-3,14-diazatricyclo[12.3.0.0$^{4,6}$]heptadec-7-en-12-yl]carbamic acid tert-butyl ester

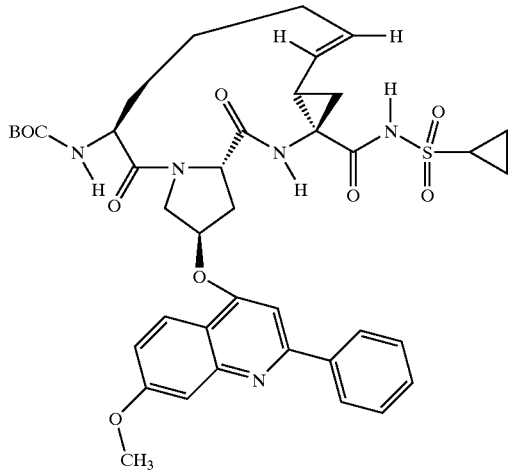

Compound 3, Example 3

Applying the procedural and purification practices of Step 1j, (144.9 mg, 0.216 mmol) of (1S,4R,6S,12S,16R)-7-trans-12-tert-butoxycarbonyl-amino-16-(7-methoxy-2-phenylquinolin-4-yloxy)-2,13-dioxo-3,14-diazatricyclo [12.3.0.0$^{4,6}$]heptadec-7-ene-4-carboxylic acid was converted to 92 mg (56%) of the product (1S,4R,6S,12S,16R)-7-trans-[4-cyclopropane-sulfonylaminocarbonyl-16-(7-methoxy-2-phenylquinolin-4-yloxy)-2,13-dioxo-3,14-diazatricyclo[12.3.0.0$^{4,6}$]-heptadec-7-en-12-yl]carbamic acid tert-butyl ester: $^1$H NMR (300 MHz, CD$_3$OD) δ 0.81–0.88 (m, 2H), 1.00–1.05 (m, 2H), 1.15–1.19 (m, 1H), 1.32 (s, 9H), 1.42 (m, 1H), 1.59–1.68 (m, 1H), 1.77–1.93 (m, 4H), 2.08–2.26 (m, 2H), 2.60–2.73 (m, 3H), 3.94 (s, 3H), 4.21–4.34 (m, 2H), 4.43 (d, J=11 Hz, 1H), 4.56–4.62 (m, 1H), 5.28–5.36 (m, 1H), 5.46–5.55 (m, 2H), 7.07 (dd, J=9.5, 2.4 Hz, 1H), 7.27 (s, 1H), 7.37 (d, J=2.4 Hz, 1H), 7.42–7.49 (m, 3H), 8.01, 8.03 (2s, 2H), 8.18 (d, J=9.5 Hz, 1H). LC-MS (Method D-retention time: 1.48), MS m/z 774 (M$^+$+1). HRMS m/z (M+H)$^+$ calcd for C$_{40}$H$_{48}$SN$_5$O$_9$: 774.3173, found 774.3173.

Step 4k: Preparation of Compound 4, Example 4 (1S,4R, 6S,12S,16R)-7-trans-Cyclopropanesulfonic acid [12-amino-16-(7-methoxy-2-phenylquinolin-4-yloxy)-2,13-dioxo-3,14-diazatricyclo [12.3.0.0$^{4,6}$]heptadec-7-ene-4-carbonyl] amide dihydrochloride

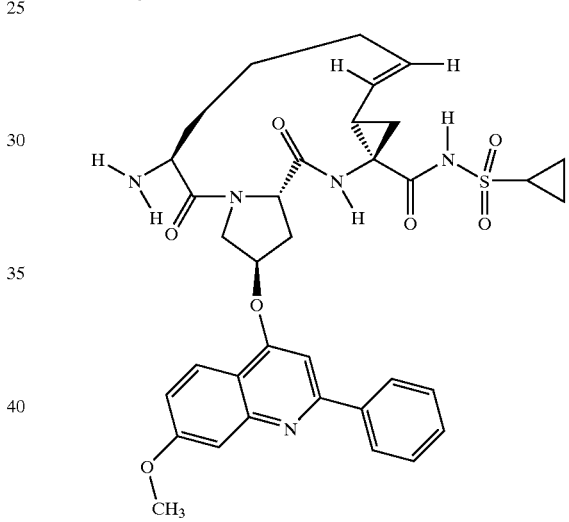

Compound 4, Example 4-(Bis HCl Salt)

A solution of 5 mL (20 mmol) of 4N HCl/dioxane was added to 10.8 mg (0.014 mmol) of (1S,4R,6S,12S,16R)-7-trans-[4-cyclopropanesulfonyl-aminocarbonyl-16-(7-methoxy-2-phenyl-quinolin-4-yloxy)-2,13-dioxo-3,14-diazatricyclo[12.3.0.0$^{4,6}$]hexa-dec-7-en-12-yl]carbamic acid tert-butyl ester, the mixture stirred 2 h, concentrated and dried (50° C.; 20 torr; 12 h) to afford 10.6 mg (~100%) of (1S,4R,6S,12S,16R)-7-trans-cyclopropanesulfonic acid [12-amino-16-(7-methoxy-2-phenylquinolin-4-yloxy)-2,13-dioxo-3,14-diazatricyclo-[12.3.0.0$^{4,6}$]heptadec-7-ene-4-carbonyl]amide dihydrochloride as a white solid: $^1$H NMR (300 MHz, CD$_3$OD) δ 0.89 (m, 1H), 1.05–2.12 (m, 11H), 2.18–2.26 (m, 1H), 2.41–2.49 (m, 1H), 2.62–2.99 (m, 2H), 4.05 (s, 3H), 4.30 (m, 2H), 4.44–4.46 (m, 2H), 5.15–5.23 (m, 1H), 5.68–5.75 (m, 1H), 5.96 brs, 1H), 7.45 (d. J=9 Hz, 1H), 7.57 (s, 1H), 7.63–7.73 (m, 4H), 8.08–8.13 (m, 2H), 8.38 (d, J=9 Hz, 1H). LC-MS (Method E-retention time: 1.10), MS m/z 674 (M$^+$+1). HRMS m/z (M+H)+calcd for C$_{35}$H$_{40}$SN$_5$O$_7$: 674.2649, found 674.2655.

EXAMPLES 5,6

Preparation of Compounds 5 and 6

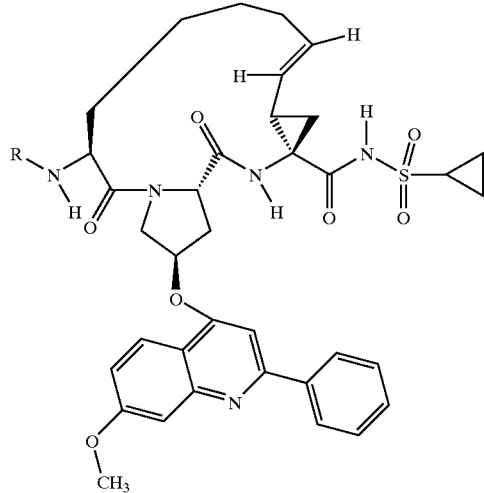

Compound 5, Example 5-R is Boc
Compound 6, Example 6-R is H (Bis HCl Salt)

Step 5g: Preparation of 1-{[1-(2(S)-tert-Butoxycarbonylamino-oct-7-enoyl)-4-(7-methoxy-2-phenylquinolin-4(R)-yloxy)pyrrolidine-2(S)-carbonyl]-1(R)-amino]-2(S)-vinylcyclopropanecarboxylic acid ethyl ester

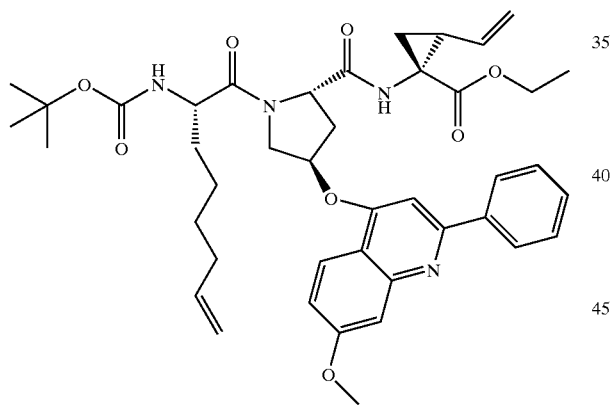

Following the procedure of Step 1g, except that (0.35 g, 1.4 mmol) of 2(S)-tert-butoxycarbonylamino-7-octenoic acid purchased from RSP Amino Acids, was coupled in place of 2(S)-tert-butoxycarbonylamino-5-hexenoic acid, to give 1-{[1-(2(S)-tert-Butoxycarbonylamino-oct-7-enoyl}-4-(7-methoxy-2-phenyl-quinolin-4(R)-yloxy)pyrrolidine-2(S)-carbonyl]-1(R)-amino]-2(S)-vinylcyclopropanecarboxylic acid ethyl ester as a yellow oil (0.58 g, 75%): $^1$H NMR (300 MHz, CDCl$_3$) δ 1.20 (t, J=7 Hz, 3H), 1.32–1.47 (m, 5H), 1.39 (s, 9H), 1.54–1.68 (m, 2H), 1.68–2.05 (m, 3H), 2.09–2.18 (m, 1H), 2.35–2.48 (m, 1H), 2.89–2.99 (m, 1H), 3.93 (s, 3H), 4.02–4.22 (m, 2H), 4.27 (d, J=11.3 Hz, 1H), 4.38–4.47 (m, 1H), 4.80–4.98 (m, 3H), 5.06–5.14 (m, 2H), 5.28 (dd, J=17.2, 1.5 Hz, 1H), 5.41 (brs, 1H), 5.63–5.81 (m, 2H), 7.03 (s, 1H), 7.07 (dd, J=9.2, 2.6 Hz, 1H), 7.41–7.57 (m, 4H), 7.98–8.04 (m, 3H). LC-MS (Method A-retention time: 1.81), MS m/z 741 (M$^+$+1).

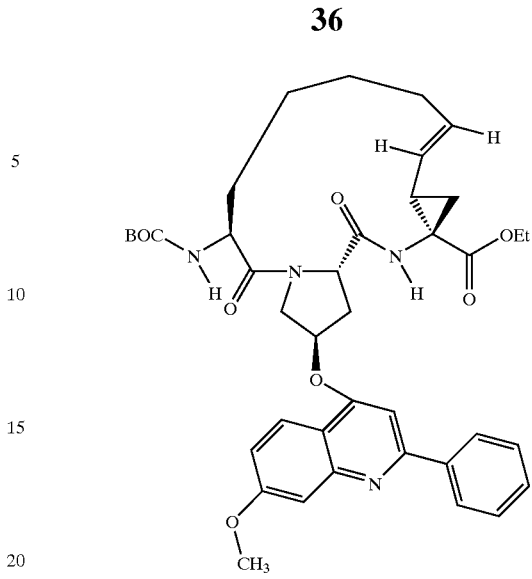

Trans or E-Isomer-
was used in this sequence

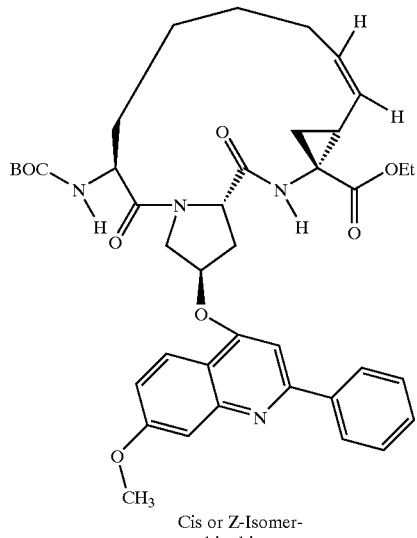

Cis or Z-Isomer-
not used in this sequence

Step 5h: Preparation of (1S,4R,6S,13S,17R)-7-trans-13-tert-butoxycarbonylamino-17-(7-methoxy-2-phenylquin-olin-4-yloxy)-2,14-dioxo-3,15-diazatricyclo-[13.3.0.0$^{4,6}$]octadec-7-ene-4-carboxylic acid ethyl ester and (1S,4R,6S,13S,17R)-7-cis-13-tert-butoxycarbonylamino-17-(7-methoxy-2-phenylquinolin-4-yloxy)-2,14-dioxo-3,15-diazatricyclo [13.3.0.0$^{4,6}$]octadec-7-ene-4-carboxylic acid ethyl ester Following the experimental and purification procedure of step 1h, 1-{[1-(2(S)-tert-butoxycarbonylamino-oct-7-enoyl)-4-(7-methoxy-2-phenylquinolin-4(R)-yloxy)-pyrrolidine-2(S)-carbonyl]-1(R)-amino]-2(S)-vinyl-cyclopropanecarboxylic acid ethyl ester (1.16 g, 1.565 mmol) was reacted with 275 mg and 225 mg portions of Grubbs catalyst to afford (1S,4R,65S,13S,17R)-7-trans-13-tert-butoxycarbonyl-amino-17-(7-methoxy-2-phenylquinolin-4-yloxy)-2,14-dioxo-3,15-diazatricyclo-[13.3.0.0$^{4,6}$]octadec-7-ene-4-carboxylic acid ethyl ester (90 mg, 8%) and (1S,4R,6S,13S,17R)-7-cis-13-tert-butoxycarbonylamino-17-(7-methoxy-2-phenylquinolin-4-yloxy)-2,14-dioxo-3,15-diaza-tricyclo[13.3.0.0$^{4,6}$]octadec-7-ene-4-carboxylic acid ethyl ester (222 mg, 20%). Data for trans- or E-olefin isomer: $^1$H NMR (500 MHz, CD$_3$OD) δ 1.14–1.48 (m, 6H), 1.21 (t, J=7.0 Hz, 3H), 1.34 (s, 9H), 1.51–1.63 (m, 2H), 1.76 (s, 1H), 1.81–1.91 (m, 2H), 2.00–2.08 (m, 1H), 2.50 (q, J=8 Hz, 1H), 2.61–2.66 (m, 1H), 2.75–2.80 (m, 1H), 3.95 (s, 3H), 4.04–4.18 (m, 2H), 4.40–4.44 (m, 1H), 4.54 (d, J=11.6 Hz, 1H), 4.79 (t, J=7.3 Hz, 1H), 5.04 (dd, J=15.6, 7.6 Hz, 1H), 5.16 (d, J=8.2 Hz, 1H), 5.46 (brs, 1H), 5.53–5.59 (m, 1H), 7.04 (s, 1H), 7.07 (dd, J=9.2, 2.4 Hz, 1H), 7.42–7.52 (m, 4H), 8.03–8.10 (m, 3H). LC-MS (Method E-retention time: 1.89), MS m/z 713 (M$^+$+1). Data for cis- or Z-olefin isomer: $^1$H NMR (300 MHz, CDCl$_3$) δ 1.15–1.62 (m, 5H), 1.21 (t, J=7 Hz, 3H), 1.38 (s, 9H), 1.91 (dd, J=8.1, 5.9 Hz, 1H), 1.97–2.02 (m, 5H), 2.33–2.41 (m, 1H), 3.03–3.11 (m, 1H), 3.95 (s, 3H), 4.06–4.18 (m, 3H), 4.27 (d, J=11 Hz, 1H), 4.54 (m, 1H), 4.93 (dd, J=8.2, 4.2 Hz, 1H), 5.27–5.40 (m, 2H), 5.71–5.80 (m, 1H), 7.05 (s, 1H), 7.08 (dd, J=9.2, 2.6 Hz, 1H), 7.43–7.53 (m, 4H), 8.02 (d, J=9.2 Hz, 1H), 8.05–8.07 (2s, 2H). LC-MS (Method E-retention time: 1.80), MS m/z 713 (M$^+$+1).

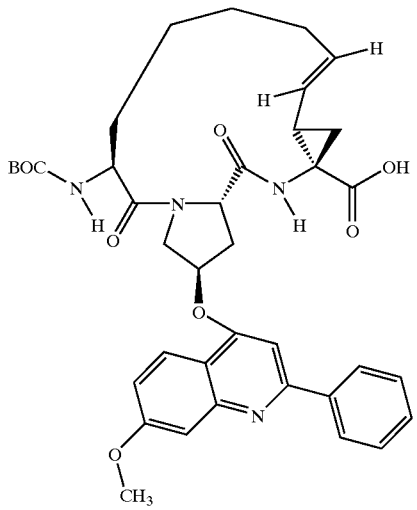

Trans or E-Isomer-
was used in this sequence

Step 5i: Preparation of (1S,4R,6S,13S,17R)-7-trans-13-tert-butoxycarbonylamino-17-(7-methoxy-2-phenylquin-olin-4-yloxy)-2,14-dioxo-3,15-diazatricyclo-[13.3.0.0$^{4,6}$]octadec-7-ene-4-carboxylic acid Following the experimental and purification procedure of Step 2i, (1S,4R,6S,13S,17R)-7-trans-13-tert-butoxycarbonyl-amino-17-(7-methoxy-2-phenylquin-olin-4-yloxy)-2,14-dioxo-3,15-diazatricyclo-[13.3.0.0$^{4,6}$]octadec-7-ene-4-carboxylic acid ethyl ester (185 mg, 0.265 mmol) was reacted with 64 mg (1.6 mmol) of LiOH in 15.5 mL of 9:5:1.5 of THF/H$_2$O/MeOH to afford (1S,4R,6S,13S,17R)-7-trans-13-tert-butoxycar-bonylamino-17-(7-methoxy-2-phenylquinolin-4-yloxy)-2,14-dioxo-3,15-diazatricyclo[13.3.0.0$^{4,6}$]octadec-7-ene-4-carboxylic acid (180 mg, 100%): $^1$H NMR (300 MHz, CD$_3$OD) δ 1.14 (s, 9H), 1.20–1.51 (m, 5H), 1.53–1.58 (m, 1H), 1.70 (dd, J=9.9, 5.1 Hz, 1H), 1.86 (brs, 1H), 2.06 (brs, 1H), 2.28–2.59 (m, 3H), 2.65–2.73 (m, 1H), 3.94 (s, 3H), 4.07 (dd, J=11.3, 2.6 Hz, 1H), 4.23 (d, J=8.4 Hz, 1H), 4.64–4.70 (m, 2H), 5.54–5.68 (m, 3H), 7.10 (dd, J=9, 2 Hz, 1H), 7.26 (s, 1H), 7.39 (d, J=2.2 Hz, 1H), 8.02, 8.04 (2s, 2H), 8.12 (d, J=9.1 Hz, 1H). LC-MS (Method E-retention time: 1.57), MS m/z 685 (M$^+$+1). HRMS m/z (M+H)$^+$ calcd for C$_{38}$H$_{45}$N$_4$O$_8$: 685.3238, found 685.3241.

Step 5j: Preparation of Compound 5, Example 5 (1S,4R,6S,13S,17R)-7-trans-[4-Cyclopropanesul-fonylamino-carbonyl-17-(7-methoxy-2-phenylquinolin-4-yloxy)-2,14-dioxo-3,15-diazatricyclo[13.3.0.0$^{4,6}$]octa-dec-7-en-13-yl] carbamic acid tert-butyl ester

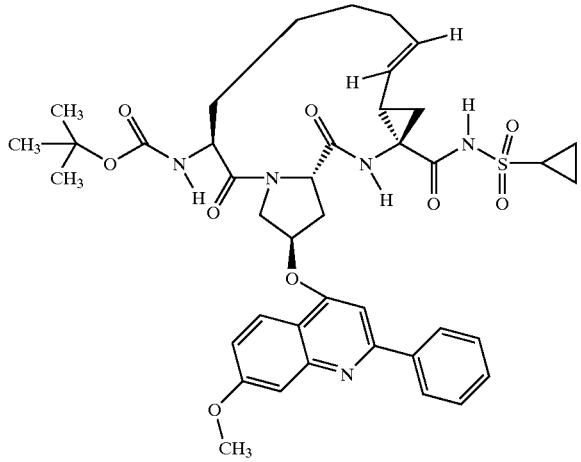

Using the procedural and purification conditions of Step 2j, 35.6 mg (0.052 mmol) of (1S,4R,6S,13S, 17R)-7-trans-13-tert-butoxycarbonyl-amino-17-(7-methoxy-2-phenylquinolin-4-yloxy)-2,14-dioxo-3,15-diazatricyclo-[13.3.0.0$^{4,6}$]octadec-7-ene-4-carboxylic acid was converted to 30 mg (73%) (1S,4R,6S,13S,17R)-7-trans-[4-cyclopropanesulfonylaminocarbonyl-17-(7-methoxy-2-phenylquinolin-4-yloxy)-2,14-dioxo-3,15-diazatricyclo-[13.3.0.0$^{4,6}$]octadec-7-ene-13-yl]carbamic acid tert-butyl ester: $^1$H NMR (300 MHz, CD$_3$OD) δ 0.85–1.51 (m, 8H), 1.16 (s, 9H), 1.64–1.76 (m, 3H), 1.87 (m, 1H), 2.10 (m, 1H), 2.32 (m, 1H), 2.44 (m, 1H), 2.52–2.72 (m, 2H), 2.83 (brs, 1H), 3.94 (s, 3H), 4.10–4.15 (m, 1H), 4.23–4.32 (m, 1H), 4.61–4.69 (m, 2H), 5.49–5.64 (m, 3H), 7.08 (dd, J=9.2, 2.2 Hz, 1H), 7.23 (s, 1H), 7.37 (d, J=2.2 Hz, 1H), 7.46–7.56 (m, 3H), 8.03–8.09 (m, 3H). LC-MS (Method E-retention time: 1.57), MS m/z 788 (M$^+$+1). HRMS m/z (M+H)+calcd for C$_{41}$H$_5$OSN$_5$O$_9$: 788.3329, found 788.3337.

Step 6k: Preparation of Compound 6, Example 6 (1S,4R, 6S,13S,17R)-7-trans-Cyclopropanesulfonic acid [13-amino-17-(7-methoxy-2-phenylquinolin-4-yloxy)-2,14-dioxo-3,15-diazatricyclo[13.3.0.0$^{4,6}$]octadec-7-ene-4-carbonyl] amide dihydrochloride

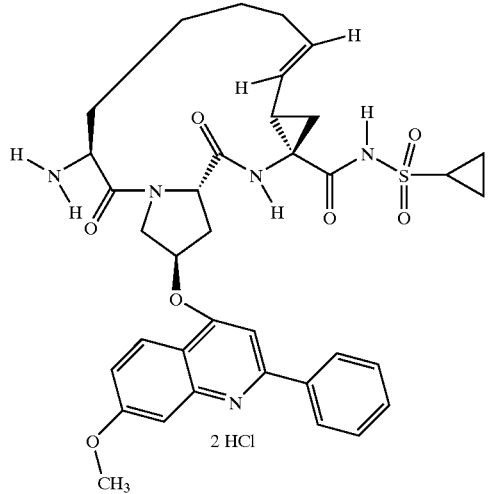

Compound 6, Example 6

A solution of 2 mL (8 mmol) of 4N HCl/dioxane was added to 10.5 mg (0.014 mmol) of (1S,4R,6S,13S,17R)-7-trans-[4-cyclopropanesufonyiaminocarbonyl-17-(7-methoxy-2-phenylquinolin-4-yloxy)-2,14-dioxo-3,15-diazatricyclo-[13.3.0.0$^{4,6}$]octadec-7-en-13-yl]carbamic acid tert-butyl ester, the mixture stirred 2 h, concentrated and dried (50° C.; 20 torr; 12 h) to afford 10.0 mg (~100%) of (1S,4R,6S,13S,17R)-7-trans-Cyclopropanesulfonic acid [13-amino-17-(7-methoxy-2-phenylquinolin-4-yloxy)-2,14-dioxo-3,15-diazatricyclo[13.3.0.0$^{4,6}$]octadec-7-ene-4-carbonyl]amide dihydrochlbride as a white solid: $^1$H NMR (300 MHz, CD$_3$OD) δ 0.86–2.03 (m, 14H), 2.17 (brs, 1H), 2.52–3.00 (m, 3H), 4.06 (s, 3H), 4.16–4.53 (m, 4H), 5.36 (t, J=10.6 Hz, 1H), 5.65–5.72 (m, 1H), 5.97 (brs, 1H), 7.44–7.47 (m, 1H), 7.59–7.74 (m, 5H), 8.12 (m, 2H), 8.38–8.41 (m, 1H). LC-MS (Method E-retention time: 1.16), MS m/z 688 (M$^+$+1). HRMS m/z (M+H)+calcd for C$_{36}$H$_{42}$SN$_5$O$_7$: 688.2805, found 688.2793.

EXAMPLES 7,8
Preparation of Compounds 7 and 8

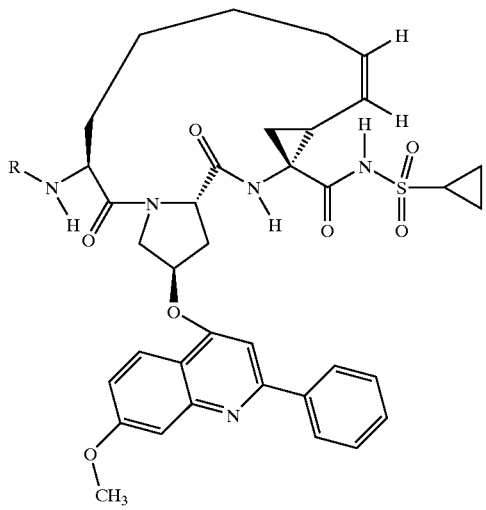

Compound 7, Example 7-R is Boc
Compound 8, Example 8-R is H

Step 7h: Preparation of (1S,4R,6S,13S,17R)-7-cis-13-tert-butoxycarbonylamino-17-(7-methoxy-2-phenylquin-olin-4-yloxy)-2,14-dioxo-3,15-diazatricyclo-[13.3.0.0$^{4,6}$]octadec-7-ene-4-carboxylic acid ethyl ester

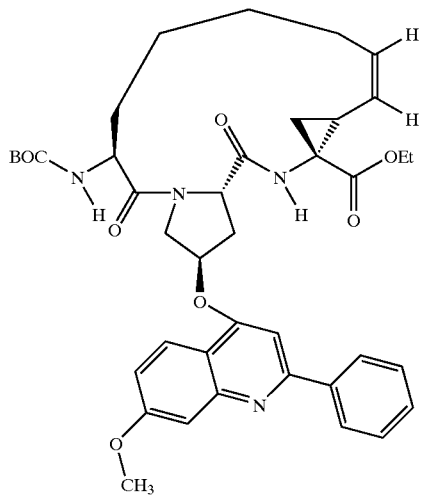

This step of this particular sequence uses the product of step 5 g as the starting point. To a solution of 1-{[1-(2(S)-tert-butoxycarbonylamino-oct-7-enoyl)-4-(7-methoxy-2-phenylquinolin-4(R)-yloxy)pyrrolidine-2(S)-carbonyl]-1 (R)-amino]-2(S)-vinylcyclopropanecarboxylic acid ethyl ester (1.44 g, 1.93 mmol) in 2.5L of Argon degassed 1,2-DCE, was added 150 mg of Grubbs catalyst, the mixture degassed under Ar and heated to reflux for 3 h. The reaction mixture was cooled to rt, the mixture degassed again, 140 mg portion of Grubbs catalyst added, and the mixture heated to reflux for 14 h. The reaction mixture was cooled again to rt, the mixture degassed again, 140 mg portion of Grubbs catalyst added, and the mixture heated to reflux for a final 4 h. The dark brown solution was concentrated in vacuo, purified by a Biotage 40 M column (eluted with 15% to 65% EtOAc in hexanes) to supply (1S,4R,6S,13S,17R)-7-cis-13-tert-butoxycarbonylamino-17-(7-methoxy-2-phenylquinolin-4-yloxy)-2,14-dioxo-3,15-diazatricyclo [13.3.0.0$^{4,6}$]octadec-7-ene-4-carboxylic acid ethyl ester (720 mg, 52%). Data for cis- or Z-olefin isomer, (1S,4R,6S,13S,17R)-7-cis-13-tert-butoxycarbonylamino-17-(7-methoxy-2-phenylquinolin-4-yloxy)-2,14-dioxo-3,15-diazatricyclo[13.3.0.0$^{4,6}$]octadec-7-ene-4-carboxylic acid ethyl ester: $^1$H NMR (300 MHz, CDCl$_3$) δ 1.15–1.62 (m, 5H), 1.21 (t, J=7 Hz, 3H), 1.38 (s, 9H), 1.91 (dd, J=8.1, 5.9 Hz, 1H), 1.97–2.02 (m, 5H), 2.33–2.41 (m, 1H), 3.03–3.11 (m, 1H), 3.95 (s, 3H), 4.06–4.18 (m, 3H), 4.27 (d, J=11 Hz, 1H), 4.54 (m, 1H), 4.93 (dd, J=8.2, 4.2 Hz, 1H), 5.27–5.40 (m, 2H), 5.71–5.80 (m, 1H), 7.05 (s, 1H), 7.08 (dd, J=9.2, 2.6 Hz, 1H), 7.43–7.53 (m, 4H), 8.02 (d, J=9.2 Hz, 1H), 8.05–8.07 (2s, 2H). LC-MS (Method E-retention time: 1.80), MS m/z 713 (M$^+$+1).

Step 7i: Preparation of (1S,4R,6S,13S,17R)-7-cis-13-tert-butoxycarbonylamino-17-(7-methoxy-2-phenylquin-olin-4-yloxy)-2,14-dioxo-3,15-diazatricyclo-[13.3.0.0$^{4,6}$]octa-dec-7-ene-4-carboxylic acid

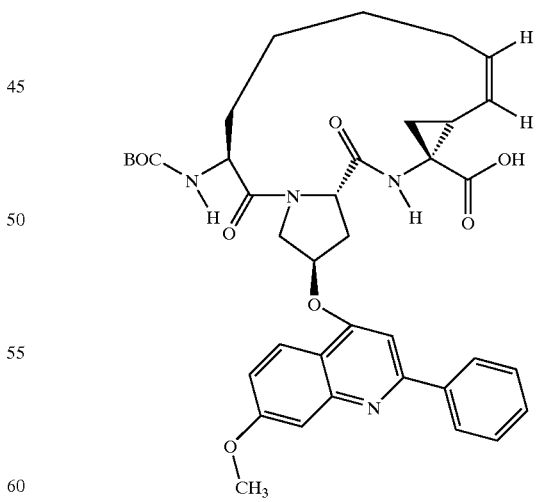

Following the experimental and purification procedure of Step 1i, (1S,4R,6S,13S,17R)-7-cis-13-tert-butoxycarbonylamino-17-(7-methoxy-2-phenyl-quinolin-4-yloxy)-2,14-dioxo-3,15-diazatricyclo [13.3.0.0$^{4,6}$]octadec- 7-ene-4-carboxylic acid ethyl ester (290 mg, 0.406 mmol) was reacted with 100 mg (2.5 mmol) of LiOH in 23.9 mL of 14.4:7.7:1.8 of THF/H$_2$O/MeOH to afford (1S,4R,6S,13S,17R)-7-cis-13-tert-butoxy-carbonylamino-17-(7-methoxy-2-phenylquin-olin-4-yloxy)-2,14-dioxo-3,15-diazatricyclo-[13.3.0.0$^{4,6}$]octadec-7-ene-4-carboxylic acid (279 mg, 100%): $^1$H NMR (300 MHz, CD$_3$OD) δ 0.97–1.05 (m, 2H), 1.14 (s, 9H), 1.20–1.55 (m, 5H), 1.60–1.73 (m, 2H), 1.85 (brs, 1H), 2.06–2.22 (m, 1H), 2.29 (brs, 1H), 2.52–2.73 (m, 2H), 3.93 (s, 3H), 4.14–4.19 (m, 1H), 4.26 (d, J=9.5 Hz, 1H), 4.56–4.67 (m, 2H), 5.47–5.53 (m, 2H), 5.71–5.78 (m, 1H), 7.08 (dd, J=9.1, 2.2 Hz, 1H), 7.22 (s, 1H), 7.37 (d, J=2.2 Hz, 1H), 7.45–7.56 (m, 3H), 8.02, 8.04 (2s, 2H), 8.09 (d, J=9.1 Hz, 1H). LC-MS (Method E-retention time: 1.60), MS m/z 685 (M$^+$+1).

Step 7j: Preparation of Compound 7, Example 7 (1S,4R,6S,13S,17R)-7-cis-[4-Cyclopropanesulfonylamino-carbonyl-17-(7-methoxy-2-phenylquinolin-4-yloxy)-2,14-dioxo-3,15-diazatricyclo[13.3.0.0$^{4,6}$]octadec-7-en-13-yl]carbamic acid tert-butyl ester

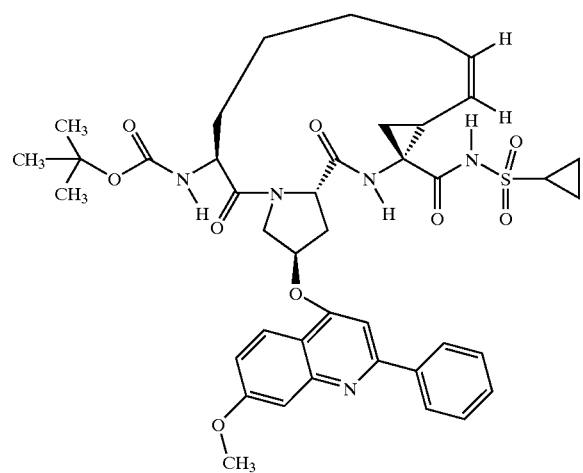

Following the procedural and purification conditions of Step 1j, 219 mg (0.31 mmol) of (1S,4R,6S,13S,17R)-7-cis-13-tert-butoxycarbonylamino-17-(7-methoxy-2-phenylquinolin-4-yloxy)-2,14-dioxo-3,15-diazatricyclo-[13.3.0.0$^{4,6}$]octadec-7-ene-4-carboxylic acid was converted to 94 mg (40%) (1S,4R,6S,13S,17R)-7-cis-[4-cyclopropanesulfonylamino-carbonyl-17-(7-methoxy-2-phenylquinolin-4-yloxy)-2,14-dioxo-3,15-diazatricyclo[13.3.0.0$^{4,6}$]octadec-7-en-13-yl]carbamic acid tert-butyl ester: $^1$H NMR (300 MHz, CD$_3$OD) δ 0.90–1.50 (m, 9H), 1.16 (s, 9H), 1.64–1.74 (m, 2H), 1.85 (brs, 1H), 2.08 (brs, 1H), 2.30 (brs, 1H), 2.44 (brs, 1H), 2.53–2.71 (m, 2H), 2.84 (brs, 1H), 3.92 (s, 3H), 4.05–4.12 (m, 1H), 4.24 (d, J=9.5 Hz, 1H), 4.60–4.69 (m, 2H), 5.44–5.63 (m, 3H), 7.06 (dd, J=9.2, 2.2 Hz, 1H), 7.20 (s, 1H), 7.35 (d, J=2.2 Hz, 1H), 7.45–7.56 (m, 3H), 8.02–8.08 (m, 3H). LC-MS (Method D-retention time: 1.55), MS m/z 788 (M$^+$+1).

Step 8k: Preparation of Compound 8, Example 8 (1S,4R,6S,13S,17R)-7-cis-Cyclopropanesulfonic acid [13-amino-17-(7-methoxy-2-phenylquinolin-4-yloxy)-2,14-dioxo-3,15-diazatricyclo[13.3.0.0$^{4,6}$]octadec-7-ene-4-carbonyl] amide dihydrochloride

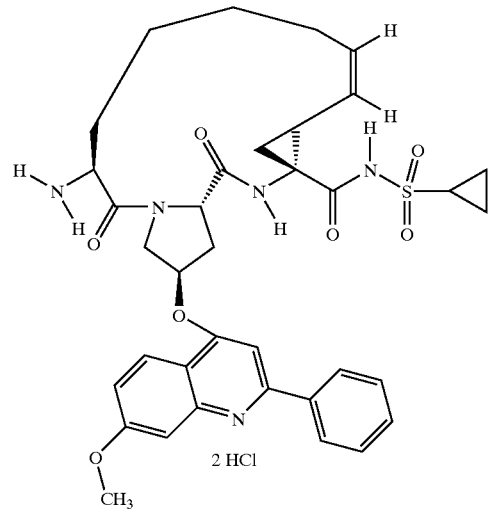

Compound 8, Example 8

A solution of 5 mL (20 mmol) of 4N HCl/dioxane was added to 21 mg (0.027 mmol) of (1S,4R,6S,13S,17R)-7-Cis-[4-Cyclopropanesulfonylaminocarbonyl-17-(7-methoxy-2-phenylquinolin-4-yloxy)-2,14-dioxo-3,15-diazatricyclo-[13.3.0.0$^{4,6}$]octadec-7-en-13-yl]carbamic acid tert-butyl ester, the mixture stirred 2 h, concentrated and dried (50° C.; 20 torr; 12 h) to afford 20 mg (~100%) of (1S,4R,6S,13S,17R)-7-cis-Cyclopropanesulfonic acid [13-amino-17-(7-methoxy-2-phenylquinolin-4-yloxy)-2,14-dioxo-3,15-diazatricy-clo[13.3.0.0$^{4,6}$]octadec-7-ene-4-carbonyl]amide dihydrochloride as a white solid: $^1$H NMR (500 MHz, CD$_3$OD) δ 1.03–1.16 (m, 3H), 1.25–1.33 (m, 2H), 1.35–1.57 (m, 3H), 1.65–1.71 (m, 2H), 1.76–1.84 (m, 1H), 1.94–2.01 (m, 1H), 2.10–2.21 (m, 2H), 2.38–2.43 (m, 1H), 2.67–2.72 (m, 1H), 2.85 (dd, J=14.6, 7.9 Hz, 1H), 2.93–2.98 (m, 1H), 4.06 (s, 3H), 4.24 (dd, J=12.2, 3.7 Hz, 1H), 4.40, 4.42 (2s, 2H), 4.80–4.81 (m, 1H), 5.53–5.57 (m, 1H), 5.67–5.74 (m, 1H), 5.95 (s, 1H), 7.45 (dd, J=9, 2 Hz, 1H), 7.57 (d, J=2 Hz, 1H), 7.61 (s, 1H), 7.70–7.77 (m, 3H), 8.09–8.10 (m, 2H), 8.37 (d, J=9.2 Hz, 1H). LC-MS (Method E-retention time: 1.21), MS m/z 688 (M$^+$+1).

EXAMPLES 9, 10
Preparation of Compounds 9 and 10

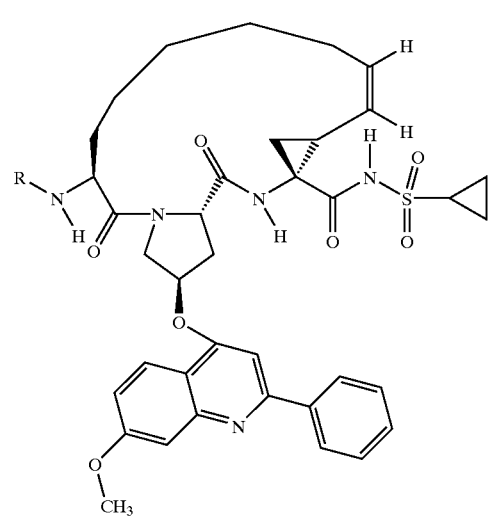

Compound 9, Example 9-R is Boc
Compound 10, Example 10-R is H (Bis HCl Salt)

Step 9g: Preparation of 1-{[1-(2(S)-tert-butoxycarbonylamino-non-8-enoyl)-4-(7-methoxy-2-phenylquinolin-4(R)-yloxy)pyrrolidine-2(S)-carbonyl]-1(R)-amino]-2(S)-vinylcyclopropanecarboxylic acid ethyl ester

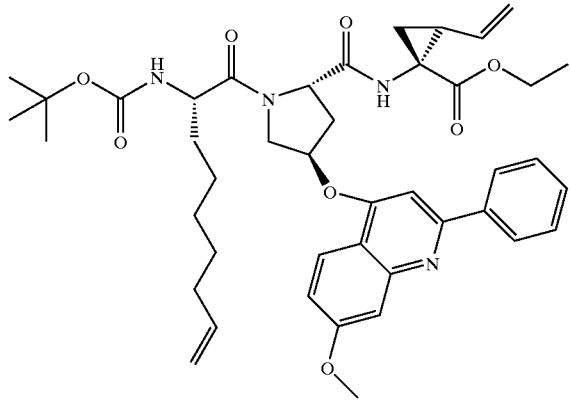

Following the procedure of Step 1 g, except that (0.78 g, 3.0 mmol) of 2(S)-tert-butoxycarbonylamino-8-nonenoic acid purchased from RSP Amino Acids, was coupled in place of 2(S)-tert-butoxycarbonylamino-5-hexenoic acid, gave 1-{[1-(2(S)-tert-butoxycarbonylamino-non-8-enoyl)-4-(7-methoxy-2-phenylquinolin-4(R)-yloxy)pyrrolidine-2(S)-carbonyl]-1(R)-amino]-2(S)-vinylcyclopropanecarboxylic acid ethyl ester as a yellow oil (1.55 g, 82%): $^1$H NMR (300 MHz, CDCl$_3$) δ 1.15–1.78 (m, 9H), 1.20 (t, J=7 Hz, 3H), 1.39 (s, 9H), 1.84 (dd, J=8.1, 5.5 Hz, 1H), 1.91–2.04 (m, 2H), 2.14 (q, J=8.8 Hz, 1H), 2.35–2.48 (m, 1H), 2.89–3.00 (m, 1H), 3.93 (s, 3H), 4.02–4.20 (m, 2H), 4.28 (d, J=11.7 Hz, 1H), 4.39–4.47 (m, 1H), 4.80–4.99 (m, 1H), 5.06–5.14 (m, 2H), 5.27 (dd, J=17, 1.3 Hz, 1H), 5.40 (brs, 1H), 5.65–5.81 (m, 2H), 7.03 (s, 1H), 7.07 (dd, J=9.1, 2.6 Hz, 1H), 7.42–7.57 (m, 4H), 7.99–8.05 (m, 3H). LC-MS (Method E-retention time: 1.79), MS m/z 755 (M$^+$+1)

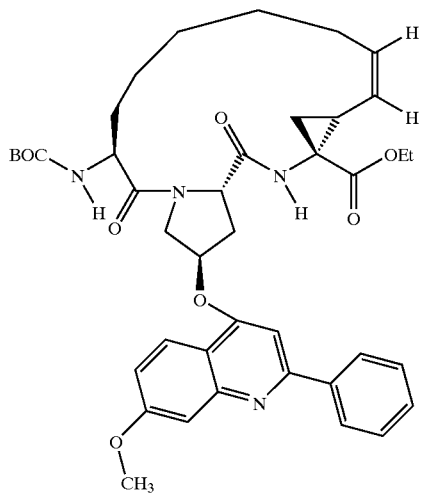

Step 9h: Preparation of (1S,4R,6S,14S,18R)-7-cis-14-tert-butoxycarbonylamino-18-(7-methoxy-2-phenylquinol-in-4-yloxy)-2,15-dioxo-3,16-diazatricyclo[14.3.0.0$^{4,6}$]-nonadec-7-ene-4-carboxylic acid ethyl ester To a solution of 1-{[1-(2(S)-tert-butoxycarbonylamino-non-8-enoyl)-4-(7-methoxy-2-phenylquinolin-4(R)-yloxy)-pyrrolidine-2(S)-carbonyl]-1(R)-amino]-2 (S)-vinylcyclopropanecarboxylic acid ethyl ester (1.50 g, 1.99 mmol) in 2.4L of Argon degassed 1,2-DCE, was added 150 mg of Grubbs catalyst, the mixture degassed under Ar and heated to reflux for 3 h. The reaction mixture was cooled to rt, the mixture degassed again, 150 mg portion of Grubbs catalyst added, and the mixture heated to reflux for 3 h. The reaction mixture was cooled again to rt, the mixture degassed again, 150 mg portion of Grubbs catalyst added, and the mixture heated to reflux for a final 9 h. The dark brown solution was concentrated in vacuo, purified by a Biotage 40 M column (eluted with 15% to 65% EtOAc in hexanes) to supply (1S,4R,6S,14S,18R)-7-cis-14-tert-butoxycarbonylamino-18-(7-methoxy-2-phenylquinolin-4-yloxy)-2,15-dioxo-3,16-diazatricyclo[14.3.0.0$^{4,6}$]nonadec-7-ene-4-carboxylic acid ethyl ester (1.08 g, 75%): $^1$H NMR (300 MHz, CDCl$_3$) δ 1.10–1.42 (m, 6H), 1.17 (t, J=7 Hz, 3H), 1.33 (s, 9H), 1.54 (dd, J=9.5, 5.5 Hz, 1H), 1.62 (m, 1H), 1.73 (dd, J=8.5, 5.5 Hz, 1H), 1.75–1.86 (m, 1H), 2.01–2.24 (m, 3H), 2.39–2.47 (m, 1H), 2.81–2.89 (m, 1H), 3.91 (s, 3H), 3.98–4.17 (m, 3H), 4.34 (d, J=11.0 Hz, 1H), 4.46 (m, 1H), 4.77 (dd, J=8.1, 5.5 Hz, 1H), 5.21–5.27 (m, 1H), 5.39 (m, 1H), 5.48–5.57 (m, 1H), 6.99 (s, 1H), 7.04 (dd, J=9.1, 2.2 Hz, 1H), 7.38 (d, J=2.2 Hz, 1H), 7.42–7.50 (m, 3H), 7.95–8.01 (m, 3H). LC-MS (Method E-retention time: 1.71), MS m/z 727 (M$^+$+1).

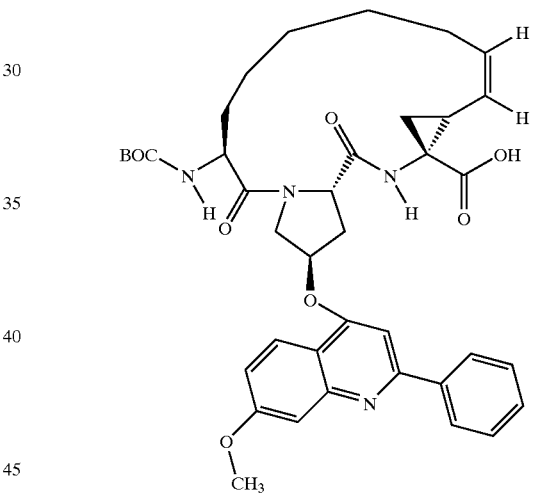

Step 9i: Preparation of (1S,4R,6S,14S,18R)-7-cis-14-tert-butoxycarbonylamino-18-(7-methoxy-2-phenylquinol-in-4-yloxy)-2,15-dioxo-3,16-diazatricyclo[14.3.0.0$^{4,6}$]-nonadec-7-ene-4-carboxylic acid Following an analogous experimental and purification procedure to Step 1i, (1S,4R,6S,14S,18R)-7-cis-14-tert-butoxycarbonylamino-18-(7-methoxy-2-phenylquinolin-4-yloxy)-2,15-dioxo-3,16-diazatricyclo[14.3.0.0$^{4,6}$]nonadec-7-ene-4-carboxylic acid ethyl ester (225 mg, 0.309 mmol) was reacted with 78 mg (2.0 mmol) of LiOH in 20.8 mL of 12.4:6.6:1.8 of THF/H$_2$O/MeOH to afford (1S,4R,6S,14S, 18R)-7-cis-14-tert-butoxycarbonylamino-18-(7-methoxy-2-phenylquinol-in-4-yloxy)-2,15-dioxo-3,16-diazatricyclo [14.3.0.0$^{4,6}$]-nonadec-7-ene-4-carboxylic acid (178 mg, 82%): $^1$H NMR (500 MHz, CD$_3$OD) δ 1.12–1.54 (m, 8H), 1.19 (s, 9H), 1.59 (dd, J=8.4, 5.0 Hz, 1H), 1.64 (dd, J=9.8, 4.9 Hz, 1H), 1.75–1.82 (m, 1H), 1.87–1.94 (m, 1H), 2.31 (q, J=9 Hz, 1H), 2.52–2.57 (m, 1H), 2.69 (dd, J=14, 7.5 Hz, 1H), 3.92 (s, 3H), 4.01 (dd, J=11.6, 3.2 Hz, 1H), 4.19 (dd, J=10.4, 2.4 Hz, 1H), 4.65 (t, J=8 Hz, 1H), 4.75 (d, J=11.6 Hz, 1H), 5.33 (t, J=9.6 Hz, 1H), 5.55–5.60 (m, 2H), 7.08 (dd, J=9.2, 2.1 Hz, 1H), 7.25 (s, 1H), 7.37 (d, J=2 Hz, 1H), 7.51–7.57 (m, 3H), 8.02–8.05 (m, 2H), 8.15 (d, J=9.2 Hz, 1H). LC-MS (Method E-retention time: 1.61), MS m/z 699 (M⁺+1). HRMS m/z (M+H)⁺ calcd for $C_{39}H_{47}N_4O_8$: 699.3394, found 699.3395.

Step 9j: Preparation of Compound 9, Example 9 (1S,4R,6S,14S,18R)-7-cis-[4-Cyclopropanesulfonylamino-carbonyl-18-(7-methoxy-2-phenylquinolin-4-yloxy)-2,15-dioxo-3,16-diazatricyclo[14.3.0.0$^{4,6}$]nonadec-7-en-14-yl]carbamic acid tert-butyl ester

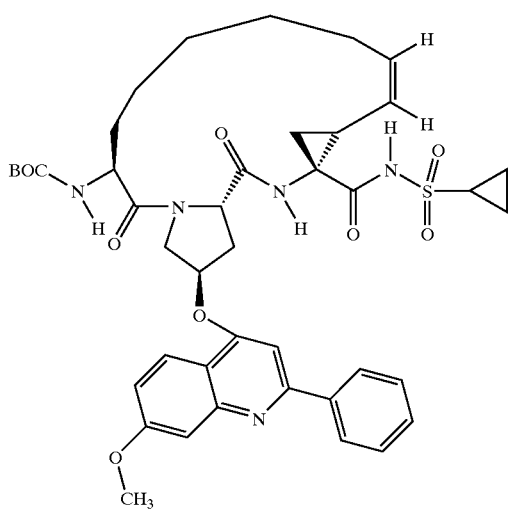

Compound 9, Example 9

Following the procedure of Step 1j, 136.5 mg (0.195 mmol) of (1S,4R,6S,13S,18R)-7-cis-14-tert-butoxycarbonylamino-18-(7-methoxy-2-phenylquinolin-4-yloxy)-2,15-dioxo-3,16-diazatricyclo-[14.3.0.0$^{4,6}$]nonadec-7-ene-4-carboxylic acid was converted to 115 mg (76%) (1S,4R,6S,13S,18R)-7-cis-[4-Cyclopropanesulfonylaminocarbonyl-18-(7-methoxy-2-phenyl-quinolin-4-yloxy)-2,15-dioxo-3,16-diazatricyclo-[14.3.0.0$^{4,6}$]nonadec-7-en-14-yl]carbamic acid tert-butyl ester: ¹H NMR (500 MHz, CD₃OD) 0.97–1.54 (m, 11H), 1.20 (s, 9H), 1.59 (m, 1H), 1.71 (m, 1H), 1.75–1.89 (m, 2H), 2.35–2.43 (m, 1H), 2.47–2.75 (m, 3H), 2.87–2.91 (m, 1H), 3.92 (s, 3H), 3.97–4.05 (m, 1H), 4.17 (d, J=10.4 Hz, 1H), 4.64 (t, J=7.6 Hz, 1H), 5.07 (m, 1H), 5.54 (brs, 1H), 5.63 (brs, 1H), 7.04 (d, J=8.6 Hz, 1H), 7.21 (brs, 1H), 7.36 (s, 1H), 7.48–7.55 (m, 3H), 8.02, 8.03 (2s, 2H), 8.15 (d, J=8.5 Hz, 1H). LC-MS (Method E-retention time: 1.64), MS m/z 802 (M⁺+1). HRMS m/z (M+H)⁺ calcd for $C_{42}H_{52}SN_5O_9$: 802.3486, found 802.3481.

Step 10k: Preparation of Compound 10, Example 10 Preparation of (1S,4R,6S,14S,18R)-7-cis-Cyclopropane-sulfonic acid [14-amino-18-(7-methoxy-2-phenylquinol-in-4-yloxy)-2,15-dioxo-3,16-diazatricyclo[14.3.0.0$^{4,6}$]-nonadec-7-ene-4-carbonyl]amide dihydrochloride

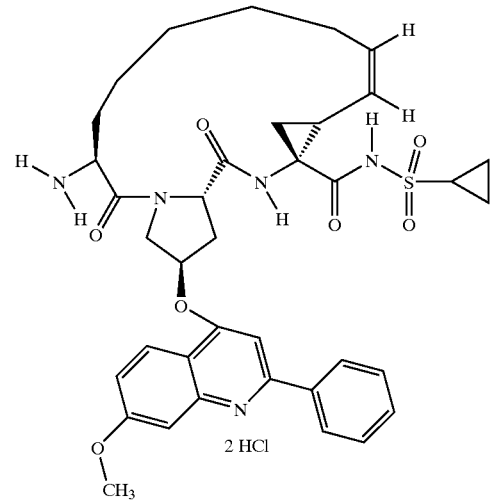

Compound 10, Example 10

A solution of 5 mL (20 mmol) of 4N HCl/dioxane was added to 26 mg (0.032 mmol) of (1S,4R,6S,13S,18R)-7-cis-[4-cyclopropanesulfonylaminocarbonyl-18-(7-methoxy-2-phenylquinolin-4-yloxy)-2,15-dioxo-3,16-diazatricyclo-[14.3.0.0$^{4,6}$]nonadec-7-en-14-yl]carbamic acid tert-butyl ester, the mixture stirred 2 h, concentrated and dried (50° C.; 20 torr; 12 h) to afford 24.0 mg (~100%) of (1S,4R,6S,14S,18R)-7-cis-cyclopropanesulfonic acid [14-amino-18-(7-methoxy-2-phenylquinolin-4-yloxy)-2,15-dioxo-3,16-diazatricyclo[14.3.0.0$^{4,6}$]nonadec-7-ene-4-carbonyl]amide dihydrochloride as a white solid: ¹H NMR (300 MHz, CD₃OD) δ 0.96–2.05 (m, 16H), 2.24–2.34 (m, 1H), 2.52 (ms, 1H), 2.73 (m, 1H), 2.91 (m, 2H), 3.57–3.74 (m, 1H), 4.06 (s, 3H), 4.17 (m, 1H), 4.37 (m, 1H), 4.48 (m 2H), 5.07–5.14 (m, 1H), 5.66–5.75 (m, 1H), 5.95 (m, 1H), 7,47 (m, 1H), 7.60–7.75 (m, 5H), 8.12 (m, 2H), 8.39–8.41 (m, 1H) LC-MS (Method E-retention time: 1.24), MS m/z 702 (M⁺+1). HRMS m/z (M+H)⁺ calcd for $C_{37}H_{44}SN_5O_7$: 702.2962, found 702.2976.

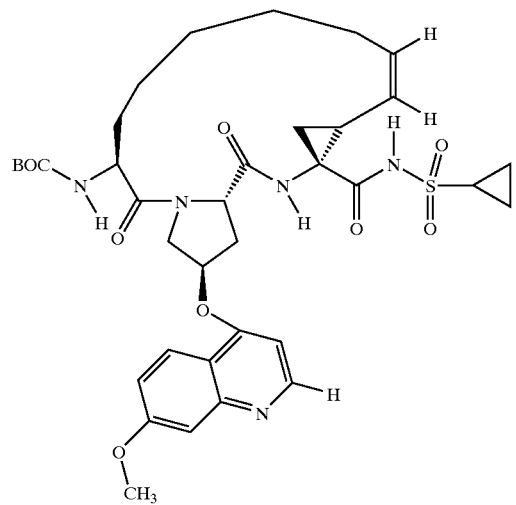

Compound 11, Example 11

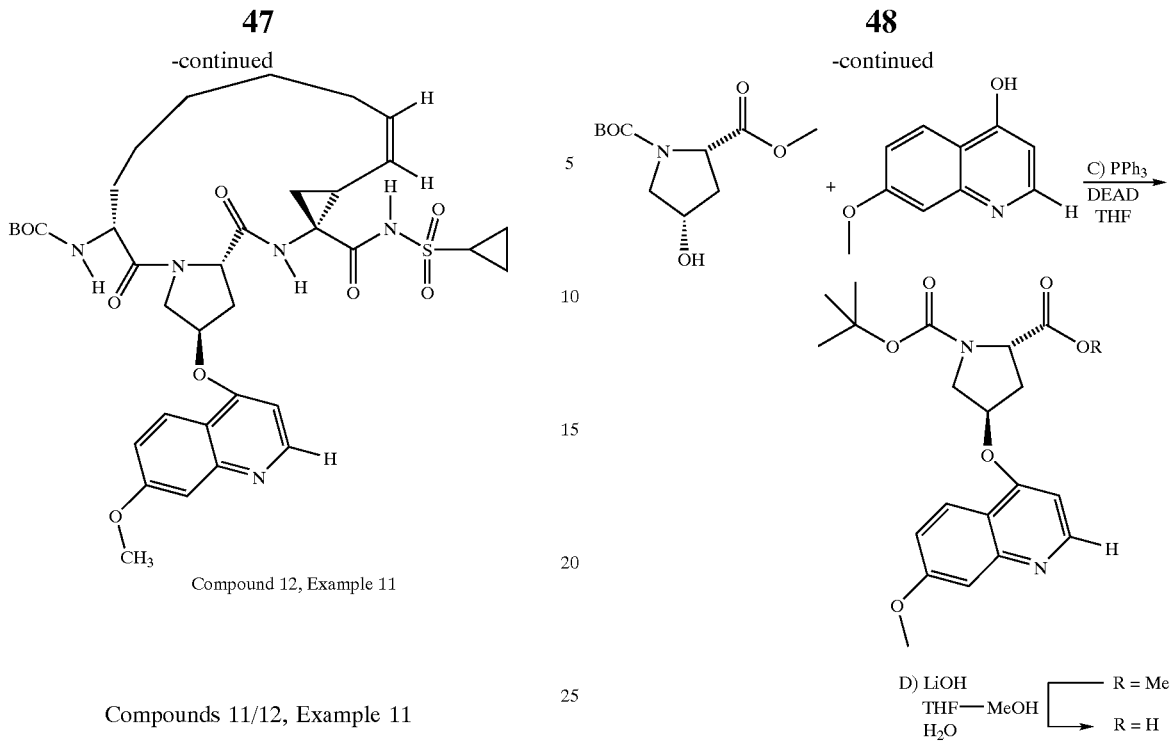

Compound 12, Example 11

Compounds 11/12, Example 11

Preparation of Compound 11, Example 11, (1S,4R,6S,13S, 18R)-7-cis-[4-Cyclopropanesulfonyl-aminocarbonyl-18-(7-methoxy-2-phenylquinolin-4-yloxy)-2,15-dioxo-3,16-diazatricyclo-[14.3.0.0$^{4,6}$]nona-dec-7-en-14-yl]carbamic acid tert-butyl ester and Compound 12, Example 11, (1S,4R,6S,13R,18R)-7-cis-[4-Cyclopropanesulfonylaminocarbonyl-18-(7-methoxy-2-phenylquinolin-4-yloxy)-2,15-dioxo-3,16-diazatri-cyclo-[14.3.0.0$^{4,6}$]nonadec-7-en-14-yl]carbamic acid tert-butyl ester was accomplished using steps 11A–J.

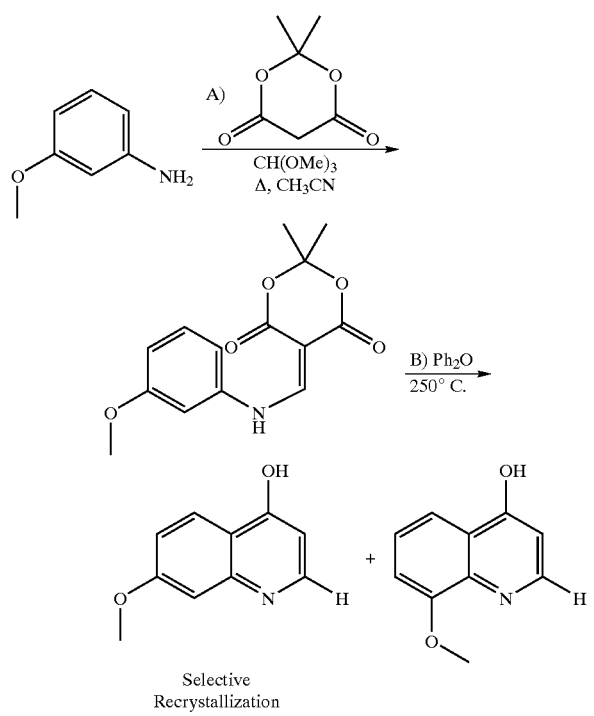

Selective Recrystallization

Steps 11A–11B: Preparation of 7-Methoxyquinolin-4-ol from m-anisidine.

Step 11A) To a solution of m-anisidine (58 g, 471 mmol) in 800 mL of CH$_3$CN was added Meldrum's acid (75 g, 518 mmol), and trimethylformate (60 g, 565 mmol). The heterogeneous mixture was refluxed for 2 h went into solution. The solvent was removed in vacuo, 30 mL of MeOH added, and the resulting precipitate filtered and washed with 10–15 mL of MeOH. The MeOH addition/filtration procedure was repeated on the concentrated mother liquor. The resulting combined solid was dried (~20 torr, 45° C. overnite) to afford (117.6 g, 90%) of the intermediate 5-[(3-Methoxyphenylamino)methylene]-2,2-dimethyl-[1,3] dioxane-4,6-dione.

Step 11B) To a solution of 500 g of Ph$_2$O heated to 250° C. was added 108.7 g (392 mmol) of 5-[(3-Methoxyphenyl-amino)methylene]-2,2-dimethyl-[1,3]dioxane-4,6-dione in portions over a 30 min period. The mixture was heated an additional 15 min, cooled to rt, diluted with 800 mL of hexanes and the resulting slurry stirred overnite. The hexanes was decanted off, the solid residue dissolved in 600 mL of MeOH at reflux, cooled to rt and the resulting solid filtered and washed with minimal CH$_2$Cl$_2$. The analogous recrystallization procedure was followed to afford a total of 20.73 g (30%) of 7-methoxyquinolin-4-ol as a light brown solid. $^1$H NMR (methanol-d$_4$) δ 3.87 (s, 3H), 6.23 d, J=7.3 Hz, 1H), 6.68 (d, J=2.4 Hz, 1H), 6.96 (dd, J=9.0, 2.4 Hz, 1H), 8.11 (d, J=9 Hz, 1H); LC-MS (retention time: 0.77, method D), MS m/z 176 (M$^+$+1).

Step 11C: Preparation of BOC-N-P2[(4R)-(7-methoxyquinoline-4-oxo)proline methyl ester]4-(7-methoxyquinolin-4yloxy)-pyrrolidine-1,2-dicarboxylic acid 1-tert-butyl ester 2-methyl ester from BOC-L-CIS-HYP-OH and 7-methoxyquinolin-4-ol.

Step 11C) To a solution of 12.24 g (49.8 mmol) of BOC-L-CIS-HYP-OH (BOC-CIS-HYP-OME, N-α-tert-butoxycarbonyl-cis-L-4-Hydroxyproline methylester) and 26.14 g (99.7 mmol) of PPh$_3$ in 200 mL of THF cooled to 0° C., was added a solution of 17.36 g (99.7 mmol) of DEAD and 8.73 g (49.8 mmol) of 7-methoxyquinolin-4-ol in 700 mL of THF over a 45 min period. The mixture was slowly allowed to warm to rt overnite, concentrated in vacuo and the residue purified over a Biotage 65M (eluted with 0% to 10% MeOH-EtOAc) to afford 12.78 g (64%) of the desired product BOC-N-P2[(4R)-(7-methoxyquinoline-4-oxo)pro-line methyl ester], 4-(7-methoxyquinolin-4yloxy)-pyrrolidine-1,2-dicarboxylic acid 1-tert-butyl ester 2-methyl ester as a colorless glass. $^1$H NMR (CDCl$_3$) δ 1.36 (s, 9H), 2.26–2.35 (m, 1H), 2.57–2.68 (m, 1H), 3.71 (s, 3H), 3.75–3.92 (m, 2H), 3.86, 3.87 (two s (rotamers) 3H), 4.41–4.53 (m, 1H), 5.09 (m, 1H), 6.52 (d, J=5.5 Hz, 1H), 7.06–7.09 (m, 1H), 7.24–7.26 (m, 1H), 7.94 (d, J=9.1 Hz, 1H), 8.50–8.56 (m, 1H); LC-MS (retention time: 1.34, method D), MS m/e 403 (M$^+$+1).

Step 11D: Preparation of BOC-N-P2[(4R)-(7-methoxyquinoline-4-oxo)proline]-OH, 4-(7-methoxyquinolin4yl-oxy)-pyrrolidine-1,2-dicarboxylic acid 1-tert-butyl ester from BOC-N-P2[(4R)-(7-methoxyquinoline-4-oxo)proline methyl ester], 4-(7-methoxyquinolin-4yloxy)-pyrrolidine-1,2-dicarboxylic acid 1-tert-butyl ester 2-methyl ester.

Step 11D) To a solution of 8.54 g (21.2 mmol) of BOC-N-P2[(4R)-(7-methoxyquinoline-4-oxo)proline methyl ester]in 600 mL of 5:1 THF/MeOH, was added a solution of 4.0 g (167 mmol) of LiOH in 150 mL of water. The mixture was stirred overnite, the pH adjusted to pH 7 using 6N aqueous HCl, and the solution concentrated until only the water layer remained. The solution was adjusted to pH 4 using 6N aqueous HCl, NaCl added to saturate the mixture and was partitioned repeatedly with first EtOAc and then THF as the product was aqueous soluble. The combined organic layers were dried (MgSO$_4$) and concentrated to afford 8.18 g (99%) of BOC-N-P2[(4R)-(7-methoxyquinoline-4-oxo)proline]-OH, 4-(7-methoxyquinolin-4yloxy)-pyrrolidine-1,2-dicarboxylic acid 1-tert-butyl ester as a white solid. $^1$H NMR (CDCl$_3$-Methanol-d$_4$) δ 1.42 (s, 9H), 2.40–2.49 (m, 1H), 2.68–2.77 (m, 1H), 3.88 (m, 2H), 3.94 (s, 3H), 4.41–4.53 (m, 1H), 5.32 (m, 1H), 6.86–6.92 (m, 1H), 7.21 (dd, J=9, 2 Hz, 1H), 7.30 (d, J=2 Hz, 1H), 8.05–8.10 (m, 1H), 8.62 (d, J=6 Hz, 1H); LC-MS (retention time 1.20, method A), MS m/z 389 (M$^+$+1).

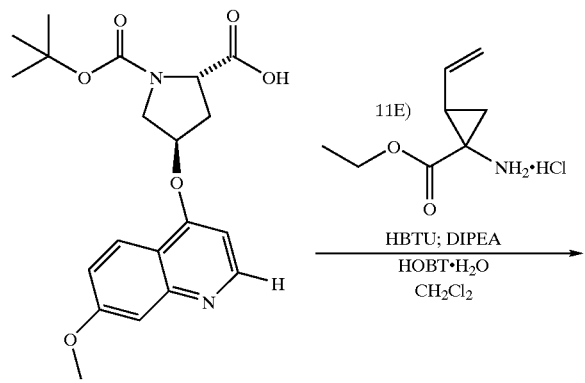

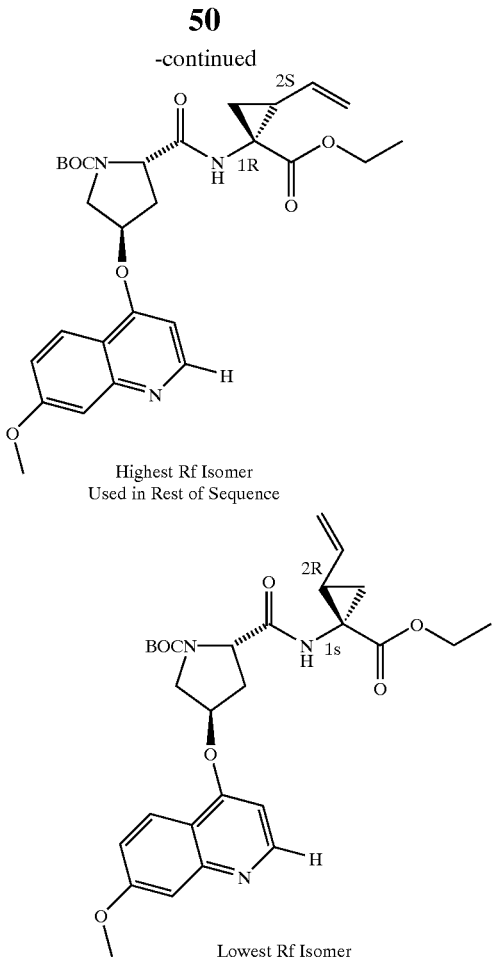

Highest Rf Isomer
Used in Rest of Sequence

Lowest Rf Isomer

Step 11E: Coupling of (1R,2S/1S,2R)-Vinyl Acca)-CO$_2$Et HCl Salt P1 Moiety with Boc (4R)-(7-methoxyquinoline-4-oxo)-S-proline P2 Moiety to make BOCN-P2[(4R)-7-methoxyquinoline-4-oxo) proline]-P1 (1R,2S/1S,2R)-vinylAcca-COOEt and chromatographic separation of BOCN-P2[(4R)-(7-methoxyquinoline-4-oxo)-S-proline]-P1 (1R,2S VinylAcca)-CO$_2$Et (most bioactive isomer) and BOCN-P2[(4R)-(7-methoxyquinoline-4-oxo)-S-proline]-P1 (1S,2R Vinyl Acca)-CO$_2$Et Diastereomers.

Step 11E) To a solution of 4.50 g (11.60 mmol) of Boc-4(R)-(7-methoxyquinoline-4-oxo)proline, 2.66 g (13.9 mmol) of the HCl salt of vinyl Acca (existing as a 1:1 mixture of diastereoisomers (1R,2S/1S,2R where cyclopropyl carboxyethyl group is syn to vinyl moiety), 10 mL (57.4 mmol) of DIPEA, and 2.13 g (13.9 mmol) of HOBT.H$_2$O in 150 mL of CH$_2$Cl$_2$ was added 5.27 g (13.9 mmol) of the coupling reagent HBTU, and the mixture stirred overnite. The solution was diluted with 200 mL of CH$_2$Cl$_2$ and was partitioned with pH 4.0 buffer (2×50 mL). The organic layer was washed with saturated aqueous NaHCO$_3$ (2×50 mL), water (2×50 mL), and brine (2×50 mL). The organic solution was dried (MgSO$_4$), concentrated and purified using a Biotage 65M column (eluted with 0% to 9% MeOH/EtOAc) to provide of BOC-NH-P2[(4R)-(7-methoxyquinoline-4-oxo)-S-proline]-P1 (1R,2S vinyl acca P1 moiety)-COOEt as the initial eluted isomer (2.21 g, 36% overall), followed by 1.13 g (19%) of pure lower Rf isomer BOC-NH-P2[(4R)-(7-methoxyquinoline-4-oxo)-S-proline]-P1 (1S,2R Vinyl Acca P1 moiety)-CO$_2$Et. Mixed fractions were also obtained. Data for BOCN-P2[(4R)-(7-methoxyquinoline-4- oxo)-S-proline]-P1 (1R,2S)-(VinylAcca)-COOEt: $^1$H NMR (CDCl$_3$) δ 1.16 (t, J=7 Hz, 3H), 1.35 (s, 9H), 1.37–1.47 (m, 1H), 1.74–1.88 (m, 1H), 2.04–2.13 (m, 1H), 2.32–2.46 (m, 1H), 2.58–2.69 (m, 1H), 3.76 (m, 1H), 3.87 (s, 3H), 4.02–4.13 (m, 2H), 4.30–4.44 (m, 1H), 5.05–5.19 (m, 2H), 5.24 (d, J=17 Hz, 1H), 5.63–5.71 (m, 1H), 6.61 (m, 1H), 7.07 (dd, J=9, 2 Hz, 1H), 7.22 (d, J=2 Hz, 1H), 7.76–7.83 (m, 1H), 7.92 (d, J=9 Hz, 1H), 8.50 (d, J=5 Hz, 1H). LC-MS (retention time: 1.38, method A), MS m/z 526 (M$^+$+1).

Data for BOC-NH-P2[(4R)-(7-methoxyquinoline-4-oxo)-S-proline]-P1 (1S,2R Vinyl Acca P1 moiety)-CO$_2$Et: $^1$H NMR (methanol-d$_4$) δ 1.23 (t, J=7 Hz, 3H), 1.38 (s, 9H), 1.45 (dd, J=9.5, 5.5 Hz, 1H), 1.77–1.87 (m, 1H), 2.10–2.16 (m, 1H), 2.37 (m, 1H), 2.73 (m, 1H), 3.77 (m, 1H), 3.90 (s, 3H), 4.07–4.15 (m, 2H), 4.46 (m, 1H), 5.10 (d, J=10 Hz, 1H), 5.21 (m, 1H), 5.27 (d, J=17 Hz, 1H), 5.69–5.76 (m, 1H), 6.64 (m, 1H), 7.10 (dd, J=9.2, 2.2 Hz, 1H), 7.27 (m, 1H), 7.95 (d, J=9.2 Hz, 1H), 8.56 (d, J=5 Hz, 1H). LC-MS (retention time: 1.45, method B), MS m/z 526 (M$^+$+1).

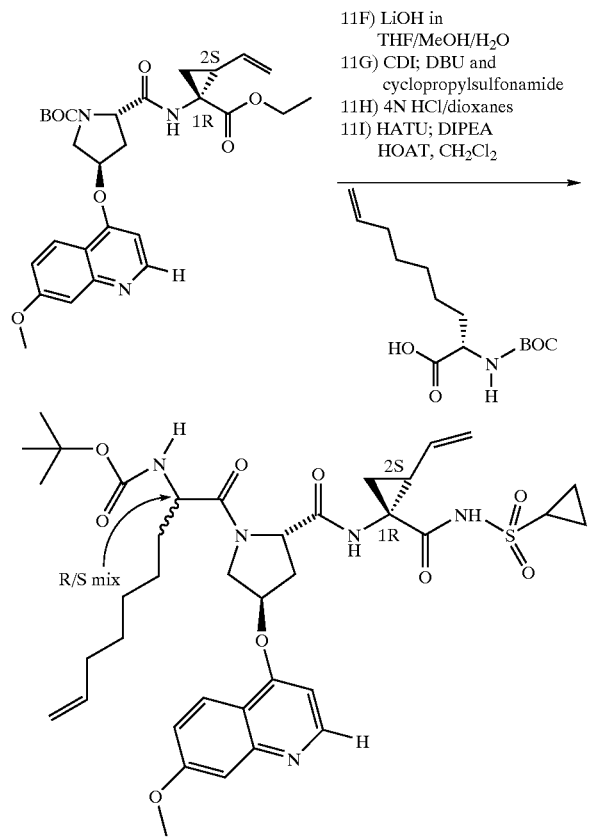

11F) LiOH in THF/MeOH/H$_2$O
11G) CDI; DBU and cyclopropylsulfonamide
11H) 4N HCl/dioxanes
11I) HATU; DIPEA HOAT, CH$_2$Cl$_2$ Step 11F: Preparation of N-BOC-P2[(4R)-(7-methoxyquinoline-4-oxo)-S-proline]-P1 (1R,2S VinylAcca)-CO$_2$H or (1R,2S) Vinyl Acca P1 Isomer of {1-[2-(1-Cyclopropanesulfonylaminocarbon-yl-2-vinylcyclopropylcarbamoyl)-4-(7-methoxyquinolin-4-yloxy)pyrrolidine-1-carbonyl]-2,2-dimethylpropyl}-carbamic acid tert-butyl ester.

Step 11F) To a solution of 794 mg (1.51 mmol) of N-BOC-P2[(4R)-(7-methoxyquinoline-4-oxo)-S-proline]-P1 (1R,2S VinylAcca)-CO$_2$Et (from step 11E) in 68 mL of 12% MeOH/THF was added a solution of 218 mg (9.08 mmol) of lithium hydroxide in 30 mL of water and the mixture stirred 16 h. The pH was adjusted to neutral by addition of 6N aqueous HCl, concentrated until only the water remained, the solution adjusted to pH 4 using aqueous 1N HCl and was then extracted with 50% THF-EtOAc (5×200-mL portions). The combined organic layers were dried (MgSO$_4$) and concentrated to afford 808 mg of crude which was dried further to provide 752 mg (100%) of N-BOC-P2[(4R)-(7-methoxyquinoline-4-oxo)-S-proline]-P1 (1R,2S VinylAcca)-CO$_2$H. $^1$H NMR (Methanol-d$_4$) δ 1.37–1.43 (m, 1H), 1.39 (s, 9H), 1.69–1.78 (m, 1H), 2.16–2.24 (m, 1H), 2.44–2.54 (m, 1H), 2.64–2.74 (m, 1H), 3.89–3.94 (m, 2H), 3.96 (s, 3H), 4.40–4.43 (m, 1H), 5.11 (d, J=10 Hz, 1H), 5.31 (d, J=17 Hz, 1H), 5.40 (m, 1H), 5.79–5.87 (m, 1H), 6.91 (s, 1H), 7.04 (d, J=6 Hz, 1H), 7.25 (dd, J=9.1, 2 Hz, 1H), 7.29 (m, 1H), 8.09 (d, J=9.1 Hz, 1H), 8.66 (d, J=6 Hz, 1H). LC-MS (retention time: 1.05, method H). MS m/z 498 (M$^+$+1)

Step 11G: Preparation of N-BOC-P2[(4R)-(7-methoxyquinoline-4-oxo)-S-proline]-P1 (1R,2S VinylAcca)-CONHSO$_2$Cyclopropane or (1R,2S) Vinyl Acca P1 Diastereomer of 2-(1-Cyclopropane-sulfonylamino-carbonyl-2-vinylcyclopropylcarbamoyl)-4-(7-methoxy-quinolin-4-yloxy)pyrrolidine-1-carboxylic acid tert-butyl ester.

Step 11G) To a solution of 399.5 mg (0.668 mmol) of N-BOC-P2[(4R)-(7-methoxyquinoline-4-oxo)-S-proline]-P1 (1R,2S VinylAcca)-CO$_2$H in THF (4 mL), was added CDI (434 mg, 2.68 mmol), and the resulting solution refluxed for 60 min and allowed to cool down to rt. Cyclopropylsulfonamide (406 mg, 3.35 mmol) was added in one portion before the addition of a neat solution of DBU (0.50 mL, 3.35 mmol). The reaction was stirred for 16 h, diluted with 50% THF-EtOAc (200 mL) and washed with brine saturated pH 4.0 buffer (2×40 mL), dried (MgSO$_4$) and chromatographed over a Biotage 25M column (eluted with 0% to 15% MeOH in CH$_2$Cl$_2$) to supply 217 mg (54%) of the desired product N-BOC-P2[(4R)-(7-methoxyquinoline-4-oxo)-S-proline]-P1 (1R,2S VinylAcca)-CONHSO$_2$Cyclopropane. $^1$H NMR (Methanol-d$_4$) δ 1.01–1.10 (m, 2H), 1.11–1.18 (m, 1H), 1.20–1.27 (m, 1H), 1.39–1.48 (m, 1H), 1.44 (s, 9H), 1.87 (dd, J=8, 5 Hz, 1H), 2.01–2.38 (m, 2H), 2.57 (dd, J=14, 7 Hz, 1H), 2.91–2.96 (m, 1H), 3.83–3.92 (m, 2H), 3.94 (s, 3H), 4.36–4.39 (m, 1H), 5.11 (d, J=10 Hz, 1H), 5.29 (d, J=17 Hz, 1H), 5.38 (m, 1H), 5.74–5.81 (m, 1H), 6.91 (d, J=5.5 Hz, 1H), 7.20 (dd, J=9.2, 2.4 Hz, 1H), 7.29 (m, 1H), 8.07 (d, J=9.2 Hz, 1H), 8.60 (d, J=5.5 Hz, 1H). LC-MS (retention time: 1.28, method I). MS m/z 601 (M$^+$+1)

Steps 11H and 11I: Preparation of BOCNH-P3 (2(S)-tert-butoxycarbonylamino-8-nonenoyl)-P2[(4R)-(7-methoxyquinoline-4-oxo)-S-proline]-P1 (1R,2S-VinylAcca)-CONHSO$_2$Cyclopropane or (1R,2S) P1 Isomer of {1-[2-(1-Cyclopropanesulfonylaminocarbonyl-2-vinylcyclopropylcarbamoyl)-4-(7-methoxyquinolin-4-yloxy)-pyrrolidine-1-carbonyl]-oct-7-enyl}carbamic acid tert-butyl ester.

Steps 11H) A total of 600 mg (1.0 mmol) of BOC-P2 [(4R)-(7-methoxyquinoline-4-oxo)-S-proline]-P1 (1R,2S Vinyl Acca-CONHSO$_2$Cyclopropane), (1R,2S) VinylAcca P1 isomer of 2-(1-Cyclopropanesulfonylaminocarbonyl-2-vinylcyclopropyl-carbamoyl)-4-(7-methoxyquinolin-4-yloxy)pyrrolidine-1-carboxylic acid tert-butyl ester, was dissolved in 4N HCl/dioxane (4 ml, 16 mmol) and was stirred for 3 h at rt. The reaction mixture was concentrated to supply the crude HN-P2[(4R)-(7-methoxyquinoline-4-oxo)-S-proline]-P1 (1R,2S Vinyl Acca)—CONHSO$_2$Cyclopropane, Bis HCl Salt: (1R,2S)-Vinyl Acca P1 isomer of 4-(7-Methoxyquinolin-4-yloxy)-pyrrolidine-2-carboxylic acid (1-cyclopropane-sulfonylaminocarbonyl-2-vinylcyclopropyl)amide dihydrochloride as a tan solid which was used immediately in Step 11I.

Step 11I) The HN-P2[(4R)-(7-methoxyquinoline-4-oxo)-S-proline]-P1 (1R,2S Vinyl Acca)-CONHSO₂Cyclopropane, Bis HCl Salt from step 11H, was suspended in 20 mL of dichloromethane. To this mixture was added 352 mg (1.30 mmol) of 2(S)-tert-butoxycarbonylamino-8-nonenoic acid purchased from RSP Amino Acids, HOAT (82 mg, 0.60 mmol), DIPEA (0.74 ml, 5.0 mmol), and HATU (494 mg, 1.30 mmol) at rt. The reaction mixture was stirred 16 h, and the majority of the CH₂Cl₂ removed in vacuo. The mixture was diluted with saturated pH 4.0 buffer (150 mL), and extracted into EtOAc (4×200 mL). The combined organic layers were dried (MgSO₄), concentrated and purified over a Biotage 40M column (eluted with 0% to 15% MeOH in CH₂Cl₂) to afford 574 mg (76%) of BOCNH-P3 (2 (R/S)-tert-butoxycarbonylamino-8-nonenoic acid)-P2[(4R)-(7-methoxyquinoline-4-oxo)-S-proline]-P1 (1R,2S-VinylAcca)-CONHSO₂Cyclopropane or (1R,2S) P1 Isomer of {1-[2-(1-Cyclopropanesulfonylaminocarbonyl-2-vinylcyclopropylcarbamoyl)-4-(7-methoxyquinolin-4-yloxy)-pyrrolidine-1-carbonyl]-oct-7-enyl}carbamic acid tert-butyl ester. LC-MS m/e 754 (retention time: 1.64, method I).

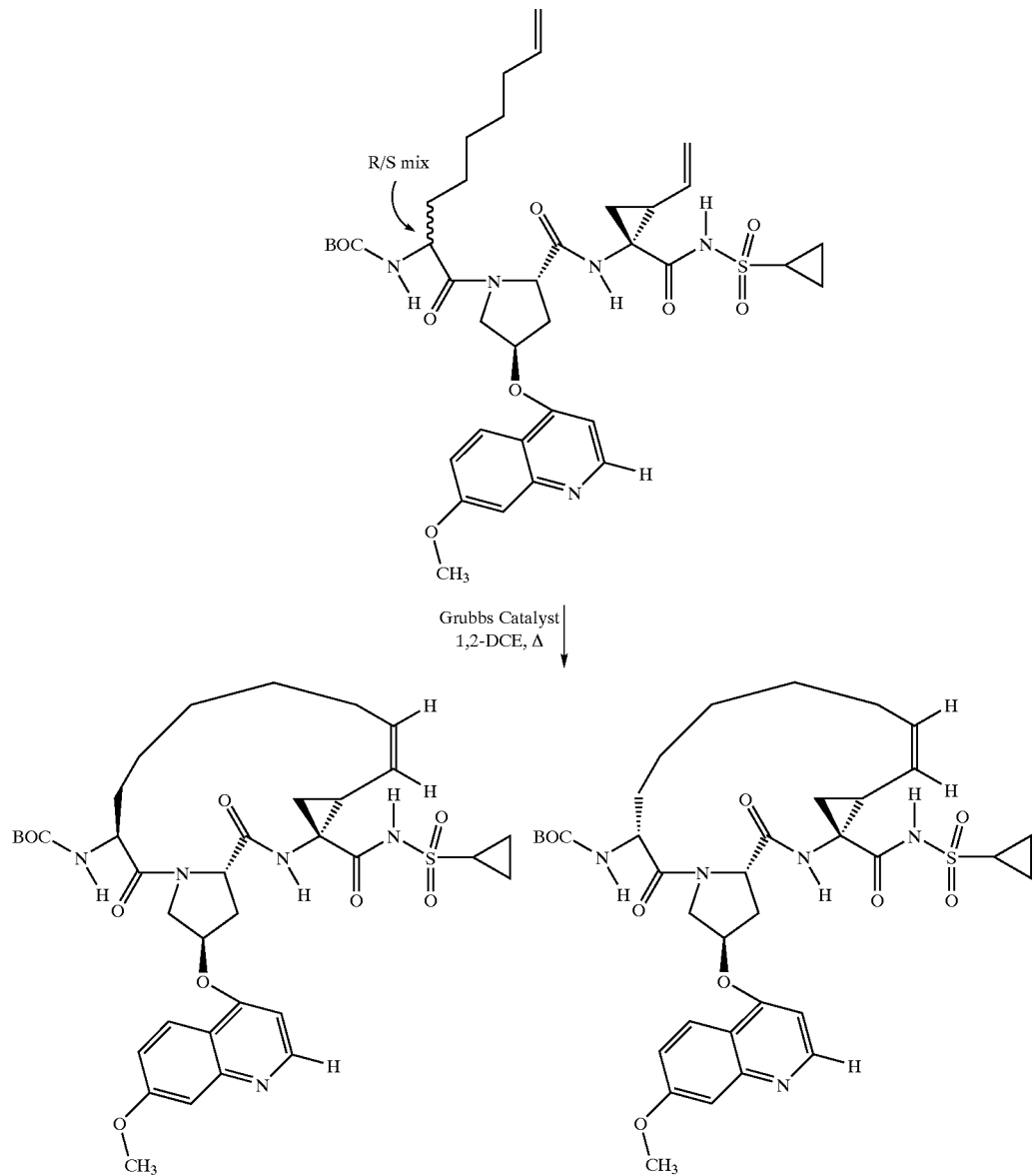

Compound 11, Example 11    Compound 12, Example 11

Preparation of Compound 11, Example 11, (1S,4R,6S,13S,18R)-7-cis-[4-Cyclopropanesulfonylaminocarbonyl-18-(7-methoxy-2-phenyl-quinolin-4-yloxy)-2,15-dioxo-3,16-diazatricyclo-[14.3.0.0⁴,⁶]nonadec-7-en-14-yl]carbamic acid tert-butyl ester and Compound 12, Example 11, (1S,4R,6S,13R,18R)-7-cis-[4-Cyclopropanesulfonyl-aminocarbonyl-18-(7-methoxy-2-phenylquinolin-4-yloxy)-2,15-dioxo-3,16-diazatricyclo[14.3.0.0⁴,⁶]-nonadec-7-en-14-yl] carbamic acid tert-butyl ester.

Step 11J) To a solution of BOCNH-P3 (2(S)-tert-butoxycarbonylamino-8-nonenoyl)-P2[(4R)-(7- methoxyquinoline-4-oxo)-S-proline]-P1 (1R,2S-VinylAcca)-CONHSO₂Cyclopropane or (1R,2S) P1 Isomer of {1-[2-(1-Cyclopropanesulfonylaminocarbonyl-2-vinylcyclopropylcarbamoyl)-4-(7-methoxyquinolin-4-yloxy)-pyrrolidine-1-carbonyl]-oct-7-enyl}carbamic acid tert-butyl ester from Step 11I (537 mg, 0.712 mmol) in 0.7L of Argon degassed 1,2-DCE, was added 60 mg of Grubbs catalyst, the mixture degassed under Ar and heated to reflux for 4 h. The reaction mixture was cooled to rt, the mixture degassed once more, an additional 60 mg portion of Grubbs catalyst added, and the mixture heated to reflux for 4 h. The reaction mixture was cooled to rt, the mixture degassed once more, and a final 60 mg portion of Grubbs catalyst added, and the mixture heated to reflux for 2 h. The mixture was cooled to rt, stirred 9 h more and the resulting dark brown solution concentrated in vacuo and purified using three Analtech 1000μ PTLC plates (20×40 cm, eluted sequentially with 0% to 3% MeOH in CH₂Cl₂ to afford 80 mg of crude product. This material was further purified using four 500μ E-Merck PTLC plates to afford 10 mg of Compound 11, Example 11, (1S,4R,6S,13S,18R)-7-cis-[4-Cyclopropanesulfonyl-aminocarbonyl-18-(7-methoxy-2-phenyl-quinolin-4-yloxy)-2,15-dioxo-3,16-diazatricyclo[14.3.0.0⁴,⁶]-nonadec-7-en-14-yl]carbamic acid tert-butyl ester and P3 Epimer Compound 12, Example 11, (1S,4R,6S,13R,18R)-7-cis-[4-Cyclopropanesulfonylaminocarbonyl-18-(7-methoxy-2-phenylquinolin-4-yloxy)-2,15-dioxo-3,16-diazatricyclo-[14.3.0.0⁴,⁶]nonadec-7-en-14-yl]carbamic acid tert-butyl ester. Data for Compound 11: ¹H NMR (CD₃OD) δ 0.87–1.10 (m, 4H), 1.15–2.01 (m, 11H), 1.21 (s, 9H), 2.19–2.29 (m, 1H), 2.45–2.73 (m, 3H), 2.83–2.92 (m, 1H), 3.93 (s, 3H), 4.11–4.17 (m, 1H), 4.20–4.29 (m, 1H), 4.60–4.69 (m, 2H), 5.21–5.27 (m, 1H), 5.47 (m, 1H), 5.54–5.63 (m, 1H), 6.96 (d, J=5.5 Hz, 1H), 7.10 (dd, J=9.5, 2.5 Hz, 1H), 7.27 (d, J=2.5 Hz, 1H), 8.17 (d, J=9.5 Hz, 1H), 8.61 (d, J=5.5 Hz, 1H). LC-MS m/e 726 (retention time: 1.57, method A). Data for Compound 12: ¹H NMR (CD₃OD) δ 0.79–0.99 (m, 2H), 1.00–1.65 (m, 9H), 1.15 (s, 9H), 1.80–2.05 (m, 4H), 2.32–2.57 (m, 2H), 2.59–2.83 (m, 2H), 2.84–2.92 (m, 1H), 3.92 (s, 3H), 4.03–4.16 (m, 1H), 4.27–4.31 (m, 1H), 4.53–4.78 (m, 2H), 5.42 (m, 3H), 6.91 (d, J=5 Hz, 1H), 7.11 (dd, J=9.2, 2.2 Hz, 1H), 7.26 (d, J=2.2 Hz, 1H), 8.11 (d, J=9.2 Hz, 1H), 8.60 (d, J=5 Hz, 1H). LC-MS m/e 726 (retention time: 1.49, method A).

EXAMPLES 12,13

Preparation of Compounds 13 and 14

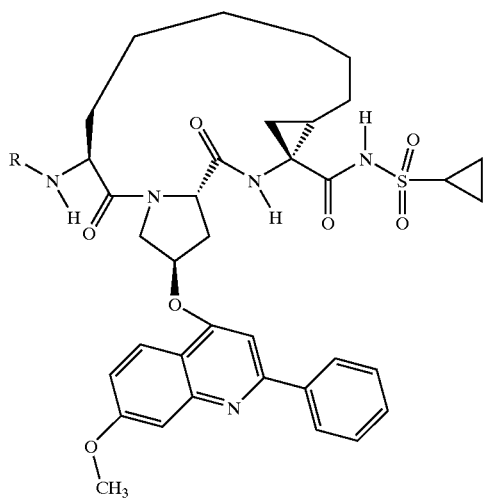

Compound 13, Example 12-R is Boc
Compound 14, Example 13-R is H

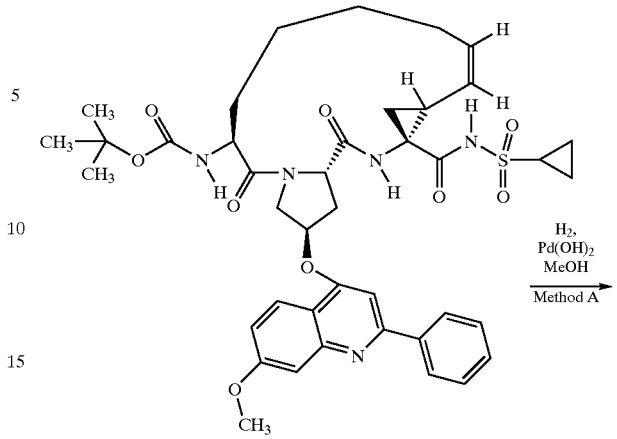

Compound 7, Example 7

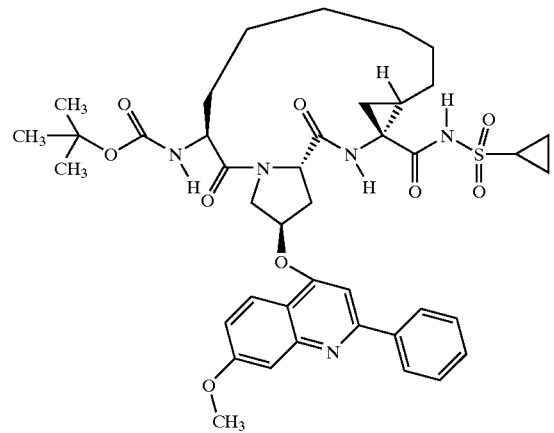

Compound 13, Example 12

Compound 13, Example 12
Preparation of (1S,4R,6R,13S,17R)-[4-Cyclopropanesulfonylaminocarbonyl-17-(7-methoxy-2-phenylquinolin-4-yloxy)-2,14-dioxo-3,15-diazatricyclo [13.3.0.0⁴,⁶]-octadec-13-yl]-carbamic acid tert-butyl ester, Compound 13, Example 12.

Method A. A solution of 30 mg (0.038 mmol) of (1S,4R,6S,13S,17R)-7-cis-[4-Cyclopropanesulfonylaminocarbonyl-17-(7-methoxy-2-phenylquinolin-4-yloxy)-2,14-dioxo-3,15-diazatricyclo [13.3.0.0⁴,⁶]octadec-7-en-13-yl]carbamic acid tert-butyl ester, Compound 7, Example 7, was dissolved in 15 mL of MeOH and then evacuated via vacuum and degassed repeatedly under Ar. To this solution was added 15 mg of 20% Pd(OH)₂/C and the mixture evacuated and put under 1 atmosphere of H₂ gas three times and finally allowed to stir under 1 atmosphere of H₂ over 45 minutes. The reaction contents were then then evacuated and put under Argon, filtered over celite and the resulting crude residue purified over preparative HPLC (column: Xterra C18 S5 30×75 mm, 35% to 80% Solvent B/A for 28 min gradient, hold time 3 min; where Solvent A is 10% MeOH/90% H₂O with 0.1% TFA, Solvent B is 90% MeOH/10% H₂O with 0.1% TFA and flow rate is 40 ml/min). Compound 13, Example 12 eluted first (8.8 mg, 29.3%), followed by 15 mg of mixed fractions containing Compound 13 and an unidentified product: ¹H NMR (methanol-d₄) δ 0.84–2.08 (m, 26H), 2.51–2.69 (m, 1H), 2.74–2.78 (m, 1H), 2.91–3.01 (m, 1H), 3.96 (s, 3H), 4.04–4.09 (m, 1H), 4.17 (d, J=11 Hz, 1H), 4.72 (t, J=8 Hz, 1H), 4.97 (d, J=12 Hz, 1H), 5.64 m, 1H), 7.13 (dd, 9, 1.6 Hz, 1H), 7.32 (s, 1H), 7.40 (d, J=1.6 Hz, 1H), 7.53–7.62 (m, 3H), 8.02–8.05 (m, 2H), 8.15 (d, J=9 Hz, 1H). LC-MS m/e 790 (retention time: 2.55, method D, except gradient time increased from 2 to 3 min).

S5, 30% to 85% Solvent B/A for 25 min gradient, hold time 5 min; where Solvent A is 10% MeOH/90% $H_2O$ with 0.1% TFA, Solvent B is 90% MeOH/10% $H_2O$ with 0.1% TFA and flow rate is 40 ml/min). The pH of the combined fractions was adjusted to neutral using 6N aqueous NaOH solution and the MeOH removed in vacuo. The solution was

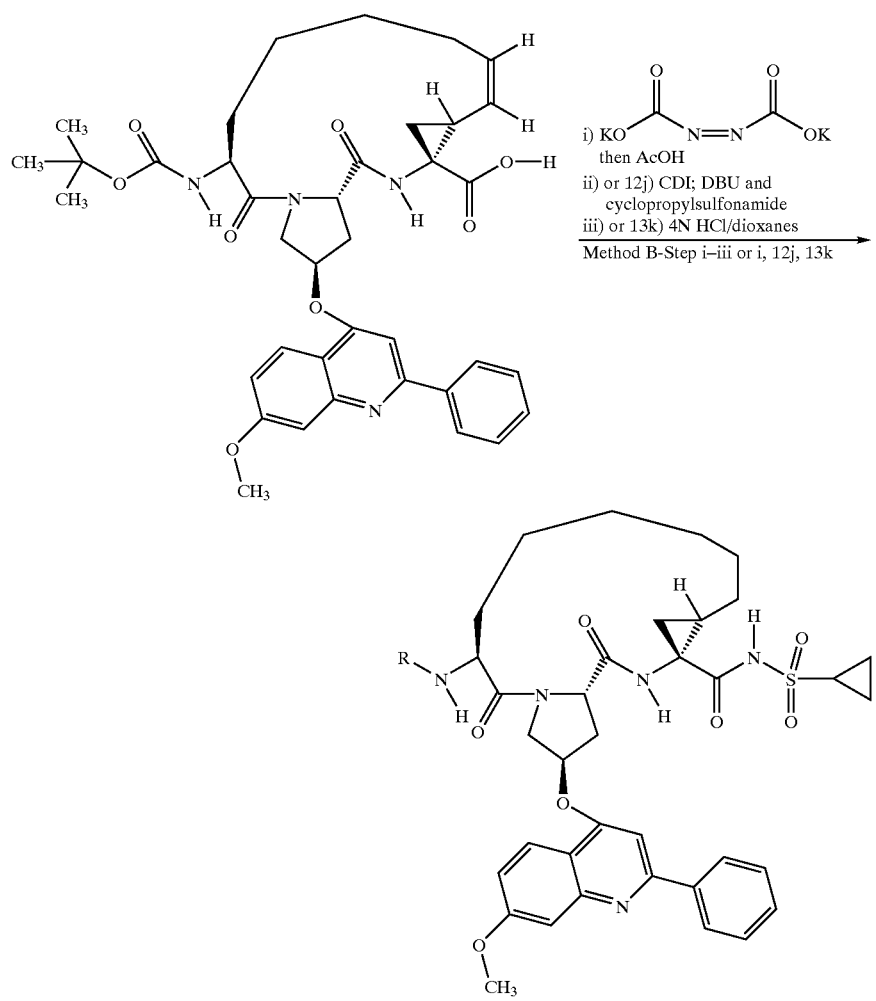

Compound 13, Example 12-R is BOC
Compound 14, Example 13-R is H

Step i of Method B) To a solution of 400 mg (0.584 mmol) of (1S,4R,6S,13S,17R)-7-cis-13-tert-butoxycarbonylamino-17-(7-methoxy-2-phenylquinolin-4-yloxy)-2,14-dioxo-3,15-diazatricyclo[13.3.0.0$^{4,6}$]octa-dec-7-ene-4-carboxylic acid and 1.90 g (11.7 mmol) of potassium diazodicarboxylate in 20 mL of MeOH, was added a solution of 1.34 mL (22.4 mmol) of glacial AcOH in 19 mL of MeOH slowly dropwise via syringe pump over 5 h, followed by stirring for an additional 6 h. To this mixture was added an additional 380 mg of potassium diazodicarboxylate (prepared as in Org. React. 1991, 40, p.91), followed by 400 μL of glacial AcOH in 4 mL of MeOH via syringe pump over 70 min. The mixture was stirred overnite, diluted with 200 mL of $Et_2O$, filtered and concentrated in vacuo. The residue was chromatographed over 20 g of $SiO_2$ (eluted with 5% MeOH/$CH_2Cl_2$) to afford 450 mg of crude which was dissolved in 12 mL of MeOH and injected six times (6×2 mL injections) onto a preparative HPLC column: Xterra C18 30×100 mm adjusted to pH 4 using 3N aqueous HCl solution, and repeatedly extracted with EtOAC. The combined extracts were dried ($MgSO_4$) and concentrated to afford 360 mg, (90%) of (1S,4R,6R,13S,17R)-13-tert-Butoxycarbonylamino-17-(7-methoxy-2-phenyl-quinolin-4-yloxy)-2,14-dioxo-3,15-diazatricyclo[13.3.0.0$^{4,6}$] octadecane-4-carboxylic acid: $^1$H NMR (methanol-$d_4$) δ 1.10 (s, 9H), 1.34 (m, 12H), 1.68 (m, 1H), 1.84 (m, 1H), 2.05 (s, 1H), 2.58 (m, 1H), 2.71 (m, 1H) 3.94 (s, 3H), 4.05 (dd, J=11.4, 2.9 Hz, 1H), 4.16 (dd, J=11.8, 2.9 Hz, 1H), 4.67 (t, J=8.1 Hz, 1H), 4.90 (m, 1H), 5.61 (s, 1H), 7.10 (dd, J=9, 2 Hz, 1H), 7.29 (s, 1H), 7.38 (d, J=2 Hz, 1H), 7.55 (m, 3H), 8.03 (d, J=6.7 Hz, 2H), 8.13 (d, J=9 Hz, 1H). LC-MS m/e 687 (retention time: 2.84, method D, except gradient time increased from 2 to 4 min). LC-MS m/e 687 (retention time: 2.84, method D, except gradient time increased from 2 to 4 min).

Step ii/12j-Method B Preparation of Compound 13, Example 12, Preparation of (1S,4R,6R,13S,17R)-[4-Cyclopropanesulfonylaminocarbonyl-17-(7-methoxy-2-phenylquinolin-4-yloxy)-2,14-dioxo-3,15-diazatricyclo[13.3.0.0⁴,⁶]octadec-13-yl]-carbamic acid tert-butyl ester, Compound 13, Example 12.

Compound 13, Example 12

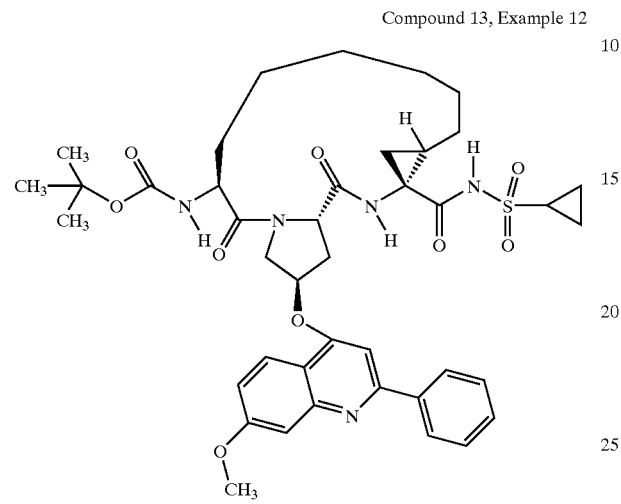

Method B-Step ii/Step 12j) Following the procedural and purification conditions of Step 1j, except preparative HPLC/Extractive workup was used instead of normal phase chromatography, 260 mg (0.38 mmol) of (1S,4R,6R,13S,17R)-13-tert-Butoxycarbonyl-amino-17-(7-methoxy-2-phenyl-quinolin-4-yloxy)-2,14-dioxo-3,15-diazatricyclo[13.3.0.04,6]octa-decane-4-carboxylic acid was converted to 192 mg (64%) (1S,4R,6R,13S,17R)-[4-Cyclopropanesulfonylamino-carbonyl-17-(7-methoxy-2-phenylquinolin-4-yloxy)-2,14-dioxo-3,15-diazatricyclo[13.3.0.0$^{4,6}$]octadec-13-yl]carbamic acid tert-butyl ester, Compound 13, Example 12 identical spectroscopically to that prepared in Method A. Representative Preparative HPLC/Extractive Workup Conditions: Xterra C18 30×100 mm S5, 35% to 100% Solvent B/A for 25 min gradient, hold time 5 min; where Solvent A is 10% MeOH/90% H$_2$O with 0.1% TFA, Solvent B is 90% MeOH/10% H$_2$O with 0.1% TFA and flow rate is 40 ml/min) The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to afford the aforementioned amount of Compound 13.

Method B-Stepiii/Step 13k: Preparation of Compound 14, Example 13, (1S,4R,6R,13S,17R)-Cyclopropanesulfonic acid [13-amino-17-(7-methoxy-2-phenylquinolin-4-yloxy)-2,14-dioxo-3,15-diazatricyclo[13.3.0.0$^{4,6}$]-octadecane-4-carbonyl]amide dihydrochloride Compound 14, Example 13

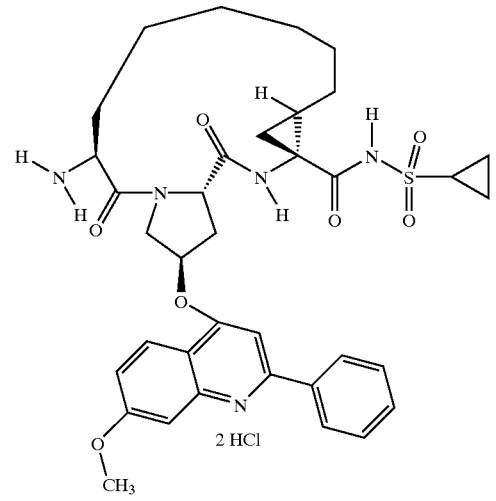

Method B-Step iii/Step 13k) A solution of 2.5 mL (10 mmol) of 4N HCl/dioxane was added to 161 mg (0.204 mmol) of (1S,4R,6R,13S)-[4-Cyclopropanesulfonylamino-carbonyl-17-(7-methoxy-2-phenylquinolin-4-yloxy)-2,14-dioxo-3,15-diazatricyclo[13.3.0.0$^{4,6}$]octadec-13-yl] carbamic acid tert-butyl ester, the mixture stirred 3 h, concentrated and dried (40° C.; 20 torr; 24 h) to afford 156 mg (~100%) of Compound 14, Example 13, (1S,4R,6R,13S,17R)-Cyclopropanesulfonic acid [13-amino-17-(7-methoxy-2-phenylquinolin-4-yloxy)-2,14-dioxo-3,15-diazatricyclo[13.3.0.0$^{4,6}$]octadecane-4-carbonyl]amide dihydrochloride as a white solid: $^1$H NMR (500 MHz, CD$_3$OD) δ 1.03–1.26 (m, 3H), 1.26–1.75 (m, 14H), 1.84 (s, 1H), 2.02 (m, 1H), 2.75 (m, 1H), 2.85 (m, 1H), 2.96 (m, 1H), 4.05 (s, 3H), 4.23 (m, 1H), 4.31 (s, 1H), 4.46 (d, J=11.29 Hz, 1H), 5.95 (s, 1H), 7.44 (d, J=8.85 Hz, 1H), 7.57 (s, 1H), 7.61 (s, 1H), 7.75 (dd, J=8.55, 7.32 Hz, 3H), 8.13 (d, J=6.71 Hz, 1H), 8.38 (d, J=9.16 Hz, 1H). LC-MS m/e 690 (retention time: 2.10, method D, except gradient time increased from 2 to 4 min).

EXAMPLES 14, 15
Preparation of Compounds 15 and 16

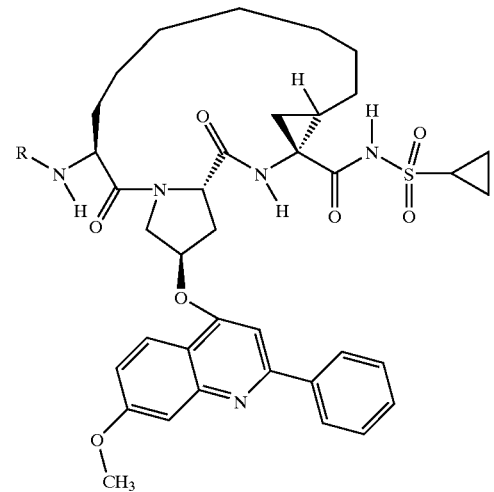

Compound 15, Example 14-R is Boc
Compound 16, Example 15-R is H (Bis HCl Salt)

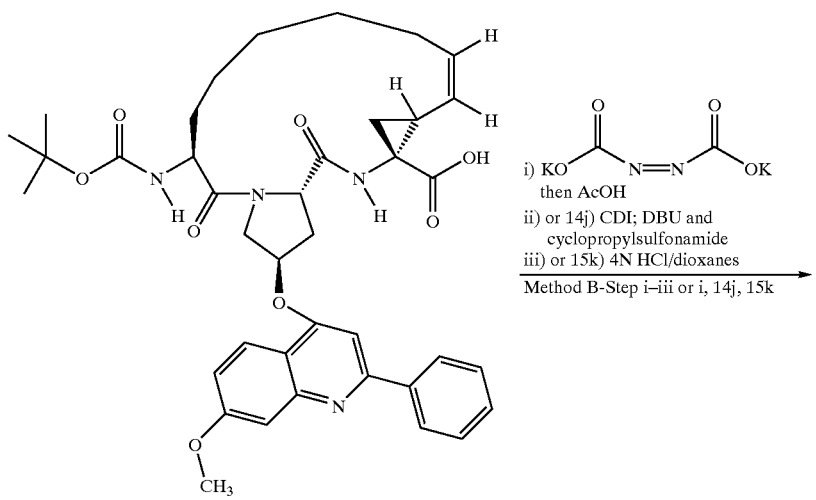

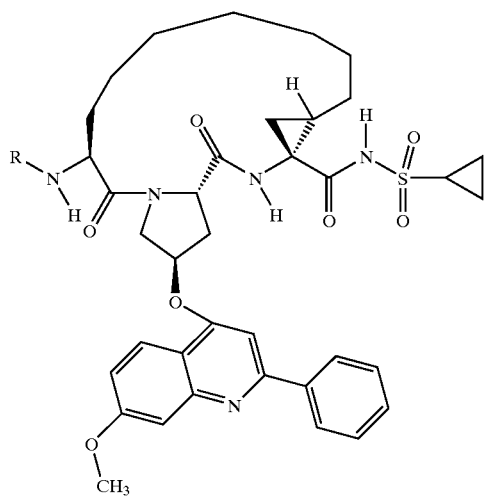

Compound 15, Example 14-R is BOC
Compound 16, Example 15-R is H

Step i of Method B) To a solution of 470 mg (0.67 mmol) of (1S,4R,6S,14S,18R)-8-cis-14-tert-butoxycarbonylamino-18-(7-methoxy-2-phenylquinolin-4-yloxy)-2,15-dioxo-3,16-diazatricyclo[14.3.0.0$^{4,6}$]nona-dec-7-ene-4-carboxylic acid and 1.90 g (11.7 mmol) of potassium diazodicarboxylate (prepared as in Org. React. 1991, 40, p.91) in 20 mL of MeOH, was added a solution of 1.34 mL (22.4 mmol) of glacial AcOH in 20 mL of MeOH slowly dropwise via syringe pump over 6.5 h. This procedure was repeated twice, but using a 12 h time interval instead of 6.5 h during which the reaction was stopped at approximately 90% completion. The mixture was concentrated in vacuo and then chromatographed over 20 g of SiO$_2$ (eluted with 5% MeOH/CH$_2$Cl$_2$). The resulting residue was dissolved in 18 mL of MeOH and injected nine times (9×2 mL injections) onto a preparative HPLC column: Xterra C18 30×100 mm S5, 30% to 75% Solvent B/A for 30 min gradient, hold time 5 min; where Solvent A is 10% MeOH/90% H$_2$O with 0.1% TFA, Solvent B is 90% MeOH/10% H$_2$O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to afford 278 mg (59%) of (1S,4R,6R,14S,18R)-14-tert-Butoxycarbonylamino-18-(7-methoxy-2-phenyl-quinolin-4-yloxy)-2,15-dioxo-3,16-diazatricyclo[14.3.0.0$^{4,6}$]nonadecane-4-carboxylic acid: $^1$H NMR (500 MHz, methanol-d$_4$) δ 1.23 (s, 9H), 1.12–1.49 (m, 11H), 1.50–1.67 (m, 4H), 1.71–1.86 (m, 2H), 2.54–2.60 (m, 1H), 2.65–2.72 (m, 1H), 3.94 (s, 3H), 4.05 (dd, J=11.29, 3.36 Hz, 1H), 4.28–4.33 (m, 1H), 4.65 (d, J=11.29 Hz, 1H), 4.70 (t, J=8.09 Hz, 1H), 5.55–5.61 (m, 1H), 7.07–7.15 (m, 1H), 7.28 (s, 1H), 7.38 (d, J=1.83 Hz, 1H), 7.50–7.59 (m, 3H), 8.04 (d, J=7.02 Hz, 2H), 8.15 (d, J=9.16 Hz, 1H). LC-MS m/e 701 (retention time: 3.01, method D, except gradient time increased from 2 to 4 min).

Step ii/14j-Method B Preparation of Compound 15, Example 14, Preparation of (1S,4R,6R,14S,18R)-[4-Cyclopropanesulfonylaminocarbonyl-18-(7-methoxy-2-phenylquinolin-4-yloxy)-2,15-dioxo-3,16-diazatricyclo-[14.3.0.0$^{4,6}$]nonadec-14-yl]carbamic acid tert-butyl ester.

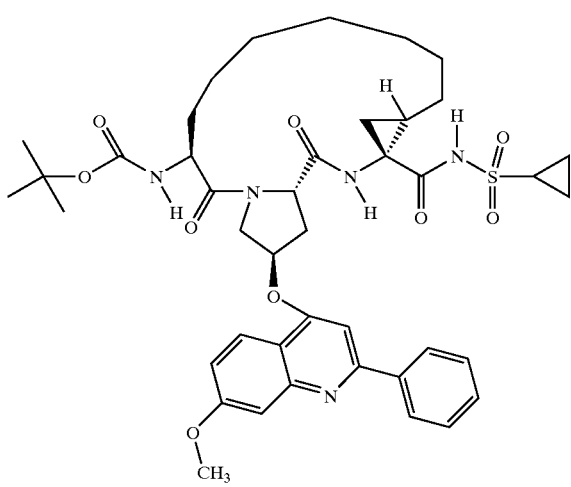

Compound 15, Example 14

Method B-Step ii/Step 14j) Following the analogous procedural and purification conditions of Steps 1j and 12j, respectively, 100 mg (0.143 mmol) of (1S,4R,6R,14S,18R)-14-tert-Butoxycarbonylamino-18-(7-methoxy-2-phenyl-quinolin-4-yloxy)-2,15-dioxo-3,16-diazatricyclo[14.3.0.0$^{4,6}$]nonadecane-4-carboxylic acid was converted to 108 mg (93%) (1S,4R,6R,14S)-[4-Cyclopropanesulfonylaminocarbonyl-18-(7-methoxy-2-phenylquinolin-4-yloxy)-2,15-dioxo-3,16-diazatricyclo-[14.3.0.0$^{4,6}$]nonadec-14-yl]carbamic acid tert-butyl ester, Compound 15, Example 14: $^1$H NMR (500 MHz, methanol-d$_4$) δ 1.20 (m, 9H) 0.83–1.83 (m, 21H), 2.48 (s, 1H), 2.73 (s, 1H), 2.95 (s, 1H), 3.94 (s, 3H), 4.04 (m, 1H), 4.24 (m, 1H), 4.67 (m, 2H), 5.60 (s, 1H), 7.12 (m, J=8.85 Hz, 1H), 7.30 (s, 1H), 7.38 (s, 1H), 7.57 (m, J=6.10 Hz, 3H), 8.03 (m, J=5.80 Hz, 2H), 8.16 (d, J=8.85 Hz, 1H). LC-MS m/e 804 (retention time: 1.73, method D.

Method B-Stepiii/Step 15k: Preparation of Compound 16, Example 15, (1S,4R,6R,14S,18R)-Cyclopropanesulfonic acid [14-amino-18-(7-methoxy-2-phenylquinolin-4-yloxy)-2,15-dioxo-3,16-diazatricyclo[14.3.0.0$^{4,6}$]-nonadecane-4-carbonyl]amide dihydrochloride

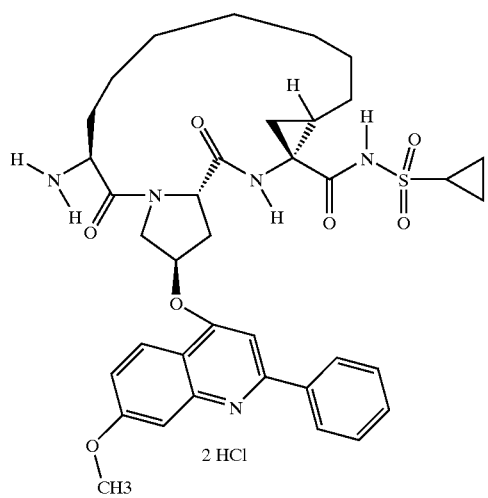

Compound 16, Example 15

Method B-Step iii/Step 15k) A solution of 2.5 mL (10 mmol) of 4N HCl/dioxane was added to 101 mg (0.126 mmol) of (1S,4R,6R,14S,18R)-[4-Cyclopropanesulfonyl-aminocarbonyl-18-(7-methoxy-2-phenylquinolin-4-yloxy)-2,15-dioxo-3,16-diazatricyclo[14.3.0.0$^{4,6}$]nona-dec-14-yl] carbamic acid tert-butyl ester (Compound 15 from Example 14), the mixture stirred 3 h, concentrated and dried (40° C.; 20 torr; 24 h) to afford 98 mg (~100%) of Compound 16, Example 15, (1S,4R,6R,14S,18R)-Cyclopropanesulfonic acid [14-amino-18-(7-methoxy-2-phenylquin-olin-4-yloxy)-2,15-dioxo-3,16-diazatricyclo[14.3.0.0$^{4,6}$] nonadecane-4-carbonyl]amide dihydrochloride as a white solid: $^1$H NMR (500 MHz, CD$_3$OD) δ 1.05–1.77 (m, 19H), 1.88 (m, 2H), 2.60 (m, 1H), 2.90 (m, 1H), 2.96 (m, 1H), 4.05 (s, 3H), 4.21 (m, 1H), 4.41 (m, 1H), 4.46 (s, 1H), 5.93 (s, 1H), 7.44 (d, J=8.55 Hz, 1H), 7.58 (s, 1H), 7.62 (s, 1H), 7.74 (m, 3H), 8.10 (m, J=7.02 Hz, 2H), 8.33 (d, J=9.16 Hz, 1H). LC-MS m/e 704 (retention time: 2.24, method D, except gradient time increased from 2 to 4 min).

Step 16j: Preparation of Compound 17, Example 16 (1S,4R,6S,13S,17R)-7-cis-[4-Cyclobutanesulfonylaminocarbonyl-17-(7-methoxy-2-phenylquinolin-4-yloxy)-2,14-dioxo-3,15-diazatricyclo[13.3.0.0$^{4,6}$]octadec-7-en-13-yl]carbamic acid tert-butyl ester

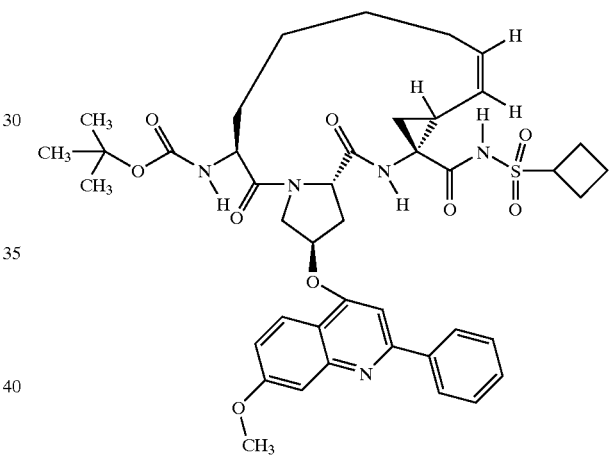

Compound 17, Example 16

Step 16j) Following the analogous procedural conditions of Steps 1j except cyclobutylsulfonamide was substituted for cyclopropylsulfonamide as well using the following preparative HPLC/Extractive Workup Purification: HPLC Column Xterra C18 30×100 mm S5, 35% to 85% Solvent B/A for 23 mm gradient, hold time 4 mm; where Solvent A is 10% MeOH/90% H$_2$O with 0.1% TFA, Solvent B is 90% MeOH/10% H$_2$O with 0.1% TFA and flow rate is 30 ml/min. The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to give the resulting conversion: 52 mg (0.076 mmol) of (1S,4R,6S,13S,17R)-7-cis-13-tert-butoxycarbonylamino-17-(7-methoxy-2-phenylquinolin-4-yloxy)-2,14-dioxo-3,15-diazatricyclo[13.3.0.0$^{4,6}$]octa-dec-7-ene-4-carboxylic acid was converted to 12 mg (20%) of (1S,4R,6S,13S,17R)-7-cis-[4-Cyclobutanesulfonylaminocarbonyl-17-(7-methoxy-2- phenylquinolin-4-yloxy)-2,14-dioxo-3,15-diazatricyclo[13.3.0.0$^{4,6}$]octadec-7-en-13-yl]carbamic acid tert-butyl ester: $^1$H NMR (500 MHz, CD$_3$OD) δ 1.18 (s, 9H), 1.23–1.56 (m, 11H), 1.76 (m, 1H), 1.98–2.13 (m, 3H), 2.15–2.34 (m, 2H), 2.48 (m, 1H), 2.62 (m, 1H), 2.74 (m, 1H), 3.98 (m, 3H), 4.29 (m, 3H), 4.66 (m, 1H), 5.41 (m, 1H), 5.64 (m, 2H), 7.12 (d, J=8.85 Hz, 1H), 7.29 (s, 1H), 7.42 (m, 1H), 7.56 (m, 3H), 8.10 (m, 3H). LC-MS (Method D-retention time: 1.61), MS m/z 802 (M$^+$+1).

Step 17j-Preparation of Compound 18, Example 17, Preparation of (1S,4R,6R,13S,17R)-[4-Cyclobutanesulfonylaminocarbonyl-17-(7-methoxy-2-phenylquinolin-4-yloxy)-2,14-dioxo-3,15-diazatricyclo[13.3.0.0$^{4,6}$]octa-dec-13-yl]carbamic acid tert-butyl ester.

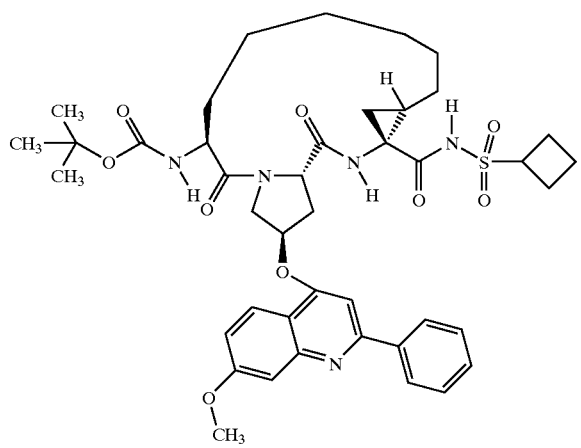

Compound 18, Example 17

Step 17j) Following the procedural and purification conditions of Step 1j, except preparative HPLC/Extractive workup was used instead of normal phase chromatography, 56 mg (0.082 mmol) of (1S,4R,6R,13S,17R)-13-tert-Butoxycarbonylamino-17-(7-methoxy-2-phenyl-quinolin-4-yloxy)-2,14-dioxo-3,15-diazatricyclo[13.3.0.04,6]octadecane-4-carboxylic acid was converted to 12 mg (20%) of (1S,4R,6R,13S,17R)-[4-Cyclobutanesulfonylaminocarbonyl-17-(7-methoxy-2-phenylquinolin-4-yloxy)-2,14-dioxo-3,15-diazatricyclo-[13.3.0.0$^{4,6}$]octadec-13-yl]carbamic acid tert-butyl ester, Compound 18, Example 17. Representative Preparative HPLC/Extractive Workup Conditions: Xterra C18 30×100 mm S5, 35% to 85% Solvent B/A for 25 min gradient, hold time 5 min; where Solvent A is 10% MeOH/90% H$_2$O with 0.1% TFA, Solvent B is 90% MeOH/10% H$_2$O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to afford the aforementioned amount of Compound 18: $^1$H NMR (500 MHz, CD$_3$OD) δ 1.07 (s, 9H), 1.22–1.62 (m, 15H), 1.63–1.78 (m, 2H), 2.04 (m, 1H), 2.52 (m, 4H), 2.87 (m, 1H), 4.04 (s, 3H), 4.14 (m, 2H), 4.36 (m, 1H), 4.78 (m, 1H), 5.07 (m, 1H), 5.82 (s, 1H), 7.32 (d, J=9.16 Hz, 1H), 7.51 (s, 1H), 7.56 (d, J=8.55 Hz, 1H), 7.72 (m, 3H), 8.08 (m, 2H), 8.32 (m, 1H). LC-MS (Method D-retention time: 1.68), MS m/z 804 (M$^+$+1)

Step 18j-Preparation of Compound 19, Example 18, Preparation of (1S,4R,6R,14S,18R)-[4-Cyclobutanesulfonylaminocarbonyl-18-(7-methoxy-2-phenylquinolin-4-yloxy)-2,15-dioxo-3,16-diazatricyclo-[14.3.0.0$^{4,6}$]nona-dec-14-yl]carbamic acid tert-butyl ester.

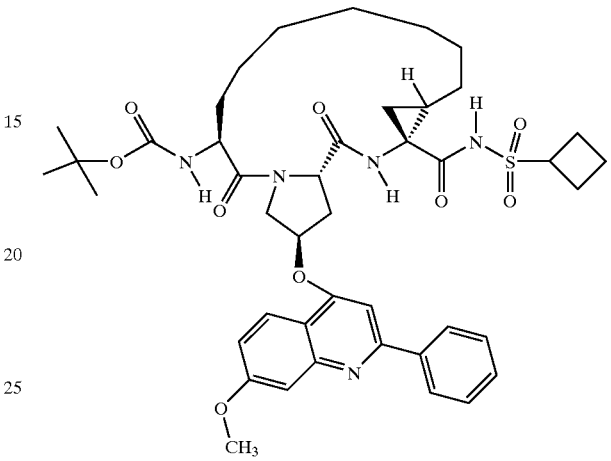

Compound 19, Example 18

Step 18j) Following the analogous procedural and purification conditions of Steps 1j and 17j, respectively, 50 mg (0.071 mmol) of (1S,4R,6R,14S, 18R)-14-tert-Butoxycarbonylamino-18-(7-methoxy-2-phenylquinolin-4-yloxy)-2,15-dioxo-3,16-dliazatricyclo[14.3.0.0$^{4,6}$]nonadecane-4-carboxylic acid was converted to 22 mg (38%) of (1S,4R,6R,14S,18R)-[4-Cyclobutanesulfonylaminocarbonyl-18-(7-methoxy-2-phenyl-quinolin-4-yloxy)-2,15-dioxo-3,16-diazatricyclo [14.3.0.0$^{4,6}$]nonadec-14-yl]carbamic acid tert-butyl ester, Compound 19, Example 18: $^1$H NMR (500 MHz, Solvent methanol-d$_4$) δ 1.21 (s, 9H), 1.14–1.88 (m, 20H), 2.35 (m, 2H), 2.53 (m, 3H), 2.83 (dd, J=13.4, 6.4 Hz, 1H), 4.01 (s, 3H), 4.12 (d, J=11.3 Hz, 1H), 4.27 (m, 1H), 4.36 (m, 1H), 4.70 (m, 1H), 5.73 (m, 1H), 7.21 (d, J=9.2 Hz, 1H), 7.41 (m, 1H), 7.46 (m, 1H), 7.64 (m, 3H), 8.08 (m, 2H), 8.25 (d, J=9.2 Hz, 1H). LC-MS m/e 818 (retention time: 1.75, method D.

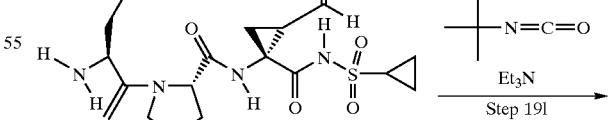
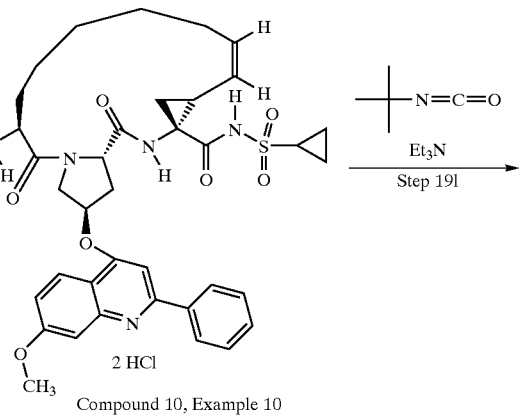

Compound 10, Example 10

-continued

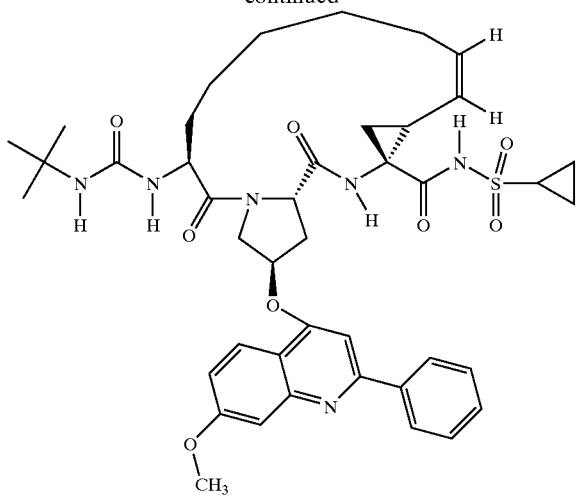

Compound 20, Example 19

Step 19l: Preparation of Compound 20, Example 19 Preparation of (1S,4R,6S,14S,18R)-7-cis-Cyclopropanesulfonic acid [14-(3-tert-butylureido)-18-(7-methoxy-2-phenyl-quinolin-4-yloxy)-2,15-dioxo-3,16-diazatricyclo[14.3.0.0$^{4,6}$]nona-dec-7-ene-4-carbonyl]amide Step 19l) To a suspension of 59 mg (0.0762 mmol) of compound 10 and 53.4 µL (0.381 mmol) of Et$_3$N in 2 mL of CH$_2$Cl$_2$, was added 24 µL (0.208 mmol) of tert-butyl isocyanate (Aldrich). The mixture was stirred 18 h, concentrated in vacuo and dissolved up in 2 mL of MeOH. This solution was injected onto a preparative HPLC using the following conditions: Column Xterra C18 30×100 mm S5, 37% to 85% Solvent B/A for 30 min gradient, hold time 5 min; where Solvent A is 10% MeOH/90% H$_2$O with 0.1% TFA, Solvent B is 90% MeOH/10% H$_2$O with 0.1% TFA and flow rate is 35 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to afford 30 mg (49%) of Compound 20, Example 19: $^1$H NMR (500 MHz, methanol-d$_4$) δ 1.03 (s, 9H) 1.11 (m, 3H) 1.30 (m, 5H) 1.49 (m, 5H) 1.65 (m, 1H) 1.78 (m, 2H) 1.91 (m, 1H) 2.41 (m, 1H) 2.69 (dd, J=14.04, 4.58 Hz, 2H) 2.85 (m, 1H) 2.94 (m, 1H) 4.07 (s, 3H) 4.13 (dd, J=12.2, 3.4 Hz, 1H) 4.25 (d, J=10.4 Hz, 1H) 4.75 (m, 1H) 4.98 (d, J=12.2 Hz, 1H) 5.11 (m, 1H) 5.74 (m, 1H) 5.91 (s, 1H) 7.40 (dd, J=9.3, 2.4 Hz, 1H) 7.55 (m, 1H) 7.67 (s, 1H) 7.77 (m, 3H) 8.10 (d, J=7.6 Hz, 1H) 8.42 (d, J=9.3 Hz, 1H). LC-MS m/e 801 (retention time: 2.88, method D, except gradient time increased from 2 to 4 min).

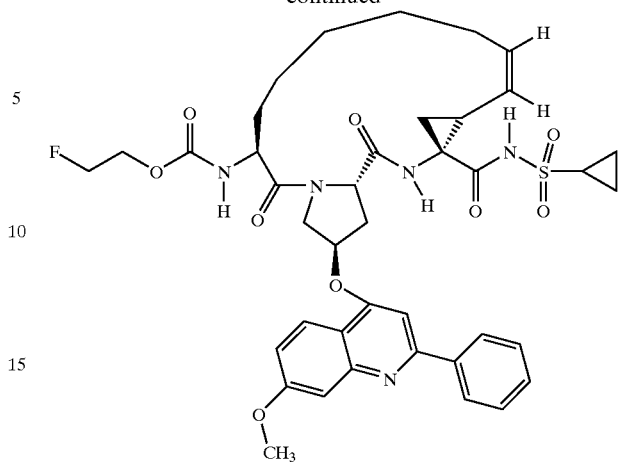

Compound 21, Example 20

Step 20l: Preparation of Compound 21, Example 20 Preparation of (1S,4R,6S,14S,18R)-7-cis-[4-Cyclopropanesulfonylaminocarbonyl-18-(7-methoxy-2-phenylquinolin-4-yloxy)-2,15-dioxo-3,16-diazatricyclo[14.3.0.0$^{4,6}$]nonadec-7-en-14-yl]carbamic acid 2-fluoroethyl ester Step 20l) To a suspension of 59 mg (0.0762 mmol) of compound 10 and 53.4 µL (0.381 mmol) of Et$_3$N in 2 mL of CH$_2$Cl$_2$, was added 20 µL (0.208 mmol) of 2-fluoroethyl chloroformate (Aldrich). The mixture was stirred 18 h, concentrated in vacuo and dissolved up in 2 mL of MeOH. This solution was injected onto a preparative HPLC using the following conditions: Column Xterra C18 30×100 mm S5, 30% to 80% Solvent B/A for 30 min gradient, hold time 2 min; where Solvent A is 10% MeOH/90% H$_2$O with 0.1% TFA, Solvent B is 90% MeOH/10% H$_2$O with 0.1% TFA and flow rate is 35 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to afford 38 mg (64%) of Compound 21, Example 20: $^1$H NMR (500 MHz, methanol-d$_4$) δ 1.05 (m, 3H) 1.25–1.89 (m, 8H) 1.62 (dd, J=9.5, 5.49 Hz, 1H) 1.74 (dd, J=8.1, 5.34 Hz, 1H) 1.84 (m, 2H) 2.39 (m, 1H) 2.66 (m, 2H) 2.83 (m, 1H) 2.91 (m, 1H) 3.87 (m, 2H) 4.06 (s, 3H) 4.09 (m, 1H) 4.22 (m, 1H) 4.30 (m, 1H) 4.40 (m, 1H) 4.71 (m, 1H) 5.08 (m, 1H) 5.70 (m, 1H) 5.91 (s, 1H) 7.41 (m, 1H) 7.53 (s, 1H) 7.65 (s, 1H) 7.73 (m, 3H) 8.07 (d, J=7.6 Hz, 2H) 8.39 (d, J=9.2 Hz, 1H). LC-MS m/e 792 (retention time: 2.66, method D, except gradient time increased from 2 to 4 min).

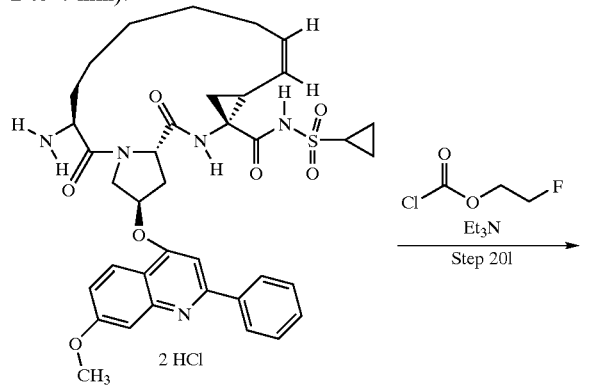

Compound 10, Example 10

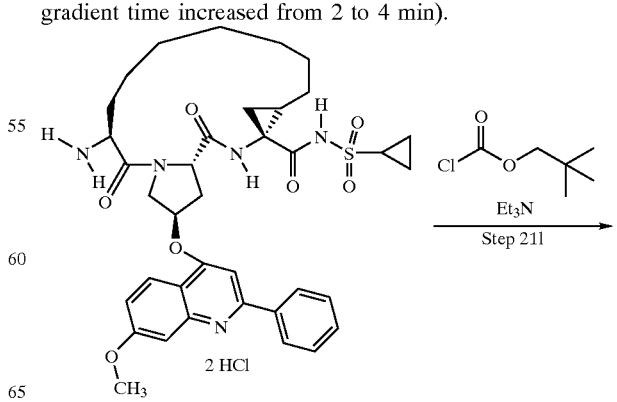

Compound 16, Example 15

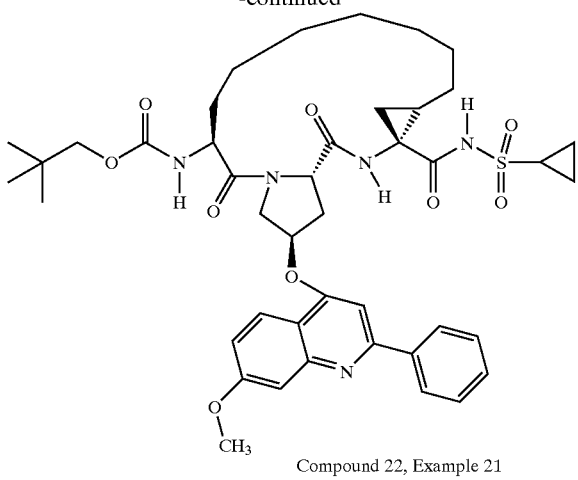

Compound 22, Example 21

Step 21l: Preparation of Compound 22, Example 21 Preparation of (1S,4R,6R,14S,18R)-[4-Cyclopropanesulfonylaminocarbonyl-18-(7-methoxy-2-phenylquinolin-4-yloxy)-2,15-dioxo-3,16-diazatricyclo[14.3.0.0$^{4,6}$]-nonadec-14-yl]carbamic acid 2,2-dimethylpropyl ester Step 21l) To a suspension of 45 mg (0.058 mmol) of compound 16 and 42 μL (0.29 mmol) of Et$_3$N in 2 mL of CH$_2$Cl$_2$, was added 26 μL (0.174 mmol) of neopentyl chloroformate (Aldrich). The mixture was stirred 18 h, concentrated in vacuo and dissolved up in 2 mL of MeOH. This solution was injected onto a preparative HPLC using the following conditions: Column Xterra C18 30×100 mm S5, 30% to 80% Solvent B/A for 29 min gradient, hold time 2 min; where Solvent A is 10% MeOH/90% H$_2$O with 0.1% TFA, Solvent B is 90% MeOH/10% H$_2$O with 0.1% TFA and flow rate is 35 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to afford 35 mg (74%) of Compound 22, Example 21: $^1$H NMR (500 MHz, methanol-d$_4$) δ 0.81 (s, 9H), 1.10–1.25 (m, 4H), 1.27–1.79 (m, 16H), 1.86 (m, 1H) 2.60 (m, 1H) 2.90 (m, 1H), 3.01 (m, 1H), 3.18 (d, J=10.1 Hz, 1H), 3.35 (m, 1H), 4.07 (m, 3H), 4.13 (m, 1H), 4.26 (m, 1H), 4.76 (m, 1H), 4.90 (m, 1H), 5.93 (m, 1H), 7.43 (m, 1H), 7.55 (m, 1H), 7.68 (m, 1H), 7.79 (m, 3H), 8.12 (m, 2H), 8.39 (d, J=9.2 Hz, 1H). LC-MS m/e 818 (retention time: 3.21, method D, except gradient time increased from 2 to 4 min).

General Procedure For Preparation of Chloroformates

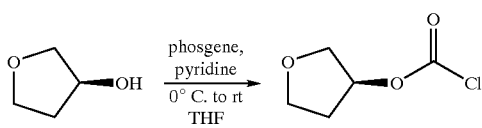

This procedure was used for the preparation of non-commercially available chloroformates. To a solution of 5.96 g (67.6 mmol) of commercially available reagents (S)-3-hydroxytetrahydrofuran and pyridine (5.8 mL; 72 mmol) in THF (150 mL) cooled to 0° C. was added a 1.93 M solution of phosgene in toluene (48 mL, 92.6 mmol over 10 min under argon. The resulting solution was allowed to warm to rt over 2 h, the resulting solid filtered, and the mother liquor carefully concentrated in vacuo at room temperature until theoretical mass was obtained. The resulting residue was dissolved in 100 mL of THF to prepare a 0.68M stock solution of 3(S)-oxo-tetrahydrofuran chloroformate that could be stored in the freezer until use. In analogous fashion, other commercially available alcohols could be converted to 0.68M stock solutions of the corresponding chloroformates.

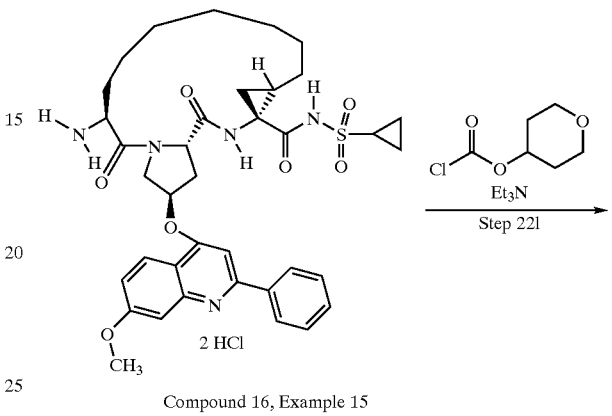

Compound 16, Example 15

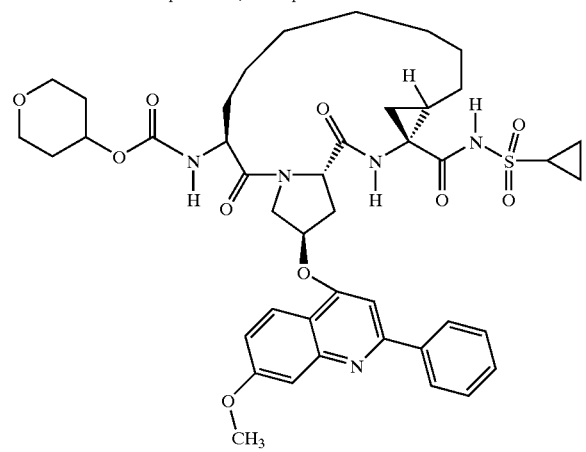

Compound 23, Example 22

Step 22l: Preparation of Compound 23, Example 22 Preparation of (1S,4R,6R,14S,18R)-[4-Cyclopropanesulfonyl-aminocarbonyl-18-(7-methoxy-2-phenylquinolin-4-yloxy)-2,15-dioxo-3,16-diazatricyclo[14.3.0.0$^{4,6}$]nonadec-14-yl] carbamic acid tetrahydro[4H]pyran-4-yl ester Step 22l) To a suspension of 45 mg (0.058 mmol) of compound 16 and 42 μL (0.29 mmol) of Et$_3$N in 2 mL of CH$_2$Cl$_2$, was added 217 μL (0.174 mmol) of ~0.8M tetrahydro[4H]pyran-4-yl chloroformate (prepared from Aldrich quality tetrahydro[4H]pyran-4-ol using the same method as in the preparation of 3(S)-oxo-tetrahydrofuran chloroformate) in CH$_2$Cl$_2$. The mixture was stirred 18 h, concentrated in vacuo and dissolved up in 2 mL of MeOH. This solution was injected onto a preparative HPLC using the following conditions: Column Xterra C18 30×100 mm S5, 30% to 80% Solvent B/A for 29 min gradient, hold time 2 min; where Solvent A is 10% MeOH/90% H$_2$O with 0.1% TFA, Solvent B is 90% MeOH/10% H$_2$O with 0.1% TFA and flow rate is 35 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$), concentrated, and rechromatographed over a Biotage 12M column (eluted with 0 to 8% MeOH/

CH$_2$Cl$_2$) to afford 14.2 mg (30%) of Compound 23, Example 22: $^1$H NMR (500 MHz, CDCl$_3$) δ 1.24 (m, 25H), 2.48 (m, 1H) 2.64 (m, 1H), 2.93 (m, 1H), 3.44 (m, 2H), 3.83 (m, 2H), 3.93 (s, 3H), 4.05 (m, 1H), 4.39 (d, J=11.3 Hz, 1H), 4.45 (t, J=6.9 Hz, 1H), 4.65 (m, 2H), 5.36 (m, 2H,) 6.95 (s, 1H), 7.02 (dd, J=9.0, 2.3 Hz, 1H), 7.49 (m, 4H), 7.93 (d, J=8.8 Hz, 1H), 8.03 (d, J=7.3 Hz, 2H), 10.26 (s, 1H). LC-MS m/e 832 (retention time: 2.90, method D, except gradient time increased from 2 to 4 min).

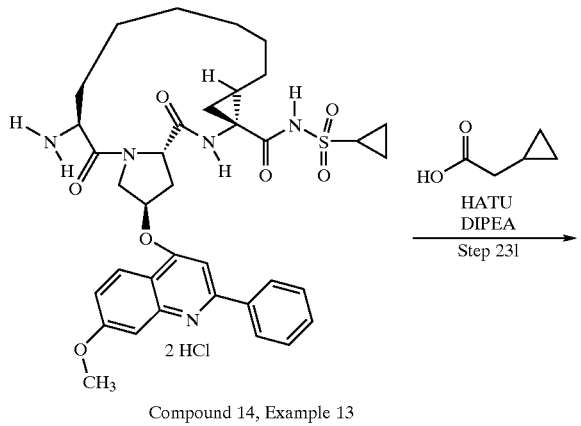

Compound 14, Example 13

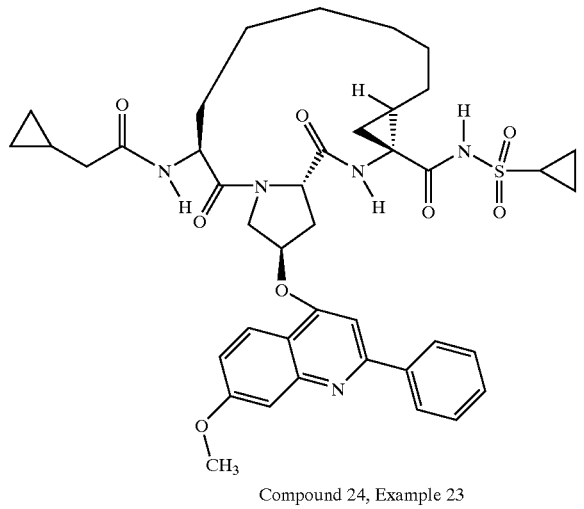

Compound 24, Example 23

Step 23l: Preparation of Compound 24, Example 23 Preparation of (1S,4R,6R,14S,17R)-N-[4-Cyclopropanesulfonylaminocarbonyl-17-(7-methoxy-2-phenylquinolin-4-yloxy)-2,14-dioxo-3,15-diazatricyclo[13.3.0.0$^{4,6}$]-octadec-13-yl]-2-cyclopropylacetamide Step 23l) To a suspension of 50 mg (0.065 mmol) of compound 14, 14 mg (0.139 mmol) of cyclopropyl acetic acid and 97 μL of DIPEA in 2 mL of CH$_2$Cl$_2$, was added 53 mg (0.139 mmol) of HATU. The mixture was stirred 18 h, concentrated in vacuo and dissolved up in 2 mL of MeOH. This solution was injected onto a preparative HPLC using the following conditions: Column Xterra C18 30×100 mm S5, 30% to 80% Solvent B/A for 30 min gradient, hold time 2 min; where Solvent A is 10% MeOH/90% H$_2$O with 0.1% TFA, Solvent B is 90% MeOH/10% H$_2$O with 0.1% TFA and flow rate is 35 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to afford 20 mg (40%) of Compound 24, Example 23: $^1$H NMR (500 MHz, methanol-d$_4$) δ −0.01 (m, 2H), 0.30 (m, 2H), 0.66 (m, 1H), 0.88 (m, 1H), 1.08 (m, 3H), 1.24–1.68 (m, 13H), 1.75 (m, 1H), 1.91 (m, 3H), 2.63 (m, 1H), 2.81 (s, 1H), 2.98 (m, 1H), 4.02 (s, 3H), 4.15 (m, 1H), 4.41 (m, 1H), 4.73 (t, J=8.1 Hz, 1H), 4.94 (d, J=11.6 Hz, 1H), 5.86 (s, 1H), 7.31 (dd, J=9.2, 2.2 Hz, 1H), 7.50 (d, J=2.2 Hz, 1H), 7.58 (s, 1H), 7.69 (m, 3H), 8.08 (m, 2H), 8.27 (d, J=9.2 Hz, 1H). LC-MS m/e 772 (retention time: 2.77, method D, except gradient time increased from 2 to 4 min).

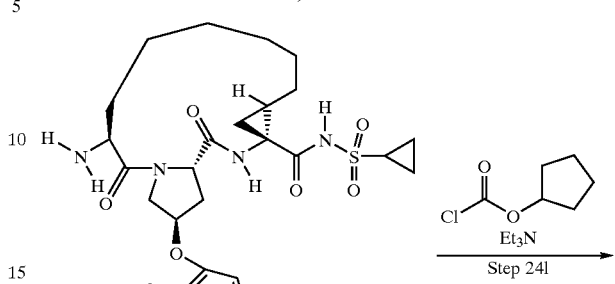

Compound 14, Example 13

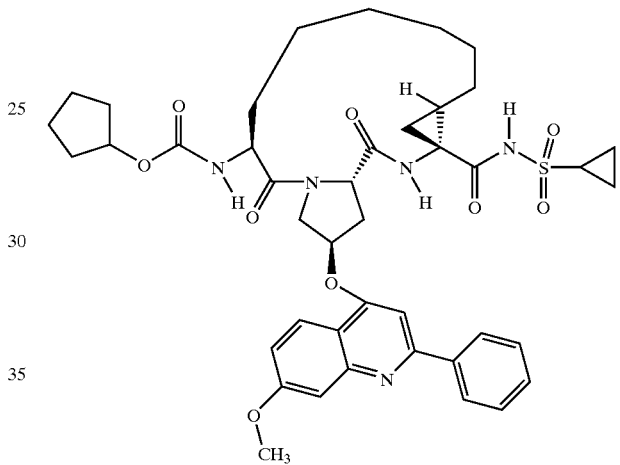

Compound 25, Example 24

Step 24l: Preparation of Compound 25, Example 24 Preparation of (1S,4R,6R,14S,17R)-[4-Cyclopropanesulfonylaminocarbonyl-17-(7-methoxy-2-phenylquinolin-4-yloxy)-2,14-dioxo-3,15-diazatricyclo[13.3.0.0$^{4,6}$]octa-dec-13-yl]carbamic acid cyclopentyl ester Step 24l) To a suspension of 50 mg (0.065 mmol) of compound 14, and 47 μL (0.32 mmol) of Et$_3$N in 2 mL of CH$_2$Cl$_2$, was added 300 μL (0.20 mmol) of ~0.67M cyclopentyl chloroformate (prepared from Aldrich quality cyclopentanol using the same method as in the preparation of 3(S)-oxo-tetrahydrofuran chloroformate) in CH$_2$Cl$_2$. The mixture was stirred 18 h, concentrated in vacuo and dissolved up in 2 mL of MeOH. This solution was injected onto a preparative HPLC using the following conditions: Column Xterra C18 30×100 mm S5, 30% to 80% Solvent B/A for 30 min gradient, hold time 2 min; where Solvent A is 10% MeOH/90% H$_2$O with 0.1% TFA, Solvent B is 90% MeOH/ 10% H$_2$O with 0.1% TFA and flow rate is 35 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated to afford 26 mg (50%) of Compound 25, Example 24: $^1$H NMR (500 MHz, methanol-d$_4$) δ 1.02–1.17 (m, 3H), 1.20–1.67 (m, 22H), 1.72 (m, 1H), 1.88 (m, 1H), 2.63 (m, 1H), 2.86 (m, 1H), 2.98 (m, 1H), 4.03 (s, 3H), 4.08 (m, 1H), 4.16 (m, 1H), 4.28 (m, 1H), 4.78 (m, 1H), 5.02 (d, J=11.0 Hz, 1H), 5.89 (m, 1H), 7.38 (m, 1H), 7.51 (d, J=2.1 Hz, 1H), 7.64 (s, 1H), 7.73 (m, 3H), 8.06 (d, J=7.6 Hz, 2H), 8.34 (d, J=9.5 Hz, 1H). LC-MS m/e 802 (retention time: 3.00, method D, except gradient time increased from 2 to 4 min).

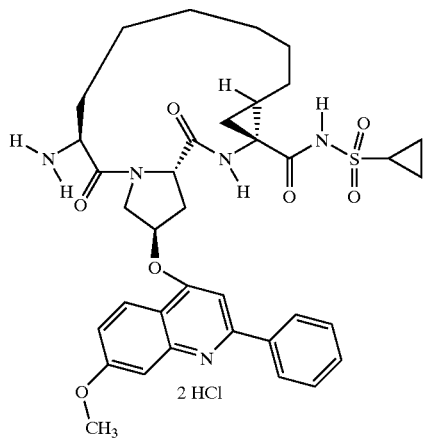

Compound 14, Example 13

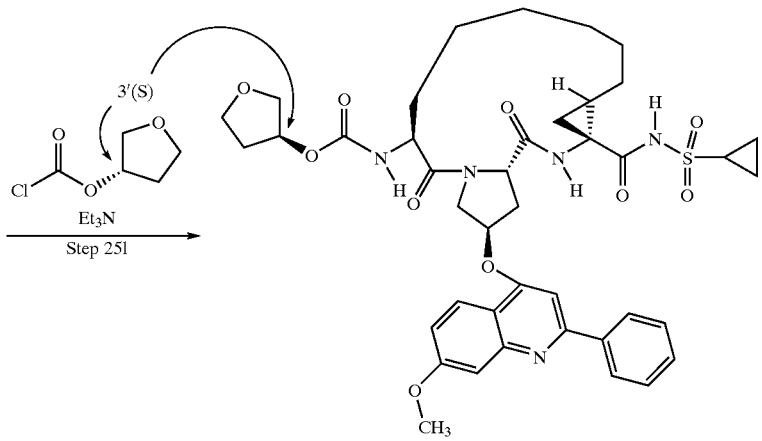

Compound 26, Example 25

Step 25l: Preparation of Compound 26, Example 25 Preparation of (1S,4R,6R,14S,17R,3'S)-[4-Cyclopropanesulfonyl-aminocarbonyl-17-(7-methoxy-2-phenylquinolin-4-yloxy)-2,14-dioxo-3,15-diazatricyclo [13.3.0.0$^{4,6}$]-octadec-13-yl]-carbamic acid tetrahydrofuran-3'-yl ester Step 25l) To a suspension of 50 mg (0.065 mmol) of compound 14, and 47 μL (0.32 mmol) of Et$_3$N in 2 mL of CH$_2$Cl$_2$, was added 300 μL (0.20 mmol) of −0.67M 3(S)-oxo-tetrahydrofuran chloroformate (prepared as described above) in CH$_2$Cl$_2$. The mixture was stirred 18 h, concentrated in vacuo and dissolved up in 2 mL of MeOH. This solution was injected onto a preparative HPLC using the following conditions: Column Xterra C18 30×100 mm S5, 30% to 80% Solvent B/A for 30 min gradient, hold time 2 min; where Solvent A is 10% MeOH/90% H$_2$O with 0.1% TFA, Solvent B is 90% MeOH/10% H$_2$O with 0.1% TFA and flow rate is 35 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined extracts were dried (MgSO$_4$) and concentrated and chromatographed over a Biotage 12M column (eluted with 0% to 8% MeOH/CH$_2$Cl$_2$) to afford 10 mg (25%) of Compound 26, Example 25: $^1$H NMR (500 MHz, CDCl$_3$) δ 1.20 (m, 18H), 1.73 (m, 2H), 1.93 (m, 2H), 2.59 (m, 1H), 2.69 (m, 1H), 2.95 (m, 1H), 3.74 (m, 3H), 3.93 (s, 3H), 4.07 (m, 1H), 4.31 (m, 1H), 4.65 (t, J=7.48 Hz, 1H), 4.71 (d, J=11.3 Hz, 1H), 4.96 (s, 1H), 5.37 (d, J=6.7 Hz, 1H), 5.43 (s, 1H), 7.02 (m, 3H), 7.50 (m, 3H), 8.07 (d, J=7.3 Hz, 2H) 10.83 (s, 1H). LC-MS m/e 804 (retention time: 2.69, method D, except gradient time increased from 2 to 4 min).

The following steps (A)–(G) show the preparation of the intermediate, the product of step (G).

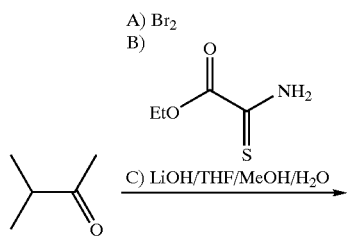

-continued

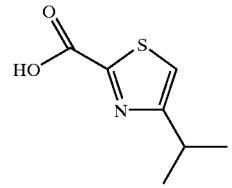

Step A) To a solution of 4.0 g (46.5 mmol) of 3-methyl-2-butanone (Aldrich) in 50 mL of MeOH was added dropwise a solution of 2.4 mL (46.5 mmol) of bromine over 40 min. The mixture was stirred 1.5 h, diluted with 300 mL of pentane, washed with sat. aqueous NaHCO$_3$, dried (MgSO$_4$) and concentrated to afford 5.81 g of impure 1-Bromo-3-methyl-butan-2-one which was taken directly into the step B.

Step B) A neat solution of 5.58 g (34 mmol) of 1-Bromo-3-methyl-butan-2-one and 4.50 g (34 mmol) of ethyl thioxamate (Aldrich) was heated at 70° C. over 18 h and then cooled to room temperature. The mixture was partitioned between sat. aqueous NaHCO$_3$ and EtOAc, the EtOAc layer dried (MgSO$_4$), concentrated and chromatographed over SiO$_2$ (eluted with 2% to 40% EtOAc/hexanes) to afford 3.4 g (48% overall) of 4-isopropylthiazole-2-carboxylic acid ethyl ester as an oil: $^1$H NMR (500 MHz, CDCl$_3$) δ 1.32 (d, J=7 Hz, 6H), 1.42 (t, J=7.2 Hz, 3H), 3.23 (m, 1H), 4.46 (q, J=7.2 Hz, 2H), 7.18 (s, 1H).

Step C) To a solution of 3.12 g (15.7 mmol) of 4-isopropylthiazole-2-carboxylic acid ethyl ester in 32 mL of 75% THF/MeOH, was added 110 mg (31.3 mmol) of LiOH in 8 mL of H$_2$O. The mixture was stirred overnite, the solution adjusted to pH 5 using 1N aqueous HCl solution and concentrated in vacuo to afford 4-isopropylthiazole-2-carboxylic acid as a white solid (2.97 g including salts) which was used directly in Step E: $^1$H NMR (500 MHz, methanol-d$_4$) δ 1.29 (d, J=6.7 Hz, 6H), 3.20 (m, 1H), 7.39 (m, 1H).

D) BCl₃/AlCl₃/AcCl
E) POCl₃/pyridine

F) 1M KOtBu/THF/Δ
G) POCl₃, Δ

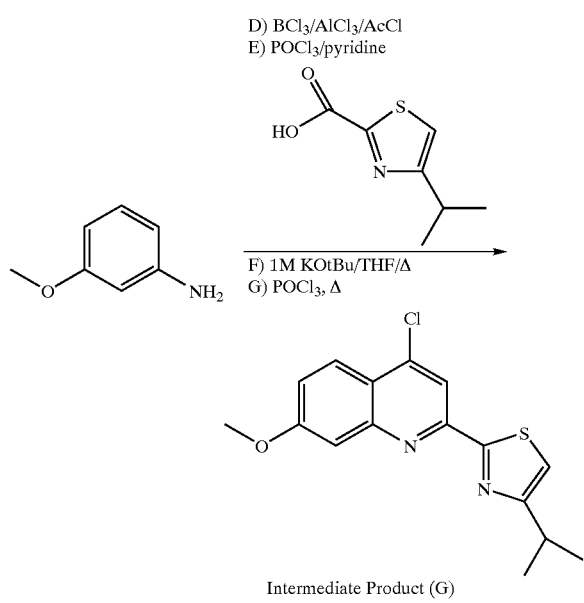

Intermediate Product (G)

Step D) To a solution of 21.8 g (172 mmol) of m-anisidine in 800 mL of CH₂Cl₂ cooled to −50° C., was added 172 mL (172 mmol) of 1M BCl₃ in heptane over 20 min to produce an amber colored mixture which was stirred 1 h. To this mixture was added 12.2 mL (172 mmol) of AcCl and 22.9 g (172 mmol) of AlCl₃. The mixture was allowed to warm to room temperature overnite, poured into ice water, the solution adjusted to pH 9 using 10% aqueous NaOH and was extracted repeatedly using EtOAC. The combined organic extracts were washed with brine, dried (MgSO₄), concentrated and the resulting solid recrystallized from the minimal amount of MeOH in CH₂Cl₂/hexanes (50%) to afford 13.4 g (47%) of slightly impure 2-amino-4-methoxybenzophenone as a crystalline solid. The solid could be taken directly into the next reaction or purified to absolute purity over SiO₂ (eluted with 0% to 14% MeOH/CH₂Cl₂): ¹H NMR (500 MHz, CDCl₃) δ 2.50 (s, 3H), 3.79 (s, 3H), 6.05 (d, J=2.4 Hz, 1H), 6.21 (dd, J=8.8, 2.4 Hz, 1H), 6.38 (m, 2H), 7.62 (d, J=8.8 Hz, 1H)

Step E) To a suspension of 2.59 g (15.7 mmol) of 2-amino-4-methoxybenzophenone (product of step D) and 2.68 g (15.7 mmol) of 4-isopropylthiazole-2-carboxylic acid (product of step C) in 75 mL of pyridine cooled to −30° C., was added 1.93 mL (23.5 mmol) of POCl₃ slowly dropwise over 5 min. The mixture was stirred 3 h, warmed to room temperature and was stirred overnite. The reaction mixture was poured into ice water, and extracted several times with EtOAc. The combined EtOAc extracts were dried (MgSO₄), concentrated and chromatographed over SiO₂ (eluted with 0% to 15% MeOH/EtOAc) to afford 2.57 g (51%) of 4-Methylthiazole-2-carboxylic acid (2-acetyl-5-methoxyphenyl)amide as a yellow solid: ¹H NMR (500 MHz, CDCl₃) δ 1.41 (d, J=6.7 Hz, 6H), 2.64 (s, 3H), 3.24 (m, 1H), 3.91 (s, 3H), 6.67 (dd, J=9, 2.5 Hz, 1H), 7.18 (s, 1H), 7.86 (d, J=9 Hz, 1H), 8.56 (d, J=2.5 Hz, 1H), 13.48 (s, 1H).

Step F) To a solution of 2.5 g (7.85 mmol) of 4-methylthiazole-2-carboxylic acid (2-acetyl-5-methoxyphenyl)amide (product of step E) in 50 mL of THF, was added 19 mL (19 mmol) of 1M KOtBu in THF. The mixture was heated to 70° C. for 3 h, cooled to rt and stirred overnight. The mixture was concentrated, cold water added to form a suspension. The mixture was then acidified to pH 4, filtered and dried. The resulting solid was chromatographed over SiO₂ (eluted with 0% to 25% MeOH in CH₂Cl₂) to afford 1.31 g (56%) of 2-(4-Isopropylthiazol-2-yl)-7-methoxyquinolin-4-ol as a beige solid: ¹H NMR (300 MHz, DMSO-D⁶) δ 1.32 (d, J=6.6 Hz, 6H), 3.14 (m, 1H), 3.89 (s, 3H), 7.06 (s, 1H), 7.38 (s, 1H), 7.51 (s, 1H), 7.99 (d, J=9.2 Hz, 1H), 11.77 (m, 1H). LC-MS m/e 301 (retention time: 1.53, method D).

Step G) A suspension of 1.3 g (4.3 mmol) of 2-(4-Isopropylthiazol-2-yl)-7-methoxyquinolin-4-ol, product of step F, in 60 mL of POCl₃ was heated to reflux for 2 h. The solvent was removed in vacuo, the residue diluted with ice cold water and the mixture adjusted to pH 9 while cooling to 0° C. This aqueous solution was extracted several times with EtOAc. The combined EtOAc extracts were washed once with brine, pH 4 buffer, dried (MgSO₄), and concentrated to afford 0.89 g (64%) of 4-Chloro-2-(4-isopropylthiazol-2-yl)-7-methoxyquinoline as a yellow solid: ¹H NMR (500 MHz, CDCl₃) δ 1.38 (d, J=7 Hz, 6H), 3.19 (m, 1H), 3.98 (s, 3H), 7.06 (s, 1H), 7.26 (m, 1H), 7.47 (d, J=2 Hz, 1H), 8.10 (d, J=9 Hz, 1H), 8.31 (s, 1H). LC-MS m/e 319 (retention time: 2.20, method D).

Preparation of Example 26, (1S,4R,6S,14S,18R)-7-cis-14-tert-butoxycarbonylamino-18-hydroxy-2,15-dioxo-3,16-diazatricyclo[14.3.0.0⁴,⁶]nonadec-7-ene-4-carboxylic acid using Steps 26i–26iv.

Example 26

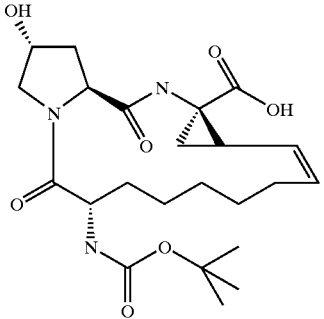

Step 26i: Preparation of 1-(2(S)-tert-Butoxycarbonylamino-non-8-enoyl)-4(R)-hydroxy-pyrrolidine-2(S)-carboxylic acid methyl ester

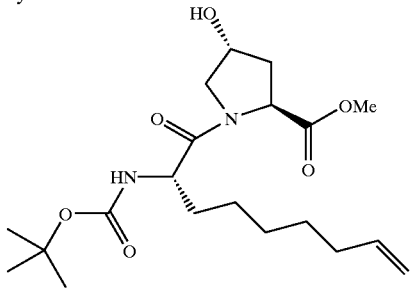

A solution of 2(S)-tert-butoxycarbonylamino-8-nonenoic acid (purchased from RSP Amino Acids)(3.5 g, 12.9 mmol) in 200 mL of DCM was treated sequentially with 4(R)-hydroxypyrrolidine-2(S)-carboxylic acid methyl ester hydrocholoride (2.15 g, 11.8 mmol), N-methyl morpholine (4.25 mL, 38.6 mmol), and HATU (5.37 g, 14.1 mmol). The reaction mixture was stirred at rt under N₂ for 3 days, and then concentrated in vacuo. The residue was partitioned between ethyl acetate and pH 4 buffer (biphthalate). The organic phase was washed with sat. aq. NaHCO₃, dried (MgSO₄), and concentrated in vacuo to give the crude product. Flash chromatography (50% ethyl acetate/hexane to 100% ethyl acetate) gave 4.7 g (~100%) of 1-(2(S)-tert-Butoxycarbonylamino-non-8-enoyl)-4(R)-hydroxy-pyrrolidine-2(S)-carboxylic acid methyl ester as a colorless oil: ¹H NMR (500 MHz, CD₃OD) δ 1.33–1.50 (m, 8H), 1.46 (s, 9H), 1.57 (m, 1H), 1.72 (m, 1H) 2.08 (m, 2H), 2.28 (m, 1H), 3.72 (s, 3H,) 3.75–3.87 (m, 2H), 4.36 (m, 1H), 4.51 (bs, 1H), 4.57 (t, J=8.2 Hz, 1H), 4.95 (d, J=10.4 Hz, 1H), 5.01

(m, 1H), 5.83 (m, 1H). LC-MS (Method J, retention time: 3.01 min), MS m/z 399 (M⁺+1).

Step 26ii: Preparation of 1-{[1-(2(S)-tert-Butoxycarbonylamino-non-8-enoyl)-4(R)-hydroxy-pyrrolidine-2(S)carbonyl]-(1R)-amino}-2(S)-vinylcyclopropanecarboxylic acid ethyl ester

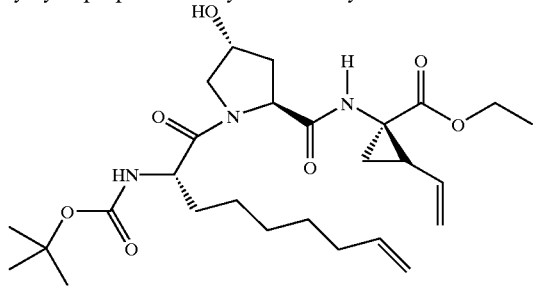

1-(2(S)-tert-Butoxycarbonylamino-non-8-enoyl)-4(R)-hydroxy-pyrrolidine-2(S)-carboxylic acid methyl ester (4.7 g, 11.8 mmol) was dissolved in THF (80 mL), methanol (20 mL), and water (40 mL). Powdered lithium hydroxide (5.6 g, 233 mmol) was added. The light yellow slurry was stirred at rt under N₂ for 16 h, and then concentrated in vacuo. The residue was partioned between ether and water. The ether phase was discarded, and the aqueous phase was treated with 1N HCl until the pH was 4. This acidic solution was extracted with EtOAc (3x). The combined EtOAc extracts were dried (MgSO₄) and concentrated in vacuo to give 4.36 g (96%) of 1-(2(S)-tert-butoxycarbonylamino-8-nonenoyl)-4(R)-hydroxy-pyrrolidine-2(S)-carboxylic acid as a white solid. This acid was then dissolved in 150 mL of DMF and (1R,2S)-1-amino-2-vinylcyclopropane carboxylic acid ethyl ester hydrochloride (2.61 g, 13.6 mmol), N-methyl morpholine (2.5 mL, 22.6 mmol), HATU (5.2 g, 13.7 mmol) was added. The reaction mixture was stirred at rt under N₂ for 16 h, and then concentrated in vacuo. The residue was partitioned between ethyl acetate and pH 4 buffer (biphthalate). The organic phase was washed with sat. aq. NaHCO₃, dried (MgSO₄), and concentrated in vacuo to give the crude product. Flash chromatography (60%–80% ethyl acetate/hexane) gave 6.0 g (98%) of 1-{[1-(2(S)-tert-Butoxycarbonylamino-non-8-enoyl)-4(R)-hydroxy-pyrrolidine-2(S)carbonyl]-(1R)-amino}-2(S)-vinylcyclopropanecarboxylic acid ethyl ester as a white solid: ¹H NMR (500 MHz, CD₃OD) δ 1.25 (t, J=7.2 Hz, 3H), 1.33–1.80 (m, 10H), 1.46 (s, 9H), 2.09 (m, 3H), 2.25 (m, 2H), 3.76 (m, 2H), 4.14 (m, 2H), 4.27 (dd, J=8.5, 5.2 Hz, 1H), 4.50 (m, 2H), 4.94 (d, J=10.1 Hz, 1H), 5.01 (dd, J=17.1, 1.8 Hz, 1H), 5.11 (dd, J=10.4, 1.8 Hz, 1H), 5.30 (d, J=15.6 Hz, 1H), 5.80 (m, 2H), 8.57 (s, 1H). LC-MS (Method J, retention time: 3.21 min), MS m/z 522 (M⁺+1).

Step 26iii: Preparation of (1S,4R,6S,14S,18R)-7-cis-14-tert-butoxycarbonylamino-18-hydroxy-2,15-dioxo-3,16-diazatricyclo[14.3.0.0$^{4,6}$]nonadec-7-ene-4-carboxylic acid ethyl ester

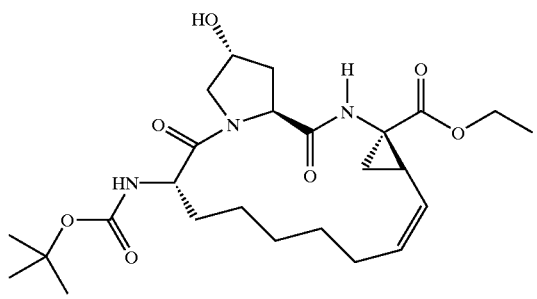

A solution of 1-{[1-(2(S)-tert-Butoxycarbonylamino-non-8-enoyl)-4(R)-hydroxy-pyrrolidine-2(S)carbonyl]-(1R)-amino}-2(S)-vinylcyclopropane-carboxylic acid ethyl ester (800 mg, 1.53 mmol) in 2 L of methylene chloride was flushed with N₂ for 0.5 h. Then tricyclohexylphosphine[1,3-bis(2,4,6-trimethyl-phenyl)-4,5-dihydroimidazol-2-ylidene][benzylidene]-ruthenium (IV) dichloride (Strem) (64 mg, 0.075 mmol) was added, and the mixture was flushed with N₂ for another 10 min. The light orange homogeneous solution was refluxed for 2 h to give a dark orange solution. The reaction mixture was cooled to rt and concentrated in vacuo to give an orange oil. Flash chromatography (ethyl acetate) gave 460 mg (61%) of (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid ethyl ester as a gray solid. ¹H NMR (500 MHz, CDCl₃) δ 1.19 (t, J=7.2 Hz, 3H), 1.42 (s, 9H), 1.22–1.8 (m, 8H), 1.87 (m, 2H), 2.03–2.22 (m, 4H), 2.63 (m, 1H), 3.65 (m, 1H), 4.09 (m, 3H), 4.45 (m, 1H), 4.56 (s, 1H), 4.82 (m, 1H), 5.23 (m, 1H), 5.51 (s, 1H), 7.16 (s, 1H). LC-MS (Method J, retention time: 2.97 min), MS m/z 494 (M⁺+1).

Step 26iv: Preparation of Example 26, (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid

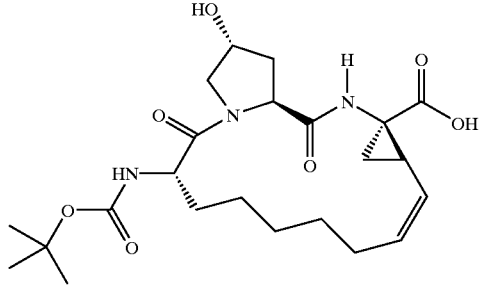

To a solution of (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid ethyl ester (493 mg, 1.0 mmol) in THF (4 mL), methanol (1 mL), and water (2 mL), was added powdered lithium hydroxide (480 mg, 20 mmol), and the light yellow slurry stirred at rt under N₂ for 16 h. The mixture was then concentrated in vacuo and the residue partioned between ether and water. The ether phase was discarded, and the aqueous phase was treated with 1 N HCl until pH 4. This acidic solution was extracted with EtOAc three times. The combined EtOAc extracts were dried (MgSO₄) and concentrated in vacuo to give 460 mg (98%) of Example 26, (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid as a gray solid. ¹H NMR (500 MHz, CD₃OD) δ ppm 1.26 (t, J=7.2 Hz, 3H), 1.35–1.52 (m, 15H), 1.57–1.68 (m, 3H), 1.79 (m, 1H), 2.04 (m, 1H), 2.16–2.41 (m, 3H), 3.80 (dd, J=10.7, 4.3 Hz, 1H), 3.88 (m, 1H), 4.38 (dd, J=8.9, 3.1 Hz, 1H), 4.55 (m, 2H), 5.39 (t, J=9.8 Hz, 1H), 5.58 (m, 1H). LC-MS (Method J, retention time: 2.64 min), MS m/z 466 (M⁺+1).

H) 1M KOtBu in THF; LaCl₃

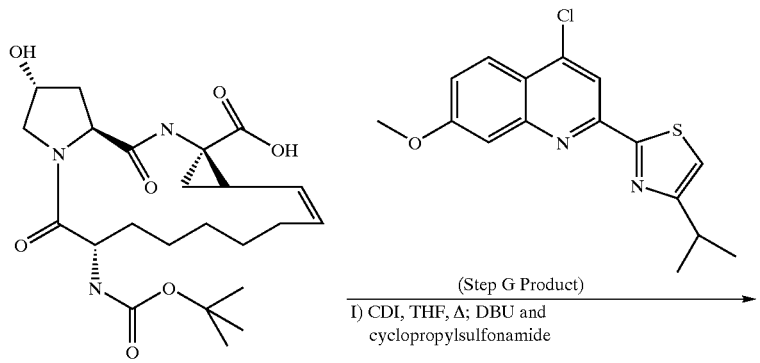

(Step G Product)
I) CDI, THF, Δ; DBU and cyclopropylsulfonamide

Example 26

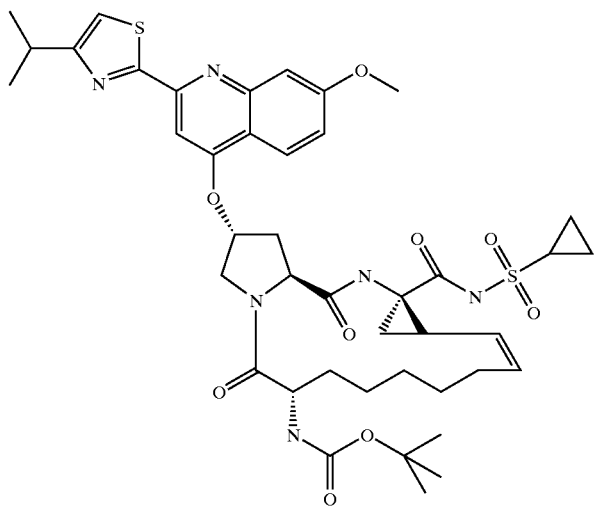

Compound 27, Example 27

Step H) To a suspension of 58 mg (0.125 mmol) of (1S,4R,6S,14S,18R)-7-cis-14-tert-butoxycarbonylamino-18-hydroxy-2,15-dioxo-3,16-diazatricyclo[14.3.0.0$^{4,6}$]-nonadec-7-ene-4-carboxylic acid, Example 26, and 31 mg (0.125 mmol) of LaCl₃ in 1.2 mL of DMF cooled to −78° C. was added 0.62 mL (0.62 mmol) of 1M KOtBU in THF, followed by 4-Chloro-2-(4-isopropylthiazol-2-yl)-7-methoxyquinoline, product of step G. The mixture was stirred one hour and warmed to rt showing little conversion to the product. Approximately 0.75 equivalent of solid KOtBU was added (10 mg), and the mixture stirred overnite. After 14 h, approximately one-half equivalent of 4-Chloro-2-(4-isopropylthiazol-2-yl)-7-methoxyquinoline (22 mg) and LaCl₃ (16 mg) were added, and the mixture stirred overnite. The mixture was quenched with pH 4 buffer and extracted into EtOAc. The combined EtOAc extracts were dried (MgSO₄), concentrated in vacuo injected onto a preparative HPLC using the following conditions: Column Xterra 30×100 mm S5, 30% to 100% Solvent B/A for 18 min gradient, hold time 5 min; where Solvent A is 10% MeOH/90% H₂O with 0.1% TFA, Solvent B is 90% MeOH/10% H₂O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined EtOAc extracts were dried (MgSO₄) and concentrated in vacuo to provide 22 mg (31%) of (1S,4R,6S,14S,18R)-7-cis-14-tert-Butoxycarbonylamino-18-[2-(2-isopropylthiazol-4-yl)-7-methoxyquinolin-4-yloxy]-2,15-dioxo-3,16-diazatricyclo[14.3.0.0$^{4,6}$]nona-dec-7-ene-4-carboxylic acid: ¹H NMR (500 MHz, Methanol-d⁴) δ 1.08–1.67 (m, 11H), 1.39 (s, 9H), 1.41 (d, J=7.0 Hz, 6H), 1.78 (m, 1H), 1.93 (m, 1H), 2.32 (q, J=9 Hz, 1H), 2.74 (m, 1H), 3.23 (m, 1H), 3.97 (m, 3H), 4.07 (d, J=9 Hz, 1H), 4.20 (d, J=8.2 Hz, 1H), 4.66 (t, J=8.2 Hz, 1H), 4.76 (d, J=11.3 Hz, 1H), 5.36 (m, 1H), 5.59 (m, 1H), 5.64 (s, 1H), 6.91 (s, 1H), 7.13 (d, J=8.9 Hz, 1H), 7.42 (s, 1H), 7.45 (s, 1H), 7.70 (s, 1H), 8.19 (d, J=8.9 Hz, 1H), 8.68 (s, 1H). LC-MS m/e 748 (retention time: 203, method D).

Step I: Preparation of Compound 27, Example 27, (1S,4R,6S,14S,18R)-7-cis-14-Cyclopropanesulfonylaminocarbonyl-18-[2-(2-isopropylthiazol-4-yl)-7-methoxy-quinolin-4-yloxy]-2,15-dioxo-3,16-diazatricyclo-[14.3.0.0$^{4,6}$]nonadec-7-en-14-yl}carbamic acid tert-butyl ester)

Step I) To a solution of 18 mg (0.024 mmol) of (1S,4R,6S,14S,18R)-7-cis-14-tert-Butoxycarbonylamino-18-[2-(2-isopropylthiazol-4-yl)-7-methoxyquinolin-4-yloxy]-2,15-dioxo-3,16-diazatricyclo[14.3.0.0$^{4,6}$]nona-dec-7-ene-4-carboxylic acid (product of Step H) in 2 mL of THF, was added CDI (29 mg, 0.036 mmol), and the resulting solution refluxed for 60 min and allowed to cool down to rt. Cyclopropylsulfonamide (4.4 mg, 0.036 mmol) was added in one portion before the addition of a neat solution of DBU (5.1 μL, 0.034 mmol). The reaction was stirred for 16 h, diluted to 2 mL of methanol and injected onto a preparative HPLC using the following conditions: Column Xterra 30×100 mm S5, 30% to 100% Solvent B/A for 30 min gradient, hold time 5 min; where Solvent A is 10% MeOH/90% H$_2$O with 0.1% TFA, Solvent B is 90% MeOH/10% H$_2$O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined EtOAc extracts were dried (MgSO$_4$) and concentrated in vacuo to provide 6.4 mg (31%) Compound 27, Example 27, as a foam: $^1$H NMR (500 MHz, Methanol-d$^4$) δ 0.96–1.56 (m, 17H), 1.18 (s, 9H), 1.61 (dd, J=9.5, 5.5 Hz, 1H), 1.72 (dd, J=8.1, 5.3 Hz, 1H), 1.84 (m, 2H), 2.38 (m, 1H), 2.61 (m, 1H), 2.70 (m, 1H), 2.80 (m, 1H), 2.90 (m, 1H), 3.24 (m, 1H), 3.96 (s, 3H), 4.07 (m, 1H), 4.15 (d, J=10.7 Hz, 1H), 4.66 (m, 1H), 4.86 (m, 1H), 5.08 (m, 1H), 5.69 (m, 2H), 7.13 (d, J=9.2 Hz, 1H), 7.43 (s, 1H), 7.45 (s, 1H), 7.70 (s, 1H), 8.20 (d, J=9.2 Hz, 1H). LC/MS m/e 851 (retention time: 1.98, method D).

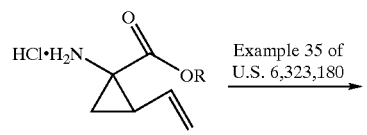

Example 35 of U.S. 6,323,180

R = Me, Example 35 of U.S. 6,323,180 was replaced with R = Et using sequence of reactions outlined in Example 35 to prepare Example 28 (this patent)

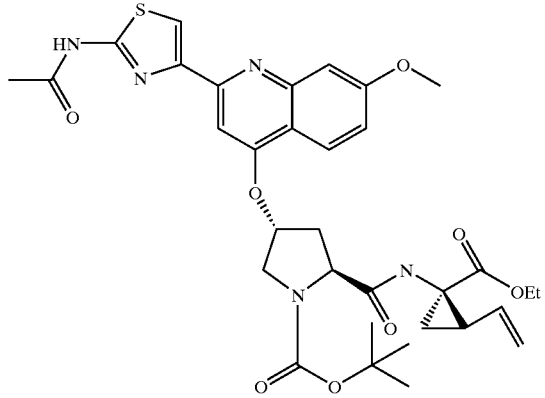

Example 28

Example 28 (which corresponds to compound 35n in U.S. Pat. No. 6,323,180 at column 83, line 45) was prepared following the sequences of Example 35 of U.S. Pat. No. 6,323,180, but using a modification where the ethyl ester of 1-amino-2-vinylcyclopropane carboxylic acid hydrochloride was coupled in place of the methyl ester analogue (i.e. compound 35i of U.S. Pat. No. 6,323,180, column 80, line 5).

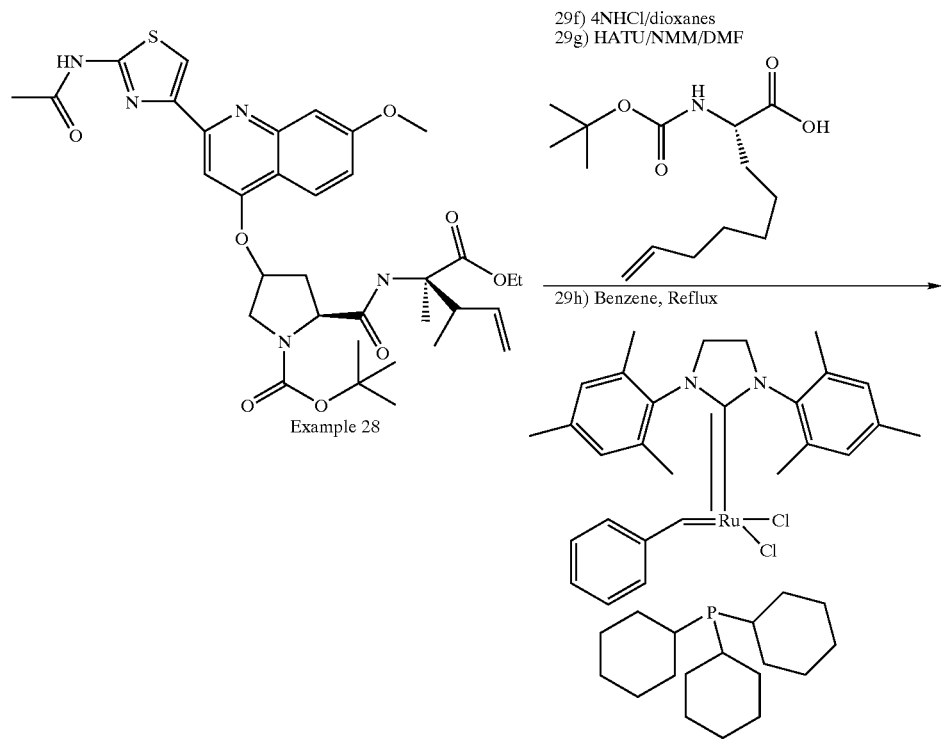

29f) 4NHCl/dioxanes
29g) HATU/NMM/DMF
29h) Benzene, Reflux
29i) LiOH/THF/MeOH/H$_2$O
29j) CDI, THF, Δ; DBU and cyclopropylsulfonamide -continued

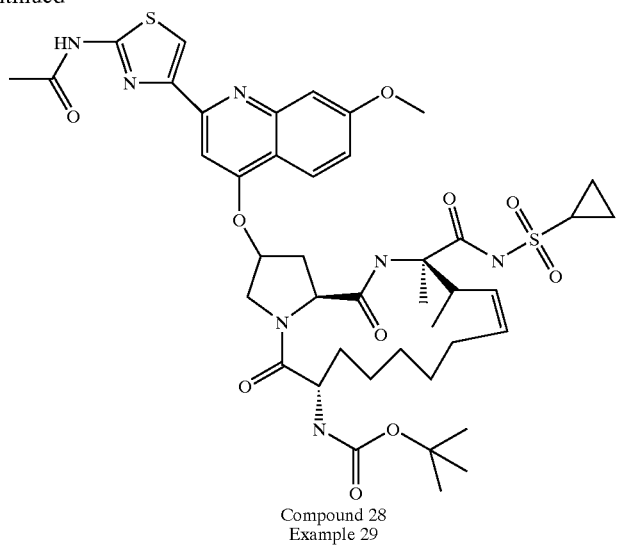

Compound 28
Example 29

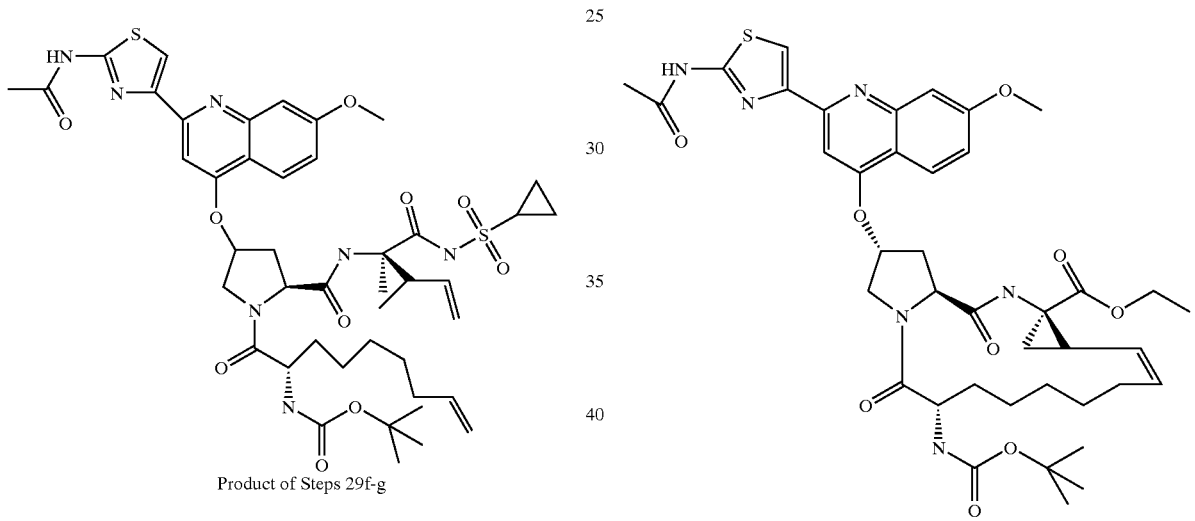

Product of Steps 29f-g

Product of Step 29h

Steps 29f–29 g) 500 mg (0.75 mmol) of Example 28 was dissolved in HCl/dioxane (4.0M; 4.5 mL) and was stirred for 2.5 h at rt. The reaction mixture was concentrated and the crude product which was directly used in the next step, 29 g. To suspension of the crude product from step 29f, 2(S)-tert-butoxycarbonyl-amino-8-nonenoic acid purchased from RSP Amino Acids (0.305 g, 1.13 mmol), NMM (0.44 ml, 4.0 mmol) in DMF (3.5 mL) was added HATU (0.43 g, 1.13 mmol). After being stirred for 2 days, the reaction mixture was diluted with EtOAc (200 mL), washed with water (50 mL), pH 4.0 buffer (50 mL), saturated aqueous NaHCO$_3$ (50 mL), dried (MgSO$_4$), and purified by a Biotage 40 M column (eluted with 0% to 5% MeOH in CH$_2$Cl$_2$) to supply the product of step 29 g, as a yellow oil (0.50 g, 81%) of approximate 80% purity by $^1$H NMR: $^1$H NMR (500 MHz, Solvent methanol-d$^4$) δ 1.32 (s, 9H), 1.07–1.67 (m, 12H), 1.74 (m, 1H), 1.88 (m, 1H), 2.02 (m, 2H), 2.26 (m, 4H), 2.42 (m, 1H), 2.78 (m, 1H), 3.94 (s, 3H), 4.15 (m, 3H), 4.49 (m, 1H), 4.66 (m, 1H), 4.83 (m, 1H), 4.89 (d, J=9.5 Hz, 1H), 4.96 (d, J=17.1 Hz, 1H), 5.10 (d, J=10.4 Hz, 1H), 5.28 (d, J=17.1 Hz, 1H), 5.47 (s, 1H), 5.76 (m, 2H), 7.09 (m, 1H), 7.37 (s, 1H), 7.55 (s, 1H), 7.95 (m, 1H). LC-MS m/e 819 (retention time: 3.30, method D, except gradient time increased from 2 to 4 min).

Step 29h: Preparation of (1S,4R,6S,14S,18R)-7-cis-18-[2-(2-Acetylaminothiazol-4-yl)-7-methoxyquinolin-4-yloxy]-14-tert-butoxycarbonylamino-2,15-dioxo-3,16-diazatricyclo[14.3.0.0$^{4,6}$]nonadec-7-ene-4-carboxylic acid ethyl ester Step 29 h) To a solution of the product of from Step 29 g (380 mg of 80% purity, assumed 0.464 mmol) in 0.7L of Argon degassed benzene, was added 60 mg of Tricyclohexylphosphine [1,3-bis(2,4,6-trimethyl-phenyl)-4,5-dihydroimidazol-2-ylidene][benzylidine]ruthenium(IV) dichloride catalyst from Strem, the mixture degassed under Ar and heated to reflux for 3 h. The reaction mixture was cooled to rt, the mixture degassed once more, an additional 60 mg portion of Tricyclohexylphosphine [1,3-bis(2,4,6-trimethyl-phenyl)-4,5-dihydroimidazol-2-ylidene][benzylidine]ruthenium(IV)dichloride catalyst added, and the mixture heated to reflux for 3 h. The reaction mixture was cooled to rt, the mixture degassed once more, and a final 5 mg portion of the catalyst added, and the mixture heated to reflux for an additional 1 h. The resulting dark brown solution was cooled to rt, concentrated in vacuo and purified over a Biotage 40M column (eluted sequentially with 0% to 10% MeOH in CH$_2$Cl$_2$) to afford 309 mg (84%) of the titled product, a portion of which was taken directly into the next reaction: LC-MS m/e 791 (retention time: 1.83, method D).

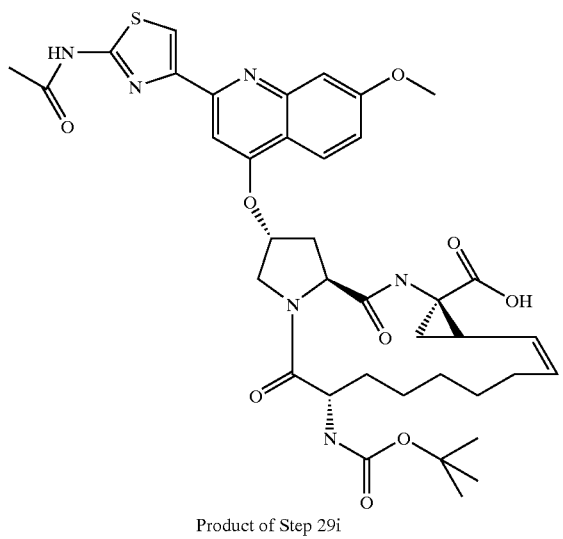

Product of Step 29i

Step 29i: Preparation of (1S,4R,6S,14S,18R)-7-cis-18-[2-(2-Acetylaminothiazol-4-yl)-7-methoxyquinolin-4-yloxy]-14-tert-butoxycarbonylamino-2,15-dioxo-3,16-diazatricyclo[14.3.0.0$^{4,6}$]nonadec-7-ene-4-carboxylic acid Step 29i) Following an analogous experimental and purification procedure to Step 1i, (1S,4R,6S,14S,18R)-7-cis-18-[2-(2-Acetylaminothiazol-4-yl)-7-methoxy-quinolin-4-yloxy]-14-tert-butoxycarbonylamino-2,15-dioxo-3,16-diazatricyclo[14.3.0.0$^{4,6}$]nonadec-7-ene-4-carboxylic ethyl ester (180 mg, 0.228 mmol) in 14 mL of THF and 3.5 mL of MeOH was reacted with 92 mg (2.3 mmol) of LiOH in 7 mL of H$_2$O to afford (1S,4R,6S,14S,18R)-7-cis-18-[2-(2-Acetylaminothiazol-4-yl)-7-methoxyquinolin-4-yloxy]-14-tert-butoxycar-bonylamino-2,15-dioxo-3,16-diazatricyclo [14.3.0.0$^{4,6}$]-nonadec-7-ene-4-carboxylic acid (150 mg, 86%): $^1$H NMR (500 MHz, CD$_3$OD, some minor broadening due to rotomers) δ 11.29 (s, 9H), 1.41 (m, 7H), 1.62 (m, 2H), 1.84 (m, 1H), 1.96 (m, 1H), 2.18 (m, 1H), 2.24 (s, 3H), 2.50 (m, 1H), 2.62 (m, 1H), 2.68 (m, 1H), 3.96 (s, 3H), 4.11 (s, 1H), 4.29 (s, 1H), 4.65 (s, 2H), 5.51 (s, 3H), 7.05 (s, 1H), 7.37 (s, 1H) 7.55 (s, 1H), 7.95 (s, 1H), 8.12 (s, 1H): LC-MS m/e 763 (retention time: 3.09, method D, except gradient time increased from 2 to 4 min).

Step 29j: Preparation of Compound 28, Example 29, (1S, 4R,6S,14S,18R)-7-cis-{18-[2-(2-Acetylaminothiazol-4-yl)-7-methoxyquinolin-4-yloxy]-4-cyclopropanesulfonylaminocarbonyl-2,15-dioxo-3,16-diazatricyclo-[14.3.0.0$^{4,6}$]nonadec-7-en-14-yl}carbamic acid tert-butyl ester Step 29j) Following an analogous experimental and purification procedure to Step 1j, 52 mg (0.068 mol) of the product from step 29i, (1S,4R,6S,14S,18R)-7-cis-18-[2-(2-Acetylaminothiazol-4-yl)-7-methoxyquinolin-4-yloxy]-14-tert-butoxycar-bonylamino-2,15-dioxo-3,16-diazatricyclo [14.3.0.0$^{4,6}$]-nonadec-7-ene-4-carboxylic acid, was reacted with 16 mg (0.095 mmol) of CDI, 12 mg (0.095 mmol) of cyclopropyl-sulfonamide and 14 μL (0.095 mmol) of DBU, to afford 25 mg (42%) of Compound 28, Example 29, (1S,4R,6S,14S,18R)-7-cis-{18-[2-(2-Acetylaminothiazol-4-yl)-7-methoxyquinolin-4-yloxy]-4-cyclopropanesulfonylaminocarbonyl-2,15-dioxo-3,16-diazatricyclo-[14.3.0.0$^{4,6}$]nonadec-7-en-14-yl}carbamic acid tert-butyl ester. To purify the compound, the compound was dissolved in 4 mL of MeOH and injected twice onto a preparative HPLC column (2×2 mL injections), afterwhich, an extractive purification was undertaken to isolate the product from the HPLC fractions: Column Xterra 30×100 mm S5, 35% to 80% Solvent B/A for 38 min gradient, hold time 2 min; where Solvent A is 10% MeOH/90% H$_2$O with 0.1% TFA, Solvent B is 90% MeOH/10% H$_2$O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined EtOAc extracts were dried (MgSO$_4$) and concentrated in vacuo to provide the product, Compound 28, Example 29: $^1$H NMR (500 MHz, Solvent methanol-d$^4$) δ 0.76–1.61 (m, 20H), 1.64 (dd, J=9.6, 5.3 Hz, 1H), 1.75 (dd, J=8.1, 5.3 Hz, 1H), 1.87 (m, 2H), 2.29 (s, 3H), 2.42 (m, 1H), 2.60 (m, 1H), 2.68 (m, 1H), 2.81 (m, 1H), 2.93 (m, 1H), 3.99 (s, 3H), 4.09 (m, 1H), 4.22 (m, 1H), 4.68 (m, 1H), 4.88 (m, 1H), 5.12 (m, 1H), 5.59 (s, 1H), 5.71 (m, 1H), 7.10 (d, J=8.6 Hz, 1H), 7.42 (s, 1H), 7.63 (s, 1H), 8.05 (s, 1H), 8.20 (d, J=8.6 Hz, 1H): LC-MS m/e 866 (retention time: 3.08, method D, except gradient time increased from 2 to 4 min).

Preparation of Example 30, Compound 29, (1S,4R,6S,14S, 18R)-7-cis-[4-Cyclopropanesulfonylaminocarbonyl-2,15-dioxo-18-(quinolin-4-yloxy)-3,16-diazatricyclo[14.3.0.0$^{4,6}$] nonadec-7-en-14-yl]carbamic acid tert-butyl ester

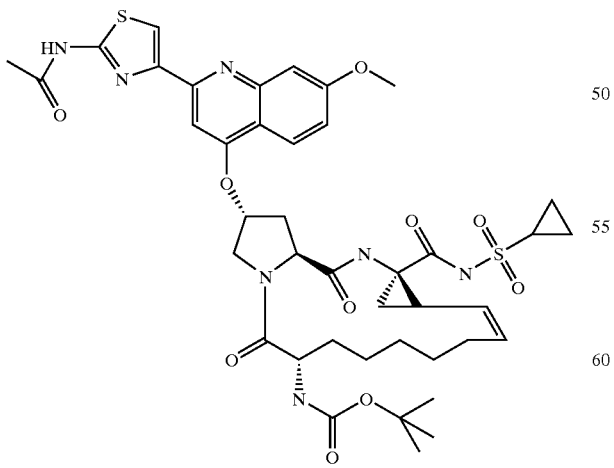

Compound 28
Example 29

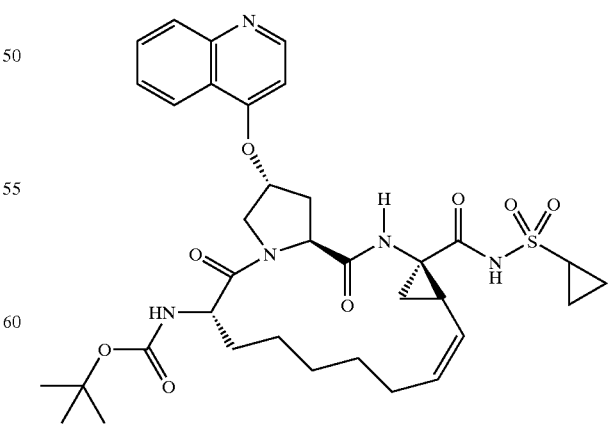

Example 30,
Compound 29

Step 30A: Preparation of 4(R)-(Quinolin-4-yloxy)-pyrrolidine-1,2(S)-dicarboxylic acid 1-tert-butyl ester

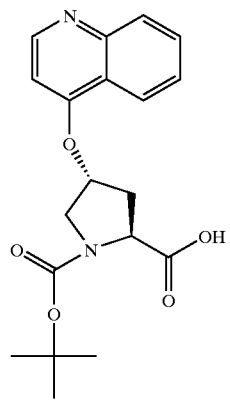

Step 30A) A suspension of Boc-L-4-hydroxyproline [N-Boc (2S,4R)-hydroxyproline](10 g, 43.3 mmol) (CHEM-IMPEX International) in DMSO (150 mL) was cooled in an ice bath for ~3 minutes, and then t-BuOK (12.1 g, 108.2 mmol) was added. The mixture was stirred for a few minutes until a solid mass formed. At this time the reaction mixture was allowed to warm to rt over 1.5 h to give a clear colorless solution. 1-Chloroquinoline (7.7 g, 47.2 mmol) was added in two portions 10 min apart. The reaction was stirred for 24 h at rt. The dark reaction mixture was partitioned between ether (500 mL) and water (700 mL). The aqueous phase was acidified to pH 4 using 4 N HCl. The resulting white precipitate was filtered and then washed with water (200 mL) to give the titled product of Step 30A as an off-white solid (13 g, 84%): $^1$H NMR (500 MHz, DMSO) δ 1.32, 1.35 (2s, 9H), 2.36 (m, 1H), 2.66 (m, 1H), 3.73 (m, 2H), 4.35 (m, 1H), 5.34 (s, 1H), 7.06 (d, J=5.2 Hz, 1H), 7.56 (t, J=8.2 Hz, 1H), 7.75 (t, J=8.2 Hz, 1H), 7.95 (d, J=8.2 Hz, 1H), 8.11 (t, J=8.2 Hz, 1H), 8.72 (d, J=5.2 Hz, 1H). LC-MS (Method J, retention time: 1.87 min), MS m/z (M$^+$+1).

Step 30B: Preparation of (2S)-(1(R)-ethoxycarbonyl-2(S)-vinylcyclopropylcarbamoyl)-4(R)-(quinolin-4-yloxy) pyrrolidine-1-carboxylic acid tert-butyl ester

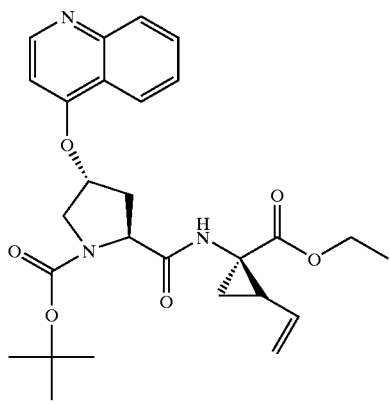

Step 30B) A stirred slurry of 4(R)-(Quinolin-4-yloxy)-pyrrolidine-1,2(S)-dicarboxylic acid 1-tert-butyl ester (5.0 g, 14 mmol) in a mixture of 100 mL of methylene chloride and 100 mL of DMF was treated sequentially with N-methyl morpholine (3 mL, 27.3 mmol), HATU (PE biosystems)(6.3 g, 16.5 mmol), and 1R,2S-1-amino-2-vinylcyclopropane carboxylic acid ethyl ester hydrochloride (3.2 g, 16.7 mmol). The solution was stirred at rt under N$_2$ for 18 h, and then concentrated in vacuo to give 10 g of a brown oil. This oil was partitioned between ethyl acetate and sat. aq. NaHCO$_3$. The organic phase was washed with brine, dried (MgSO$_4$), and concentrated in vacuo. Flash chromatography (10% MeOH in ethyl acetate) gave 7.0 g (100%) of the titled product of Step 30B as a yellow solid: $^1$H NMR (300 MHz, CD$_3$OD) δ 1.25 (t, J=7.3 Hz, 3H), 1.44, 1.39 (2 s, 10H), 1.79 (m, 1H), 2.20 (m, 1H), 2.43 (m, 1H), 2.71 (m, 1H), 3.92 (m, 2H), 4.15 (q, J=7.3 Hz, 2H), 4.42 (m, 1H), 5.11 (m, 1H), 5.29–5.39 (m, 2H), 5.75 (m, 1H), 7.05 (d, J=5.5 Hz, 1H), 7.57 (t, J=8.1 Hz, 1H), 7.76 (t, J=8.4 Hz, 1H), 7.95 (d, J=8.4 Hz, 1H), 8.16 (d, J=8.4 Hz, 1H), 8.69 (d, J=5.5 Hz, 1H). LC-MS (Method J, retention time: 2.35 min), MS m/z 496 (M$^+$+1).

Step 30C: Preparation of 1-{[4(R)-(Quinolin-4-yloxy)-pyrrolidine-2(S)-carbonyl]-1(R)-amino}-2(S)-vinylcyclopropanecarboxylic acid ethyl ester bis hydrochloride

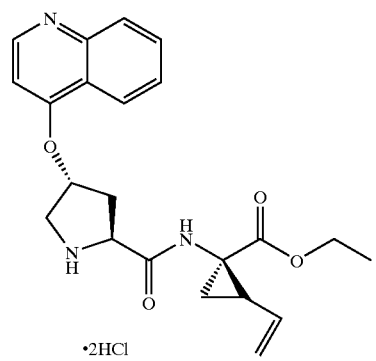

Step 30C) A stirred slurry of (2S)-(1(R)-ethoxycarbonyl-2(S)-vinylcyclopropylcarbamoyl)-4(R)-(quinolin-4-yloxy) pyrrolidine-1-carboxylic acid tert-butyl ester (7.0 g, 14.1 mmol) was treated with 150 mL (300 mmol) of 2 N HCl/ether (Aldrich) for 24 h. The reaction mixture was concentrated in vacuo to give 7.0 g (94%)of the titled product from step 30C as a yellow solid: $^1$H NMR (500 MHz, CD$_3$OD) δ 1.28 (t, J=7.0 Hz, 3H), 1.52 (dd, J=5.5 Hz, 4.0 Hz, 1H), 1.65 (dd, J=7.6 Hz, 6.7 Hz, 1H), 1.83 (dd, J=5.5 Hz, 2.7 HZ, 1H), 2.29 (q, J=8.8 Hz, 1H), 2.65 (m, 1H), 3.02 (m, 2H), 4.00 (s, 2H), 4.20 (q, J=7.0 Hz, 2H), 4.74 (dd, J=7.6 HZ, 2.7 Hz, 1H), 5.17 (d, J=10.4 Hz, 1H), 5.35 (d, J=17.1 Hz, 1H), 5.81 (m, 1H), 5.95 (m, 1H), 7.69 (d, J=6.7 Hz, 1H), 7.98 (t, J=8.2 Hz, 1H), 8.19 (m, 2H), 8.66 (d, J=8.2 Hz, 1H), 9.14 (d, J=6.7 Hz, 1H). LC-MS (Method J, retention time: 1.34 min), MS m/z 396 (M$^+$+1-2HCl).

Step 30D: Preparation of 1-{[1-(2(S)-tert-Butoxycarbonylamino-non-8-enoyl)-4(R)-(quinolin-4-yloxy)pyrrolidine-2(S)-carbonyl]-1(R)-amino}-2(S)-vinylcyclopropanecarboxylic acid ethyl ester

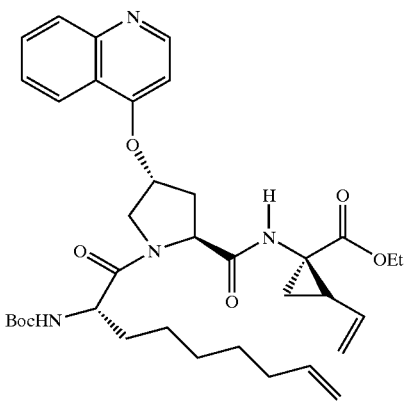

Step 30D) A solution of 2(S)-tert-butoxycarbonylamino-8-nonenoic acid (1.3 g, 4.79 mmol, purchased from RSP Amino Acids) dissolved in 100 mL of dichloromethane was treated sequentially with 1-{[4(R)-(Quinolin-4-yloxy)pyrrolidine-2(S)-carbonyl]-1(R)-amino}-2(S)-vinylcyclopropanecarboxylic acid ethyl ester bis hydrochloride (2.0 g, 4.28 mmol), N-methyl morpholine (1.5 mL, 13.6 mmol), and HATU (PE biosystems)(1.92 g, 5.05 mmol). The reaction mixture was stirred at rt under $N_2$ for 16 h, and then concentrated in vacuo. The residue was partitioned between ethyl acetate and pH 4 buffer (biphthalate). The organic phase was washed with sat. aq. $NaHCO_3$, dried ($MgSO_4$), and concentrated in vacuo to give 2.2 g of the crude product. Flash chromatography (10% methanol/ethyl acetate) gave 2.0 g (73%) of the titled product of Step 30D as a yellow solid: $^1$H NMR (500 MHz, $CD_3OD$) δ 1.27 (s, 9H), 1.21–1.45 (m, 10H), 1.63 (dd, J=11.29, 6.71 Hz, 2H) 1.75 (m, 1H) 2.04 (m, 2H) 2.28 (q, J=8.75 Hz, 1H) 2.44 (m, 1H) 2.76 (m, 1H) 4.01–4.25 (m, 4H) 4.55 (d, J=12.21 Hz, 1H) 4.67 (t, J=8.55 Hz, 1H) 4.93 (d, J=10.07 Hz, 1H) 5.00 (d, J=15.26 Hz, 1H) 5.12 (dd, J=10.38, 1.83 Hz, 1H) 5.31 (dd, J=17.24, 1.68 Hz, 1H) 5.51 (s, 1H) 5.79 (m, 2H) 7.08 (d, J=5.49 Hz, 1H) 7.56 (t, J=7.32 Hz, 1H) 7.77 (t, J=7.48 Hz, 1H) 7.97 (d, J=8.54 Hz, 1H) 8.27 (d, J=8.55 Hz, 1H) 8.73 (d, J=5.19 Hz, 1H). LC-MS (Method J, retention time: 3.06 min), MS m/z 649 ($M^+$+1).

Step 30E: Preparation of (1S,4R,6S,14S,18R)-7-cis-[14-tert-Butoxycarbonylamino-2,15-dioxo-18-(quinolin-4-yloxy)-3,16-diaza-tricyclo[14.3.0.0$^{4,6}$]nonadec-7-ene-4-carboxylic acid ethyl ester

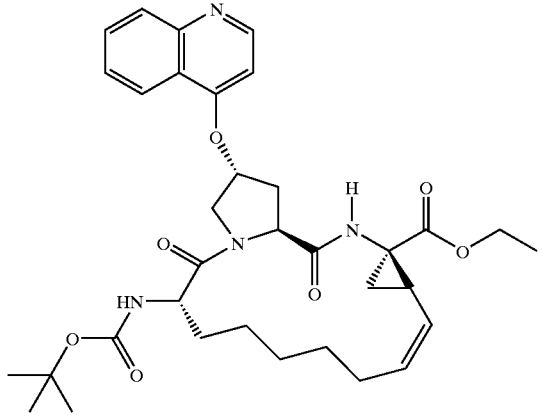

Step 30E) A solution of 1-{[1-(2(S)-tert-Butoxycarbonylamino-non-8-enoyl)-4(R)-(quinolin-4-yloxy)pyrrolidine-2(S)-carbonyl]-1(R)-amino}-2(S)-vinylcyclopropanecarboxylic acid ethyl ester (1.6 g, 2.46 mmol)in 2 L of methylene chloride was flushed with $N_2$ for 0.5 h. Then tricyclohexylphosphine[1,3-bis(2,4,6-trimethylphenyl)-4,5-dihydroimidazol-2-ylidene]-[benzylidene]-ruthenium (IV) dichloride (Strem) (150 mg, 0.17 mmol) was added, and the mixture was flushed with $N_2$ for another 10 min. The light orange homogeneous solution was refluxed for 16 h. Another 50 mg of the Ru catalyst was added, and the reaction mixture was refluxed for another 8 h. Finally, another 50 mg of the Ru catalyst was added and stirring was continued for 3 days at rt. The reaction mixture was concentrated in vacuo to give 1.7 g of an orange oil. Flash chromatography (ethyl acetate to 5% methanol in ethyl acetate) gave 1.1 g (68%) of the titled product of Step 30E as a white solid: $^1$H NMR (500 MHz, $CD_3OD$), δ 1.19 (s, 9H), 1.26 (t, J=7.0 Hz, 3H), 1.29–1.59 (m, 7H), 1.63 (dd, J=8.5 Hz, 4.8 Hz, 1H), 1.67 (dd, J=9.5 Hz, 4.8 Hz, 1H), 1.78–1.85 (m, 1H), 1.92–1.99 (m, 1H), 2.50 (m, 2H), 2.70 (m, 1H), 2.85 (q, J=8.8 Hz, 1H), 4.06 (d, J=11.9 Hz, 1H), 4.10–4.18 (m, 2H), 4.23 (d, J=10.7 Hz, 1H), 4.68 (m, 1H), 4.79 (d, J=11.3 Hz, 1H), 5.37 (t, J=10.1 Hz, 1H), 5.53 (s, 1H), 5.64 (m, 1H), 7.08 (d, J=5.5 Hz, 1H), 7.52 (t, J=7.6 Hz, 1H), 7.75 (t, J=8.2 Hz, 1H), 7.95 (d, J=8.2 Hz, 1H), 8.72 (d, J=5.5 Hz, 1H). (LC-MS (Method J, retention time: 2.71 min), MS m/z 621 ($M^+$+1).

Step 30F, Preparation of (1S,4R,6S,14S,18R)-7-cis-[14-tert-Butoxycarbonylamino-2,15-dioxo-18-(quinolin-4-yloxy)-3,16-diaza-tricyclo[14.3.0.0$^{4,6}$]nonadec-7-ene-4-carboxylic acid

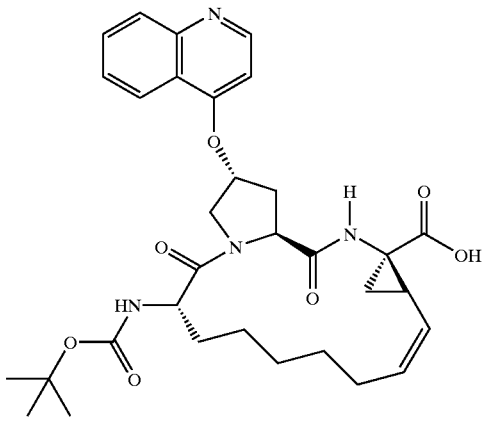

Step 30F) A solution of (1S,4R,6S,14S,18R)-7-cis-[14-tert-Butoxycarbonylamino-2,15-dioxo-18-(quinolin-4-yloxy)-3,16-diazatricyclo[14.3.0.0$^{4,6}$]nonadec-7-ene-4-carboxylic acid ethyl ester (1.10 g, 1.77 mmol) was dissolved in the mixed solvent system: THF (8 mL), methanol (2 mL), and water (4 mL). Powdered lithium hydroxide (425 mg, 17.7 mmol) was added. The light yellow slurry was stirred at rt under $N_2$ for 16 h, and then concentrated in vacuo. The residue was partitioned between ether and water. The ether phase was discarded, and the aqueous phase was treated with 1 N HCl until the pH was 4. This acidic solution was extracted with ethyl acetate four times. The combined ethyl acetate extracts were dried ($MgSO_4$) and concentrated in vacuo to give the product of step 30F (0.90 g, 86w) as a white solid: $^1$H NMR (300 MHz, $CD_3OD$) δ 1.16 (s, 9H), 1.24 (m, 1H), 1.33–1.55 (m, 6H), 1.61 (m, 2H), 1.79 (m, 1H), 1.92 (m, 1H), 2.32 (q, J=8.8 Hz, 1H), 2.58 (m, 2H), 2.68 (m, 1H), 4.05 (d, J=10.6 Hz, 1H), 4.22 (m, 1H), 4.64 (t, J=8.8 Hz, 1H), 4.74 (m, 1H), 5.36 (t, J=10.6 Hz, 1H), 5.49 (s, 1H), 5.61 (m, 1H), 7.07 (d, J=5.5 Hz, 1H), 7.49 (t, J=7.7 Hz, 1H), 7.73 (t, J=7.7 Hz, 1H), 7.92 (d, J=8.8 Hz, 1H), 8.30 (d, J=8.8 Hz, 1H), 8.70 (d, J=5.5 Hz, 1H). LC-MS (Method J, retention time: 2.54 min), MS m/z 593 ($M^+$+1).

Step 30G: Preparation of Compound 29 of Example 30, (1S,4R,6S,14S,18R)-7-cis-[4-Cyclopropanesulfonylaminocarbonyl-2,15-dioxo-18-(quinolin-4-yloxy)-3,16-diazatricyclo[14.3.0.0$^{4,6}$]nonadec-7-en-14-yl]-carbamic acid tert-butyl ester

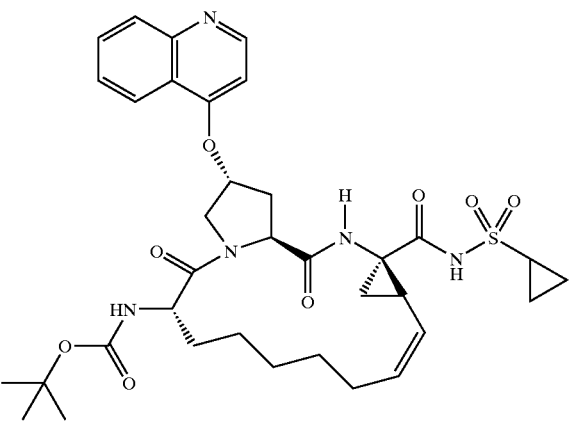

Compound 29
Example 30

Step 30G) To a solution of (1S,4R,6S,14S,18R)-7-cis-14-tert-Butoxycarbonylamino-2,15-dioxo-18-(quinolin-4-yloxy)-3,16-diazatricyclo[14.3.0.0$^{4,6}$]-nonadec-7-ene-4-carboxylic acid (100 mg, 0.17 mmol,) was dissolved in 3 mL of THF was added CDI (38 mg, 0.24 mmol), and the mixture heated to reflux for one hour. The mixture was cooled to rt and treated sequentially with cyclopropylsulfonamide (29 mg, 0.24 mmol) and DBU (36 mg, 0.24 mmol). After stirring for 24 h at rt, THF was removed by rotary evaporation. The residue was partitioned between ethyl acetate and pH 4 buffer. The organic phase was dried (MgSO$_4$) and concentrated in vacuo to give the crude product. Flash chromatography (10% MeOH/methylene chloride) gave 50 mg (42%) of the titled product, Compound 29 of Example 30, (1S,4R,6S,14S,18R)-7-cis-[4-Cyclopropanesulfonyl-aminocarbonyl-2,15-dioxo-18-(quinolin-4-yloxy)-3,16-diazatricyclo[14.3.0.0$^{4,6}$]nonadec-7-en-14-yl]carbamic acid tert-butyl ester as a white powder: $^1$H NMR (500 MHz, CD$_3$OD) δ 1.01 (m, 1H), 1.18 (s, 9H), 1.07–1.60 (m, 10H), 1.65 (dd, J=9.5 Hz, 5.2 Hz, 1H), 1.76 (dd, J=8.2 Hz, 5.5 Hz, 1H), 1.86 (m, 2H), 2.40 (m, 1H), 2.58 (m, 1H), 2.68 (m, 1H), 2.76 (m, 1H), 2.93 (m, 1H), 4.07 (d, J=10.7 Hz, 1H), 4.19 (m, 1H), 4.68 (dd, J=7.3 Hz, 1.81 Hz, 1H), 4.85 (m, 1H), 5.14 (t, J=7.6 Hz, 1H), 5.55 (s, 1H), 5.70 (m, 1H), 6.68 (d, J=5.8 Hz, 1H), 7.09 (d, J=5.2 Hz, 1H), 7.51 (t, J=7.0 Hz, 1H), 7.76 (t, J=7.0 Hz, 1H), 7.95 (d, J=8.2 Hz, 1H), 8.33 (d, J=8.2 Hz, 1H), 8.72 (d, J=5.5 Hz, 1H). LC-MS (Method A, retention time: 2.58 min), MS m/z 696 (M$^+$+1)

Example 31, Preparation of Compound 30, (1S,4R,6S,14S,18R)-7-cis-[4-Methanesulfonylaminocarbonyl-2,15-dioxo-18-(quinolin-4-yloxy)-3,16-diazatricyclo[14.3.0.0$^{4,6}$]nonadec-7-en-14-yl]-carbamic acid tert-butyl ester

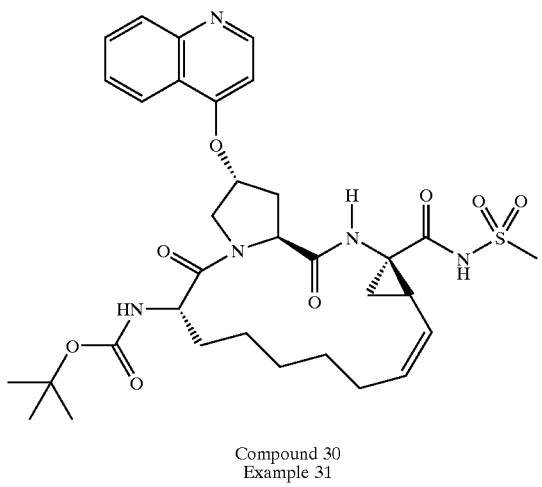

Compound 30
Example 31

(1S,4R,6S,14S,18R)-7-cis-[14-tert-butoxycarbonylamino-2,15-dioxo-18-(quinolin-4-yloxy)-3,16-diaza tricyclo[14.3.0.0$^{4,6}$]nonadec-7-ene-4-carboxylic acid, the product of Step F in Example 30 (50 mg, 0.075 mmol) was reacted in analogous fashion with methanesulfonamide (12 mg, 0.12 mmol) as described in the preceding procedure above to give 10 mg (20%) of (1S,4R,6S,14S,18R)-7-cis-[4-methanesulfonylaminocarbonyl-2,15-dioxo-18-(quinolin-4-yloxy)-3,16-diazatricyclo[14.3.0.0$^{4,6}$]-nonadec-7-en-14-yl]-carbamic acid tert-butyl ester as a white solid: $^1$H NMR (300 MHz, CDCl$_3$) δ 1.26 (s, 9H), 1.22–1.94 (m, 11H), 2.27 (m, 1H), 2.55 (m, 1H), 2.67 (m, 2H), 3.17 (s, 3H), 4.05 (m, 1H), 4.27 (m, 1H), 4.61 (t, J=8.1 Hz, 1H), 4.73 (d, J=11.0 Hz, 1H), 4.96–5.02 (m, 2H), 5.35 (s, 1H), 5.71 (q, J=8.8 Hz, 1H), 6.73 (d, J=5.1 Hz, 1H), 6.93 (bs, 1H), 7.43 (t, J=7.7 Hz, 1H), 7.69 (t, J=7.7 Hz, 1H), 8.06 (d, J=8.8 Hz, 1H), 8.15 (d, J=7.7 Hz, 1H), 8.77 (d, J=5.5 Hz, 1H). LC-MS (Method A, retention time: 2.43 min), MS m/z 670 (M$^+$+1).

Preparation of Example 32, 2(S)-tert-butoxycarbonylamino-3-pentenylsulfanylpropionic acid methyl ester (Example 32) for use in Example 33.

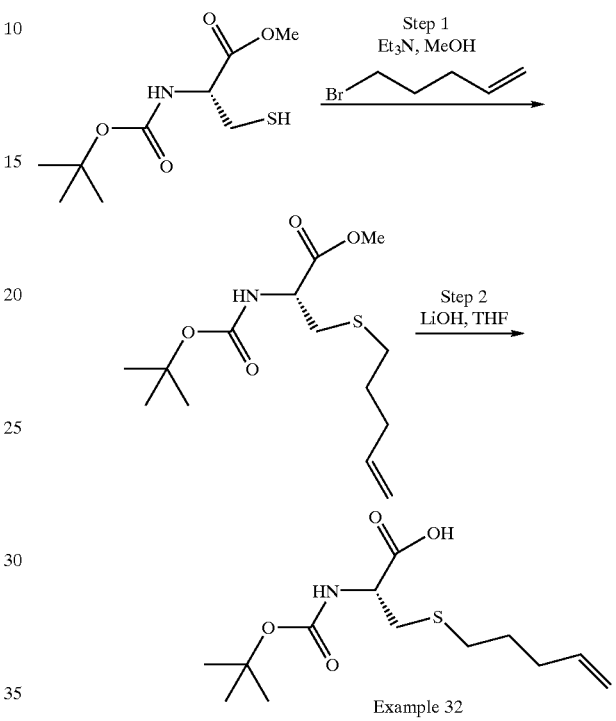

Example 32

Step 1: To a solution of N-Boc-cysteine methyl ester (3.36 g, 0.014 mol) in methanol (166 mL) at RT was added triethylamine (10.8 mL) and 1-bromopent-4-ene (3.19 g, 21 mmol, 1.5 equivalents) and the resulting solution was stirred at room temperature overnight. The mixture was then concentrated in vacuo and the resulting residual mixture was purified using flash chromatography (hexane, ethyl acetate gradient) to provide 1.76 g (41%) of the desired thioether. $^1$H NMR (500 MHz, CDCl$_3$) δ 1.43 (s, 9H), 1.64 (m, 2H), 2.11 (m, 2H), 2.51 (m, 2H), 2.95 (m, 2H), 3.75 (s, 3H), 4.51 (m, 1H), 4.95–5.03 (m, 2H), 5.34 (m, 1H), 5.80 (1H, m). LC-MS (Method H, except gradient time was 3 min., and flow rate was 4 ml/min, retention time: 2.29 min), MS m/z 304 (M$^+$+1).

Step 2: The thioether product of step 1 (9.51 g, 31.4 mmol) was added to a mixture of 1M LiOH in water (200 mL) and THF (200 mL) and the resulting mixture was stirred at room temperature overnight. The reaction mixture was then acidified using 1N hydrochloric acid and the resulting mixture was extracted several times with ethyl acetate. The extracts were combined, dried over magnesium sulfate, and concentrated in vacuo to provide the desired-acid which was used as is in the next reaction.

Preparation of Example 33, Compound 31, (1S,4R,6S,14S,18R)-7-cis-[4-Cyclopropanesulfonylaminocarbonyl-18-(7-methoxy-2-phenyl-quinolin-4-yloxy)-2,15-dioxo-12-thia-3,16-diazatricyclo[14.3.0.0$^{4,6}$]nonadec-7-en-14-yl]-carbamic acid tert-butyl ester.

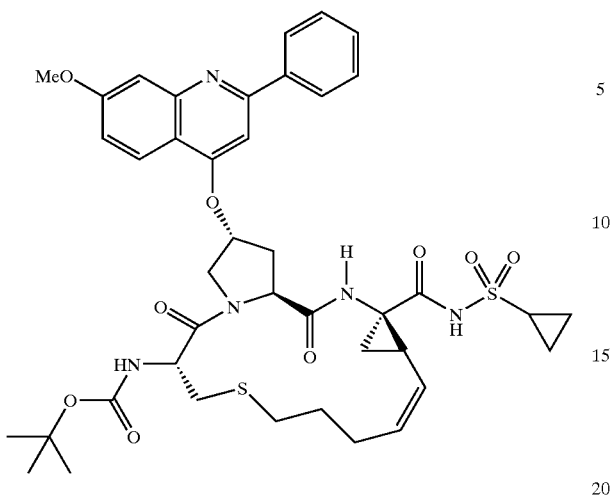

Compound 31
Example 33

Step 33A, Preparation of 1-{[1-(2(S)-tert-Butoxycarbonylamino-3-pent-4-enylsulfanylpropionyl)-4(R)-(7-methoxy-2-phenylquinolin-4-yloxy)pyrrolidine-2(S)-carbonyl]-1(R)-amino}-2(S)-vinylcyclopropanecarboxylic acid ethyl ester.

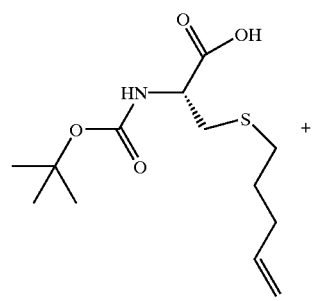

Step 33A) Note: the product of Step 1f (1-{[4-(7-Methoxy-2-phenylquinolin-4(R)-yloxy)pyrrolidine-2(S)-carbonyl]-1(R)-amino}-2(S)-vinylcyclopropanecarboxylic acid ethyl ester was used as starting material for the preparation of Compound 31. The carboxylic acid (282 mg, 976 μmol) of example 32 was added to a DMF solution containing HATU (445 mg, 1.17 mmol, 1.2 eq.), NMM (375 uL, 3.42 mmol, 3.5 eq.) and the TFA salt of the product of step 1f (600 mg, 976 mmol, 1 eq.) and the resulting solution was stirred at room temperature over night. The resulting mixture was quenched by the addition of pH 4 buffer and the resulting mixture was extracted (3×) with ethyl acetate. The extracts were combined, washed with brine, dried over magnesium sulfate and concentrated in vacuo. The crude product mixture was purified by flash chromatography (hexane, ethyl acetate) to provide the product of Step 33A (753 mg, 84%). $^1$H NMR (500 MHz, CDCl$_3$) δ 1.20–1.25 (m, 3H), 1.36 (s, 9H), 1.54–1.68 (m, 4H), 1.88 (m, 1H), 2.10–2.20 (m, 3H), 2.55–2.64 (m, 2H), 2.73–2.97 (m, 3H), 4.08–4.15 (m, 3H), 4.35 (m, 1H), 4.68 (m, 1H), 4.90–5.04 (m, 3H), 5.10 (m, 1H), 5.27–5.44 (m, 3H), 5.68–5.82 (m, 2H), 7.05–7.09 (m, 2H), 7.42–7.59 (m, 4H), 7.92–8.19 (m, 3H).

Step 33B, Preparation of 14-tert-Butoxycarbonylamino-18-(7-methoxy-2-phenyl-quinolin-4-yloxy)-2,15-dioxo-12-thia-3,16-diaza-tricycio[14.3.0.0$^{4,6}$]nonadec-7-ene-4-carboxylic acid ethyl ester

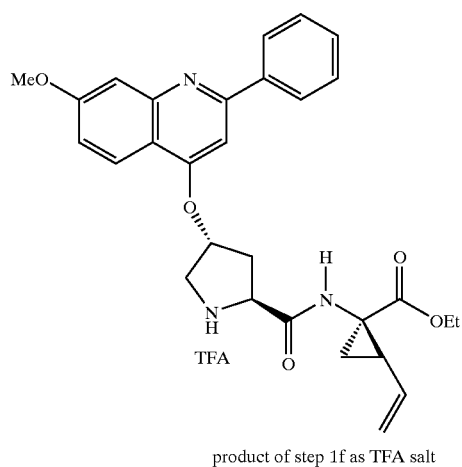

product of step 1f as TFA salt

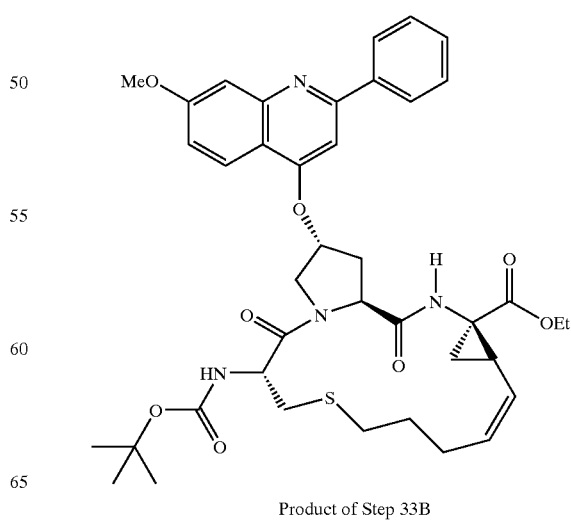

Product of Step 33B

Step. 33B) The tripeptide ester product of step 33A (390 mg, 505 μmol) was dissolved in degassed (nitrogen purged) dichloroethane (145 mL), Tricyclohexylphosphine[1,3-bis (2,4,6-trimethylphenyl)-4,5-dihydroimidazol-2-ylidene]-[benzylidene]-ruthenium (TV) dichloride (Strem) (45 mg, 53 mmol) was added, and the reaction mixture was heated to 45 C and maintained at this temperature for 5 hr. At this time, additional ruthenium catalyst (45 mg, 53 mmol)was added to the reaction mixture and heating was maintained overnight. The reaction mixture was then concentrated in vacuo and purified by flash chromatography (hexanes, ethyl acetate) to provide 159.4 mg (42%) of the desired olefin metathesis cyclization product of Step 33B. $^1$H NMR (500 MHz, CDCl$_3$) δ 1.24 (t, J=7 Hz, 3H), 1.37 (m, 1H), 1.41 (s, 9H), 1.50–1.75 (m, 3H), 1.85 (m, 1H), 1.96 (m, 1H), 2.13 (m, 1H), 2.21–2.45 (m, 3H), 2.52 (m, 1H), 2.81 (m, 1H), 3.07–3.15 (m, 3H), 4.12–4.25 (m, 3H), 4.85 (m, 1H), 5.09 (m, 1H), 5.37–5.42 (m, 2H), 5.5 (m, 1H), 5.6 (m, 1H), 7.05 (s, 1H), 7.09 (m, 1H), 7.40–7.58 (m, 4H), 8.00–8.10 (m, 3H).). LC-MS (Method H, except gradient time was 2 min, flow rate was 5 ml/min, and retention time: 1.55 min), MS m/z 745 (M$^+$+1).

Step 33C, Preparation of (1S,4R,6S,14S,18R)-7-cis-14-tert-Butoxycarbonylamino-18-(7-methoxy-2-phenyl-quinolin-4-yloxy)-2,15-dioxo-12-thia-3,16-diazatricyclo[14.3.0.0$^{4,6}$]nonadec-7-ene-4-carboxylic acid

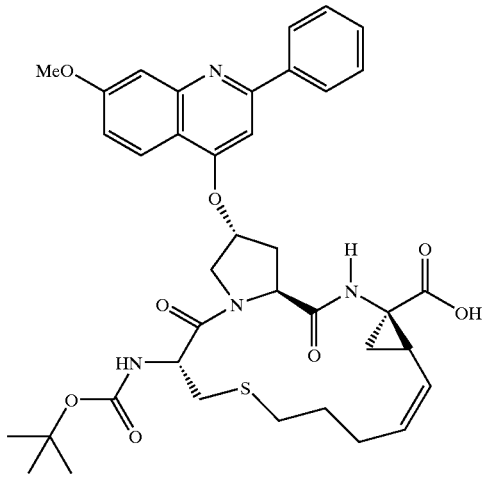

Product of Step 33C

Step 33C) The macrocycle tripeptide ester product of step 33B (149.8 mg, 201 μmol)was dissolved in a mixture of THF(40.1 mL), MeOH(1.9 mL), H$_2$O(0.45 mL) containing LiOH (97 mg, 4.04 mmol) and the resulting mixture was at stirred at room temperature overnight. The reaction was quenched by the addition of aqueous HCl (0.1N) and the resulting mixture was extracted with ethyl acetate. The organic extracts were dried with magnesium sulfate and concentrated in vacuo to provide a crude product mixture that was purified using flash chromotography (ethyl acetate, then 10% MeOH/CH$_2$Cl$_2$ as eluent) to provide the desired macrocycle carboxylic acid (109.3 mg, 76%). $^1$H NMR (500 MHz, DMSO-d$_6$) δ 1.1 (m, 1H), 1.16 (s, 9H), 1.36 (m, 1H), 1.41–1.55 (m, 3H), 1.60 (m, 1H), 1.95 (m, 1H), 2.27 (m, 1H), 2.32–2.43 (m, 2H), 2.45–2.60 (m, 3H), 2.71 (m, 1H), 2.90 (m, 1H), 3.92 (s, 3H), 4.05 (m, 1H), 4.25–4.55 (m, 2H), 5.42–5.70 (m, 3H), 7.10 (m, 1H), 7.19 (m, 1H), 7.32–7.62 (m, 3H), 7.75 (m, 1), 8.04 (m, 1H), 8.24–8.30 (m, 2H), 8.50 (s, 1H). LC-MS (Method H, except gradient time was 2 min., and flow rate was 5 ml/min, retention time: 1.48 min), MS m/z 717 (M$^+$+1).

Step 33D, Preparation of Example 33, Compound 31, (1S, 4R,6S,14S,18R)-7-cis-[4-Cyclopropanesulfonylaminocarbonyl-18-(7-methoxy-2-phenyl-quinolin-4-yloxy)-2,15-dioxo-12-thia-3,16-diazatricyclo[14.3.0.0$^{4,6}$]nonadec-7-en-14-yl]-carbamic acid tert-butyl ester Compound 31

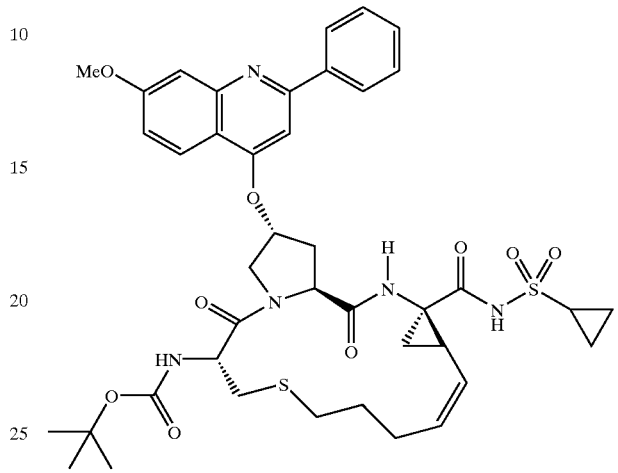

Step 33D) The macrocycle acid product of step 33C (77.9 mg, 109 mmol, 1 eq.) was dissolved in THF (770 μL) and CDI (21.1 mg, 130 mmol, 1.2 eq.) was added. The mixture was then heated to reflux and maintained at that temperature for 2 h. The reaction mixture was then cooled to room temperature, cyclopropylsulfonamide (15.5 mg, 128 mmol, 1.2 eq) and DBU (18.7 uL, 125 mmol, 1.2 eq) were added, and the resulting mixture was stirred at room temperature overnight. LC/MS analysis indicated the product mixture consisted of a mixture of starting material and desired product. The resulting mixture was partitioned between methylene chloride and 1N aqueous HCl, followed by back extraction of the aqueous layer. The combined extracts were dried over magnesium sulfate and concentrated in vacuo. The mixture of starting material and desired product was then resubjected to the above described reaction conditions using identical amounts of reagents. After the duration of the reaction the reaction mixture was worked up as before and then further purified by chromatography (Biotage 12M column, 75% ethyl acetate/hexane) to provide the desired macrocycle sulfonamide, Example 33, Compound 31, (1S, 4R,6S,14S,18R)-7-cis-[4-Cyclopropanesulfonylaminocarbonyl-18-(7-methoxy-2-phenyl-quinolin-4-yloxy)-2,15-dioxo-12-thia-3,16-diazatricyclo[14.3.0.0$^{4,6}$]nonadec-7-en-14-yl]-carbamic acid tert-butyl ester (30.6 mg, 34%). $^1$H NMR (500 MHz, methanol-d$_4$) δ 0.90–1.50 (m, 7H), 1.24 (2, 9H), 1.55 (m, 1H), 2.60–2.67 (m, 2H), 2.83 (m, 1H), 2.15 (m, 1H), 2.30–2.47 (m, 2H), 2.5–2.9 (m, 7H), 3.8 (s, 3H), 4.22 (m, 1H), 4.35–4.41 (m, 2H), 4.7 (m, 1H), 5.38 (m, 1H), 5.48–5.68 (m, 2H), 6.82 (m, 1H), 7.06 (m, 1H), 7.25 (s, 1H), 7.35 (s, 1H), 7.49–7.60 (m, 3H), 8.03–8.15 (m, 3H). LC-MS (Method H, except gradient time was 2 min., flow rate was 5 ml/min, and retention time: 1.48 min), MS m/z 820 (M$^+$+1)

Example 34, Preparation of Compound 32, (1S,4R,6S,14S, 18R)-7-cis-[4-Cyclopropanesulfonylaminocarbonyl-18-(7-methoxy-2-phenyl-quinolin-4-yloxy)-2,12,12,15-tetraoxo-12,16-thia-3,16-diazatricyclo[14.3.0.0$^{4,6}$]nonadec-7-en-14-yl]carbamic acid tert-butyl ester

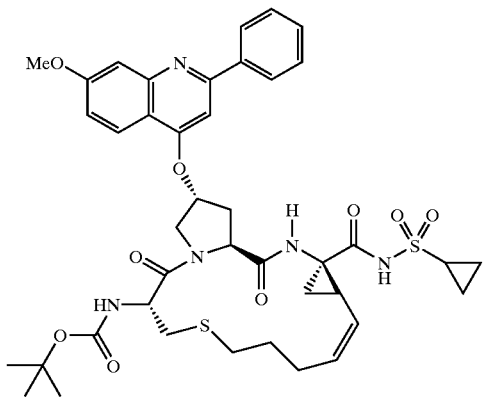

Compound 31
Example 33

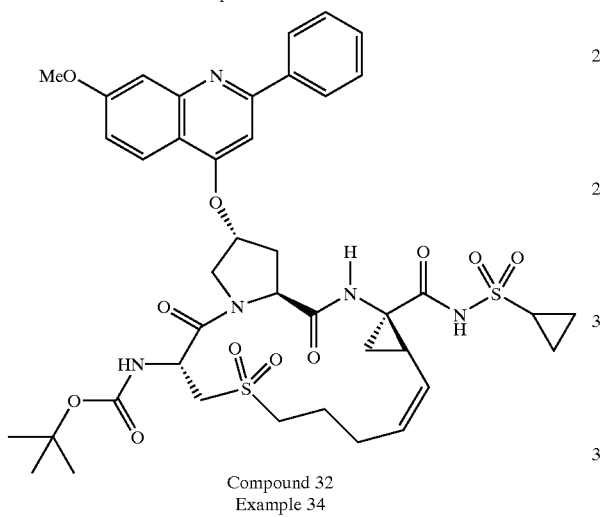

Compound 32
Example 34

Oxone Step) To a solution of Compound 31 (9.5 mg, 11.6 mmole) in methanol (0.276 mL) was added pH 7 buffer (0.093 mL) and the solution was cooled in an ice bath. Oxone (21 mg, 34.8 mmol, 3 eq.) was added and the reaction was equilibrated to room temperature and stirred for two hours. Water was then added to the reaction mixture and the resulting mixture was extracted with three times with ethyl acetate. The combined organic extracts were concentratd in vacuo and the crude product was purified by preparative TLC (Hexane: Ethyl acetate, 1:3 eluent)to provide the desired product Example 34, Compound 32, (1S,4R,6S,14S,18R)-7-cis-[4-Cyclopropanesulfonyl-aminocarbonyl-18-(7-methoxy-2-phenyl-quinolin-4-yloxy)-2,12,12,15-tetraoxo-12,16-thia-3,16-diazatricyclo[14.3.0.0$^{4,6}$]nonadec-7-en-14-yl]carbamic acid tert-butyl ester (9.8 mg, 32%). $^1$H NMR (500 MHz, methanol-d$_4$) δ 0.74–0.94 (m, 3H), 1.0–1.08 (m, 2H), 1.26 (s, 9H), 1.22–1.33 (m, 2H), 1.58 (m, 1H), 1.76–1.82 (m, 2H), 2.04 (m, 1H), 2.17 (m, 1H), 2.32–2.40 (m, 2H), 2.60 (m, 1H), 2.82–2.89 (m, 2H), 3.65–3.78 (m, 2H), 3.95 (s, 3H), 4.38–4.45 (m, 2H), 4.75–4.99 (m, 3H), 5.48–5.62 (m, 3H), 7.14 (m, 1H),7.29 (s, 1H), 7.42 (m, 1H), 7.46–7.58 (m, 3H), 8.06–8.18 (m, 3H). LC-MS (Method H, except gradient time was 2 min, flow rate was 5 ml/min, and retention time: 1.29 min), MS m/z 852 (M$^+$+1).

Example 35, Preparation of Compound 33, (1S,4R,6S,14S,18R)-7-cis-[4-Cyclopropanesulfonylaminocarbonyl-2,15-dioxo-18-(8-trifluoromethylquinol-in-4-yloxy)-3,16-diazatricyclo[14.3.0.04,6]nonadec-7-en-14-yl]-carbamic acid tert-butyl ester

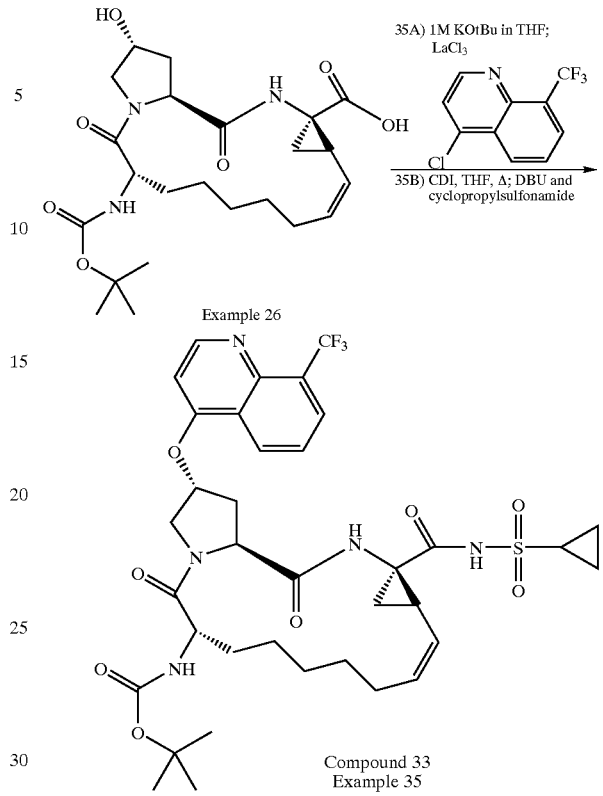

Example 26

Compound 33
Example 35

Steps 35A–B) Compound 33, Example 35, was prepared by analogy using the chemistry described in the preparation of Compound 27 using Example 26 as starting material: Data for Compound 33: $^1$H NMR (500 MHz, CD$_3$OD) δ ppm 1.02 (m, 1H), 1.09 (sr 9H), 1.05–1.60 (m, 10H), 1.64 (dd, J=9.5, 5.5 Hz, 1H), 1.75 (dd, J=8.2, 5.5 Hz, 1H), 1.84 (bs, 2H), 2.43 (q, J=8.5 Hz, 1H), 2.59 (m, 1H), 2.71 (m, 1H), 2.79 (m, 1H), 2.94 (m, 1H), 4.03 (m, 1H), 4.13 (d, J=10.7 Hz, 1H), 4.71 (dd, J=9.6, 7.2 Hz, 1H), 4.88 (m, 1H), 5.11 (t, J=9.3 Hz, 1H), 5.57 (s, 1H), 5.72 (q, J=8.9 Hz, 1H), 7.19 (d, J=5.5 Hz, 1H), 7.60 (t, J=7.6 Hz, 1H), 8.13 (d, J=7.0 Hz, 1H), 8.58 (d, J=8.2 Hz, 1H), 8.84 (d, J=5.2 Hz, 1H). LC-MS (Method J, retention time: 3.09 min), MS m/z 764 (M$^+$+1).

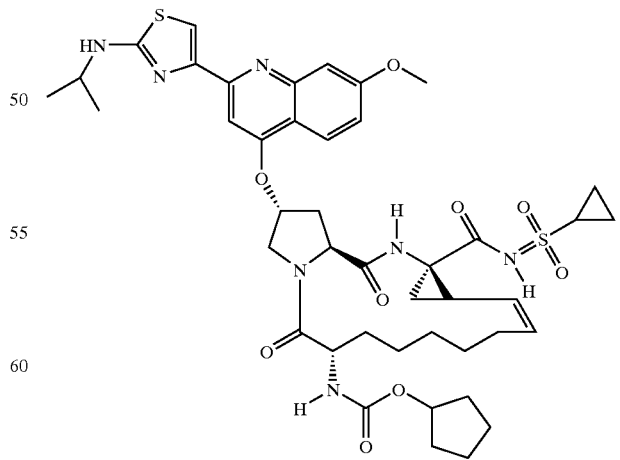

Compound 34
Example 36

Method A: Preparation of Compound 34, Example 36, (1S,4R,6S,14S,18R)-7-cis-{18-[2-(2-Acetylaminothiazol-4-yl)-7-methoxyquinolin-4-yloxy]-4-cyclopropanesulfonylaminocarbonyl-2,15-dioxo-3,16-diazatricyclo-[14.3.0.0^{4,6}]-nonadec-7-en-14-yl}carbamic acid tert-butyl ester was accomplished uing Steps 36A–36N
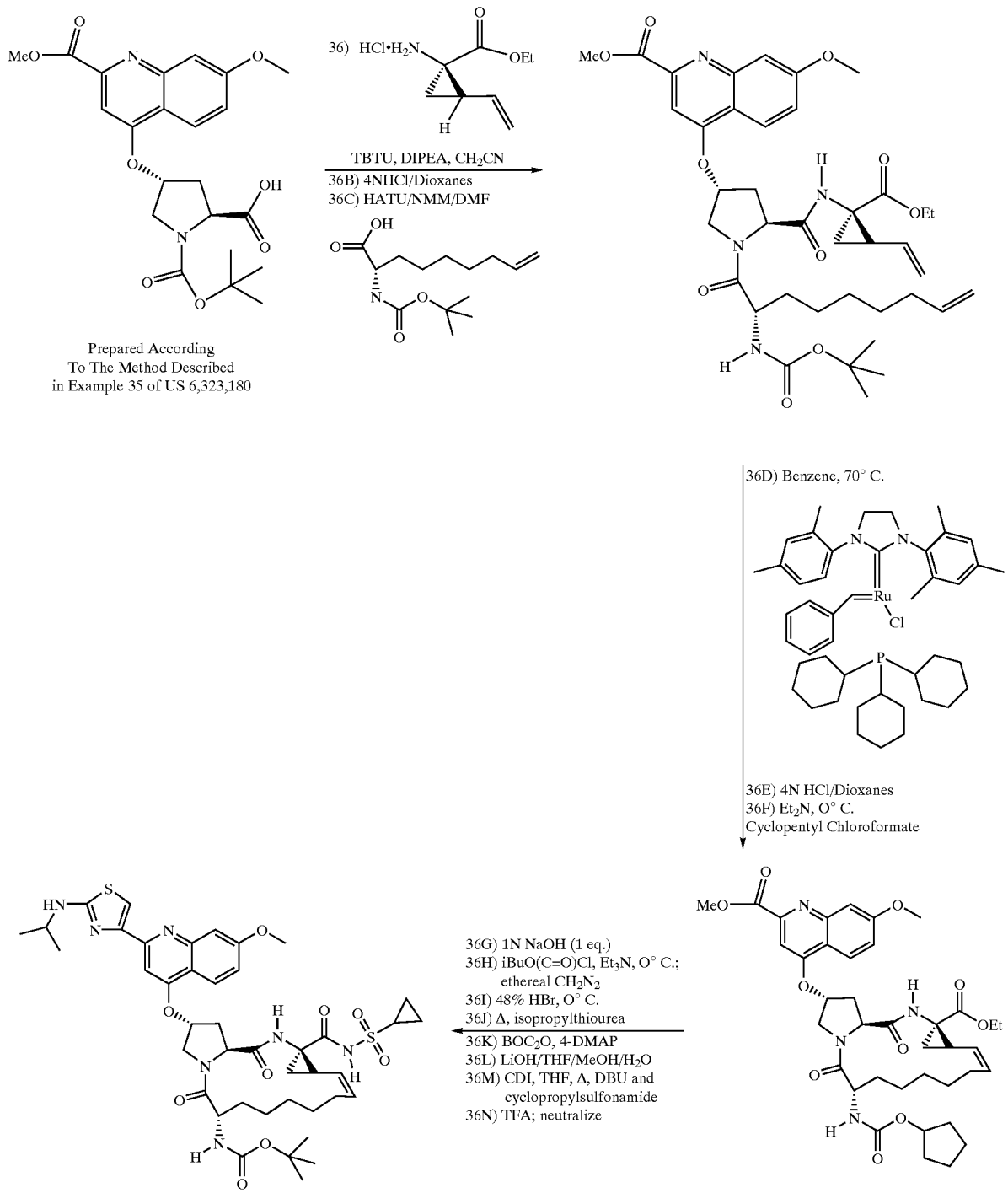

Preparation of 4(R)-(7-Methoxy-2-methoxycarbonylquinolin-4-yloxy)pyrrolidine-1,2(S)-dicarboxylic acid 1-tert-butyl ester

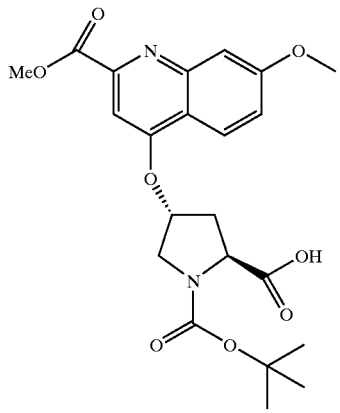

This compound was prepared following the sequences of Example 35 of U.S. Pat. No. 6,323,180.

Step 36A: Preparation of 2(S)-(1(R)-ethoxycarbonyl-2(S)-vinylcyclopropylcarbamoyl)-4(R)-(7-methoxy-2-methoxycarbonylquinolin-4-yloxy)pyrrolidine-1-carboxylic acid tert-butyl ester

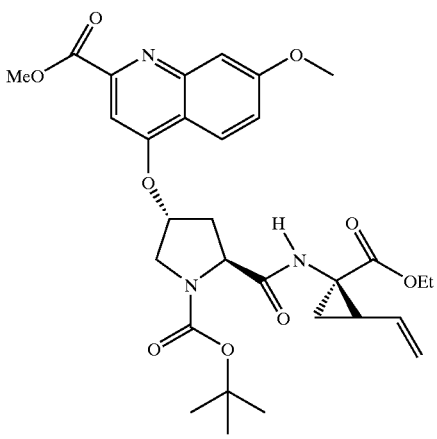

To a solution of (1R,2S)-1-amino-2-vinylcyclopropane carboxylic acid ethyl ester hydrochloride (1.24 g, 6.47 mmol), DIPEA (4.18 mL, 32.35 mmol), and 4(R)-(7-Methoxy-2-methoxycarbonylquinolin-4-yloxy)-pyrrolidine-1,2(S)-dicarboxylic acid 1-tert-butyl ester (2.95 g, 6.61 mmol) in 35 mL of acetonitrile at RT, was added TBTU (2.76 g, 8.59 mmol, purchased from Aldrich). The reaction mixture was stirred at rt under $N_2$ for 14 h, and then concentrated in vacuo. The residue was partitioned between ethyl acetate and sat. aq. $NaHCO_3$ (2×75 mL), dried ($MgSO_4$), and the organics were concentrated in vacuo to give the crude product. Flash chromatography over a Biotage 65M column (eluted with 40%–95% ethyl acetate/hexane) gave 3.45 g (91%): $^1$H NMR (500 MHz, Methanol-$d^4$, rotamers~1/2) δ 1.28 (m, 3H), 1.42 (s, 4H), 1.47 (s, 6H), 1.80 (m, 1H), 2.24 (q, J=8.6 Hz, 1H), 2.48 (m, 1H), 2.74 (m, 1H), 3.94 (m, 2H), 3.99 (s, 3H), 4.07 (s, 3H), 4.20 (m, 2H), 4.45 (m, 1H), 5.15 (m, 1H), 5.33 (m, 1H), 5.47 (s, 1H), 5.81 (m, 1H), 7.31 (m, 1H), 7.52 (s, 1H), 7.56 (d, J=1.5 Hz, 1H), 8.10 (d, J=9 Hz, 1H). LC-MS m/e 588 (retention time: 4.76, method D, except gradient time increased from 2 to 8 min and hold time increased from 1 to 2 min).

Step 36B: Preparation of 2(S)-(1(R)-ethoxycarbonyl-2(S)-vinylcyclopropylcarbamoyl)-4(R)-(7-methoxy-2-methoxycarbonylquinolin-4-yloxy)pyrrolidine dihydrochloride

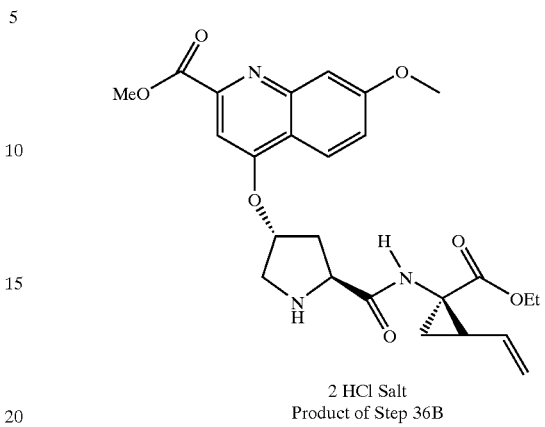

2 HCl Salt
Product of Step 36B

A solution of 3.05 g (5.23 mmol) of 4(R)-(7-Methoxy-2-methoxycarbonylquinolin-4-yloxy)-pyrrolidine-1,2(S)-dicarboxylic acid 1-tert-butyl ester was stirred in 26 mL (116.5 mmol) of 4N HCl in dioxanes but solidified after 10 min. To this mixture was added an additional 26 mL (116.5 mmol) of 4N HCl in dioxanes, the resulting suspension chopped up to allow free stirring and the mixture stirred 3.5 h. The reaction mixture was concentrated and was azeotroped several time with dioxanes (4×100 mL) to afford the titled compound of Step 36B. The resulting solid was then used directly in the next reaction: $^1$H NMR (500 MHz, Methanol-$d^4$) δ 1.25 (t, J=7.0 Hz, 3H) 1.49 (dd, J=9.0, 5.34 Hz, 1H) 1.79 (dd, J=7.6, 5.5 Hz, 1H), 2.27 (q, J=8.6 Hz, 1H), 2.61 (m, 1H), 3.00 (m, 1H), 3.97 (s, 2H), 4.08 (s, 3H), 4.16 (m, 5H), 4.70 (m, 1H), 5.13 (d, J=10.4 Hz, 1H), 5.32 (d, J=17.1 Hz, 1H), 5.78 (m, 1H), 6.01 (s, 1H), 7.58 (m, 1H), 7.70 (s, 1H), 7.91 (s, 1H), 8.55 (d, J=9 Hz, 1H). LC-MS (Method D, retention time: 1.12 min), MS m/z 484 (M$^+$+1).

Step 36C: Preparation of 1-{[1-(2(S)-tert-butoxycarbonylamino-non-8-enoyl)-4-(7-methoxy-2-methoxycarbonylquinolin-4(R)-yloxy)pyrrolidine-2(S)-carbonyl]-1(R)-amino]-2(S)-vinylcyclopropanecarboxylic acid ethyl ester

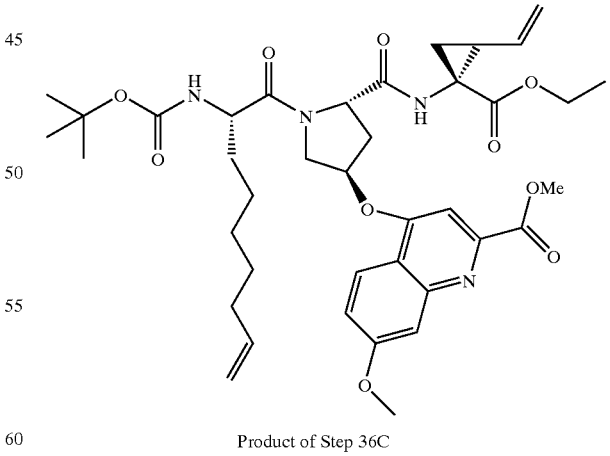

Product of Step 36C

A solution of 2(S)-tert-butoxycarbonyl-amino-8-nonenoic acid (2.13 g, 7.84 mmol, purchased from RSP Amino Acids) dissolved in 18 mL of N,N-dimethylformamide was treated sequentially with 2(S)-(1(R)-ethoxycarbonyl-2(S)-vinylcyclopropylcarbamoyl)-4(R)-(7-methoxy-2-methoxycarbonylquinolin-4-yloxy)pyrrolidine dihydrochloride (the product of step 36C-assumed 5.23 mmol), N-methyl morpholine (4.76 mL, 47 mmol), and HATU (PE biosystems)(2.97 g, 7.84 mmol). The reaction mixture was stirred at rt for 16 h, and then concentrated in vacuo. The residue was partitioned between 80% ethyl acetate/hexanes (400 mL) and water (100 mL). The organic phase was washed with pH 4 buffer (100 mL), sat. aq. NaHCO$_3$ (100 mL), dried (MgSO$_4$), and concentrated in vacuo. The residue was chromatographed over a Biotage 65M column (eluted with 50% to 100% ethyl acetate/hexanes) gave 3.43 g (89%) of the titled product of Step 36C as a foam: $^1$H NMR (500 MHz, Methanol-d$^4$) δ 1.17–1.48 (m, 10H), 1.30 (s, 9H), 1.55 (m, 1H), 1.64 (m, 1H), 1.76 (dd, J=7.9, 5.2 Hz, 1H), 2.03 (q, J=7.2 Hz, 2H), 2.28 (q, J=8.8 Hz, 1H), 2.44 (m, 1H), 2.75 (dd, J=14.3, 7.9 Hz, 1H), 3.98 (s, 3H), 4.07 (s, 3H), 4.15 (m, 4H), 4.51 (d, J=11.9 Hz, 1H), 4.68 (m, 1H), 4.93 (d, J=10.4 Hz, 1H), 4.99 (dd, J=17.1, 1.5 Hz, 1H), 5.12 (dd, J=10.4, 1.8 Hz, 1H), 5.31 (dd, J=17.1, 1.5 Hz, 1H), 5.57 (s, 1H), 5.80 (m, 2H), 7.26 (dd, J=9.2, 2.4 Hz, 1H), 7.51 (m, 1H), 7.58 (s, 1H), 8.17 (d, J=9.2 Hz, 1H). LC-MS (Method D, retention time: 1.87 min), MS m/z 737 (M$^+$+1).

Step 36D: Preparation of (1S,4R,6S,14S,18R)-7-cis-14-tert-Butoxycarbonylamino-18-(7-methoxy-2-methoxycarbonylquinolin-4-yloxy)-2,15-dioxo-3,16-diazatricyclo-[14.3.0.0$^{4,6}$]nonadec-7-ene-4-carboxylic acid ethyl ester

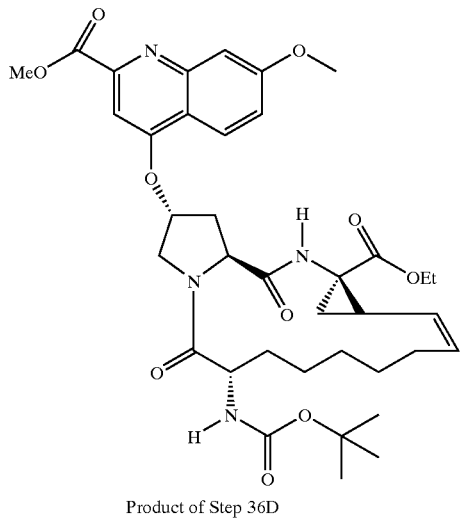

Product of Step 36D

To a solution of 1-{[1-(2(S)-tert-butoxycarbonylamino-non-8-enoyl)-4-(7-methoxy-2-carbomethoxyquinolin-4(R)-yloxy)-pyrrolidine-2(S)-carbonyl]-1(R)-amino]-2(S)-vinylcyclopropanecarboxylic acid ethyl ester (1.65 g, 2.24 mmol) in 1.4L of Argon degassed benzene, was added 200 mg of Tricyclohexylphosphine [1,3-bis(2,4,6-trimethyl-phenyl)-4,5-dihydroimidazol-2-ylidene]-[benzylidine] ruthenium(IV)dichloride catalyst, the mixture was degassed under Ar and heated to reflux for 3 h. The reaction mixture was cooled to rt, the mixture degassed again, 240 mg portion of Tricyclohexylphosphine [1,3-bis(2,4,6-trimethyl-phenyl)-4,5-dihydroimidazol-2-ylidene][benzylidine] ruthenium(IV)dichloride catalyst was added, and the mixture was heated to reflux for 3 h. The entire reaction sequence was repeated again using the exact same conditions. The combined dark brown solutions (resulting from 2×1.65 g metatheses reactions of 1-{[1-(2(S)-tert-butoxycarbonylamino-non-8-enoyl)-4-(7-methoxy-2-carbomethoxyquinolin-4(R)-yloxy)-pyrrolidine-2(S)-carbonyl]-1(R)-amino]-2(S)-vinylcyclopropanecarboxylic acid ethyl ester) were, concentrated in vacuo, purified over a Biotage 65 M column (eluted with 50% to 100% EtOAc in hexanes) to supply 2.00 g (63% yield,>99% pure) of the titled compound of Step 36D as a foam which solidified to a glass: $^1$H NMR (500 MHz, Methanol-d$^4$) δ 1.16–1.59 (m, 7H), 1.20 (s, 9H), 1.26 (t, J=7.0 Hz, 3H), 1.61 (dd, J=8.4, 5.04 Hz, 1H), 1.67 (dd, J=9.6, 5.0 Hz, 1H), 1.80 (m, 1H), 1.95 (m, 1H), 2.34 (q, J=8.8 Hz, 1H), 2.57 (m, 2H), 2.70 (m, 1H), 3.97 (s, 3H), 4.06 (s, 3H), 4.01–4.25 (m, 4H), 4.67 (t, J=8.2 Hz, 1H), 4.74 (d, J=11.3 Hz, 1H), 5.37 (m, 1H), 5.60 (m, 2H), 7.18 (d, J=9.2 Hz, 1H), 7.47 (s, 1H), 7.53 (s, 1H), 8.18 (d, J=9.2 Hz, 1H). LC-MS (Method D except gradient time increased from 2 to 4 min, retention time: 3.03 min), MS m/z 709 (M$^+$+1).

Step 36E: Preparation of (1S,4R,6S,14S,18R)-7-cis-14-Amino-18-(7-methoxy-2-methoxycarbonylquinolin-4-yloxy)-2,15-dioxo-3,16-diaza-tricyclo[14.3.0.0$^{4,6}$]nonadec-7-ene-4-carboxylic acid ethyl ester dihydrochloride

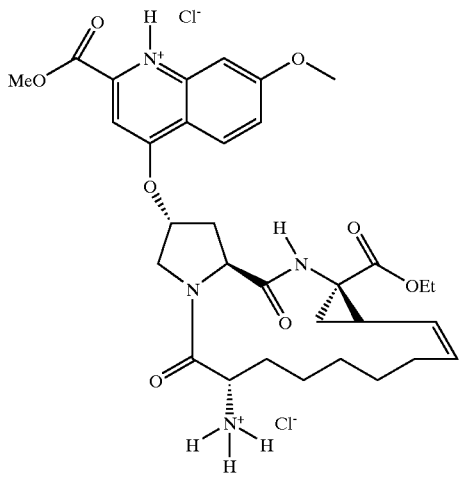

Product of Step 36E

A solution of 1.60 g (2.26 mmol) of (1S,4R,6S,14S,18R)-7-cis-14-tert-Butoxycarbonylamino-18-(7-methoxy-2-methoxycarbonylquinolin-4-yloxy)-2,15-dioxo-3,16-diazatricyclo-[14.3.0.0$^{4,6}$]nonadec-7-ene-4-carboxylic acid ethyl ester (product of step 36D) in 17 mL (68 mmol) of 4N HCl/dioxanes was stirred. After 20 min. the reaction mixture solidified and 10 mL of CH$_2$Cl$_2$ was added. The resulting solid suspension was then chopped up to aid stirring, which proceeded for an additional 1 h. After this time period the reaction was still not complete, so an additional portion of 4 mL (16 mmol) of 4N HCl/dioxanes was added and the mixture was stirred for an additional 1 h. The reaction mixture was then concentrated in vacuo to provide the product of Step 36E as a solid which was taken directly into step 36F: $^1$H NMR (500 MHz, Methanol-d$^4$) δ 1.27 (m, 3H), 1.27–1.64 (m, 7H), 1.94 (m, 2H), 2.16 (m, 1H), 2.28 (q, J=9.2 Hz, 1H), 2.31 (m, 1H), 2.72 (m, 1H), 2.84 (m, 1H), 4.10 (m, 3H), 4.16 (m, 3H), 4.22 (s, 3H), 4.44 (m, 2H), 4.84 (m, 1H), 5.65 (m, 1H), 5.99 (s, 1H), 7.58 (dd, J=9.2, 2.1 Hz, 1H), 7.73 (d, J=2.1 Hz, 1H), 7.95 (s, 1H), 8.45 (d, J=9.2 Hz, 1H). LC-MS (Method D except gradient time increased from 2 to 4 min, retention time: 2.12 min), MS m/z 609 (M$^+$+1)

Step 36F: Preparation of (1S,4R,6S,14S,18R)-7-cis-14-Cyclopentyloxycarbonylamino-18-(7-methoxy-2-methoxycarbonylquinolin-4-yloxy)-2,15-dioxo-3,16-diazatricyclo[14.3.0.0$^{4,6}$]nonadec-7-ene-4-carboxylic acid ethyl ester

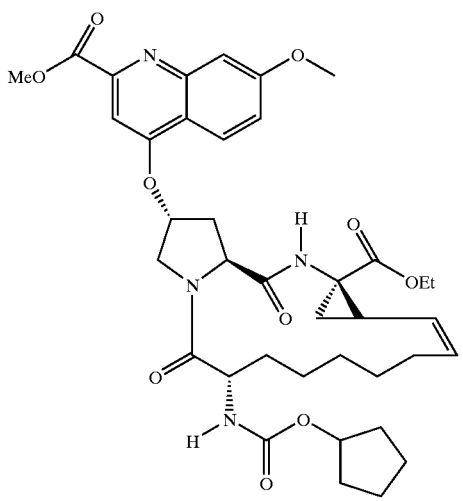

Product of Step 36F

To a slurry of (1S,4R,6S,14S,18R)-7-cis-14-Amino-18-(7-methoxy-2-methoxycarbonylquinolin-4-yloxy)-2,15-dioxo-3,16-diaza-tricyclo[14.3.0.0$^{4,6}$]nonadec-7-ene-4-carboxylic acid ethyl ester dihydrochloride (product from step 36E-assumed 2.26 mmol) in 15 mL of THF cooled to 0° C., was added 2 mL of Et$_3$N, followed by 5.7 mL (4.52 mmol) of freshly prepared 0.8M cyclopentyl chloroformate (prepared as described above). The mixture was stirred for 30 min then partitioned between 125 mL of ethyl acetate and 40 mL of a saturated aqueous NaHCO$_3$ solution. The ethyl acetate layer was dried (MgSO$_4$), concentrated and the crude residue chromatographed over a biotage 65M column (eluted with 0% to 100% CH$_2$Cl$_2$/EtOAc) to afford 1.40 g (86%) of the product of Step 36F as a white foam: $^1$H NMR (500 MHz, Methanol-d$^4$) δ 1.23 (t, J=7.2 Hz, 3H), 1.32–1.69 (m, 17H), 1.79 (m, 1H), 1.93 (m, 1H), 2.31 (q, J=9.2 Hz, 1H), 2.52 (m, 2H), 2.67 (m, 1H), 3.94 (s, 3H), 4.03 (m, 1H), 4.04 (s, 3H), 4.11 (m, 2H), 4.23 (dd, J=10.4, 2.75 Hz, 1H), 4.54 (m, 1H), 4.66 (m, 2H), 5.33 (t, J=9.6 Hz, 1H), 5.58 (m, 2H), 7.17 (dd, J=9.2, 2 Hz, 1H), 7.45 (d, J=2 Hz, 1H), 7.52 (s, 1H), 8.15 (d, J=9.2 Hz, 1H). LC-MS (Method D except gradient time increased from 2 to 4 min, retention time: 3.12 min), MS m/z 721 (M$^+$+1)

Step 36G: Preparation of (1S,4R,6S,14S,18R)-7-cis-18-(2-Carboxy-7-methoxyquinolin-4-yloxy)-14-cyclopentyloxycarbonylamino-2,15-dioxo-3,16-diazatricyclo[14.3.0.0$^{4,6}$]-nonadec-7-ene-4-carboxylic acid ethyl ester sodium salt

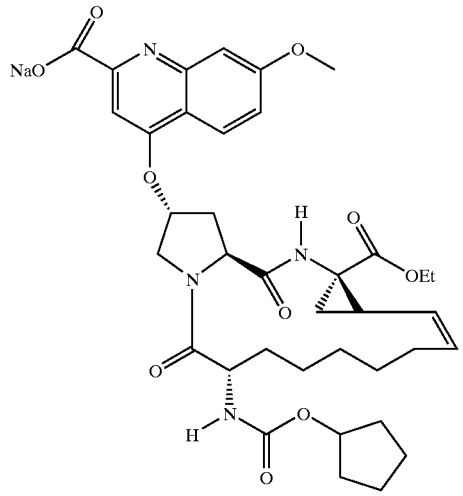

Product of Step 36G

To a solution of 1.37 g (1.90 mmol) of (1S,4R,6S,14S,18R)-7-cis-14-Cyclopentyloxycarbonylamino-18-(7-methoxy-2-methoxy-carbonylquinolin-4-yloxy)-2,15-dioxo-3,16-diazatricyclo[14.3.0.0$^{4,6}$]nonadec-7-ene-4-carboxylic acid ethyl ester (product from step 36G) in 23 mL of 2:1:1 THF/MeOH/H$_2$O was added 2.1 mL (2.1 mmol) of 1M aqueous NaOH. The solution was stirred 60 min at room temperature, glacial AcOH added dropwise until the solution pH was neutral and then the mixture concentrated in vacuo. The solid residue was dissolved in 100 mL of 30% THF/CH$_2$Cl$_2$, dried (MgSO$_4$), and concentrated to afford approximately 1.90 mmol of the product of Step 36G which was taken directly into the next reaction (Step 36H): $^1$H NMR (500 MHz, Methanol-d$^4$) δ 1.22 (t, J=7.0 Hz, 3H), 1.25–1.71 (m, 15H), 1.79 (m, 1H), 1.87 (m, 2H), 1.94 (m, 1H), 2.30 (q, J=9.0 Hz, 1H), 2.50 (m, 2H), 2.72 (m, 1H), 3.95 (s, 3H), 4.10 (m, 3H), 4.26 (m, 1H), 4.64 (m, 2H), 4.70 (d, J=11.3 Hz, 1H), 5.34 (t, J=9.6 Hz, 1H), 5.59 (m, 2H), 7.16 (d, J=8.4 Hz, 1H), 7.52 (s, 1H), 7.56 (s, 1H), 8.20 (d, J=8.4 Hz, 1H). LC-MS (Method D except gradient time increased from 2 to 4 min, retention time: 3.07 min), MS m/z 707 (M$^+$+1).

Step 36H: Preparation of (1S,4R,6S,14S,18R)-7-cis-14-Cyclopentyloxycarbonylamino-18-[2-(2-diazoacetyl)-7-methoxyquinolin-4-yloxy]-2,15-dioxo-3,16-diazatricyclo-[14.3.0.0$^{4,6}$]nonadec-7-ene-4-carboxylic acid ethyl ester

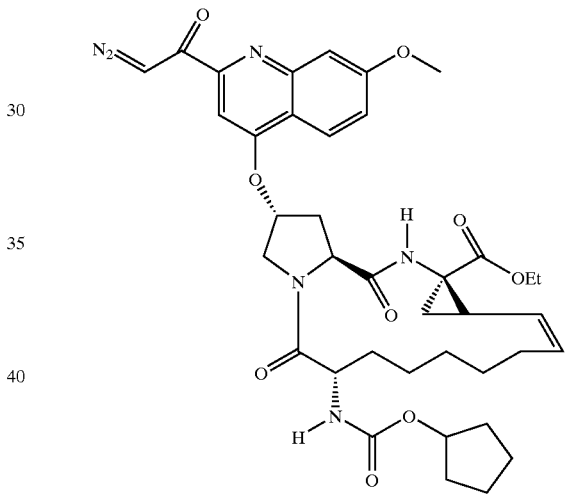

Product of Step 36H

To a solution of (1S,4R,6S,14S,18R)-7-cis-18-(2-Carboxy-7-methoxyquinolin-4-yloxy)-14-cyclopentyloxycarbonylamino-2,15-dioxo-3,16-diazatricyclo[14.3.0.0$^{4,6}$]-nonadec-7-ene-4-carboxylic acid ethyl ester sodium salt (1.90 mmol, product from step 36G) in 12 mL of THF cooled to 0° C., was added 0.37 mL (2.66 mmol) of Et$_3$N, followed by 0.35 mL (2.66 mmol) of isobutylchloroformate. The solution was stirred 80 min, and an ethereal solution of approximately 40 mL of diazomethane added [prepared by adding 2.18 g (14.89 mmol) of 1-methyl-3-nitro-1-nitrosoguanidine in small portions to a rapidly stirring solution 40 mL of Et$_2$O and 30 mL of 40% aqueous KOH solution and then decanting off the CH$_2$N$_2$/Et$_2$O layer into the mixed anhydride reaction mixture]. The mixture was then stirred 30 min at 0° C., 2 h at room temperature, and then concentrated in vacuo. The residue was dissolved in 200 mL of EtOAc, washed with saturated aqueous NaHCO$_3$ (2×75 mL), brine (2×75 mL), dried (MgSO$_4$), and concentrated to afford approximately 1.20 g (1.64 mmol, 86% over two steps) of the product of Step 36H which was taken directly into the next reaction (Step 36I): ¹H NMR (500 MHz, Methanol-d⁴)) 1.23 (t, J=7 Hz, 3H), 1.30–1.73 (m, 17H), 1.79 (m, 1H), 1.94 (m, 1H), 2.31 (q, J=9 Hz, 1H), 2.53 (m, 2H), 2.65 (m, 1H), 3.94 (s, 3H), 4.07 (m, 3H), 4.25 (m, 1H), 4.63 (m, 3H), 5.33 (t, J=9.6 Hz, 1H), 5.52 (s, 1H), 5.58 (m, 1H), 7.15 (dd, J=9.2, 2 Hz, 1H), 7.37 (s, 1H), 7.45 (s, 1H), 8.14 (d, J=9.2 Hz, 1H). LC-MS (Method D except gradient time increased from 2 to 4 min, retention time: 3.31 min), MS m/z 731 (M⁺+1).

Step 36I: Preparation of (1S,4R,6S,14S,18R)-7-cis-18-[2-(2-Bromoacetyl)-7-methoxyquinolin-4-yloxy]-14-cyclopentyloxycarbonylamino-2,15-dioxo-3,16-diazatricyclo-[14.3.0.0⁴,⁶]nonadec-7-ene-4-carboxylic acid ethyl ester

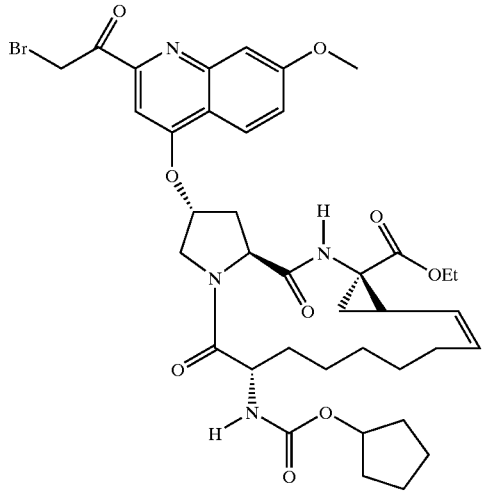

Product of Step 36I

To a solution of 1.20 g (1.64 mmol) of (1S,4R,6S,14S,18R)-7-cis-14-Cyclopentyloxycarbonylamino-18-[2-(2-diazoacetyl)-7-methoxyquinolin-4-yloxy]-2,15-dioxo-3,16-diazatricyclo-[14.3.0.0⁴,⁶]nonadec-7-ene-4-carboxylic acid ethyl ester (product of step 36H) in 17 mL of THF cooled to 0° C., was added 1.25 mL of 48% aqueous HBr. The mixture was stirred 70 min, diluted with 250 mL of EtOAc, washed with saturated aqueous NaHCO₃ (2×75 mL), brine (2×75 mL), dried (MgSO₄), and concentrated to afford approximately 1.18 g (99%) of the product of step 36I as a yellow foam. The material was taken directly into the next reaction (step 36J) without further purification: ¹H NMR (500 MHz, CDCl₃) 1.20–1.82 (m, 19H), 1.88 (m, 2H), 2.19 (m, 3H), 2.38 (m, 1H), 3.06 (m, 1H), 3.97 (s, 3H), 4.13 (m, 4H), 4.57 (m, 1H), 4.93 (m, 2H), 5.01 (m, 2H), 5.25 (m, 1H), 5.38 (s, 1H), 5.52 (m, 1H), 7.22 (dd, J=9.2, 2 Hz, 1H), 7.35 (s, 1H), 7.40 (s, 1H), 8.08 (d, J=9.2 Hz, 1H). LRMS m/z (M+H)⁺ 785.3.

Step 36J: Preparation of (1S,4R,6S,14S,18R)-7-cis-14-Cyclopentyloxycarbonylamino-18-[2-(2-isopropylaminothiazol-4-yl)-7-methoxy-quinolin-4-yloxy]-2,15-dioxo-3,16-diazatricyclo[14.3.0.0⁴,⁶]nonadec-7-ene-4-carboxylic acid ethyl ester

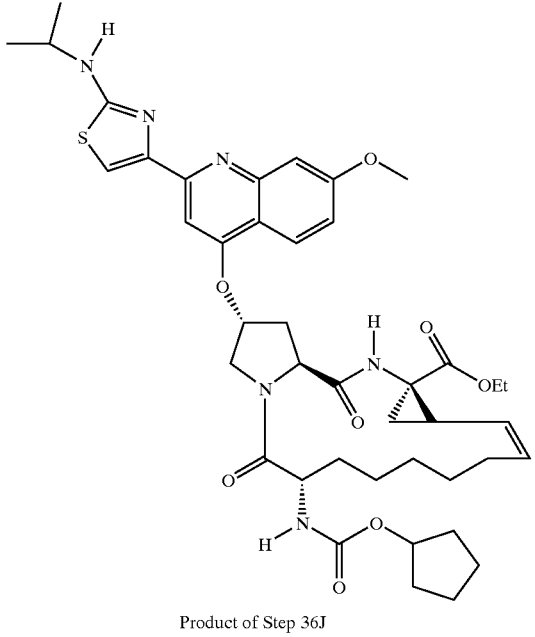

Product of Step 36J

A solution of 1.18 g (1.62 mmol) of (1S,4R,6S,14S,18R)-7-cis-18-[2-(2-Bromoacetyl)-7-methoxyquinolin-4-yloxy]-14-cyclopentyloxycarbonylamino-2,15-dioxo-3,16-diazatricyclo[14.3.0.0⁴,⁶]nonadec-7-ene-4-carboxylic acid ethyl ester (product of step 36I) and 382 mg (3.23 mmol) of isopropyl thiourea in 10 mL of isopropanol was heated to 80° C. for 1.5 h, cooled to RT, and concentrated in vacuo. The residue was diluted with 250 mL of EtOAc, washed with saturated aqueous NaHCO₃ (2×75 mL), brine (2×75 mL), dried (MgSO₄), and concentrated in vacuo. The crude residue was chromatographed over a biotage 65M column (eluted with 0% to 15% CH₂Cl₂/MeOH) to afford the desired product contaminated with isopropyl thiourea (~1.2 grams). The residue was then dissolved in a total volume of 26 mL of 75% DMSO/MeOH and purified by preparative HPLC by injection thirteen times (13×2 mL), afterwhich, an extractive purification was undertaken to isolate 900 mg (1.12 mmol, 69.4% yield) of the product from step 36J from the combined HPLC fractions: Column Xterra 30×100 mm S5, 50% to 100% Solvent B/A for 10 min gradient, hold time 2 min; where Solvent A is 10% MeOH/90% H₂O with 0.1% TFA, Solvent B is 90% MeOH/10% H₂O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined EtOAc extracts were dried (MgSO₄) and concentrated in vacuo to isolate the pure product: ¹H NMR (500 MHz, Methanol-d⁴) δ 1.22 (t, J=7.0 Hz, 3H), 1.25–1.73 (m, 16H), 1.31 (d, J=6.41 Hz, 6H), 1.80 (m, 1H), 1.98 (m, 1H), 2.31 (q, J=8.8 Hz, 1H), 2.50 (m, 2H), 2.69 (dd, J=13, 8 Hz, 1H), 3.93 (s, 3H), 4.07 (m, 5H), 4.29 (m, 1H), 4.67 (m, 3H), 5.33 (t, J=9.5 Hz, 1H), 5.52 (s, 1H), 5.58 (m, 1H), 7.05 (d, J=9 Hz, 1H), 7.37 (d, J=2 Hz, 1H), 7.48 (s, 1H), 7.51 (s, 1H), 8.10 (d, J=9 Hz, 1H). LC-MS (Method D except gradient time increased from 2 to 4 min, retention time: 3.33 min), MS m/z 803 (M⁺+1).

Method A Step 36K: Preparation of (1S,4R,6S,14S,18R)-7-cis-18-{2-[2-(tert-Butoxycarbonylisopropylamino)thiazol-4-yl]-7-methoxy-quinolin-4-yloxy}-14-cyclopentyloxycarbonylamino-2,15-dioxo-3,16- diazatricyclo-[14.3.0.0$^{4,6}$]nonadec-7-ene-4-carboxylic acid ethyl ester

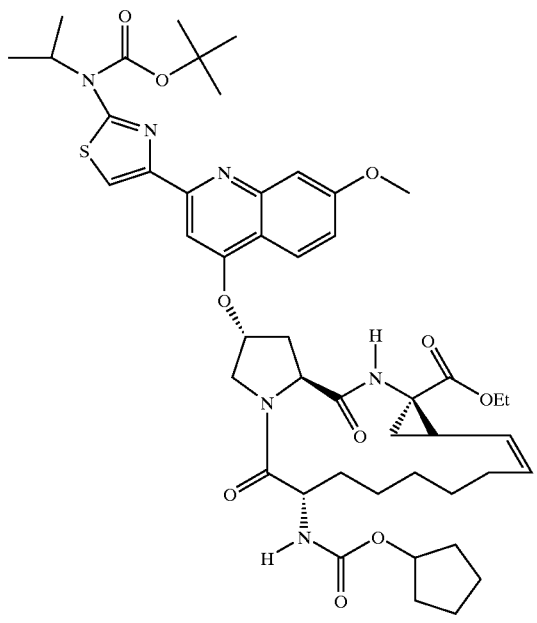

Product of Method A Step 36K

To a solution of 106 mg (0.132 mmol) of (1S,4R,6S,14S, 18R)-7-cis-14-Cyclopentyloxycarbonylamino-18-[2-(2-isopropylaminothiazol-4-yl)-7-methoxyquinolin-4-yloxy]-2,15-dioxo-3,16-diazatricyclo[14.3.0.0$^{4,6}$]nonadec-7-ene-4-carboxylic acid ethyl ester (product of step 36J), 0.043 mL (0.311 mmol) of Et$_3$N, and 3.5 mg (0.00019 mmol) of 4-DMAP in 1 mL of acetonitrile, was added 54 mg (0.245 mmol) of (BOC)$_2$O, and the mixture stirred for 3 h at RT. The residue was then diluted with MeOH until a total volume of 4 mL was obtained and the mixture purified by preparative HPLC using two injections (2×2 mL), afterwhich, an extractive purification was undertaken to isolate 22 mg (21%) of recovered (1S,4R,6S,14S,18R)-7-cis-14-Cyclopentyloxycarbonylamino-18-[2-(2-isopropylaminothiazol-4-yl)-7-methoxyquinolin-4-yloxy]-2,15-dioxo-3,16-diazatricyclo[14.3.0.0$^{4,6}$]nonadec-7-ene-4-carboxylic acid ethyl ester (product of step 36J) and 60 mg (64% yield based on recovered SM) of the desired product from step 36K via Method A from the respective combined HPLC fractions. Conditions: Column Xterra 30×100 mm S5, 45% to 100% Solvent B/A for 18 min gradient, hold time 4 min; where Solvent A is 10% MeOH/90% H$_2$O with 0.1% TFA, Solvent B is 90% MeOH/10% H$_2$O with 0.1% TFA and flow rate is 30 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined EtOAc extracts were dried (MgSO$_4$) and concentrated in vacuo to isolate the respective compounds: $^1$H NMR (500 MHz, Methanol-d$^4$) δ 1.25 (t, J=7.2 Hz, 3H), 1.28–1.74 (m, 23H), 1.65 (s, 9H), 1.82 (m, 1H), 1.98 (m, 1H), 2.33 (q, J=8.9 Hz, 1H), 2.51 (m, 1H), 2.60 (m, 1H), 2.72 (m, 1H), 3.96 (s, 3H), 4.08 (m, 4H), 4.28 (d, J=9.5 Hz, 1H), 4.70 (m, 2H), 5.36 (m, 1H), 5.61 (m, 3H), 7.12 (d, J=9.2 Hz, 1H), 7.46 (s, 1H), 7.60 (s, 1H), 8.17 (d, J=9.2 Hz, 1H), 8.22 (s, 1H). LC (Method D except gradient time increased from 2 to 4 min, retention time: 3.69 min).

Method A Step 36L: Preparation of (1S,4R,6S,14S,18R)-7-cis-18-{2-[2-(tert-Butoxycarbonylisopropylamino)thiazol-4-yl]-7-methoxyquinolin-4-yloxy}-14-cyclopentyloxycarbonylamino-2,15-dioxo-3,16-diazatricyclo-[14.3.0.0$^{4,6}$]nonadec-7-ene-4-carboxylic acid

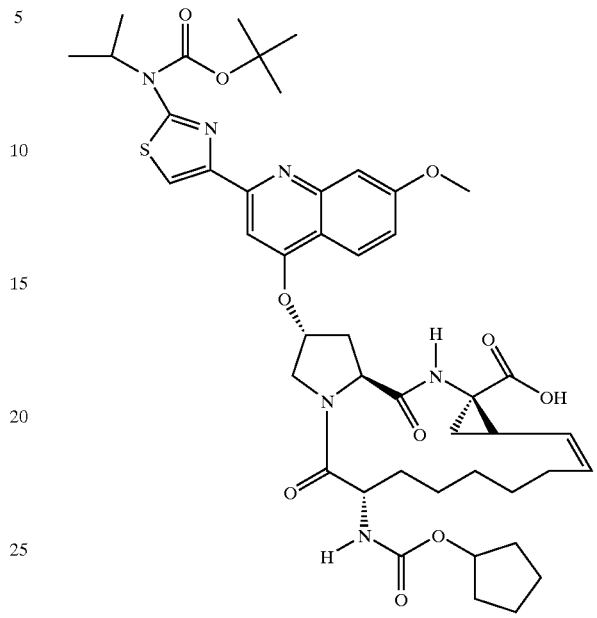

Product of Method A Step 36L

To a solution of 60 mg (0.066 mmol) of (1S, 4R,6S,14S, 18R)-7-cis-18-{2-[2-(tert-Butoxycarbonylisopropylamino)thiazol-4-yl]-7-methoxyquinolin-4-yloxy}-14-cyclopentyloxy-carbonylamino-2,15-dioxo-3,16-diazatricyclo-[14.3.0.0$^{4,6}$]nonadec-7-ene-4-carboxylic acid ethyl ester (product of step 36K, Method A) in 6.9 mL of 2:1 THF/MeOH, was added a solution of 25 mg (1.04 mmol) of LiOH in 2.3 mL of H$_2$O. The mixture was stirred for two days, the pH of the solution adjusted to neutral by the dropwise addition of 3N aqueous HCl solution, and the MeOH concentrated in vacuo. The solution was adjusted to pH 4 by the dropwise addition of 3N aqueous HCl solution and was extracted into EtOAc (3×25 mL). The combined organic layers were dried (MgSO$_4$), concentrated in vacuo. The residue was then diluted with 4 mL of MeOH and the mixture purified by preparative HPLC using two injections (2×2 mL), afterwhich, an extractive purification was undertaken to isolate 40 mg (69% yield) of the Method A product from step 36L from the respective combined HPLC fractions. HPLC/Extractive Workup Procedure: Column Xterra 30×100 mm S5, 50% to 90% Solvent B/A for 25 min gradient, hold time 3 min; where Solvent A is 10% MeOH/90% H$_2$O with 0.1% TFA, Solvent B is 90% MeOH/10% H$_2$O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined EtOAc extracts were dried (MgSO$_4$) and concentrated in vacuo to isolate the product of step 36L: LC-MS (Method E except gradient time increased from 2 to 4 min, retention time: 3.77 min), MS m/z 875 (M$^+$+1). A total of 25 mg was taken directly into Step 36M).

Method A Steps 36M–36N: Preparation of Compound 34, Example 36, (1S,4R,6S,14S,18R)-7-cis-{4-Cyclopropaneulfonylaminocarbonyl-18-[2-(2-isopropylaminothiazol-4-yl)-7-methoxyquinolin-4-yloxy]-

2,15-dioxo-3,16-diazaricyclo-[14.3.0.0$^{4,6}$]nonadec-7-en-14-yl}carbamic acid cyclopentyl ester, from the Method A Product of Step 36L Compound 34

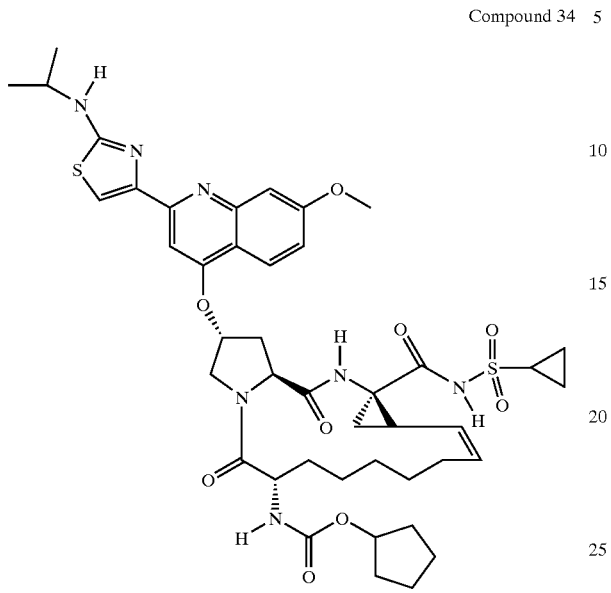

To a solution of 25 mg (28.5 mmol) of the macrocycle acid product of step 36L, (1S,4R,6S,14S,18R)-7-cis-18-{2-[2-(tert-butoxycarbonylisopropylamino)thiazol-4-yl]-7-methoxyquinolin-4-yloxy}-14-cyclopentyloxycarbonylamino-2,15-dioxo-3,16-diazatricyclo[14.3.0.0$^{4,6}$]nonadec-7-ene-4-carboxylic acid, was dissolved in THF (1 mL) and CDI (9 mg, 57 mmol, 2 eq.) was added. The mixture was then heated to 60° C. for 45 min. The reaction mixture was then cooled to room temperature, cyclopropylsulfonamide (7 mg, 57 mmol, 2 eq) and DBU (9 mg, 57 mmol, 2 eq) were added, and the resulting mixture was stirred at room temperature overnight. The resulting mixture was partitioned between EtOAc and water, followed by back extraction of the aqueous layer. The combined extracts were dried over magnesium sulfate and concentrated in vacuo. This crude material of step 36M was reacted with 3 mL of 67% TFA/CH$_2$Cl$_2$ for 3 h, concentrated in vacuo, and the residue dissolved in 4 mL of MeOH. This solution was purified by preparative HPLC using two injections (2×2 mL), afterwhich, an extractive purification was undertaken to isolate 11 mg of recovered carboxylic acid precursor, followed by 14 mg (56% yield, but 79% based on recovered carboxylic acid) of the product from step 36N (Method A), Compound 34, Example 36, from the respective combined HPLC fractions. HPLC/Extractive Workup Procedure: Column Xterra 30×75 mm S5, 40% to 100% Solvent B/A for 30 min gradient, hold time 2 min; where Solvent A is 10% MeOH/90% H$_2$O with 0.1% TFA, Solvent B is 90% MeOH/10% H$_2$O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAC. The combined EtOAc extracts were dried (MgSO$_4$) and concentrated in vacuo to isolate compound 34: For data, see aditional Method B Preparation of Compound 34, Example 36 (Method B, Step 34M).

Method B (Steps 36L–36M): Preparation of Compound 34, Example 36, (1S,4R,6S,14S,18R)-7-cis-{4-Cyclopropanesulfonylaminocarbonyl-18-[2-(2-isopropylaminothiazol-4-yl)-7-methoxy-quinolin-4-yloxy]-2,15-dioxo-3,16-diazatricyclo[14.3.0.0$^{4,6}$]nonadec-7-en-14-yl}carbamic acid cyclopentyl ester, from the Method a Product of Step 36J

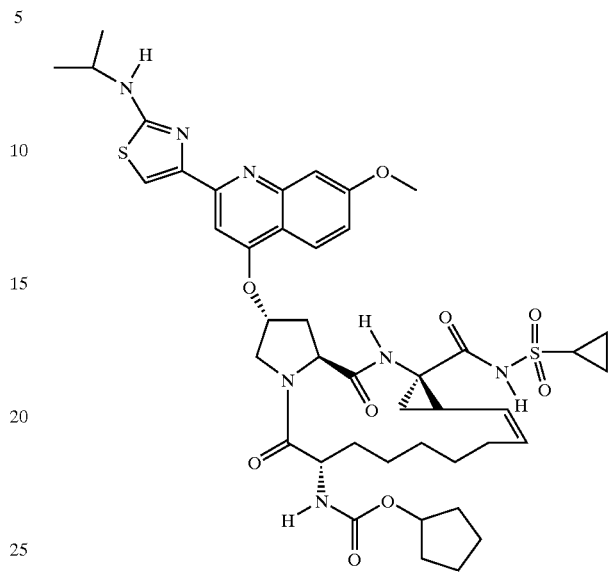

Method A Prep. of Compound 354, Example 36

Method B Step 36L: Preparation of (1S,4R,6S,14S,18R)-7-cis-14-Cyclopentyloxycarbonylamino-18-[2-(2-isopropylaminothiazol-4-yl)-7-methoxy-quinolin-4-yloxy]-2,15-dioxo-3,16-diaza-tricyclo[14.3.0.0$^{4,6}$]nonadec-7-ene-4-carboxylic acid from the Method a Product of Step 36J

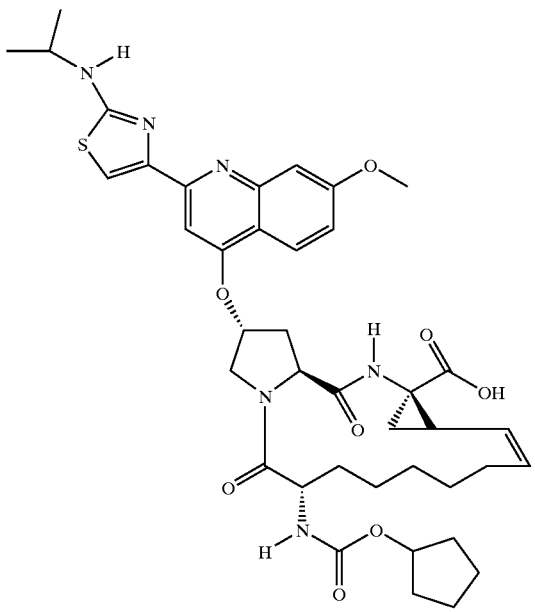

Product of Method B Step 36L

To a solution of 695 mg (0.866 mmol) of (1S,4R,6S,14S,18R)-7-cis-(1S,4R,6S,14S,18R)-7-cis-14-Cyclopentyloxycarbonylamino-18-[2-(2-isopropylaminothiazol-4-yl)-7-methoxyquinolin-4-yloxy]-2,15-dioxo-3,16-diaza-tricyclo[14.3.0.0$^{4,6}$]nonadec-7-ene-4-carboxylic acid ethyl ester (Method A product of step 36J) in a solution containing THF (57 mL), MeOH (14 mL), was added a solution of 311 mg (13 mmol) of LiOH in H$_2$O (20 mL). The mixture was stirred for 14 h, the pH of the solution adjusted to neutral by the dropwise addition of 3N aqueous HCl solution, and the MeOH concentrated in vacuo. The solution was adjusted to pH 4 by the dropwise addition of 3N aqueous HCl solution and was extracted into EtOAc (5×100 mL). The combined organic layers were dried (MgSO$_4$), concentrated in vacuo to afford 657 mg (98%) of the Method B product of Step 36L as a yellow solid: $^1$H NMR (500 MHz, Methanol-d$^4$) δ 1.18–1.71 (m, 32H), 1.79 (m, 1H), 1.92 (m, 1H), 2.30 (q, J=9 Hz, 1H), 2.55 (m, 1H), 2.64 (m, 1H), 2.77 (m, 1H), 4.02 (s, 3H), 4.04 (m, 1H), 4.15 (m, 2H), 4.40 (s, 1H), 4.71 (m, 1H), 4.80 (m, 1H), 5.36 (m, 1H), 5.61 (m, 1H), 5.81 (s, 1H), 7.30 (d, J=9 Hz, 1H), 7.73 (s, 2H), 8.16 (s, 1H), 8.29 (d, J=9 Hz, 1H). LC-MS (Method D except gradient time increased from 2 to 4 min, retention time: 3.21 min), MS m/z 775 (M$^+$+1).

Method B Step 36M, Preparation of Compound 34, Example 36, (1S,4R,6S,14S,18R)-7-cis-{4-Cyclopropanesulfonylaminocarbonyl-18-[2-(2-isopropylaminothiazol-4-yl)-7-methoxyquinolin-4-yloxy]-2,15-dioxo-3,16-diazatricyclo-[14.3.0.0$^{4,6}$]nonadec-7-en-14-yl}carbamic acid cyclopentyl ester, from the Method B Product of Step 36L

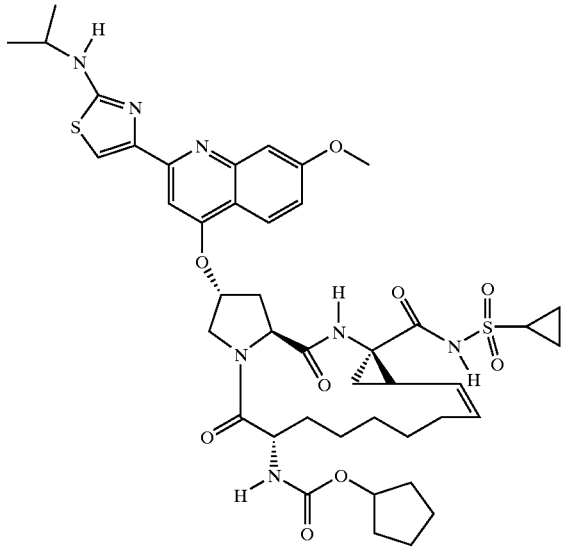

Compound 34, Product of Method B Step 36M

To a solution of 66 mg (85.2 mmol) of the Method B acid product of step 36L, (1S,4R,6S,14S,18R)-7-cis-(1S,4R,6S,14S,18R)-7-cis-14-Cyclopentyloxycarbonylamino-18-[2-(2-isopropyl-aminothiazol-4-yl)-7-methoxy-quinolin-4-yloxy]-2,15-dioxo-3,16-diazatricyclo[14.3.0.0$^{4,6}$]-nonadec-7-ene-4-carboxylic acid, was dissolved in THF (1 mL) and CDI (21 mg, 130 mmol, 1.5 eq) was added. The mixture was then heated to 60° C. for 45 min. The reaction mixture was then cooled to room temperature, cyclopropylsulfonamide (21 mg, 170 mmol, 2 eq) and DBU (19 mg, 130 mmol, 1.5 eq) were added, and the resulting mixture was stirred at room temperature overnight. The resulting mixture was partitioned between EtOAc and water, followed by back extraction of the aqueous layer. The combined extracts were dried over magnesium sulfate and concentrated in vacuo. This residue was dissolved in 6 mL of MeOH. This solution was purified by preparative HPLC using two injections (3×2 mL), afterwhich, an extractive purification was undertaken to isolate 51 mg (68% yield) of the product from step 36M (Method B), Compound 34, Example 36, from the respective combined HPLC fractions. In addition, 20 mg more of compound 34 of 80% purity (~20% yield) was isolated from earlier eluting fractions where the impurity was the carboxylic acid precursor. HPLC/Isolation Procedure: Column Xterra 30×75 mm S5, 40% to 90% Solvent B/A for 32 min gradient, hold time 4 min; where Solvent A is 10% MeOH/90% H$_2$O with 0.1% TFA, Solvent B is 90% MeOH/10% H$_2$O with 0.1% TFA and flow rate is 40 ml/min). The pH of the combined fractions was adjusted to neutral using 6N aqueous NaOH solution and the MeOH removed in vacuo. The solution was adjusted to pH 4 using 3N aqueous HCl solution, and repeatedly extracted with EtOAc. The combined EtOAc extracts were dried (MgSO$_4$) and concentrated in vacuo to isolate the desired product of step 36N: $^1$H NMR (500 MHz, Methanol-d$^4$) δ 0.83–1.66 (m, 23H), 1.32 (d, J=6 Hz, 6H), 1.72 (dd, J=8., 5.34 Hz, 1H), 1.81 (m, 2H), 2.34 (m, 1H), 2.62 (m, 2H), 2.76 (m, 1H), 2.89 (s, 1H), 4.07 (m, 2H), 4.18 (d, J=9.77 Hz, 1H), 4.49 (s, 1H), 4.68 (t, J=8.09 Hz, 1H), 4.77 (m, 1H), 5.09 (s, 1H), 5.67 (m, 2H), 7.19 (d, J=9.2 Hz, 1H), 7.56 (s, 1H), 7.60 (s, 1H), 7.91 (s, 1H), 8.21 (d, J=9.2 Hz, 1H). LC-MS (Method D, retention time: 1.82 min), MS m/z 877 (M$^+$+1).

EXAMPLE 37

Preparation of Compounds Defined in Table 1 and Table 2 of Example 37

Each of the Compounds shown in Table 1 and Table 2 of Example 37 are tripeptide acyl sulfonamides. These compounds can each be prepared from the corresponding carboxylic acid in a sulfonamide coupling process which converts the carboxylic acid to the said acyl sulfonamide. Examples of this process are found in the present application in the synthesis of Compounds 1 through 34. The carboxylic acids which are used as starting materials for the formation of the acyl sulfonamides shown in Table 1 can be prepared (for one example, see steps 9a–9i of Example 9 for the preparation of the carboxylic acid of step 9i) by the methods described in the present application and also from the teachings of International Application PCT/CA00/00353 (Publication No, WO 00/59929).

Table 1 of Example 37
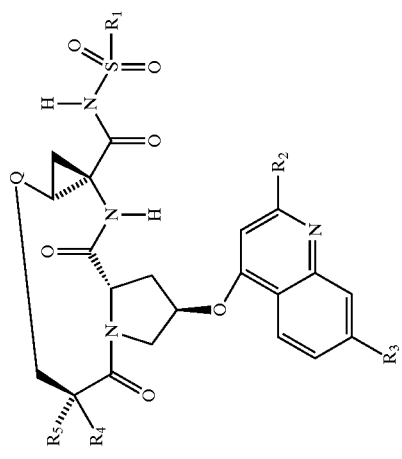
| Cmp | R₁ | R₂ | R₃ | R₅ | R₄ | Q |
|---|---|---|---|---|---|---|
| 35 | cyclopropyl | thiazole | OMe | H | cyclopentyl-O-C(O)-NH- | alkenyl chain |
| 36 | cyclopropyl | 4-isopropyl-thiazole | OMe | H | cyclopentyl-O-C(O)-NH- | alkenyl chain |
| 37 | cyclobutyl | 4-isopropyl-thiazole | OMe | H | cyclopentyl-O-C(O)-NH- | alkenyl chain |

-continued
Table 1 of Example 37
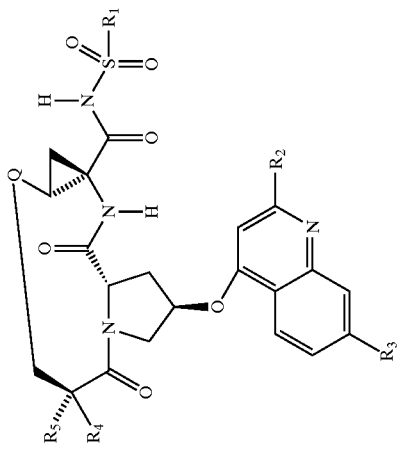
| Cmp | R₁ | R₂ | R₃ | R₅ | R₄ | Q |
|---|---|---|---|---|---|---|
| 38 | cyclobutyl | 4-isopropylthiazol-2-yl | OMe | H | cyclopentyl-O-C(O)-NH- | (8-carbon chain) |
| 39 | cyclopropyl | 4-isopropylthiazol-2-yl | OMe | H | cyclopentyl-O-C(O)-NH- | (8-carbon chain) |
| 40 | cyclopropyl | 4-isopropylthiazol-2-yl | OMe | H | cyclopentyl-O-C(O)-NH- | (7-carbon chain) |

-continued

Table 1 of Example 37

| Cmp | R₁ | R₂ | R₃ | R₅ | R₄ | Q |
|---|---|---|---|---|---|---|
| 41 | cyclopropyl | 4-isopropylthiazol-2-yl | OMe | H | cyclopentyl-O-C(O)-NH- | cis-CH₂CH₂CH=CHCH₂- |
| 42 | cyclobutyl | 4-isopropylthiazol-2-yl | OMe | H | cyclopentyl-O-C(O)-NH- | cis-CH₂CH₂CH=CHCH₂- |
| 43 | cyclobutyl | 4-isopropylthiazol-2-yl | OMe | H | cyclopentyl-O-C(O)-NH- | -(CH₂)₅- |

-continued
Table 1 of Example 37
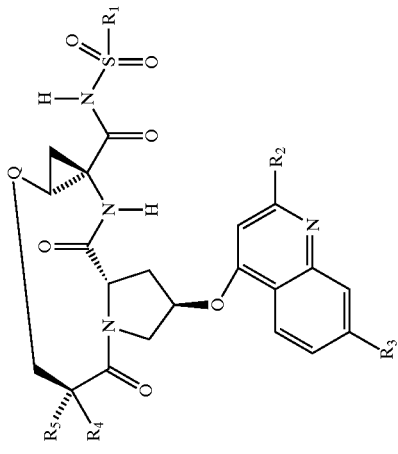
| Cmp | R₁ | R₂ | R₃ | R₅ | R₄ | Q |
|---|---|---|---|---|---|---|
| 44 | Me | 4-isopropyl-thiazol-2-yl | OMe | H | cyclopentyl-O-C(O)-NH- | cis-alkenyl chain |
| 45 | Me | 4-isopropyl-thiazol-2-yl | OMe | H | cyclopentyl-O-C(O)-NH- | alkyl chain |
| 46 | Me | 4-isopropyl-thiazol-2-yl | OMe | H | cyclopentyl-O-C(O)-NH- | cis-alkenyl chain |

-continued
Table 1 of Example 37
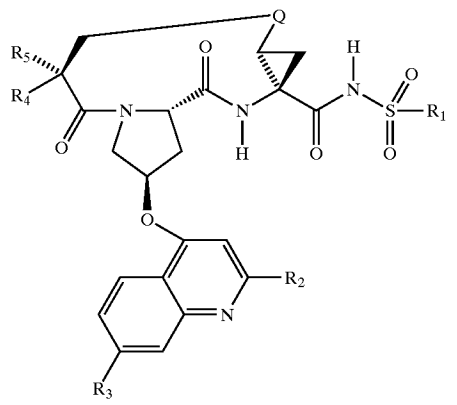
| Cmp | R₁ | R₂ | R₃ | R₅ | R₄ | Q |
|---|---|---|---|---|---|---|
| 47 | Me | 4-isopropyl-thiazol-2-yl | OMe | H | NHC(O)O-cyclopentyl | (CH₂)₇— chain |
| 48 | Me | 4-isopropyl-thiazol-2-yl | OMe | H | NHC(O)O-tBu | alkenyl chain |
| 49 | Me | 4-isopropyl-thiazol-2-yl | OMe | H | NHC(O)O-tBu | alkyl chain |

-continued
Table 1 of Example 37
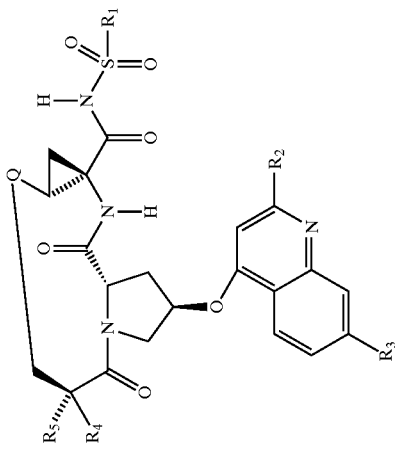
| Cmp | R₁ | R₂ | R₃ | R₅ | R₄ | Q |
|---|---|---|---|---|---|---|
| 50 | Me | 4-isopropyl-thiazol-2-yl | OMe | H | NHC(O)O-tBu | (Z)-alkenyl chain |
| 51 | Me | 4-isopropyl-thiazol-2-yl | OMe | H | NHC(O)O-tBu | alkyl chain |
| 52 | cyclopropyl | 4-isopropyl-thiazol-2-yl | OMe | H | NHC(O)O-tBu | alkyl chain |

-continued
Table 1 of Example 37
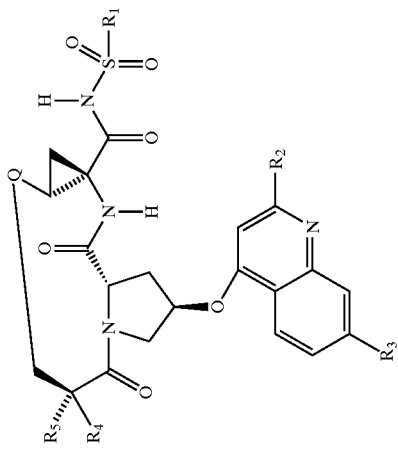
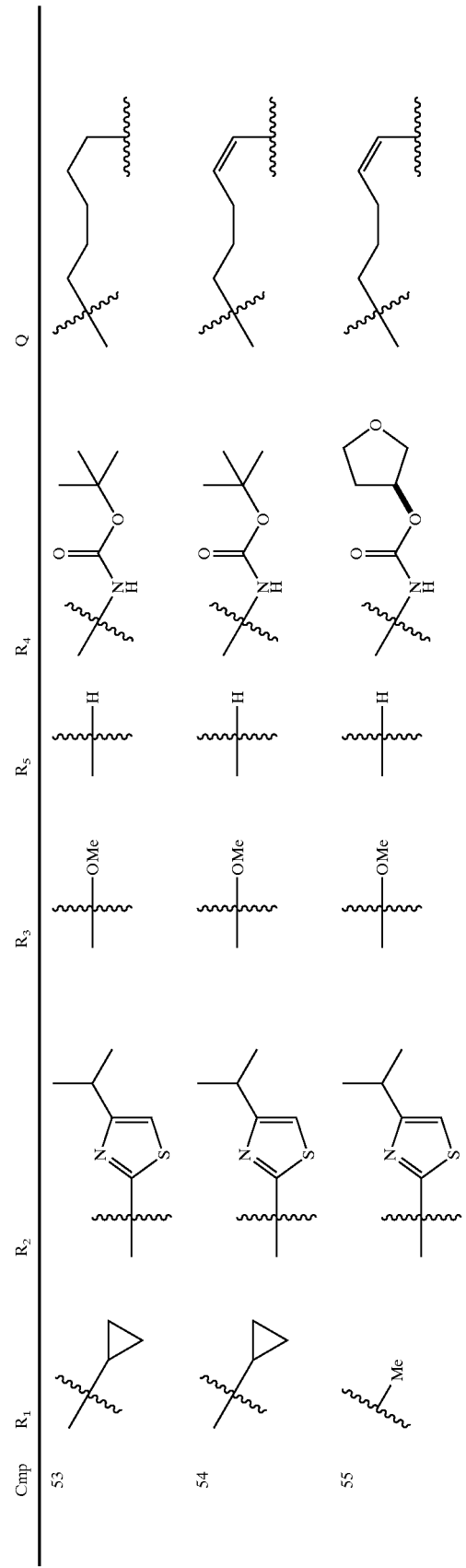

-continued

Table 1 of Example 37

| Cmp | R₁ | R₂ | R₃ | R₅ | R₄ | Q |
|---|---|---|---|---|---|---|
| 56 | Me | 4-isopropyl-thiazol-2-yl | OMe | H | tetrahydrofuran-3-yl-O-C(O)-NH- | saturated alkyl chain |
| 57 | Me | 4-isopropyl-thiazol-2-yl | OMe | H | tetrahydrofuran-3-yl-O-C(O)-NH- | alkenyl chain (cis double bond) |
| 58 | Me | 4-isopropyl-thiazol-2-yl | OMe | H | tetrahydrofuran-3-yl-O-C(O)-NH- | saturated alkyl chain |

-continued

Table 1 of Example 37

| Cmp | R₁ | R₂ | R₃ | R₅ | R₄ | Q |
|---|---|---|---|---|---|---|
| 59 | cyclopropyl | 4-isopropyl-thiazol-2-yl | OMe | H | tetrahydrofuran-3-yl-O-C(O)-NH- | (saturated chain) |
| 60 | cyclobutyl | 4-isopropyl-thiazol-2-yl | OMe | H | tetrahydrofuran-3-yl-O-C(O)-NH- | (saturated chain) |
| 61 | cyclopropyl | 4-isopropyl-thiazol-2-yl | OMe | H | tetrahydrofuran-3-yl-O-C(O)-NH- | (chain with cis double bond) |

-continued

Table 1 of Example 37

| Cmp | R₁ | R₂ | R₃ | R₅ | R₄ | Q |
|---|---|---|---|---|---|---|
| 62 | cyclopropyl | 4-isopropyl-thiazol-2-yl | OMe | H | tetrahydrofuran-3-yl-O-C(O)-NH- | pentyl chain |
| 63 | cyclobutyl | 4-isopropyl-thiazol-2-yl | OMe | H | tetrahydrofuran-3-yl-O-C(O)-NH- | pentenyl chain (cis) |
| 64 | cyclopropyl | 4-isopropyl-thiazol-2-yl | OMe | H | tetrahydrofuran-3-yl-O-C(O)-NH- | hexenyl chain |

-continued
Table 1 of Example 37
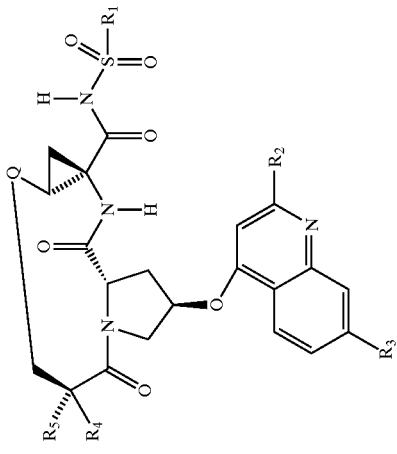
| Cmp | R₁ | R₂ | R₃ | R₅ | R₄ | Q |
|---|---|---|---|---|---|---|
| 65 | cyclobutyl | 4-isopropyl-thiazol-2-yl | OMe | H | tetrahydrofuran-3-yloxycarbonylamino | -(CH₂)₆- |
| 66 | Me | 4-isopropyl-thiazol-2-yl | OMe | H | tetrahydropyran-4-yloxycarbonylamino | -(CH₂)₂-CH=CH-(CH₂)₂- |
| 67 | Me | 4-isopropyl-thiazol-2-yl | OMe | H | tetrahydropyran-4-yloxycarbonylamino | -(CH₂)₆- |

-continued
Table 1 of Example 37
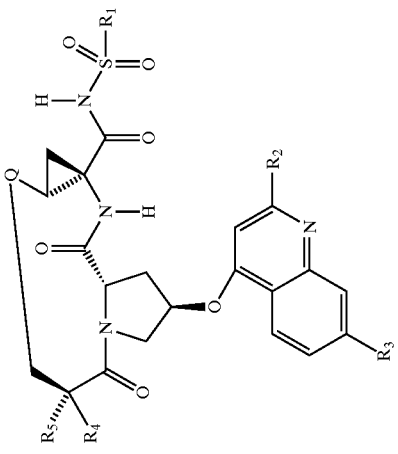
| Cmp | R1 | R2 | R3 | R5 | R4 | Q |
|---|---|---|---|---|---|---|
| 68 | Me | 4-isopropyl-thiazol-2-yl | OMe | H | tetrahydropyran-4-yl-O-C(O)-NH- | (Z)-alkenyl chain |
| 69 | Me | 4-isopropyl-thiazol-2-yl | OMe | H | tetrahydrofuran-3-yl-O-C(O)-NH- | alkyl chain |
| 70 | cyclopropyl | 4-isopropyl-thiazol-2-yl | OMe | H | tetrahydropyran-4-yl-O-C(O)-NH- | alkyl chain |

-continued
Table 1 of Example 37
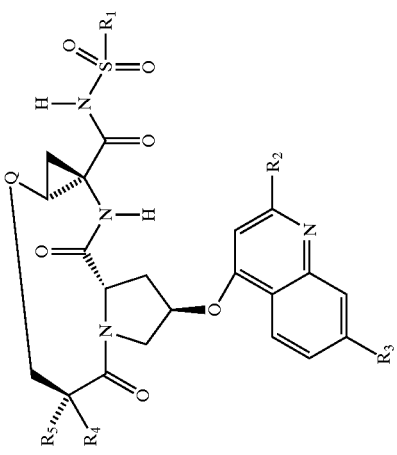
| Cmp | R₁ | R₂ | R₃ | R₅ | R₄ | Q |
|---|---|---|---|---|---|---|
| 71 | cyclobutyl | 4-isopropylthiazol-2-yl | OMe | H | tetrahydropyran-4-yl-O-C(O)-NH- | (saturated chain) |
| 72 | cyclopropyl | 4-isopropylthiazol-2-yl | OMe | H | tetrahydropyran-4-yl-O-C(O)-NH- | (chain with cis double bond) |
| 73 | cyclopropyl | 4-isopropylthiazol-2-yl | OMe | H | tetrahydropyran-4-yl-O-C(O)-NH- | (saturated chain) |

-continued
Table 1 of Example 37
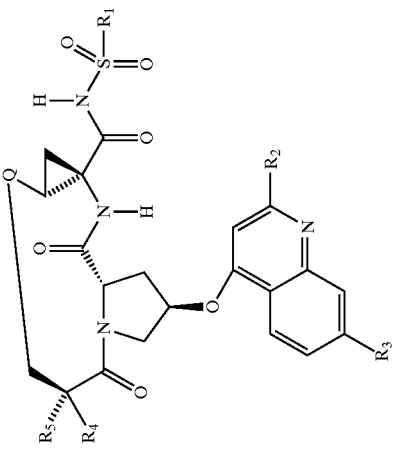
| Cmp | R₁ | R₂ | R₃ | R₅ | R₄ | Q |
|---|---|---|---|---|---|---|
| 74 | cyclobutyl | 4-isopropyl-thiazol-2-yl | OMe | H | tetrahydropyran-4-yl-O-C(O)-NH- | cis-alkenyl chain |
| 75 | cyclopropyl | 4-isopropyl-thiazol-2-yl | OMe | H | tetrahydropyran-4-yl-O-C(O)-NH- | alkenyl chain |
| 76 | cyclobutyl | 4-isopropyl-thiazol-2-yl | OMe | H | tetrahydropyran-4-yl-O-C(O)-NH- | saturated alkyl chain |

-continued
Table 1 of Example 37
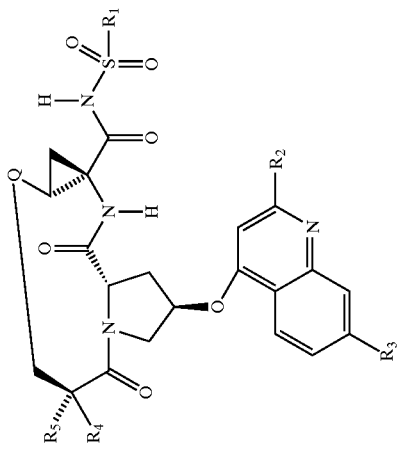
| Cmp | R1 | R2 | R3 | R5 | R4 | Q |
|---|---|---|---|---|---|---|
| 77 | Me | 4-isopropyl-thiazol-2-yl | OMe | H | NHC(O)OCH2CH2F | cis-CH2CH2CH=CHCH2- |
| 78 | Me | 4-isopropyl-thiazol-2-yl | OMe | H | NHC(O)OCH2CH2F | -(CH2)5- |
| 79 | Me | 4-isopropyl-thiazol-2-yl | OMe | H | NHC(O)OCH2CH2F | cis-CH2CH=CH(CH2)3- |

-continued
Table 1 of Example 37
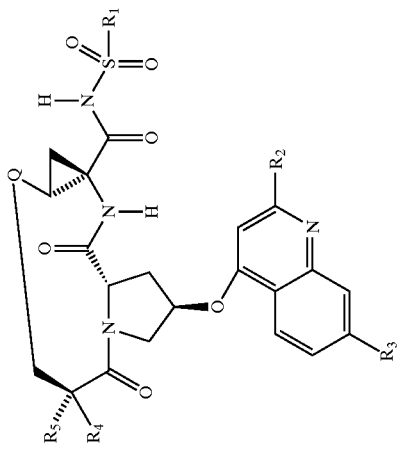
| Cmp | R₁ | R₂ | R₃ | R₅ | R₄ | Q |
|---|---|---|---|---|---|---|
| 80 | Me | 4-isopropyl-thiazol-2-yl | OMe | H | OC(O)NH-CH₂CH₂F | (CH₂)₇ |
| 81 | cyclobutyl | 4-isopropyl-thiazol-2-yl | OMe | H | OC(O)NH-CH₂CH₂F | (CH₂)₇ |
| 82 | cyclopropyl | 4-isopropyl-thiazol-2-yl | OMe | H | OC(O)NH-CH₂CH₂F | CH₂CH=CHCH₂CH₂CH₂ |

-continued
Table 1 of Example 37
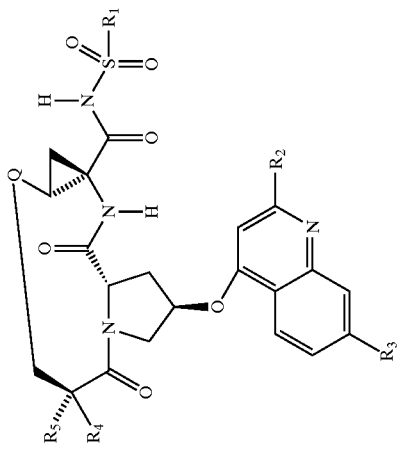
| Cmp | R₁ | R₂ | R₃ | R₅ | R₄ | Q |
|---|---|---|---|---|---|---|
| 83 | cyclopropyl | 4-isopropyl-thiazol-2-yl | OMe | H | NHC(O)OCH₂CH₂F | -(CH₂)₆- |
| 84 | cyclobutyl | 4-isopropyl-thiazol-2-yl | OMe | H | NHC(O)OCH₂CH₂F | cis -CH₂CH=CHCH₂- chain |
| 85 | cyclopropyl | 4-isopropyl-thiazol-2-yl | OMe | H | NHC(O)OCH₂CH₂F | cis -CH₂CH₂CH=CHCH₂- chain |

-continued
Table 1 of Example 37
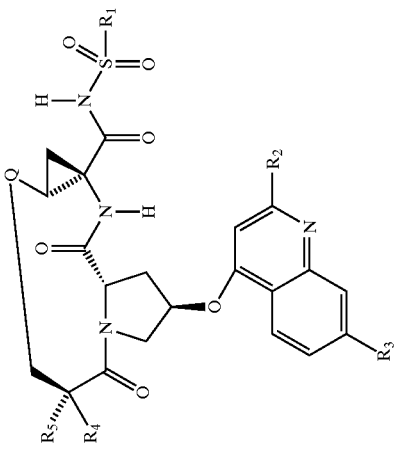
| Cmp | R₁ | R₂ | R₃ | R₅ | R₄ | Q |
|---|---|---|---|---|---|---|
| 86 | cyclobutyl | 4-isopropylthiazol-2-yl | OMe | H | -NHC(O)OCH₂CH₂F | -(CH₂)₆- |
| 87 | cyclopropyl | 4-isopropylthiazol-2-yl | OMe | H | -NHC(O)OCH₂CH₂F | -CH₂CH=CH(CH₂)₃- |
| 88 | Me | 4-isopropylthiazol-2-yl | OMe | H | -NHC(O)NHC(CH₃)₃ | -CH₂CH=CH(CH₂)₃- |

-continued
Table 1 of Example 37
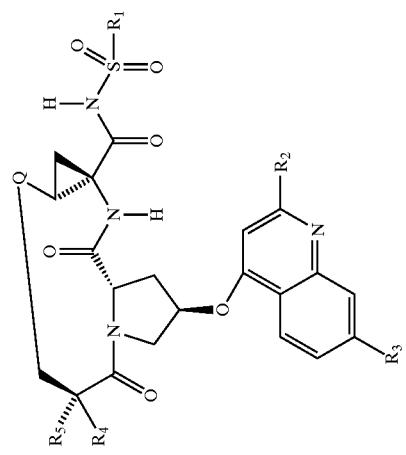
| Cmp | R₁ | R₂ | R₃ | R₅ | R₄ | Q |
|---|---|---|---|---|---|---|
| 89 | Me | 4-isopropyl-thiazol-2-yl | OMe | H | NHC(O)NH-tBu | n-heptyl |
| 90 | Me | 4-isopropyl-thiazol-2-yl | OMe | H | NHC(O)NH-tBu | cis-hept-2-enyl |
| 91 | Me | 4-isopropyl-thiazol-2-yl | OMe | H | NHC(O)NH-tBu | n-heptyl |

-continued
Table 1 of Example 37
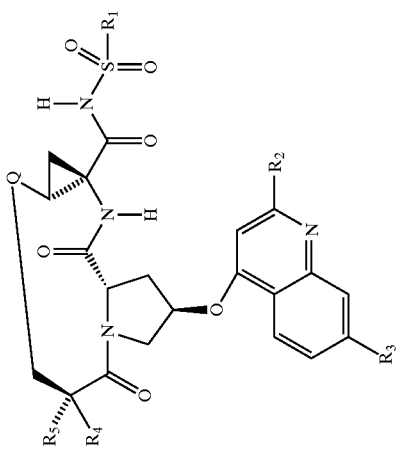
| Cmp | R₁ | R₂ | R₃ | R₅ | R₄ | Q |
|---|---|---|---|---|---|---|
| 92 | cyclobutyl | 4-isopropylthiazol-2-yl | OMe | H | t-Bu-NHC(O)NH- | (CH₂)₈ chain |
| 93 | cyclopropyl | 4-isopropylthiazol-2-yl | OMe | H | t-Bu-NHC(O)NH- | chain with cis double bond |
| 94 | cyclopropyl | 4-isopropylthiazol-2-yl | OMe | H | t-Bu-NHC(O)NH- | saturated chain |

-continued

Table 1 of Example 37

| Cmp | R₁ | R₂ | R₃ | R₅ | R₄ | Q |
|---|---|---|---|---|---|---|
| 95 | cyclobutyl | 4-isopropyl-thiazol-2-yl | OMe | H | C(=O)NH-tBu (urea) | cis-alkenyl chain |
| 96 | cyclopropyl | 4-isopropyl-thiazol-2-yl | OMe | H | C(=O)NH-tBu (urea) | cis-alkenyl chain |
| 97 | cyclobutyl | 4-isopropyl-thiazol-2-yl | OMe | H | C(=O)NH-tBu (urea) | saturated alkyl chain |

-continued
Table 1 of Example 37
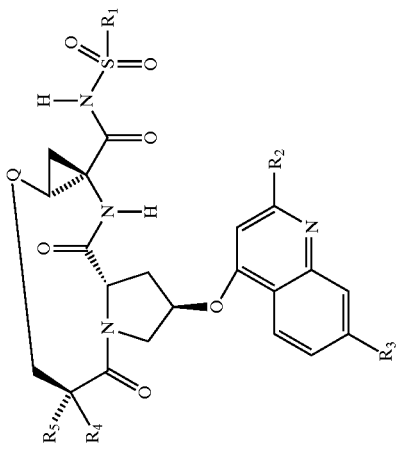
| Cmp | R₁ | R₂ | R₃ | R₅ | R₄ | Q |
|---|---|---|---|---|---|---|
| 98 | cyclopropyl | 4-isopropyl-thiazol-2-yl | OMe | H | tert-butyl-NHC(O)NH- | (Z)-alkenyl chain |
| 99 | Me | 4-isopropyl-thiazol-2-yl | OMe | H | cyclopropyl-CH₂-C(O)NH- | (Z)-alkenyl chain |
| 100 | Me | 4-isopropyl-thiazol-2-yl | OMe | H | cyclopropyl-CH₂-C(O)NH- | alkyl chain |

-continued
Table 1 of Example 37
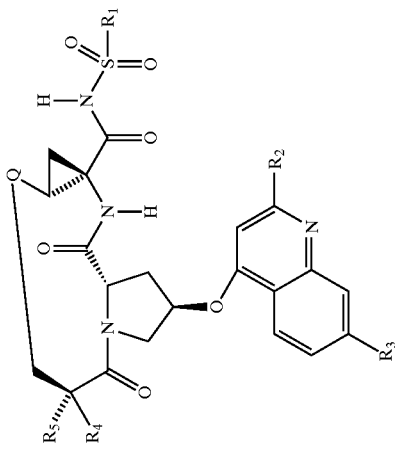
| Cmp | R₁ | R₂ | R₃ | R₅ | R₄ | Q |
|---|---|---|---|---|---|---|
| 101 | Me | 4-isopropyl-thiazol-2-yl | OMe | H | CH₂C(O)NH-cyclopropylmethyl | cis-alkenyl chain |
| 102 | Me | 4-isopropyl-thiazol-2-yl | OMe | H | CH₂C(O)NH-cyclopropylmethyl | alkyl chain |
| 103 | cyclobutyl | 4-isopropyl-thiazol-2-yl | OMe | H | CH₂C(O)NH-cyclopropylmethyl | alkyl chain |

-continued
Table 1 of Example 37
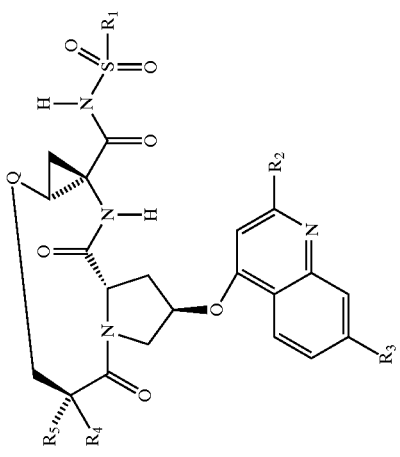
| Cmp | R₁ | R₂ | R₃ | R₅ | R₄ | Q |
|---|---|---|---|---|---|---|
| 104 | cyclopropyl | 4-isopropylthiazol-2-yl | OMe | H | cyclopropyl-CH₂-C(O)NH- | (with cis double bond) |
| 105 | cyclopropyl | 4-isopropylthiazol-2-yl | OMe | H | cyclopropyl-CH₂-C(O)NH- | (saturated) |
| 106 | cyclobutyl | 4-isopropylthiazol-2-yl | OMe | H | cyclopropyl-CH₂-C(O)NH- | (with cis double bond) |

-continued
Table 1 of Example 37
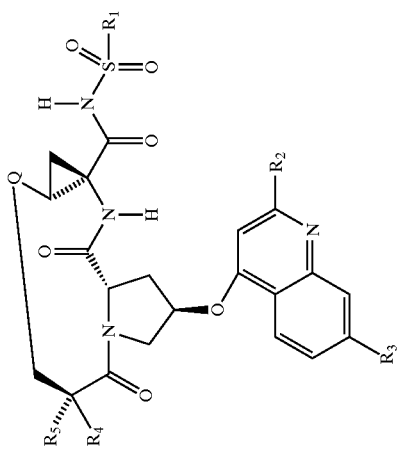
| Cmp | R₁ | R₂ | R₃ | R₅ | R₄ | Q |
|---|---|---|---|---|---|---|
| 107 | cyclopropyl | 4-isopropyl-thiazol-2-yl | OMe | H | C(O)NH-CH₂-cyclopropyl | cis-alkene chain |
| 108 | cyclobutyl | 4-isopropyl-thiazol-2-yl | OMe | H | C(O)NH-CH₂-cyclopropyl | alkyl chain |
| 109 | cyclopropyl | 4-isopropyl-thiazol-2-yl | OMe | H | C(O)NH-CH₂-cyclopropyl | cis-alkene chain |

-continued
Table 1 of Example 37
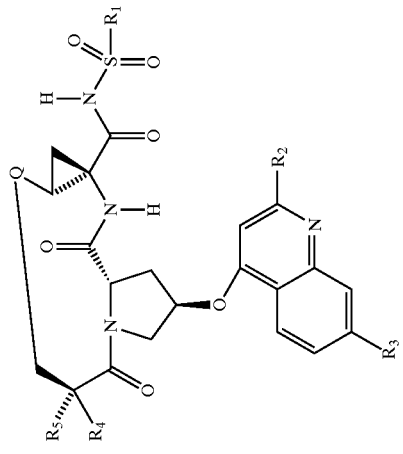
| Cmp | R₁ | R₂ | R₃ | R₅ | R₄ | Q |
|---|---|---|---|---|---|---|
| 110 | Me | 4-isopropyl-thiazol-2-yl | OMe | H | NHC(O)OCH₂C(CH₃)₃ | (Z)-CH₂CH₂CH=CHCH₂- chain |
| 111 | Me | 4-isopropyl-thiazol-2-yl | OMe | H | NHC(O)OCH₂C(CH₃)₃ | saturated alkyl chain |
| 112 | Me | 4-isopropyl-thiazol-2-yl | OMe | H | NHC(O)OCH₂C(CH₃)₃ | (Z)-alkenyl chain |

-continued
Table 1 of Example 37
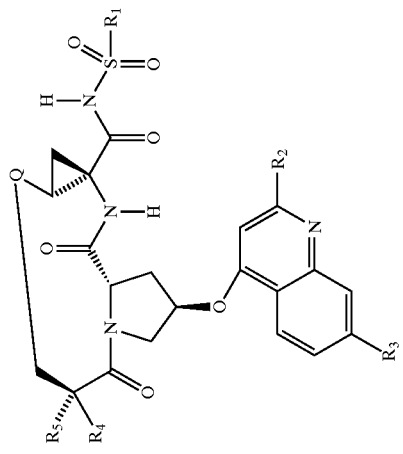
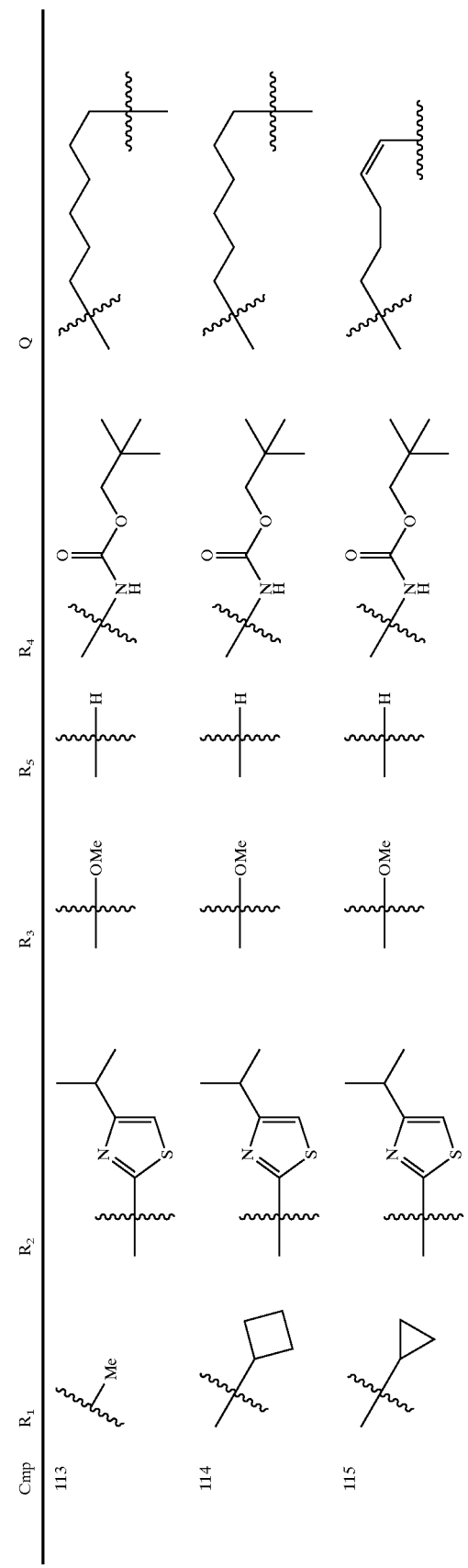
| Cmp | R₁ | R₂ | R₃ | R₅ | R₄ | Q |
|---|---|---|---|---|---|---|
| 113 | Me | 4-isopropyl-thiazol-2-yl | OMe | H | neopentyloxycarbonylamino | |
| 114 | cyclobutyl | 4-isopropyl-thiazol-2-yl | OMe | H | neopentyloxycarbonylamino | |
| 115 | cyclopropyl | 4-isopropyl-thiazol-2-yl | OMe | H | neopentyloxycarbonylamino | |

-continued
Table 1 of Example 37
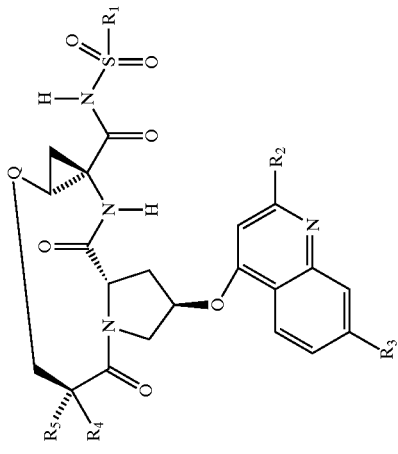
| Cmp | R₁ | R₂ | R₃ | R₅ | R₄ | Q |
|---|---|---|---|---|---|---|
| 116 | cyclopropyl | 4-isopropyl-thiazol-2-yl | OMe | H | NHC(O)O-neopentyl | saturated chain |
| 117 | cyclobutyl | 4-isopropyl-thiazol-2-yl | OMe | H | NHC(O)O-neopentyl | cis-alkene chain |
| 118 | cyclopropyl | 4-isopropyl-thiazol-2-yl | OMe | H | NHC(O)O-neopentyl | cis-alkene chain |

Table 1 of Example 37
| Cmp | R₁ | R₂ | R₃ | R₅ | R₄ | Q |
|---|---|---|---|---|---|---|
| 119 | cyclobutyl | 4-isopropyl-thiazol-2-yl | OMe | H | neopentyl carbamate | alkyl chain |
| 120 | cyclopropyl | 4-isopropyl-thiazol-2-yl | OMe | H | neopentyl carbamate | alkenyl chain |
| 121 | cyclopropyl | 2-(isopropylamino)-thiazol-4-yl | OMe | H | cyclohexyl carbamate | alkenyl chain |
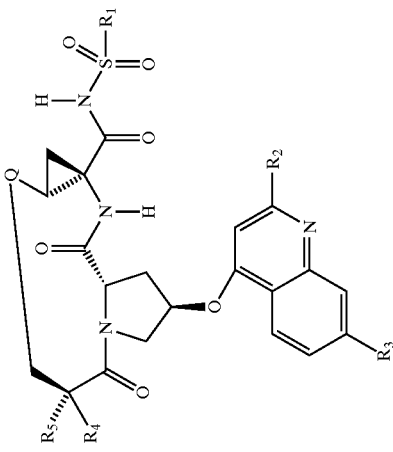

-continued
Table 1 of Example 37
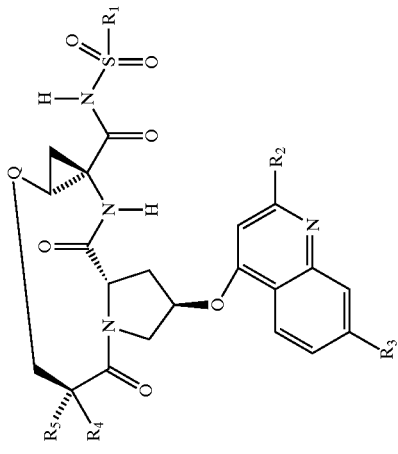
| Cmp | R₁ | R₂ | R₃ | R₅ | R₄ | Q |
|-----|----|----|----|----|----|----|
| 122 | cyclobutyl | 2-(isopropylamino)thiazol-4-yl | OMe | H | cyclopentyl-O-C(O)-NH- | cis-alkenyl chain |
| 123 | cyclobutyl | 2-(isopropylamino)thiazol-4-yl | OMe | H | cyclopentyl-O-C(O)-NH- | alkyl chain |
| 124 | cyclopropyl | 2-(isopropylamino)thiazol-4-yl | OMe | H | cyclopentyl-O-C(O)-NH- | alkyl chain |
| 125 | cyclopropyl | 2-(isopropylamino)thiazol-4-yl | OMe | H | cyclopentyl-O-C(O)-NH- | alkyl chain |

-continued
Table 1 of Example 37
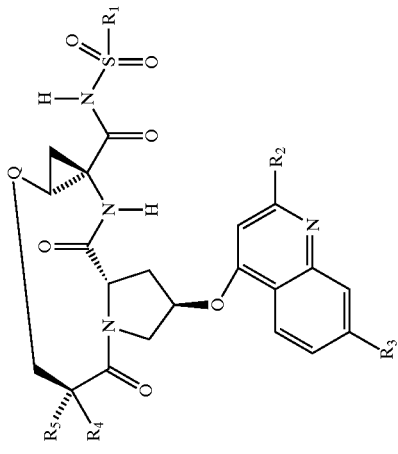
| Cmp | R₁ | R₂ | R₃ | R₅ | R₄ | Q |
|---|---|---|---|---|---|---|
| 126 | cyclopropyl | isopropyl-NH-thiazole | OMe | H | cyclopentyl-O-C(O)-NH | cis-alkenyl chain |
| 127 | cyclobutyl | isopropyl-NH-thiazole | OMe | H | cyclopentyl-O-C(O)-NH | alkyl chain |
| 128 | cyclobutyl | isopropyl-NH-thiazole | OMe | H | cyclopentyl-O-C(O)-NH | alkyl chain |
| 129 | Me | isopropyl-NH-thiazole | OMe | H | cyclopentyl-O-C(O)-NH | cis-alkenyl chain |

-continued

Table 1 of Example 37

| Cmp | R₁ | R₂ | R₃ | R₅ | R₄ | Q |
|---|---|---|---|---|---|---|
| 130 | Me | 2-(isopropylamino)thiazol-4-yl | OMe | H | cyclopentyloxycarbonylamino | saturated chain |
| 131 | Me | 2-(isopropylamino)thiazol-4-yl | OMe | H | cyclopentyloxycarbonylamino | chain with double bond |
| 132 | Me | 2-(isopropylamino)thiazol-4-yl | OMe | H | cyclopentyloxycarbonylamino | chain with double bond |
| 133 | Me | 2-(isopropylamino)thiazol-4-yl | OMe | H | t-butyloxycarbonylamino | chain with double bond |

-continued
Table 1 of Example 37
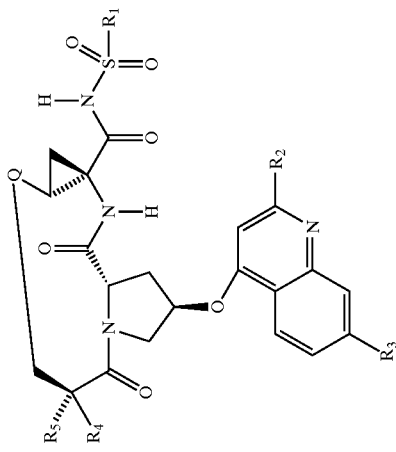
| Cmp | R₁ | R₂ | R₃ | R₅ | R₄ | Q |
|---|---|---|---|---|---|---|
| 134 | Me | 2-(isopropylamino)thiazol-4-yl | OMe | H | NHBoc | n-octyl |
| 135 | Me | 2-(isopropylamino)thiazol-4-yl | OMe | H | NHBoc | hex-2-enyl |
| 136 | Me | 2-(isopropylamino)thiazol-4-yl | OMe | H | NHBoc | n-heptyl |
| 137 | cyclopropyl | 2-(isopropylamino)thiazol-4-yl | OMe | H | NHBoc | n-octyl |

-continued
Table 1 of Example 37
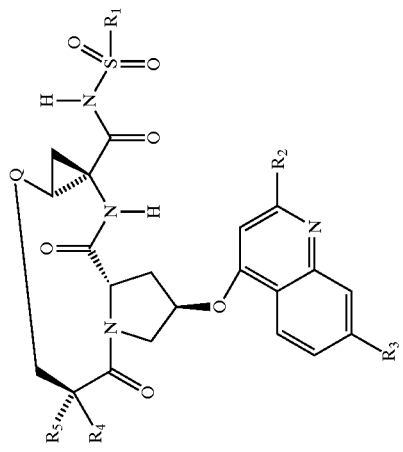
| Cmp | R₁ | R₂ | R₃ | R₅ | R₄ | Q |
|---|---|---|---|---|---|---|
| 138 | cyclopropyl | 2-(isopropylamino)thiazol-4-yl | OMe | H | tBuO-C(O)NH- | (saturated chain) |
| 139 | cyclopropyl | 2-(isopropylamino)thiazol-4-yl | OMe | H | tBuO-C(O)NH- | (cis alkene) |
| 140 | Me | 2-(isopropylamino)thiazol-4-yl | OMe | H | (tetrahydrofuran-3-yl)O-C(O)NH- | (cis alkene) |
| 141 | Me | 2-(isopropylamino)thiazol-4-yl | OMe | H | (tetrahydrofuran-3-yl)O-C(O)NH- | (saturated chain) |

Table 1 of Example 37
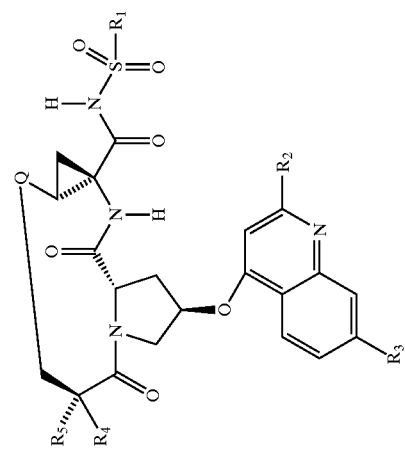
| Cmp | R₁ | R₂ | R₃ | R₅ | R₄ | Q |
|---|---|---|---|---|---|---|
| 142 | Me | isopropyl-aminothiazole | OMe | H | THF-O-C(O)NH- | alkenyl chain |
| 143 | Me | isopropyl-aminothiazole | OMe | H | THF-O-C(O)NH- | alkyl chain |
| 144 | cyclopropyl | isopropyl-aminothiazole | OMe | H | THF-O-C(O)NH- | alkyl chain |
| 145 | cyclobutyl | isopropyl-aminothiazole | OMe | H | THF-O-C(O)NH- | alkyl chain |

-continued

Table 1 of Example 37

| Cmp | R₁ | R₂ | R₃ | R₅ | R₄ | Q |
|---|---|---|---|---|---|---|
| 146 | cyclopropyl | isopropylamino-thiazolyl | OMe | H | tetrahydrofuranyl-O-C(O)-NH | cis-alkenyl chain |
| 147 | cyclopropyl | isopropylamino-thiazolyl | OMe | H | tetrahydrofuranyl-O-C(O)-NH | alkyl chain |
| 148 | cyclobutyl | isopropylamino-thiazolyl | OMe | H | tetrahydrofuranyl-O-C(O)-NH | cis-alkenyl chain |
| 149 | cyclopropyl | isopropylamino-thiazolyl | OMe | H | tetrahydrofuranyl-O-C(O)-NH | diene chain |

-continued

Table 1 of Example 37

| Cmp | R₁ | R₂ | R₃ | R₅ | R₄ | Q |
|---|---|---|---|---|---|---|
| 150 | cyclobutyl-CH₂- | isopropyl-NH-thiazolyl | OMe | H | tetrahydrofuran-3-yloxycarbonylamino | (macrocycle linker, saturated) |
| 151 | Me | isopropyl-NH-thiazolyl | OMe | H | tetrahydropyran-4-yloxycarbonylamino | (macrocycle linker, with double bond) |
| 152 | Me | isopropyl-NH-thiazolyl | OMe | H | tetrahydropyran-4-yloxycarbonylamino | (macrocycle linker, saturated) |
| 153 | Me | isopropyl-NH-thiazolyl | OMe | H | tetrahydropyran-4-yloxycarbonylamino | (macrocycle linker, with double bond) |

-continued

Table 1 of Example 37

| Cmp | R₁ | R₂ | R₃ | R₅ | R₄ | Q |
|---|---|---|---|---|---|---|
| 154 | Me | isopropyl-aminothiazole | OMe | H | tetrahydropyran-4-yl carbamate | alkyl chain |
| 155 | cyclopropyl | isopropyl-aminothiazole | OMe | H | tetrahydropyran-4-yl carbamate | alkyl chain |
| 156 | cyclobutyl | isopropyl-aminothiazole | OMe | H | tetrahydropyran-4-yl carbamate | alkyl chain |
| 157 | cyclopropyl | isopropyl-aminothiazole | OMe | H | tetrahydropyran-4-yl carbamate | alkenyl chain |

-continued

Table 1 of Example 37

| Cmp | R₁ | R₂ | R₃ | R₅ | R₄ | Q |
|---|---|---|---|---|---|---|
| 158 | cyclopropyl | 2-(isopropylamino)thiazol-4-yl | OMe | H | tetrahydropyran-4-yloxycarbonylamino | heptyl |
| 159 | cyclobutyl | 2-(isopropylamino)thiazol-4-yl | OMe | H | tetrahydropyran-4-yloxycarbonylamino | heptenyl |
| 160 | cyclopropyl | 2-(isopropylamino)thiazol-4-yl | OMe | H | tetrahydropyran-4-yloxycarbonylamino | heptenyl |
| 161 | cyclobutyl | 2-(isopropylamino)thiazol-4-yl | OMe | H | tetrahydropyran-4-yloxycarbonylamino | heptyl |

-continued
Table 1 of Example 37
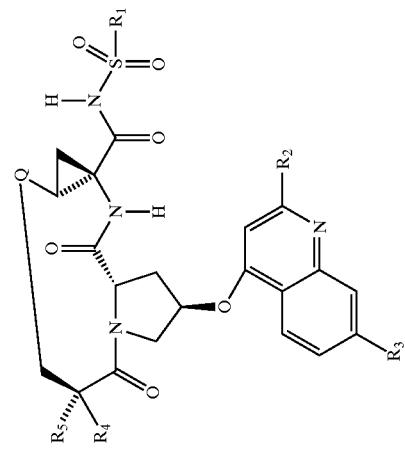
| Cmp | R1 | R2 | R3 | R5 | R4 | Q |
|---|---|---|---|---|---|---|
| 162 | Me | 2-(isopropylamino)thiazol-4-yl | OMe | H | NHC(O)OCH2CH2F | cis-alkenyl chain |
| 163 | Me | 2-(isopropylamino)thiazol-4-yl | OMe | H | NHC(O)OCH2CH2F | alkyl chain |
| 164 | Me | 2-(isopropylamino)thiazol-4-yl | OMe | H | NHC(O)OCH2CH2F | cis-alkenyl chain |
| 165 | Me | 2-(isopropylamino)thiazol-4-yl | OMe | H | NHC(O)OCH2CH2F | alkyl chain |

-continued

Table 1 of Example 37

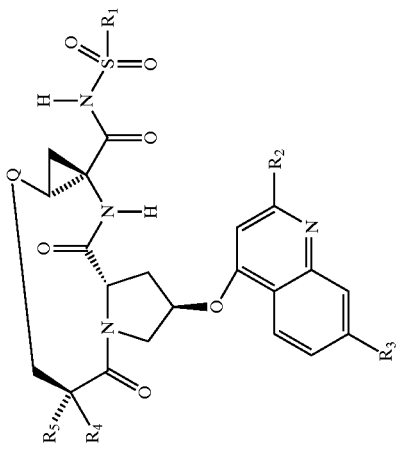

| Cmp | R<sub>1</sub> | R<sub>2</sub> | R<sub>3</sub> | R<sub>5</sub> | R<sub>4</sub> | Q |
|---|---|---|---|---|---|---|
| 166 | cyclobutyl | 2-(isopropylamino)thiazol-4-yl | OMe | H | NHC(O)OCH₂CH₂F | (saturated chain) |
| 167 | cyclopropyl | 2-(isopropylamino)thiazol-4-yl | OMe | H | NHC(O)OCH₂CH₂F | (chain with cis alkene) |
| 168 | cyclopropyl | 2-(isopropylamino)thiazol-4-yl | OMe | H | NHC(O)OCH₂CH₂F | (saturated chain) |
| 169 | cyclobutyl | 2-(isopropylamino)thiazol-4-yl | OMe | H | NHC(O)OCH₂CH₂F | (chain with cis alkene) |

-continued
Table 1 of Example 37
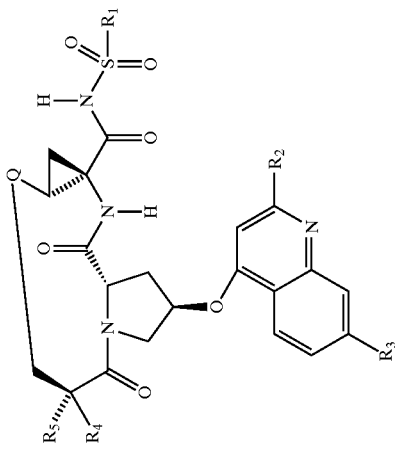

US 6,867,185 B2
-continued
Table 1 of Example 37
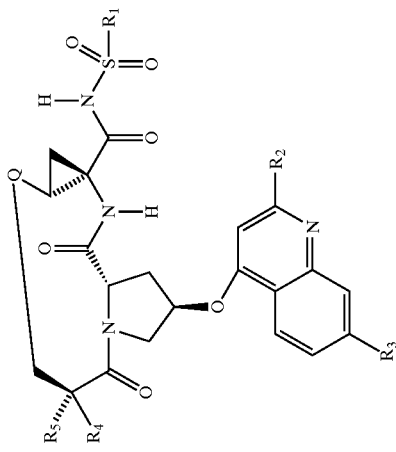
| Cmp | R₁ | R₂ | R₃ | R₅ | R₄ | Q |
|---|---|---|---|---|---|---|
| 174 | Me | 2-(isopropylamino)thiazol-4-yl | OMe | H | NHC(O)NHtBu | (CH₂)₆ |
| 175 | Me | 2-(isopropylamino)thiazol-4-yl | OMe | H | NHC(O)NHtBu | CH₂CH=CH(CH₂)₃ |
| 176 | Me | 2-(isopropylamino)thiazol-4-yl | OMe | H | NHC(O)NHtBu | (CH₂)₅ |
| 177 | cyclobutyl | 2-(isopropylamino)thiazol-4-yl | OMe | H | NHC(O)NHtBu | (CH₂)₅ |

-continued

Table 1 of Example 37

| Cmp | R₁ | R₂ | R₃ | R₅ | R₄ | Q |
|---|---|---|---|---|---|---|
| 178 | cyclopropyl | isopropyl-NH-thiazole | OMe | H | t-Bu-NH-C(O)-NH- | (cis-alkenyl chain) |
| 179 | cyclopropyl | isopropyl-NH-thiazole | OMe | H | t-Bu-NH-C(O)-NH- | (alkyl chain) |
| 180 | cyclobutyl | isopropyl-NH-thiazole | OMe | H | t-Bu-NH-C(O)-NH- | (cis-alkenyl chain) |
| 181 | cyclopropyl | isopropyl-NH-thiazole | OMe | H | t-Bu-NH-C(O)-NH- | (alkenyl chain) |

-continued

Table 1 of Example 37

| Cmp | R₁ | R₂ | R₃ | R₅ | R₄ | Q |
|---|---|---|---|---|---|---|
| 182 | cyclobutyl | isopropyl-NH-thiazole | OMe | H | tBu-NH-C(O)-NH- | pentyl chain |
| 183 | cyclopropyl | isopropyl-NH-thiazole | OMe | H | tBu-NH-C(O)-NH- | cis-alkenyl chain |
| 184 | Me | isopropyl-NH-thiazole | OMe | H | cyclopropyl-CH₂-C(O)-NH- | cis-alkenyl chain |
| 185 | Me | isopropyl-NH-thiazole | OMe | H | cyclopropyl-CH₂-C(O)-NH- | pentyl chain |

-continued

Table 1 of Example 37

| Cmp | R₁ | R₂ | R₃ | R₅ | R₄ | Q |
|---|---|---|---|---|---|---|
| 186 | Me | isopropyl-aminothiazole | OMe | H | cyclopropyl-CH₂-C(O)NH | cis-alkenyl chain |
| 187 | Me | isopropyl-aminothiazole | OMe | H | cyclopropyl-CH₂-C(O)NH | alkyl chain |
| 188 | cyclobutyl | isopropyl-aminothiazole | OMe | H | cyclopropyl-CH₂-C(O)NH | alkyl chain |
| 189 | cyclopropyl | isopropyl-aminothiazole | OMe | H | cyclopropyl-CH₂-C(O)NH | cis-alkenyl chain |

-continued
Table 1 of Example 37
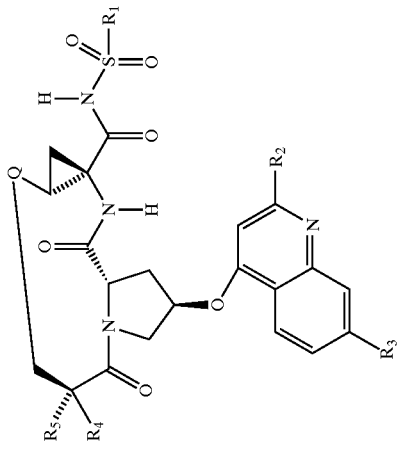
| Cmp | R₁ | R₂ | R₃ | R₅ | R₄ | Q |
|---|---|---|---|---|---|---|
| 190 | cyclopropyl | isopropylamino-thiazole | OMe | H | CH₂-cyclopropyl-C(O)NH- | alkyl chain |
| 191 | cyclobutyl | isopropylamino-thiazole | OMe | H | CH₂-cyclopropyl-C(O)NH- | alkenyl chain |
| 192 | cyclopropyl | isopropylamino-thiazole | OMe | H | CH₂-cyclopropyl-C(O)NH- | alkenyl chain |
| 193 | cyclobutyl | isopropylamino-thiazole | OMe | H | CH₂-cyclopropyl-C(O)NH- | alkyl chain |

Table 1 of Example 37

| Cmp | R1 | R2 | R3 | R5 | R4 | Q |
|---|---|---|---|---|---|---|
| 194 | cyclopropyl | isopropyl-NH-thiazole | OMe | H | cyclopropyl-CH2-C(O)NH- | alkenyl chain |
| 195 | Me | isopropyl-NH-thiazole | OMe | H | neopentyl-O-C(O)NH- | alkenyl chain |
| 196 | Me | isopropyl-NH-thiazole | OMe | H | neopentyl-O-C(O)NH- | alkyl chain |
| 197 | Me | isopropyl-NH-thiazole | OMe | H | neopentyl-O-C(O)NH- | alkenyl chain |

-continued

Table 1 of Example 37

| Cmp | R₁ | R₂ | R₃ | R₅ | R₄ | Q |
|---|---|---|---|---|---|---|
| 198 | Me | 2-(isopropylamino)thiazol-4-yl | OMe | H | NHC(O)OCH₂C(CH₃)₃ | cis-alkene chain |
| 199 | cyclobutyl | 2-(isopropylamino)thiazol-4-yl | OMe | H | NHC(O)OCH₂C(CH₃)₃ | alkyl chain |
| 200 | cyclopropyl | 2-(isopropylamino)thiazol-4-yl | OMe | H | NHC(O)OCH₂C(CH₃)₃ | cis-alkene chain |
| 201 | cyclopropyl | 2-(isopropylamino)thiazol-4-yl | OMe | H | NHC(O)OCH₂C(CH₃)₃ | alkyl chain |

-continued
Table 1 of Example 37
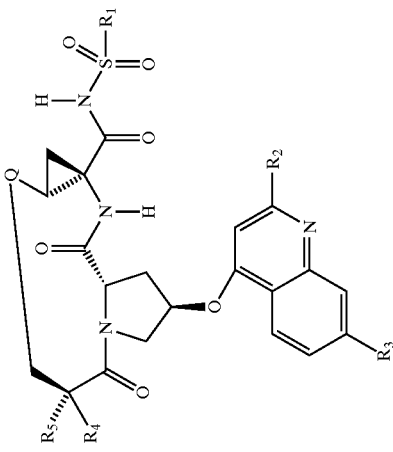
| Cmp | R₁ | R₂ | R₃ | R₅ | R₄ | Q |
|---|---|---|---|---|---|---|
| 202 | cyclobutyl | 2-(isopropylamino)thiazol-4-yl | OMe | H | NHC(O)OCH₂C(CH₃)₃ | cis-alkenyl chain |
| 203 | cyclopropyl | 2-(isopropylamino)thiazol-4-yl | OMe | H | NHC(O)OCH₂C(CH₃)₃ | saturated chain |
| 204 | cyclobutyl | 2-(isopropylamino)thiazol-4-yl | OMe | H | NHC(O)OCH₂C(CH₃)₃ | saturated chain |
| 205 | cyclopropyl | 2-(isopropylamino)thiazol-4-yl | OMe | H | NHC(O)OCH₂C(CH₃)₃ | cis-alkenyl chain |

Table 2 of Example 37

| Cmp | R₁ | R₂ | R₃ | R₅ | R₄ | Z |
|---|---|---|---|---|---|---|
| 206 | cyclopropyl | oxazol-4-yl | OMe | H | cyclopentyl-O-C(O)-NH- | cis-alkene chain |
| 207 | cyclopropyl | oxazol-4-yl | OMe | H | cyclopentyl-O-C(O)-NH- | alkyl chain |
| 208 | cyclobutyl | oxazol-4-yl | OMe | H | cyclopentyl-O-C(O)-NH- | cis-alkene chain |
| 209 | cyclobutyl | oxazol-4-yl | OMe | H | cyclopentyl-O-C(O)-NH- | alkyl chain |

-continued
Table 2 of Example 37
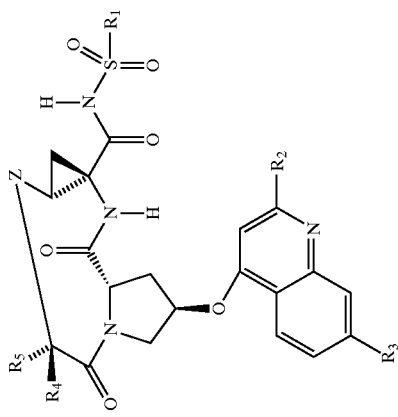
| Cmp | R₁ | R₂ | R₃ | R₅ | R₄ | Z |
|---|---|---|---|---|---|---|
| 210 | Me | oxazole | OMe | H | cyclopentyl-O-C(O)-NH- | -CH₂-CH=CH-CH₂-CH₂- |
| 211 | Me | oxazole | OMe | H | cyclopentyl-O-C(O)-NH- | -CH₂-CH₂-CH₂-CH₂-CH₂- |
| 212 | cyclopropyl | oxazole | OMe | H | cyclopentyl-O-C(O)-NH- | -CH₂-CH=CH-CH₂-O-CH₂- |
| 213 | cyclopropyl | oxazole | OMe | H | cyclopentyl-O-C(O)-NH- | -CH₂-CH₂-CH₂-O-CH₂- |

-continued
Table 2 of Example 37
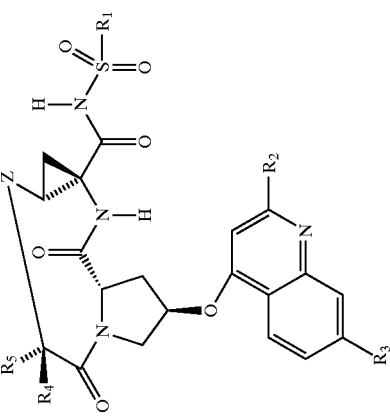
| Cmp | R₁ | R₂ | R₃ | R₅ | R₄ | Z |
|---|---|---|---|---|---|---|
| 214 | cyclopropyl | oxazole | OMe | H | cyclopentyl-O-C(O)-NH- | Me-O-CH₂-CH=CH-CH₂- |
| 215 | cyclopropyl | oxazole | OMe | H | cyclopentyl-O-C(O)-NH- | Me-S-CH₂-CH=CH-CH₂- |
| 216 | cyclopropyl | oxazole | OMe | H | cyclopentyl-O-C(O)-NH- | O-CH₂-CH₂-CH=CH- |
| 217 | cyclopropyl | oxazole | OMe | H | cyclopentyl-O-C(O)-NH- | S-CH₂-CH₂-CH=CH- |

-continued
Table 2 of Example 37
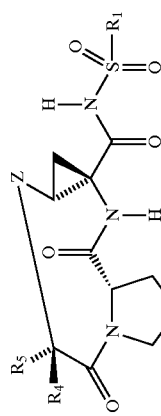
| Cmp | R₁ | R₂ | R₃ | R₅ | R₄ | Z |
|---|---|---|---|---|---|---|
| 218 | cyclopropyl | oxazole | OMe | H | cyclopentyl-O-C(O)-NH- | -CH₂-CH₂-CH=CH-CH₂-S(O)₂- |
| 219 | cyclopropyl | oxazole | OMe | H | cyclopentyl-O-C(O)-NH- | -CH(Me)-CH₂-CH₂-CH=CH-CH₂-O- |
| 220 | cyclopropyl | 2-(isopropylamino)thiazole | OMe | H | cyclopentyl-O-C(O)-NH- | -CH₂-CH₂-CH₂-CH₂-CH₂-O- |

-continued
Table 2 of Example 37
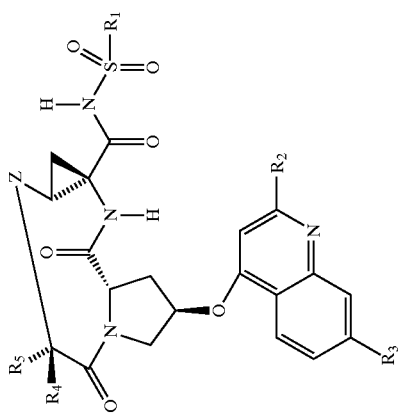
| Cmp | R1 | R2 | R3 | R5 | R4 | Z |
|---|---|---|---|---|---|---|
| 221 | cyclopropyl | 2-(isopropylamino)thiazol-4-yl | OMe | H | cyclopentyl-O-C(O)-NH- | -CH2-O-CH2-CH=CH- |
| 222 | cyclopropyl | 2-(isopropylamino)thiazol-4-yl | OMe | H | cyclopentyl-O-C(O)-NH- | -CH2-S-CH2-CH=CH- |
| 223 | cyclopropyl | 2-(isopropylamino)thiazol-4-yl | OMe | H | cyclopentyl-O-C(O)-NH- | -CH2-S(O)2-CH2-CH=CH- |

-continued
Table 2 of Example 37
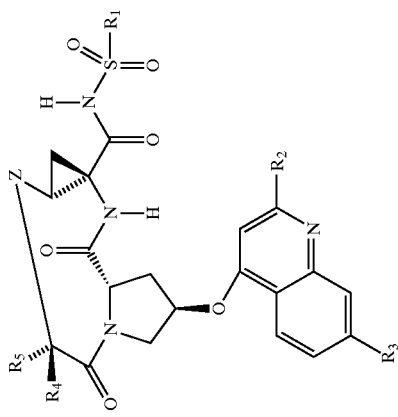
| Cmp | R₁ | R₂ | R₃ | R₅ | R₄ | Z |
|---|---|---|---|---|---|---|
| 224 | cyclopropyl | 2-(isopropylamino)-4-thiazolyl | OMe | H | cyclopentyl-O-C(O)-NH- | -CH₂CH₂CH₂CH₂-S(O)₂-CH₂- |
| 225 | cyclopropyl | 2-(isopropylamino)-4-thiazolyl | OMe | H | cyclopentyl-O-C(O)-NH- | -CH(Me)-O-CH₂CH₂-CH=CH- |
| 226 | cyclopropyl | 2-(isopropylamino)-4-thiazolyl | OMe | H | cyclopentyl-O-C(O)-NH- | -CH(Me)-O-CH₂CH₂CH₂CH₂- |

Table 2 of Example 37
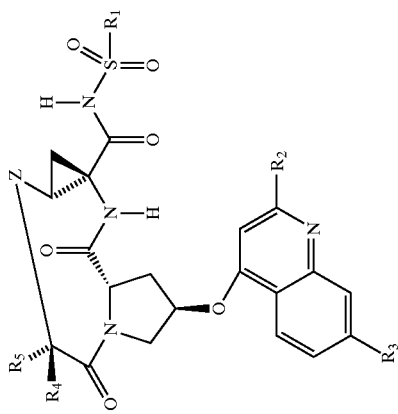
| Cmp | R₁ | R₂ | R₃ | R₅ | R₄ | Z |
|---|---|---|---|---|---|---|
| 227 | cyclobutyl | 2-(isopropylamino)thiazol-4-yl-methyl | OMe | H | cyclopentyl-O-C(=O)-NH- | -CH₂-O-(CH₂)₃- |
| 228 | cyclobutyl | 2-(isopropylamino)thiazol-4-yl-methyl | OMe | H | cyclopentyl-O-C(=O)-NH- | -CH₂-O-CH₂-CH=CH- |
| 229 | cyclobutyl | 2-(isopropylamino)thiazol-4-yl-methyl | OMe | H | cyclopentyl-O-C(=O)-NH- | -CH₂-S-CH₂-CH=CH- |

-continued

Table 2 of Example 37

| Cmp | R₁ | R₂ | R₃ | R₅ | R₄ | Z |
|---|---|---|---|---|---|---|
| 230 | cyclobutyl | 2-(isopropylamino)thiazol-4-yl | OMe | H | cyclopentyl-O-C(O)-NH- | -S(O)₂-(CH₂)₄- |
| 231 | cyclobutyl | 2-(isopropylamino)thiazol-4-yl | OMe | H | cyclopentyl-O-C(O)-NH- | -S(O)₂-CH₂-CH=CH-CH₂- |
| 232 | cyclobutyl | 2-(isopropylamino)thiazol-4-yl | OMe | H | cyclopentyl-O-C(O)-NH- | -CH(Me)-O-CH₂-CH=CH- |

-continued

Table 2 of Example 37

| Cmp | R₁ | R₂ | R₃ | R₅ | R₄ | Z |
|---|---|---|---|---|---|---|
| 233 | cyclobutyl-CH₂- | isopropyl-NH-thiazolyl- | OMe | H | cyclopentyl-O-C(O)-NH- | -CH₂CH₂CH₂CH₂-O-CH₂- |
| 234 | Me | isopropyl-NH-thiazolyl- | OMe | H | cyclopentyl-O-C(O)-NH- | -CH₂-CH=CH-CH₂-O-CH₂- |
| 235 | Me | isopropyl-NH-thiazolyl- | OMe | H | cyclopentyl-O-C(O)-NH- | -CH₂-CH=CH-CH₂-S-CH₂- |

-continued
Table 2 of Example 37
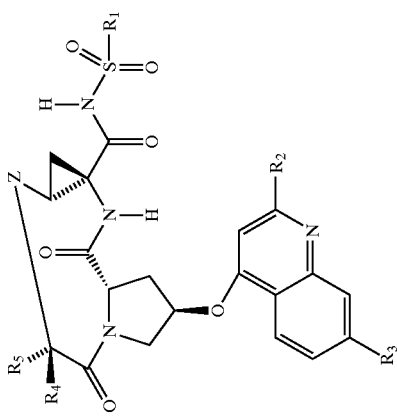
| Cmp | R₁ | R₂ | R₃ | R₅ | R₄ | Z |
|---|---|---|---|---|---|---|
| 236 | Me | 2-(isopropylamino)thiazol-4-yl | OMe | H | cyclopentyl-O-C(O)-NH- | -CH₂-S(O)₂-CH₂CH₂-CH=CH- (cis) |
| 237 | Me | 2-(isopropylamino)thiazol-4-yl | OMe | H | cyclopentyl-O-C(O)-NH- | -CH₂-S(O)₂-(CH₂)₄- |
| 238 | Me | 2-(isopropylamino)thiazol-4-yl | OMe | H | cyclopentyl-O-C(O)-NH- | -CH(Me)-O-CH₂-CH=CH- |

-continued

Table 2 of Example 37

| Cmp | R₁ | R₂ | R₃ | R₅ | R₄ | Z |
|---|---|---|---|---|---|---|
| 239 | Me | isopropylamino-thiazolyl | OMe | H | cyclopentyl-O-C(O)NH- | Me-O-(CH₂)ₙ- |
| 240 | cyclopropyl | isopropylamino-thiazolyl | OMe | H | (tetrahydrofuran-3-yl)-O-C(O)NH- | -O-CH₂-CH=CH-CH₂- |
| 241 | cyclopropyl | isopropylamino-thiazolyl | OMe | H | (tetrahydrofuran-3-yl)-O-C(O)NH- | -S-CH₂-CH=CH-CH₂- |

-continued

Table 2 of Example 37

| Cmp | R₁ | R₂ | R₃ | R₅ | R₄ | Z |
|---|---|---|---|---|---|---|
| 242 | cyclopropyl | 2-(isopropylamino)thiazol-4-yl | OMe | H | tetrahydrofuran-3-yloxycarbonylamino | -CH₂CH₂CH₂-S(O)₂-CH₂- (cis alkene linker) |
| 243 | cyclopropyl | 2-(isopropylamino)thiazol-4-yl | OMe | H | tetrahydrofuran-3-yloxycarbonylamino | -CH₂CH₂CH₂-O-CH(Me)- (cis alkene linker) |
| 244 | cyclopropyl | 2-(isopropylamino)thiazol-4-yl | OMe | H | tetrahydrofuran-3-yloxycarbonylamino | -CH₂CH₂CH₂CH₂-O-CH₂- |

-continued
Table 2 of Example 37
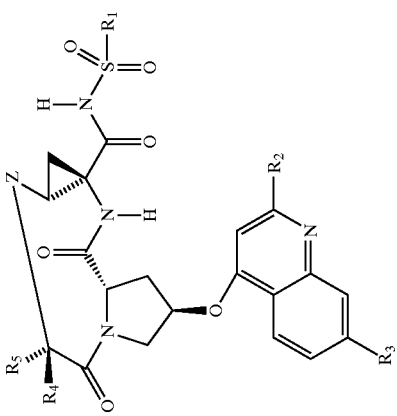
| Cmp | R₁ | R₂ | R₃ | R₅ | R₄ | Z |
|---|---|---|---|---|---|---|
| 245 | cyclopropyl | 2-(isopropylamino)-4-thiazolyl | OMe | H | tetrahydrofuran-3-yl-O-C(O)NH- | -S(O)₂-(CH₂)₄- |
| 246 | cyclopropyl | 2-(isopropylamino)-4-thiazolyl | OMe | H | tetrahydrofuran-3-yl-O-C(O)NH- | -CH(Me)-O-(CH₂)₄- |
| 247 | cyclobutyl | 2-(isopropylamino)-4-thiazolyl | OMe | H | tetrahydrofuran-3-yl-O-C(O)NH- | -CH₂-O-CH₂-CH=CH- |

Table 2 of Example 37
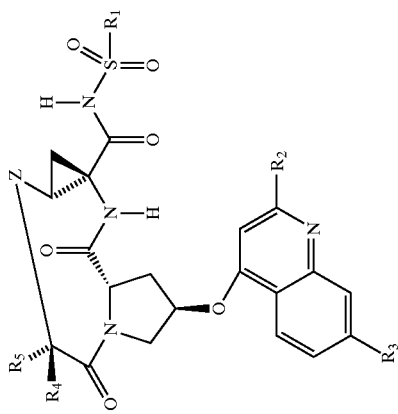
| Cmp | R₁ | R₂ | R₃ | R₅ | R₄ | Z |
|---|---|---|---|---|---|---|
| 248 | cyclobutyl | isopropyl-aminothiazole | OMe | H | tetrahydrofuranyl-O-C(O)NH | -CH₂-S-CH₂-CH=CH- |
| 249 | cyclobutyl | isopropyl-aminothiazole | OMe | H | tetrahydrofuranyl-O-C(O)NH | -CH₂-SO₂-CH₂-CH=CH- |
| 250 | cyclobutyl | isopropyl-aminothiazole | OMe | H | tetrahydrofuranyl-O-C(O)NH | -CH(Me)-O-CH₂-CH=CH- |

-continued
Table 2 of Example 37
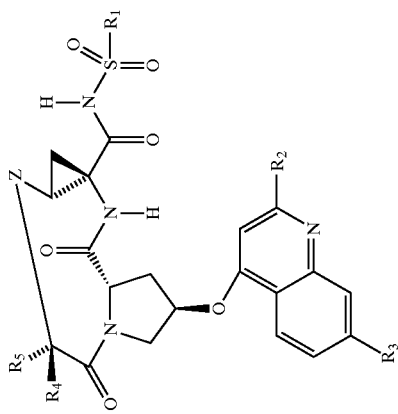
| Cmp | R₁ | R₂ | R₃ | R₅ | R₄ | Z |
|---|---|---|---|---|---|---|
| 251 | Me | 2-(isopropylamino)thiazol-4-yl-methyl | OMe | H | tetrahydrofuran-3-yloxycarbonylamino | -CH₂-O-CH₂-CH=CH- |
| 252 | Me | 2-(isopropylamino)thiazol-4-yl-methyl | OMe | H | tetrahydrofuran-3-yloxycarbonylamino | -CH₂-S-CH₂-CH=CH- |
| 253 | Me | 2-(isopropylamino)thiazol-4-yl-methyl | OMe | H | tetrahydrofuran-3-yloxycarbonylamino | -CH₂-S(O)₂-CH₂-CH=CH- |

-continued

Table 2 of Example 37

| Cmp | R₁ | R₂ | R₃ | R₅ | R₄ | Z |
|---|---|---|---|---|---|---|
| 254 | Me | isopropylaminothiazole | OMe | H | tetrahydrofuran-3-yl carbamate | MeO-CH₂CH₂-CH=CH- |
| 255 | cyclopropyl | isopropylaminothiazole | OMe | H | tetrahydropyran-4-yl carbamate | O-CH₂CH₂-CH=CH- |
| 256 | cyclopropyl | isopropylaminothiazole | OMe | H | tetrahydropyran-4-yl carbamate | S-CH₂CH₂-CH=CH- |

Table 2 of Example 37

| Cmp | R₁ | R₂ | R₃ | R₅ | R₄ | Z |
|---|---|---|---|---|---|---|
| 257 | cyclopropyl | 2-(isopropylamino)thiazol-4-yl | OMe | H | tetrahydropyran-4-yl-O-C(O)-NH- | -CH₂CH₂CH₂-CH=CH-CH₂-S(O)₂- |
| 258 | cyclopropyl | 2-(isopropylamino)thiazol-4-yl | OMe | H | tetrahydropyran-4-yl-O-C(O)-NH- | -CH₂CH₂CH₂-CH=CH-CH₂-O-C(Me)- |
| 259 | cyclopropyl | 2-(isopropylamino)thiazol-4-yl | OMe | H | (3S)-tetrahydrofuran-3-yl-O-C(O)-NH- | -(CH₂)₅-O-C- |

-continued
Table 2 of Example 37
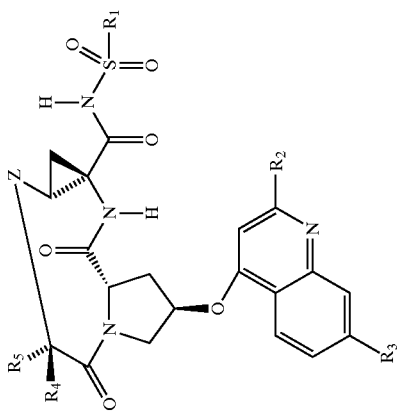
| Cmp | R₁ | R₂ | R₃ | R₅ | R₄ | Z |
|---|---|---|---|---|---|---|
| 260 | cyclopropyl | 2-(isopropylamino)thiazol-4-yl | OMe | H | tetrahydropyran-4-yl-O-C(O)-NH- | -(CH₂)₄-S(O)₂- |
| 261 | cyclopropyl | 2-(isopropylamino)thiazol-4-yl | OMe | H | tetrahydropyran-4-yl-O-C(O)-NH- | -(CH₂)₄-CH(OMe)- |
| 262 | cyclobutyl | 2-(isopropylamino)thiazol-4-yl | OMe | H | tetrahydropyran-4-yl-O-C(O)-NH- | -CH₂CH=CHCH₂-O- |

-continued

Table 2 of Example 37

| Cmp | R₁ | R₂ | R₃ | R₅ | R₄ | Z |
|---|---|---|---|---|---|---|
| 263 | cyclobutyl | 2-(isopropylamino)-4-methylthiazol-5-yl | OMe | H | tetrahydropyran-4-yl-O-C(O)-NH- | -CH₂-S-CH₂-CH₂-CH=CH- |
| 264 | cyclobutyl | 2-(isopropylamino)-4-methylthiazol-5-yl | OMe | H | tetrahydropyran-4-yl-O-C(O)-NH- | -CH₂-S(O)₂-CH₂-CH₂-CH=CH- |
| 265 | cyclobutyl | 2-(isopropylamino)-4-methylthiazol-5-yl | OMe | H | tetrahydropyran-4-yl-O-C(O)-NH- | -CH(Me)-O-CH₂-CH₂-CH=CH- |

-continued

Table 2 of Example 37

| Cmp | R₁ | R₂ | R₃ | R₅ | R₄ | Z |
|---|---|---|---|---|---|---|
| 266 | Me | isopropylamino-thiazolyl | OMe | H | tetrahydropyran-4-yl carbamate | -CH₂-O-CH₂-CH=CH- |
| 267 | Me | isopropylamino-thiazolyl | OMe | H | tetrahydropyran-4-yl carbamate | -CH₂-S-CH₂-CH=CH- |
| 268 | Me | isopropylamino-thiazolyl | OMe | H | tetrahydropyran-4-yl carbamate | -CH₂-S(O)₂-CH₂-CH=CH- |

-continued

Table 2 of Example 37

| Cmp | R₁ | R₂ | R₃ | R₅ | R₄ | Z |
|---|---|---|---|---|---|---|
| 269 | Me | 4-isopropylamino-thiazol-2-yl | OMe | H | tetrahydropyran-4-yl-O-C(O)NH- | Me-O-CH₂CH₂CH=CH- |
| 270 | cyclopropyl | 4-isopropylamino-thiazol-2-yl | OMe | H | 2-fluoroethyl-O-C(O)NH- | -O-CH₂CH₂CH=CH- |
| 271 | cyclopropyl | 4-isopropylamino-thiazol-2-yl | OMe | H | 2-fluoroethyl-O-C(O)NH- | -S-CH₂CH₂CH=CH- |

-continued
Table 2 of Example 37
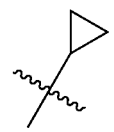
| Cmp | R<sub>1</sub> | R<sub>2</sub> | R<sub>3</sub> | R<sub>5</sub> | R<sub>4</sub> | Z |
|---|---|---|---|---|---|---|
| 272 | cyclopropyl | isopropyl-NH-thiazole | OMe | H | NHC(O)OCH₂CH₂F | sulfone-linked chain |
| 273 | cyclopropyl | isopropyl-NH-thiazole | OMe | H | NHC(O)OCH₂CH₂F | Me-CH-O-linked chain |
| 274 | cyclopropyl | isopropyl-NH-thiazole | OMe | H | NHC(O)OCH₂CH₂F | O-linked chain |

-continued
Table 2 of Example 37
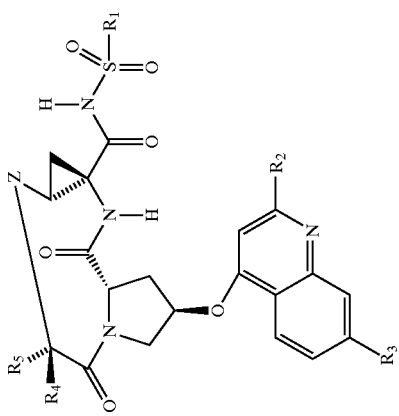
| Cmp | R₁ | R₂ | R₃ | R₅ | R₄ | Z |
|---|---|---|---|---|---|---|
| 275 | cyclopropyl | isopropyl-thiazolyl-NH | OMe | H | 2-fluoroethyl carbamate | sulfone-linked alkyl |
| 276 | cyclopropyl | isopropyl-thiazolyl-NH | OMe | H | 2-fluoroethyl carbamate | methoxy-linked alkyl |
| 277 | cyclobutyl | isopropyl-thiazolyl-NH | OMe | H | 2-fluoroethyl carbamate | alkenyl-O-linked |

-continued

Table 2 of Example 37

| Cmp | R1 | R2 | R3 | R5 | R4 | Z |
|---|---|---|---|---|---|---|
| 278 | cyclobutyl | 2-(isopropylamino)-4-thiazolyl | OMe | H | NHC(O)O-CH2CH2F | -CH2-S-CH2-CH=CH- |
| 279 | cyclobutyl | 2-(isopropylamino)-4-thiazolyl | OMe | H | NHC(O)O-CH2CH2F | -CH2-S(O)2-CH2-CH=CH- |
| 280 | cyclobutyl | 2-(isopropylamino)-4-thiazolyl | OMe | H | NHC(O)O-CH2CH2F | -CH(Me)-O-CH2-CH=CH- |

Table 2 of Example 37

| Cmp | R$_1$ | R$_2$ | R$_3$ | R$_5$ | R$_4$ | Z |
|---|---|---|---|---|---|---|
| 281 | Me | 2-(isopropylamino)thiazol-4-yl | OMe | H | NHC(O)OCH$_2$CH$_2$F | -CH$_2$OCH$_2$-CH=CH- |
| 282 | Me | 2-(isopropylamino)thiazol-4-yl | OMe | H | NHC(O)OCH$_2$CH$_2$F | -CH$_2$SCH$_2$-CH=CH- |
| 283 | Me | 2-(isopropylamino)thiazol-4-yl | OMe | H | NHC(O)OCH$_2$CH$_2$F | -CH$_2$S(O)$_2$CH$_2$-CH=CH- |

-continued
Table 2 of Example 37
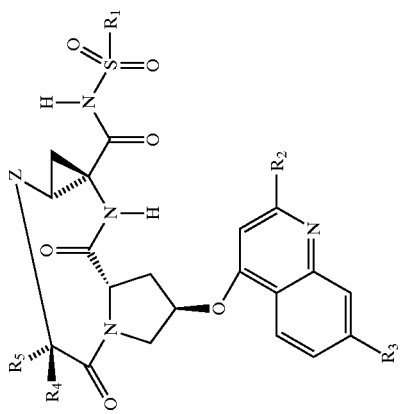
| Cmp | R₁ | R₂ | R₃ | R₅ | R₄ | Z |
|---|---|---|---|---|---|---|
| 284 | Me | 2-(isopropylamino)-4-thiazolyl | OMe | H | NH-C(O)-O-CH₂CH₂F | -OCH₂-CH=CH-CH₂-, Me-O- |
| 285 | cyclopropyl | 2-(isopropylamino)-4-thiazolyl | OMe | H | NH-C(O)-NH-tBu | -OCH₂-CH=CH-CH₂-CH₂-O- |
| 286 | cyclopropyl | 2-(isopropylamino)-4-thiazolyl | OMe | H | NH-C(O)-NH-tBu | -SCH₂-CH=CH-CH₂-CH₂- |

-continued

Table 2 of Example 37

| Cmp | R₁ | R₂ | R₃ | R₅ | R₄ | Z |
|---|---|---|---|---|---|---|
| 287 | cyclopropyl | isopropyl-NH-thiazole | OMe | H | t-Bu-NH-C(O)-NH- | -CH₂CH₂-S(O)₂-CH₂- (cis alkene linker) |
| 288 | cyclopropyl | isopropyl-NH-thiazole | OMe | H | t-Bu-NH-C(O)-NH- | -CH(Me)-O-CH₂CH₂- (cis alkene linker) |
| 289 | cyclopropyl | isopropyl-NH-thiazole | OMe | H | t-Bu-NH-C(O)-NH- | -O-CH₂CH₂CH₂- |

-continued
Table 2 of Example 37
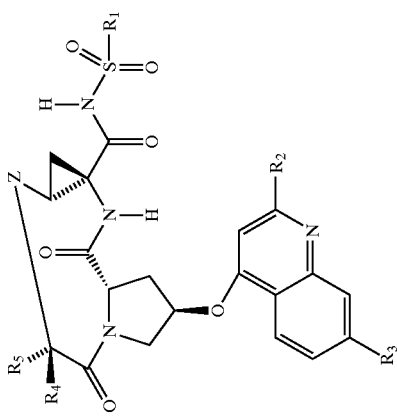
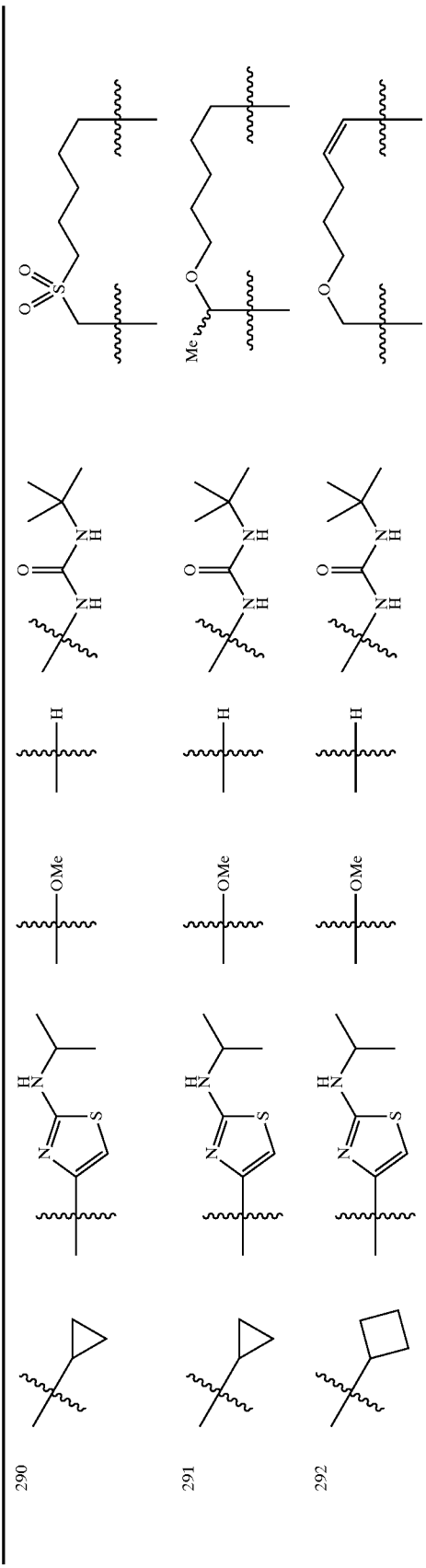

-continued
Table 2 of Example 37
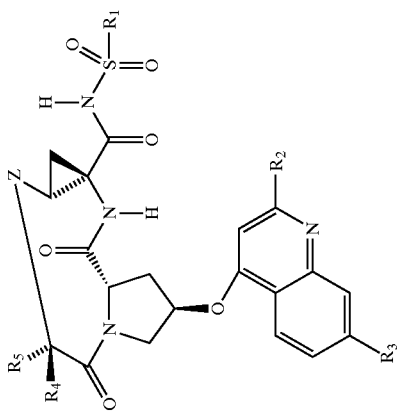
| Cmp | R₁ | R₂ | R₃ | R₅ | R₄ | Z |
|---|---|---|---|---|---|---|
| 293 | cyclobutyl | 2-(isopropylamino)thiazol-4-yl | OMe | H | t-Bu-NHC(O)NH- | -CH₂-S-CH₂-CH=CH-CH₂- |
| 294 | cyclobutyl | 2-(isopropylamino)thiazol-4-yl | OMe | H | t-Bu-NHC(O)NH- | -CH₂-S(O)₂-CH₂-CH=CH-CH₂- |
| 295 | cyclobutyl | 2-(isopropylamino)thiazol-4-yl | OMe | H | t-Bu-NHC(O)NH- | -CH(Me)-O-CH₂-CH=CH-CH₂- |

-continued

Table 2 of Example 37

| Cmp | R₁ | R₂ | R₃ | R₅ | R₄ | Z |
|---|---|---|---|---|---|---|
| 296 | Me | isopropylamino-thiazole | OMe | H | t-Bu-NHC(O)NH- | -CH₂-O-CH₂-CH=CH- |
| 297 | Me | isopropylamino-thiazole | OMe | H | t-Bu-NHC(O)NH- | -CH₂-S-CH₂-CH=CH- |
| 298 | Me | isopropylamino-thiazole | OMe | H | t-Bu-NHC(O)NH- | -CH₂-S(O)₂-CH₂-CH₂-CH=CH- |

-continued
Table 2 of Example 37
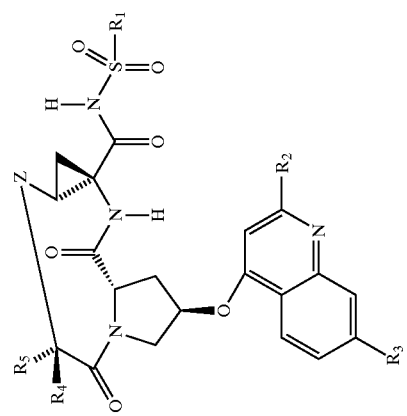
| Cmp | R1 | R2 | R3 | R5 | R4 | Z |
|---|---|---|---|---|---|---|
| 299 | Me | isopropyl-NH-thiazole | OMe | H | t-Bu-NH-C(O)-NH- | Me-O-CH2CH2-CH=CH- |
| 300 | cyclopropyl | isopropyl-NH-thiazole | OMe | H | cyclopropyl-CH2-C(O)-NH- | O-CH2CH2-CH=CH- |
| 301 | cyclopropyl | isopropyl-NH-thiazole | OMe | H | cyclopropyl-CH2-C(O)-NH- | S-CH2CH2-CH=CH- |

-continued
Table 2 of Example 37
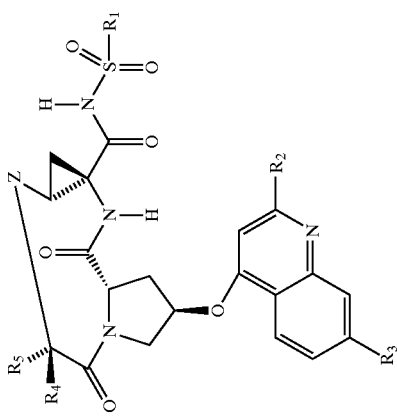
| Cmp | R₁ | R₂ | R₃ | R₅ | R₄ | Z |
|---|---|---|---|---|---|---|
| 302 | | | OMe | H | | |
| 303 | | | OMe | H | | |
| 304 | | | OMe | H | | |

-continued
Table 2 of Example 37
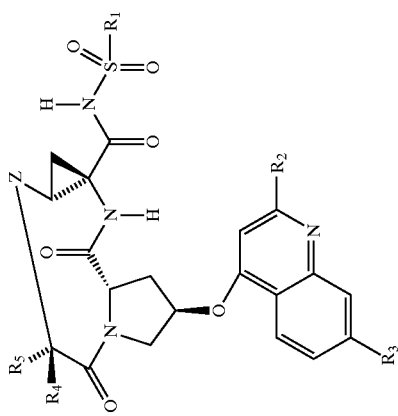
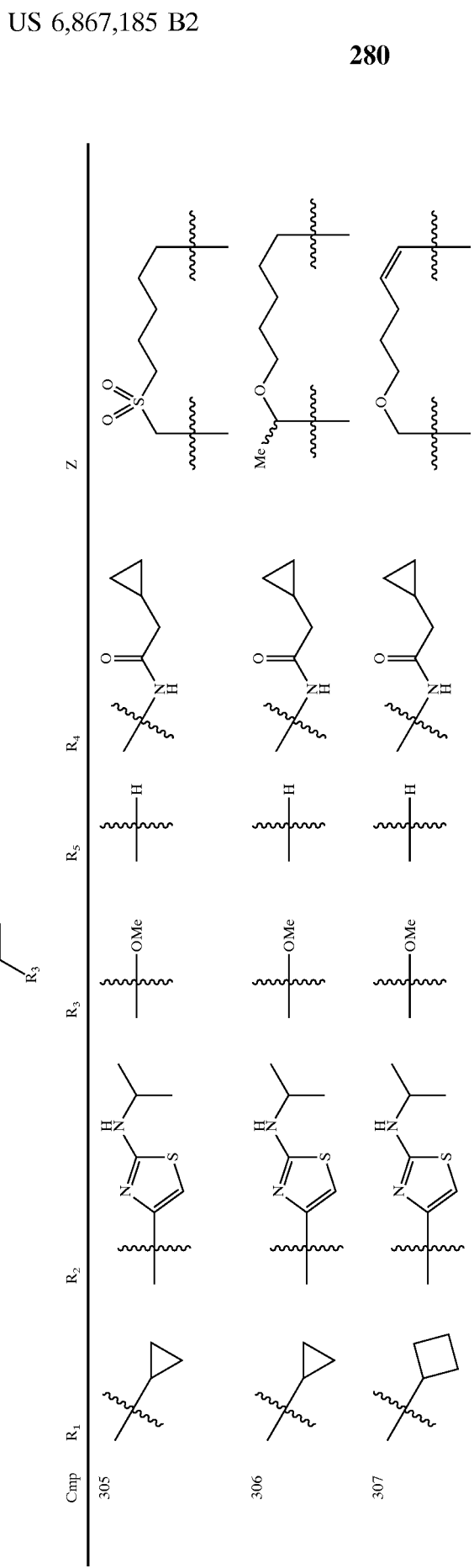

-continued

Table 2 of Example 37

-continued

Table 2 of Example 37

| Cmp | R1 | R2 | R3 | R5 | R4 | Z |
|---|---|---|---|---|---|---|
| 311 | cyclobutyl | 2-(isopropylamino)thiazol-4-yl | OMe | H | cyclopropylmethyl-C(O)NH- | -CH2-O-CH2-CH=CH-CH2- |
| 312 | Me | 2-(isopropylamino)thiazol-4-yl | OMe | H | cyclopropylmethyl-C(O)NH- | -CH2-S-CH2-CH=CH-CH2- |
| 313 | Me | 2-(isopropylamino)thiazol-4-yl | OMe | H | cyclopropylmethyl-C(O)NH- | -CH2-S(O)2-CH2-CH=CH-CH2- |

-continued

Table 2 of Example 37

| Cmp | R₁ | R₂ | R₃ | R₅ | R₄ | Z |
|---|---|---|---|---|---|---|
| 314 | Me | 2-(isopropylamino)thiazol-4-yl | OMe | H | cyclopropylacetamido | MeO-CH(−)-CH₂CH₂CH=CH- |
| 315 | cyclopropyl | 2-(isopropylamino)thiazol-4-yl | OMe | H | neopentyloxycarbonylamino | O-CH₂CH₂CH=CH- |
| 316 | cyclopropyl | 2-(isopropylamino)thiazol-4-yl | OMe | H | neopentyloxycarbonylamino | S-CH₂CH₂CH=CH- |

-continued
Table 2 of Example 37
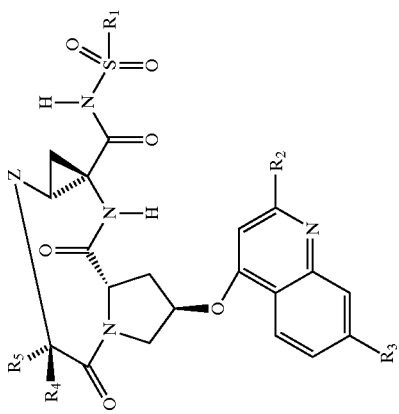
| Cmp | R₁ | R₂ | R₃ | R₅ | R₄ | Z |
|---|---|---|---|---|---|---|
| 317 | 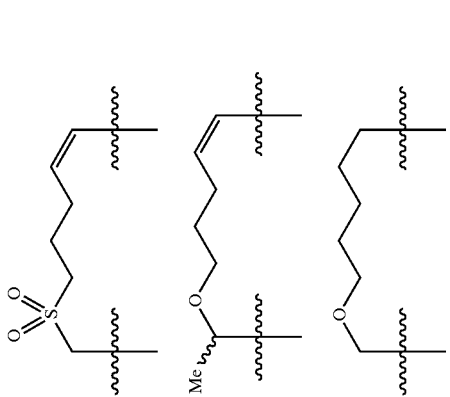 | | OMe | H | | 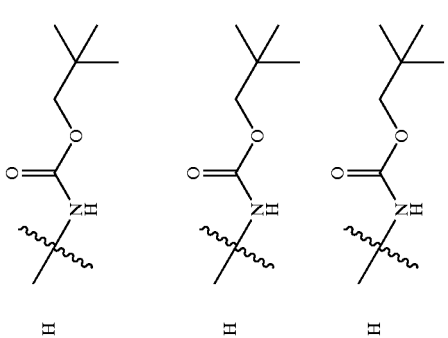 |
| 318 | | | OMe | H | | |
| 319 | | | OMe | H | | 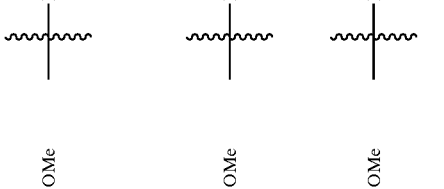 |
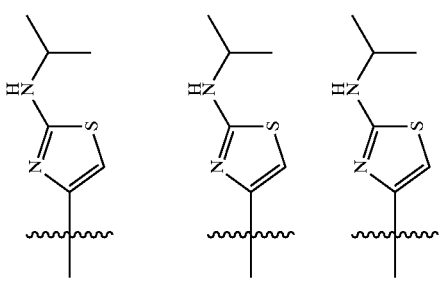

-continued
Table 2 of Example 37
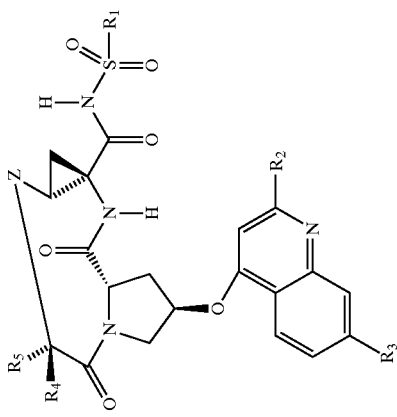
| Cmp | R1 | R2 | R3 | R5 | R4 | Z |
|---|---|---|---|---|---|---|
| 320 | cyclopropyl | 2-(isopropylamino)thiazol-4-yl | OMe | H | neopentyloxycarbonylamino | -(CH2)4-SO2-CH2- |
| 321 | cyclopropyl | 2-(isopropylamino)thiazol-4-yl | OMe | H | neopentyloxycarbonylamino | -(CH2)4-O-CH(Me)- |
| 322 | cyclobutyl | 2-(isopropylamino)thiazol-4-yl | OMe | H | neopentyloxycarbonylamino | -(CH2)3-CH=CH-CH2-O- |

-continued
Table 2 of Example 37
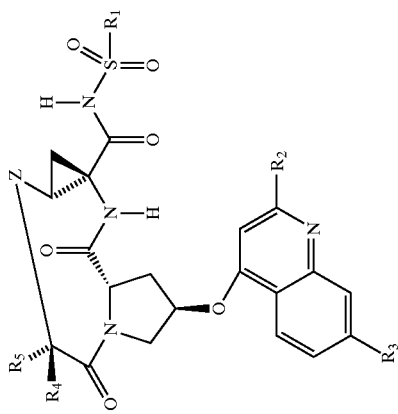
| Cmp | R₁ | R₂ | R₃ | R₅ | R₄ | Z |
|---|---|---|---|---|---|---|
| 323 | cyclobutyl | 2-(isopropylamino)-4-thiazolyl | OMe | H | neopentyl carbamate | -CH₂-S-CH₂-CH=CH- |
| 324 | cyclobutyl | 2-(isopropylamino)-4-thiazolyl | OMe | H | neopentyl carbamate | -CH₂-S(O)₂-CH₂-CH=CH- |
| 325 | cyclobutyl | 2-(isopropylamino)-4-thiazolyl | OMe | H | neopentyl carbamate | -CH(Me)-O-CH₂-CH=CH- |

-continued

Table 2 of Example 37

| Cmp | R₁ | R₂ | R₃ | R₅ | R₄ | Z |
|---|---|---|---|---|---|---|
| 326 | Me | 2-(isopropylamino)-4-methylthiazol-5-yl | OMe | H | NH-C(O)-O-CH₂-C(CH₃)₃ | -CH₂-O-CH₂-CH=CH- |
| 327 | Me | 2-(isopropylamino)-4-methylthiazol-5-yl | OMe | H | NH-C(O)-O-CH₂-C(CH₃)₃ | -CH₂-S-CH₂-CH=CH- |
| 328 | Me | 2-(isopropylamino)-4-methylthiazol-5-yl | OMe | H | NH-C(O)-O-CH₂-C(CH₃)₃ | -CH₂-S(O)₂-CH₂-CH=CH- |

-continued

Table 2 of Example 37

| Cmp | R₁ | R₂ | R₃ | R₅ | R₄ | Z |
|---|---|---|---|---|---|---|
| 329 | Me | NH-isopropyl-thiazole | OMe | H | neopentyl carbamate | Me-O-CH₂-CH=CH- |
| 330 | cyclopropyl | isopropyl-thiazole | OMe | H | cyclopentyl carbamate | O-CH₂-CH₂-CH=CH- |
| 331 | cyclopropyl | isopropyl-thiazole | OMe | H | cyclopentyl carbamate | S-CH₂-CH₂-CH=CH- |

-continued

Table 2 of Example 37

| Cmp | R₁ | R₂ | R₃ | R₅ | R₄ | Z |
|-----|----|----|----|----|----|----|
| 332 | cyclopropyl | 4-isopropyl-thiazol-2-yl | OMe | H | cyclopentyl-O-C(O)-NH- | -CH₂-CH=CH-CH₂-S(O)₂-CH₂- |
| 333 | cyclopropyl | 4-isopropyl-thiazol-2-yl | OMe | H | cyclopentyl-O-C(O)-NH- | -CH(Me)-CH₂-CH=CH-CH₂-O-CH₂- |
| 334 | cyclopropyl | 4-isopropyl-thiazol-2-yl | OMe | H | cyclopentyl-O-C(O)-NH- | -CH₂-CH₂-CH₂-CH₂-CH₂-O-CH₂- |

-continued

Table 2 of Example 37

| Cmp | R₁ | R₂ | R₃ | R₅ | R₄ | Z |
|---|---|---|---|---|---|---|
| 335 | cyclopropyl | 4-isopropylthiazol-2-yl | OMe | H | cyclopentyl-O-C(O)-NH- | -(CH₂)₄-SO₂-CH₂- |
| 336 | cyclopropyl | 4-isopropylthiazol-2-yl | OMe | H | cyclopentyl-O-C(O)-NH- | -(CH₂)₄-CH(Me)-O-CH₂- |
| 337 | cyclobutyl | 4-isopropylthiazol-2-yl | OMe | H | cyclopentyl-O-C(O)-NH- | -CH₂-CH=CH-CH₂-O-CH₂- |

-continued

Table 2 of Example 37

| Cmp | R₁ | R₂ | R₃ | R₅ | R₄ | Z |
|---|---|---|---|---|---|---|
| 338 | cyclobutyl | 4-isopropyl-thiazol-2-yl | OMe | H | cyclopentyl-O-C(O)-NH- | -CH₂-S-CH₂-CH=CH-CH₂- |
| 339 | cyclobutyl | 4-isopropyl-thiazol-2-yl | OMe | H | cyclopentyl-O-C(O)-NH- | -CH₂-S(O)₂-CH₂-CH=CH-CH₂- |
| 340 | cyclobutyl | 4-isopropyl-thiazol-2-yl | OMe | H | cyclopentyl-O-C(O)-NH- | -CH(Me)-O-CH₂-CH₂-CH=CH-CH₂- |

-continued
Table 2 of Example 37
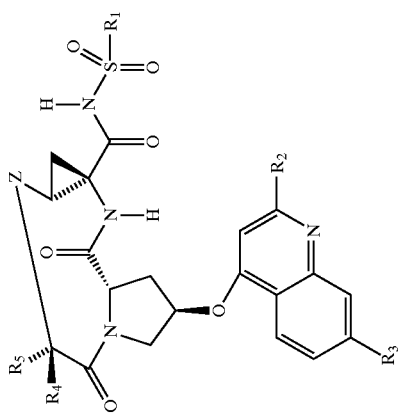
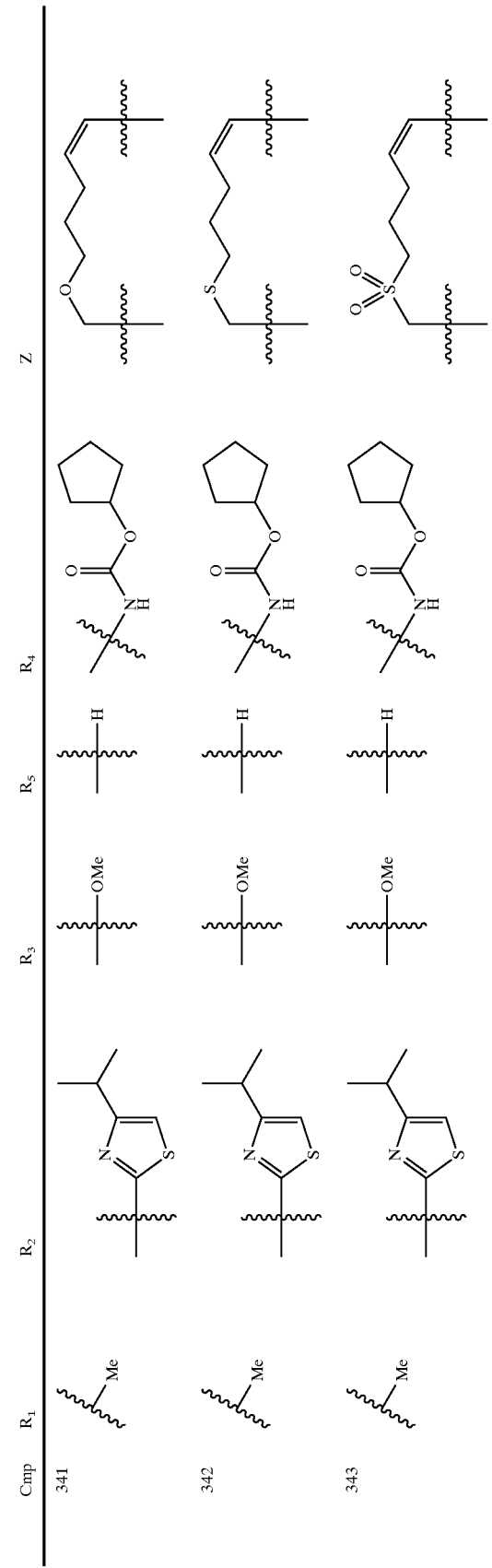
| Cmp | R₁ | R₂ | R₃ | R₅ | R₄ | Z |
|---|---|---|---|---|---|---|
| 341 | Me | 4-isopropylthiazol-2-yl | OMe | H | cyclopentyl carbamate | -CH₂-O-CH₂CH₂CH=CH- |
| 342 | Me | 4-isopropylthiazol-2-yl | OMe | H | cyclopentyl carbamate | -CH₂-S-CH₂CH₂CH=CH- |
| 343 | Me | 4-isopropylthiazol-2-yl | OMe | H | cyclopentyl carbamate | -CH₂-SO₂-CH₂CH₂CH=CH- |

-continued

Table 2 of Example 37

| Cmp | R₁ | R₂ | R₃ | R₅ | R₄ | Z |
|---|---|---|---|---|---|---|
| 344 | Me | 4-isopropyl-thiazol-2-yl | OMe | H | cyclopentyl-O-C(O)-NH- | MeO-CH₂-CH₂-CH=CH- |
| 345 | cyclopropyl | 4-isopropyl-thiazol-2-yl | OMe | H | (tetrahydrofuran-3-yl)-O-C(O)-NH- | O-CH₂-CH₂-CH=CH- |
| 346 | cyclopropyl | 4-isopropyl-thiazol-2-yl | OMe | H | (tetrahydrofuran-3-yl)-O-C(O)-NH- | S-CH₂-CH₂-CH=CH- |

-continued

Table 2 of Example 37

| Cmp | R₁ | R₂ | R₃ | R₅ | R₄ | Z |
|---|---|---|---|---|---|---|
| 347 | cyclopropyl | 4-isopropylthiazol-2-yl | OMe | H | (tetrahydrofuran-3-yl)oxycarbonylamino | -CH₂-CH₂-CH=CH-CH₂-SO₂-CH₂- |
| 348 | cyclopropyl | 4-isopropylthiazol-2-yl | OMe | H | (tetrahydrofuran-3-yl)oxycarbonylamino | -CH₂-CH₂-CH=CH-CH₂-CH(Me)-O-CH₂- |
| 349 | cyclopropyl | 4-isopropylthiazol-2-yl | OMe | H | (tetrahydrofuran-3-yl)oxycarbonylamino | -CH₂-CH₂-CH₂-CH₂-CH₂-O-CH₂- |

Table 2 of Example 37

-continued

Table 2 of Example 37

| Cmp | R$_1$ | R$_2$ | R$_3$ | R$_5$ | R$_4$ | Z |
|---|---|---|---|---|---|---|
| 353 | cyclobutyl | 4-isopropyl-thiazol-2-yl | OMe | H | tetrahydrofuran-3-yl-O-C(O)-NH- | -CH$_2$-S-CH$_2$-CH=CH- |
| 354 | cyclobutyl | 4-isopropyl-thiazol-2-yl | OMe | H | tetrahydrofuran-3-yl-O-C(O)-NH- | -CH$_2$-S(O)$_2$-CH$_2$-CH=CH- |
| 355 | cyclobutyl | 4-isopropyl-thiazol-2-yl | OMe | H | tetrahydrofuran-3-yl-O-C(O)-NH- | -CH(Me)-O-CH$_2$-CH=CH- |

-continued
Table 2 of Example 37
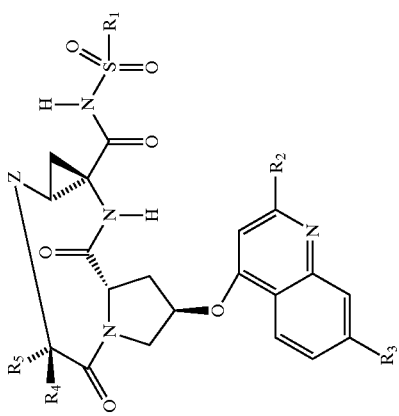
| Cmp | R₁ | R₂ | R₃ | R₅ | R₄ | Z |
|---|---|---|---|---|---|---|
| 356 | cyclobutyl | 4-isopropylthiazol-2-yl | OMe | H | tetrahydrofuran-3-yl-O-C(O)NH- | -CH₂-O-CH₂CH₂-CH=CH- |
| 357 | Me | 4-isopropylthiazol-2-yl | OMe | H | tetrahydrofuran-3-yl-O-C(O)NH- | -CH₂-S-CH₂CH₂-CH=CH- |
| 358 | Me | 4-isopropylthiazol-2-yl | OMe | H | tetrahydrofuran-3-yl-O-C(O)NH- | -CH₂-S(O)₂-CH₂CH₂-CH=CH- |

-continued
Table 2 of Example 37
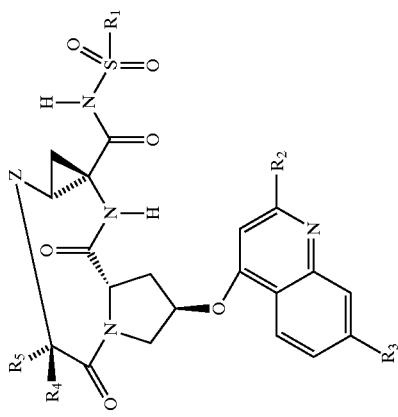
| Cmp | R1 | R2 | R3 | R5 | R4 | Z |
|---|---|---|---|---|---|---|
| 359 | Me | 4-isopropylthiazol-2-yl | OMe | H | tetrahydrofuran-3-yl-O-C(O)-NH | Me-O-CH(—)-CH2CH2-CH=CH- |
| 360 | cyclopropyl | 4-isopropylthiazol-2-yl | OMe | H | tetrahydropyran-4-yl-O-C(O)-NH | -O-CH2-...-CH=CH- |
| 361 | cyclopropyl | 4-isopropylthiazol-2-yl | OMe | H | tetrahydropyran-4-yl-O-C(O)-NH | -S-CH2CH2-CH=CH- |

-continued

Table 2 of Example 37

| Cmp | R₁ | R₂ | R₃ | R₅ | R₄ | Z |
|---|---|---|---|---|---|---|
| 362 | cyclopropyl | 4-isopropyl-thiazol-2-yl | OMe | H | tetrahydropyran-4-yl-O-C(O)-NH- | -S(O)₂-CH₂CH₂CH₂-CH=CH- (cis) |
| 363 | cyclopropyl | 4-isopropyl-thiazol-2-yl | OMe | H | tetrahydropyran-4-yl-O-C(O)-NH- | -CH(Me)-O-CH₂CH₂CH₂-CH=CH- (cis) |
| 364 | cyclopropyl | 4-isopropyl-thiazol-2-yl | OMe | H | tetrahydropyran-4-yl-O-C(O)-NH- | -CH₂-O-CH₂CH₂CH₂CH₂CH₂- |

-continued
Table 2 of Example 37
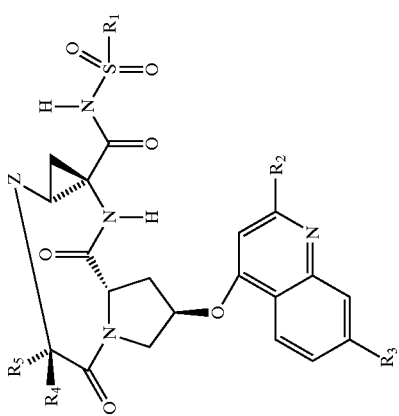
| Cmp | R₁ | R₂ | R₃ | R₅ | R₄ | Z |
|---|---|---|---|---|---|---|
| 365 | cyclopropyl | 4-isopropylthiazol-2-yl | OMe | H | tetrahydropyran-4-yl-O-C(O)-NH- | -S(O)₂-(CH₂)₄- |
| 366 | cyclopropyl | 4-isopropylthiazol-2-yl | OMe | H | tetrahydropyran-4-yl-O-C(O)-NH- | -CH(Me)-O-(CH₂)₄- |
| 367 | cyclobutyl | 4-isopropylthiazol-2-yl | OMe | H | tetrahydropyran-4-yl-O-C(O)-NH- | -CH₂-O-CH₂-CH=CH- |

-continued

Table 2 of Example 37

| Cmp | R₁ | R₂ | R₃ | R₅ | R₄ | Z |
|---|---|---|---|---|---|---|
| 368 | cyclobutyl | 4-isopropylthiazol-2-yl | OMe | H | tetrahydropyran-4-yl-O-C(O)-NH- | -S-CH₂-CH=CH-CH₂- |
| 369 | cyclobutyl | 4-isopropylthiazol-2-yl | OMe | H | tetrahydropyran-4-yl-O-C(O)-NH- | -S(O)₂-CH₂-CH=CH-CH₂- |
| 370 | cyclobutyl | 4-isopropylthiazol-2-yl | OMe | H | tetrahydropyran-4-yl-O-C(O)-NH- | -CH(Me)-O-CH₂-CH=CH-CH₂- |

-continued
Table 2 of Example 37
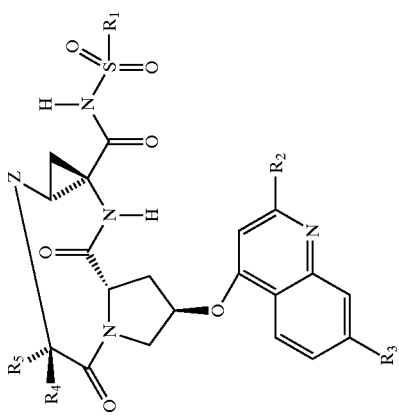
| Cmp | R1 | R2 | R3 | R5 | R4 | Z |
|---|---|---|---|---|---|---|
| 371 | Me | 4-isopropyl-thiazol-2-yl | OMe | H | tetrahydropyran-4-yl-O-C(O)NH- | 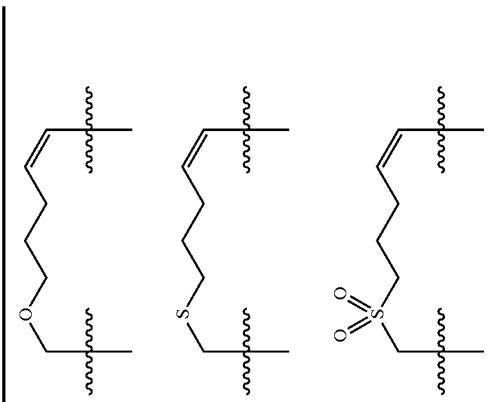 |
| 372 | Me | 4-isopropyl-thiazol-2-yl | OMe | H | tetrahydropyran-4-yl-O-C(O)NH- | 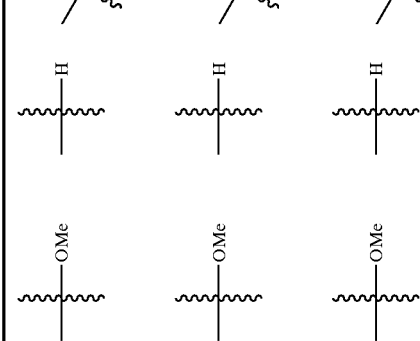 |
| 373 | Me | 4-isopropyl-thiazol-2-yl | OMe | H | tetrahydropyran-4-yl-O-C(O)NH- | 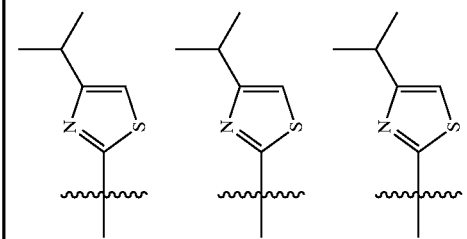 |

-continued
Table 2 of Example 37
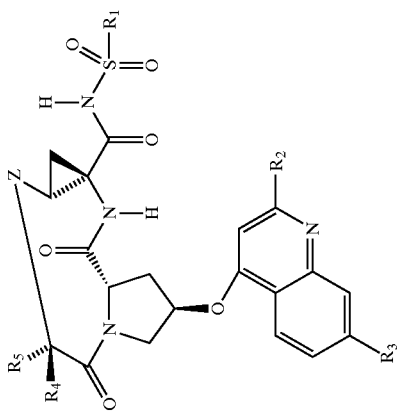
| Cmp | R₁ | R₂ | R₃ | R₅ | R₄ | Z |
|---|---|---|---|---|---|---|
| 374 | Me | 4-isopropyl-thiazol-2-yl | OMe | H | tetrahydropyran-4-yl-O-C(O)-NH- | Me-O-CH(Me)-...-CH=CH-CH₂- |
| 375 | cyclopropyl | 4-isopropyl-thiazol-2-yl | OMe | H | 2-fluoroethyl-O-C(O)-NH- | O-CH₂-...-CH=CH-CH₂- |
| 376 | cyclopropyl | 4-isopropyl-thiazol-2-yl | OMe | H | 2-fluoroethyl-O-C(O)-NH- | S-CH₂-...-CH=CH-CH₂- |

-continued
Table 2 of Example 37
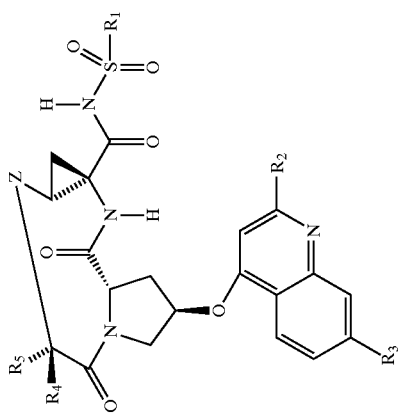
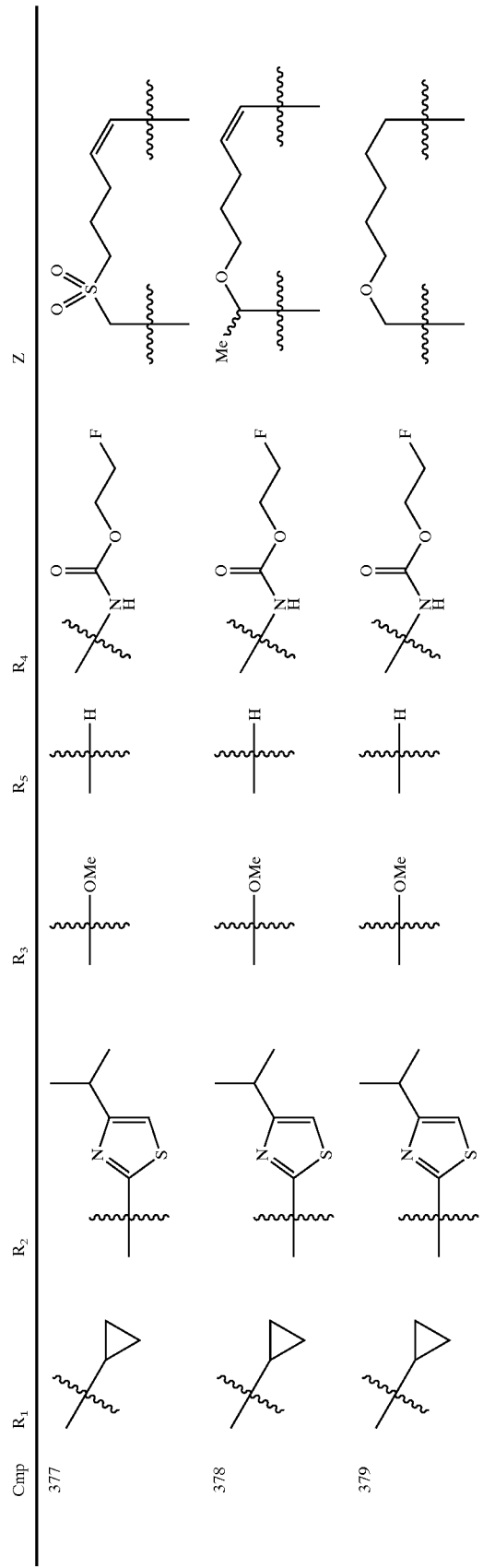
| Cmp | R₁ | R₂ | R₃ | R₅ | R₄ | Z |
|---|---|---|---|---|---|---|
| 377 | cyclopropyl | 4-isopropylthiazol-2-yl | OMe | H | NHC(O)OCH₂CH₂F | -CH₂-CH=CH-CH₂-S(O)₂-CH₂- |
| 378 | cyclopropyl | 4-isopropylthiazol-2-yl | OMe | H | NHC(O)OCH₂CH₂F | -CH₂-CH=CH-CH₂-CH(Me)-O-CH₂- |
| 379 | cyclopropyl | 4-isopropylthiazol-2-yl | OMe | H | NHC(O)OCH₂CH₂F | -CH₂-CH₂-CH₂-CH₂-CH₂-O-CH₂- |

-continued

Table 2 of Example 37

| Cmp | R₁ | R₂ | R₃ | R₅ | R₄ | Z |
|---|---|---|---|---|---|---|
| 380 | cyclopropyl | 4-isopropyl-thiazol-2-yl | OMe | H | NHC(O)O-CH₂CH₂F | -(CH₂)₄-SO₂- |
| 381 | cyclopropyl | 4-isopropyl-thiazol-2-yl | OMe | H | NHC(O)O-CH₂CH₂F | -CH(Me)-O-(CH₂)₄- |
| 382 | cyclobutyl | 4-isopropyl-thiazol-2-yl | OMe | H | NHC(O)O-CH₂CH₂F | -CH₂-O-CH₂-CH=CH-CH₂- |

-continued
Table 2 of Example 37
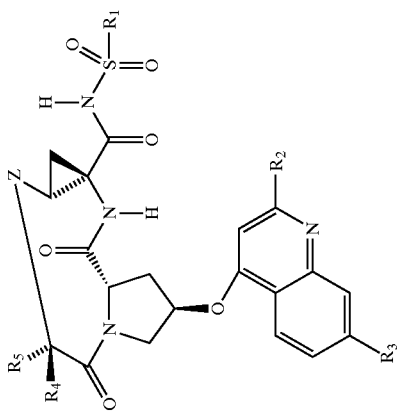
| Cmp | R₁ | R₂ | R₃ | R₅ | R₄ | Z |
|---|---|---|---|---|---|---|
| 383 | cyclobutyl | 4-isopropyl-thiazol-2-yl | OMe | H | NHC(O)O-CH₂CH₂F | -CH₂-S-CH₂-CH=CH- |
| 384 | cyclobutyl | 4-isopropyl-thiazol-2-yl | OMe | H | NHC(O)O-CH₂CH₂F | -CH₂-S(O)₂-CH₂-CH=CH- |
| 385 | cyclobutyl | 4-isopropyl-thiazol-2-yl | OMe | H | NHC(O)O-CH₂CH₂F | -CH(Me)-O-CH₂-CH=CH- |

-continued
Table 2 of Example 37
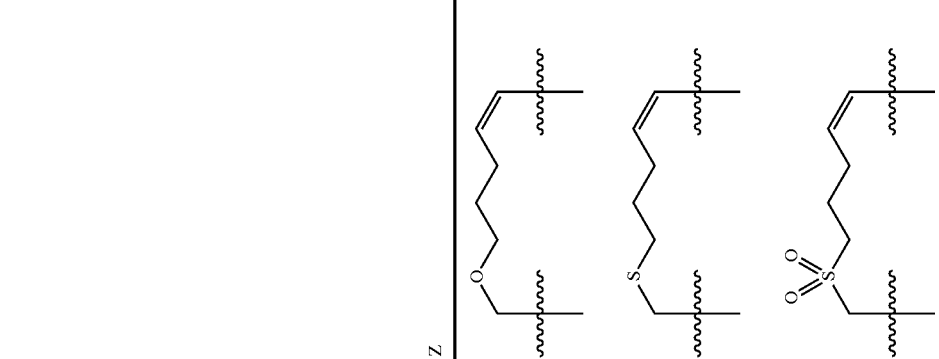
| Cmp | R1 | R2 | R3 | R5 | R4 | Z |
|---|---|---|---|---|---|---|
| 386 | Me | 4-isopropyl-thiazol-2-yl | OMe | H | NHC(O)OCH2CH2F | -CH2OCH2CH=CH- |
| 387 | Me | 4-isopropyl-thiazol-2-yl | OMe | H | NHC(O)OCH2CH2F | -CH2SCH2CH=CH- |
| 388 | Me | 4-isopropyl-thiazol-2-yl | OMe | H | NHC(O)OCH2CH2F | -CH2S(O)2CH2CH=CH- |

-continued

Table 2 of Example 37

| Cmp | R₁ | R₂ | R₃ | R₅ | R₄ | Z |
|---|---|---|---|---|---|---|
| 389 | Me | 4-isopropyl-thiazol-2-yl | OMe | H | 2-fluoroethoxycarbonylamino | CH(Me)-O-CH₂-CH=CH- |
| 390 | cyclopropyl | 4-isopropyl-thiazol-2-yl | OMe | H | tert-butyl-NH-C(O)-NH | CH₂-O-CH₂-CH₂-CH=CH- |
| 391 | cyclopropyl | 4-isopropyl-thiazol-2-yl | OMe | H | tert-butyl-NH-C(O)-NH | CH₂-S-CH₂-CH₂-CH=CH- |

-continued

Table 2 of Example 37

| Cmp | R₁ | R₂ | R₃ | R₅ | R₄ | Z |
|---|---|---|---|---|---|---|
| 392 | cyclopropyl | 4-isopropyl-thiazol-2-yl | OMe | H | t-butyl urea | -CH₂-CH₂-CH=CH-CH₂-SO₂- |
| 393 | cyclopropyl | 4-isopropyl-thiazol-2-yl | OMe | H | t-butyl urea | -CH₂-CH₂-CH=CH-CH₂-CH(Me)-O- |
| 394 | cyclopropyl | 4-isopropyl-thiazol-2-yl | OMe | H | t-butyl urea | -CH₂-CH₂-CH₂-CH₂-CH₂-O- |

-continued

Table 2 of Example 37

| Cmp | R₁ | R₂ | R₃ | R₅ | R₄ | Z |
|---|---|---|---|---|---|---|
| 395 | cyclopropyl | 4-isopropyl-thiazol-2-yl | OMe | H | t-BuNHC(O)NH- | -(CH₂)₄-S(O)₂-CH₂- |
| 396 | cyclopropyl | 4-isopropyl-thiazol-2-yl | OMe | H | t-BuNHC(O)NH- | -(CH₂)₄-CH(Me)-O-CH₂- |
| 397 | cyclobutyl | 4-isopropyl-thiazol-2-yl | OMe | H | t-BuNHC(O)NH- | -CH₂-CH=CH-CH₂-O-CH₂- |

-continued

Table 2 of Example 37

| Cmp | R₁ | R₂ | R₃ | R₅ | R₄ | Z |
|---|---|---|---|---|---|---|
| 398 | cyclobutyl | 4-isopropyl-thiazol-2-yl | OMe | H | tBu-NHC(O)NH- | -CH₂-S-CH₂CH₂CH=CH- |
| 399 | cyclobutyl | 4-isopropyl-thiazol-2-yl | OMe | H | tBu-NHC(O)NH- | -CH₂-S(O)₂-CH₂CH₂CH=CH- |
| 400 | cyclobutyl | 4-isopropyl-thiazol-2-yl | OMe | H | tBu-NHC(O)NH- | -CH(Me)-O-CH₂CH₂CH=CH- |

-continued

Table 2 of Example 37

| Cmp | R₁ | R₂ | R₃ | R₅ | R₄ | Z |
|---|---|---|---|---|---|---|
| 401 | Me | 4-isopropyl-thiazol-2-yl | OMe | H | NHC(O)NH-tBu | -CH₂-O-CH₂-CH=CH- |
| 402 | Me | 4-isopropyl-thiazol-2-yl | OMe | H | NHC(O)NH-tBu | -CH₂-S-CH₂-CH=CH- |
| 403 | Me | 4-isopropyl-thiazol-2-yl | OMe | H | NHC(O)NH-tBu | -CH₂-S(O)₂-CH₂-CH=CH- |

-continued

Table 2 of Example 37

| Cmp | R₁ | R₂ | R₃ | R₅ | R₄ | Z |
|---|---|---|---|---|---|---|
| 404 | Me | 4-isopropyl-thiazol-2-yl | OMe | H | tBu-NHC(O)NH- | -CH(Me)-O-CH₂-CH₂-CH=CH- |
| 405 | cyclopropyl | 4-isopropyl-thiazol-2-yl | OMe | H | cyclopropyl-CH₂-C(O)NH- | -CH₂-O-CH₂-CH₂-CH=CH- |
| 406 | cyclopropyl | 4-isopropyl-thiazol-2-yl | OMe | H | cyclopropyl-CH₂-C(O)NH- | -CH₂-S-CH₂-CH₂-CH=CH- |

-continued

Table 2 of Example 37

| Cmp | R1 | R2 | R3 | R5 | R4 | Z |
|---|---|---|---|---|---|---|
| 407 | cyclopropyl | 4-isopropylthiazol-2-yl | OMe | H | cyclopropylacetamide | -CH2CH2CH2S(O)2- |
| 408 | cyclopropyl | 4-isopropylthiazol-2-yl | OMe | H | cyclopropylacetamide | -CH2CH2CH2OCH(Me)- |
| 409 | cyclopropyl | 4-isopropylthiazol-2-yl | OMe | H | cyclopropylacetamide | -CH2CH2CH2CH2O- |

-continued

Table 2 of Example 37

| Cmp | R₁ | R₂ | R₃ | R₅ | R₄ | Z |
|---|---|---|---|---|---|---|
| 410 | cyclopropyl | 4-isopropylthiazol-2-yl | OMe | H | cyclopropyl-CH₂-C(O)NH- | -(CH₂)₄-S(O)₂- |
| 411 | cyclopropyl | 4-isopropylthiazol-2-yl | OMe | H | cyclopropyl-CH₂-C(O)NH- | -(CH₂)₄-CH(Me)-O- |
| 412 | cyclobutyl | 4-isopropylthiazol-2-yl | OMe | H | cyclopropyl-CH₂-C(O)NH- | -CH₂-CH=CH-(CH₂)₂-O- |

-continued

Table 2 of Example 37

| Cmp | R₁ | R₂ | R₃ | R₅ | R₄ | Z |
|---|---|---|---|---|---|---|
| 413 | cyclobutyl | 4-isopropyl-thiazol-2-yl | OMe | H | cyclopropylmethyl-C(O)NH- | -S-CH₂-CH=CH-CH₂- |
| 414 | cyclobutyl | 4-isopropyl-thiazol-2-yl | OMe | H | cyclopropylmethyl-C(O)NH- | -S(O)₂-CH₂-CH=CH-CH₂- |
| 415 | cyclobutyl | 4-isopropyl-thiazol-2-yl | OMe | H | cyclopropylmethyl-C(O)NH- | -O-CH(Me)-CH₂-CH=CH-CH₂- |

-continued

Table 2 of Example 37

| Cmp | R₁ | R₂ | R₃ | R₅ | R₄ | Z |
|-----|----|----|-----|-----|-----|----|
| 416 | Me | 4-isopropyl-thiazol-2-yl | OMe | H | cyclopropylmethyl-C(O)NH- | -CH₂OCH₂CH₂CH=CH- |
| 417 | Me | 4-isopropyl-thiazol-2-yl | OMe | H | cyclopropylmethyl-C(O)NH- | -CH₂SCH₂CH₂CH=CH- |
| 418 | Me | 4-isopropyl-thiazol-2-yl | OMe | H | cyclopropylmethyl-C(O)NH- | -CH₂S(O)₂CH₂CH₂CH=CH- |

-continued

Table 2 of Example 37

| Cmp | R₁ | R₂ | R₃ | R₅ | R₄ | Z |
|---|---|---|---|---|---|---|
| 419 | Me | 4-isopropyl-thiazol-2-yl | OMe | H | -C(O)NH-CH₂-cyclopropyl | -O-CH(Me)-CH₂-CH₂-CH=CH- |
| 420 | cyclopropyl | 4-isopropyl-thiazol-2-yl | OMe | H | -NHC(O)O-CH₂-C(Me)₃ | -O-CH₂-CH₂-CH₂-CH=CH- |
| 421 | cyclopropyl | 4-isopropyl-thiazol-2-yl | OMe | H | -NHC(O)O-CH₂-C(Me)₃ | -S-CH₂-CH₂-CH₂-CH=CH- |

-continued
Table 2 of Example 37
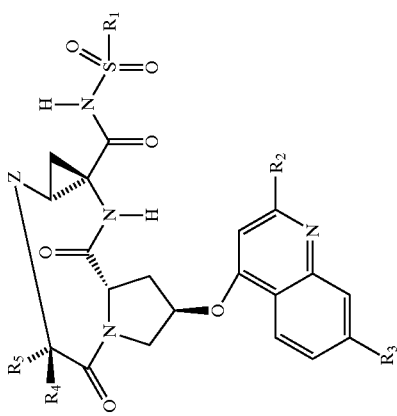
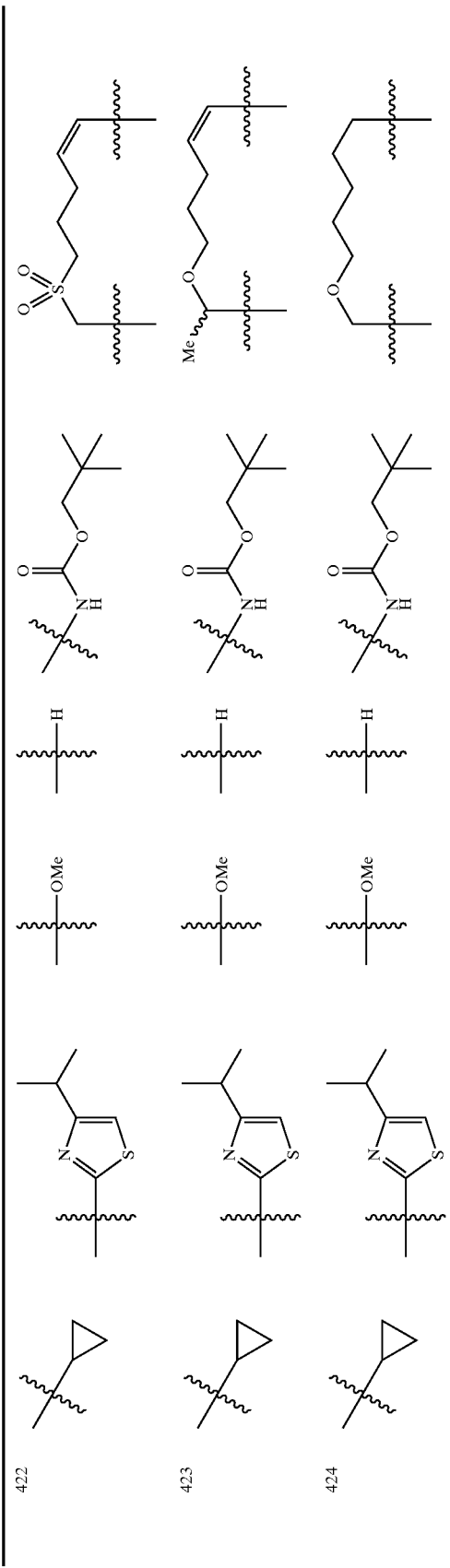

-continued

Table 2 of Example 37

| Cmp | R₁ | R₂ | R₃ | R₅ | R₄ | Z |
|---|---|---|---|---|---|---|
| 425 | cyclopropyl | 4-isopropyl-thiazol-2-yl | OMe | H | neopentyl carbamate | -(CH₂)₄-SO₂- |
| 426 | cyclopropyl | 4-isopropyl-thiazol-2-yl | OMe | H | neopentyl carbamate | -(CH₂)₄-CH(Me)-O- |
| 427 | cyclobutyl | 4-isopropyl-thiazol-2-yl | OMe | H | neopentyl carbamate | -CH₂-CH=CH-CH₂-O-CH₂- |

-continued
Table 2 of Example 37
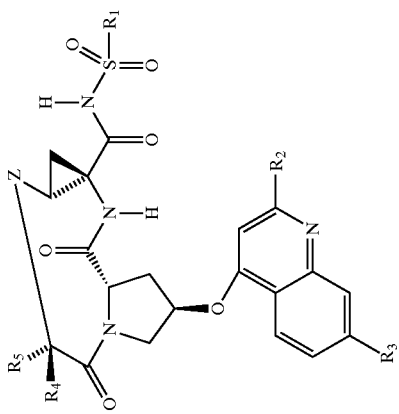
| Cmp | R₁ | R₂ | R₃ | R₅ | R₄ | Z |
|---|---|---|---|---|---|---|
| 428 | cyclobutyl-CH₂- | 4-isopropyl-thiazol-2-yl | OMe | H | neopentyl-O-C(O)-NH- | -CH₂-S-CH₂-CH=CH- |
| 429 | cyclobutyl-CH₂- | 4-isopropyl-thiazol-2-yl | OMe | H | neopentyl-O-C(O)-NH- | -CH₂-S(O)₂-CH₂-CH₂-CH=CH- |
| 430 | cyclobutyl-CH₂- | 4-isopropyl-thiazol-2-yl | OMe | H | neopentyl-O-C(O)-NH- | -CH(Me)-O-CH₂-CH₂-CH=CH- |

-continued
Table 2 of Example 37
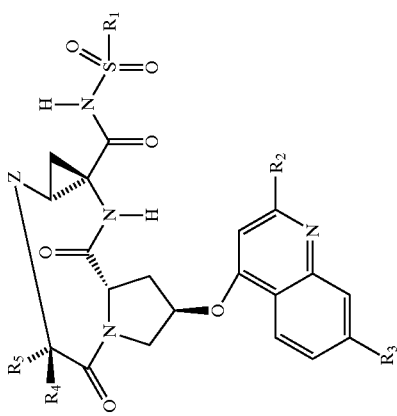
| Cmp | R₁ | R₂ | R₃ | R₅ | R₄ | Z |
|-----|----|----|----|----|----|----|
| 431 | Me | 4-isopropyl-thiazol-2-yl | OMe | H | neopentyloxycarbonylamino | -CH₂-O-CH₂-CH=CH- |
| 432 | Me | 4-isopropyl-thiazol-2-yl | OMe | H | neopentyloxycarbonylamino | -CH₂-S-CH₂-CH=CH- |
| 433 | Me | 4-isopropyl-thiazol-2-yl | OMe | H | neopentyloxycarbonylamino | -CH₂-S(O)₂-CH₂-CH=CH- |

-continued

Table 2 of Example 37

| Cmp | R$_1$ | R$_2$ | R$_3$ | R$_5$ | R$_4$ | Z |
|---|---|---|---|---|---|---|
| 434 | Me | 4-isopropyl-thiazol-2-yl | OMe | H | neopentyloxycarbonylamino | MeO-CH-(chain)- |
| 435 | cyclopropyl | pyrrol-1-yl | OMe | H | cyclopentyloxycarbonylamino | alkenyl chain |
| 436 | cyclopropyl | pyrazol-1-yl | OMe | H | cyclopentyloxycarbonylamino | alkenyl chain |

-continued

Table 2 of Example 37

| Cmp | R₁ | R₂ | R₃ | R₅ | R₄ | Z |
|---|---|---|---|---|---|---|
| 437 | cyclopropyl | 3-Me-pyrazolyl | OMe | H | cyclopentyl-O-C(O)-NH- | alkenyl chain |
| 438 | cyclopropyl | 4-Me-pyrazolyl | OMe | H | cyclopentyl-O-C(O)-NH- | alkenyl chain |
| 439 | cyclopropyl | pyrazolyl | OMe | H | cyclopentyl-O-C(O)-NH- | alkenyl chain |

-continued

Table 2 of Example 37

| Cmp | R₁ | R₂ | R₃ | R₅ | R₄ | Z |
|---|---|---|---|---|---|---|
| 440 | cyclopropyl | N-methylimidazole | OMe | H | cyclopentyl-O-C(O)-NH | alkenyl chain |
| 441 | cyclopropyl | 5-methyl-oxadiazole | OMe | H | cyclopentyl-O-C(O)-NH | alkenyl chain |
| 442 | cyclopropyl | 3-methyl-oxadiazole | OMe | H | cyclopentyl-O-C(O)-NH | alkenyl chain |

Table 2 of Example 37

| Cmp | R₁ | R₂ | R₃ | R₅ | R₄ | Z |
|---|---|---|---|---|---|---|
| 443 | cyclopropyl | pyridin-2-yl | OMe | H | cyclopentyl-O-C(O)-NH- | alkenyl chain |
| 444 | cyclopropyl | 6-methylpyridin-2-yl | OMe | H | cyclopentyl-O-C(O)-NH- | alkenyl chain |
| 445 | cyclopropyl | 5-methoxypyridin-2-yl | OMe | H | cyclopentyl-O-C(O)-NH- | alkenyl chain |

-continued
Table 2 of Example 37
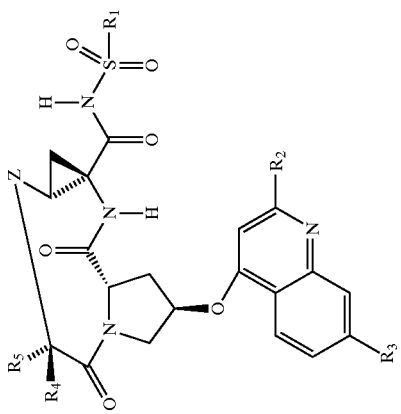
| Cmp | R₁ | R₂ | R₃ | R₅ | R₄ | Z |
|---|---|---|---|---|---|---|
| 446 | cyclopropyl | OMe | OMe | H | cyclopentyl-O-C(O)-NH- | alkenyl chain |
| 447 | cyclopropyl | CH₂OMe | OMe | H | cyclopentyl-O-C(O)-NH- | alkenyl chain |

Preparation of Compound 441

A nonlimiting example of the above coupling process is shown for the preparation of compound 441 (where $R_1=$

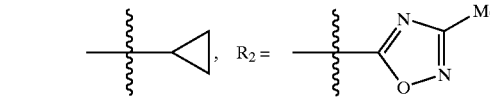

$R_3=$OMe, $R_5=$H,

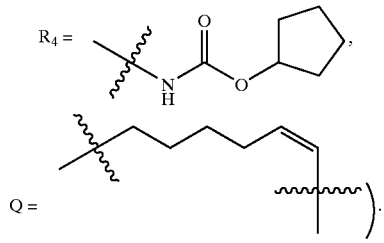

The starting material carboxylic acid Compound 441A can be prepared as described in International Application PCT/CA00/00353 (Publication No, WO 00/59929) or Example 9 herein.

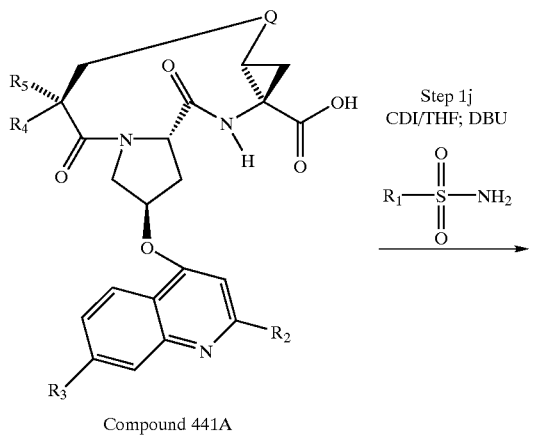

Compound 441A

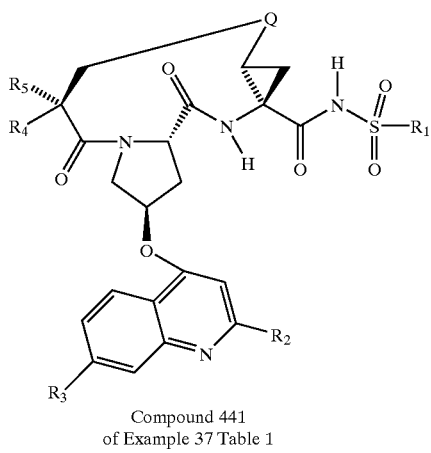

Compound 441
of Example 37 Table 1

In the sulfonamide coupling step a tripeptide carboxylic acid, for example 441A (where

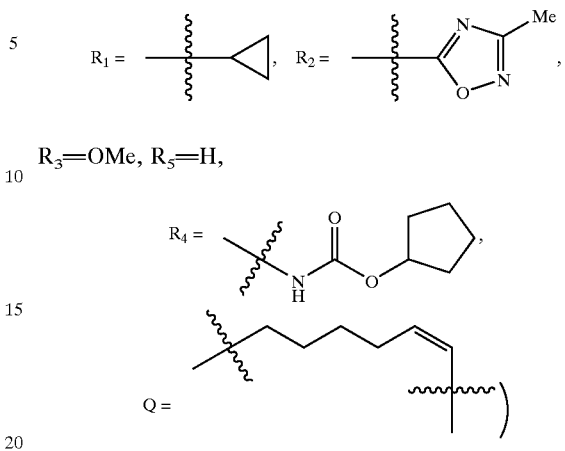

$R_3=$OMe, $R_5=$H, is dissolved in a suitable solvent, as for example THF or dichloroethane, under an in inert atmosphere, as example argon or nitrogen. A suitable coupling reagent is then added. A non-limiting example of a coupling reagent is carbonyldiimidazole. The resulting solution is then stirred at room temperature for approximately 30 min and then heated at reflux for a period of 30 min. The solution is then cooled to room temperature and a sulfonamide is then added. In the present example cyclopropylsulfonamide is added in one portion, followed by the addition of a base. An example of a base used in this transformation is DBU. The resulting reaction is stirred for 24 h, after which it is subjected to a work-up procedure. This work-up procedure can involve first diluting the reaction mixture with an organic solvent such as ethyl acetate then washing the resulting mixture with an aqueous solution as for example an aqueous solution buffered to a pH of four. The organic phase is then separated and washed with brine. The organic extract is then dried ($MgSO_4$) and concentrated under vacuum to provide a crude product. The crude product can be purified using conventional practices, such as but not limited to, flash chromatography, preparative thin layer chromatography (TLC) or reverse phase chromatography to provide the desire acylsulfonamide compound 441.

EXAMPLE 38

Biological Studies
Recombinant HCV NS3/4A Protease Complex FRET Peptide Assay

The purpose of this in vitro assay was to measure the inhibition of HCV NS3 protease complexes, derived from the BMS, $H_{77}C$ or J4L6S strains, as described below, by compounds of the present invention. This assay provides an indication of how effective compounds of the present invention would be in inhibiting HCV proteolytic activity.

Serum from an HCV-infected patient was obtained from Dr. T. Wright, San Francisco Hospital. An engineered full-length cDNA (compliment deoxyribonucleic acid) template of the HCV genome (BMS strain) was constructed from DNA fragments obtained by reverse transcription-PCR (RT-PCR) of serum RNA (ribonucleic acid) and using primers selected on the basis of homology between other genotype 1a strains. From the determination of the entire genome sequence, a genotype 1a was assigned to the HCV isolate according to the classification of Simmonds et al. (See P Simmonds, K A Rose, S Graham, S W Chan, F McOmish, B C Dow, E A Follett, P L Yap and H Marsden, J. Clin. Microbiol., 31 (6), 1493–1503 (1993)). The amino acid sequence of the nonstructural region, NS2-5B, was shown to be >97% identical to HCV genotype 1a ($H_{77}C$) and 87% identical to genotype 1b (J4L6S). The infectious clones, $H_{77}C$ (1a genotype) and J4L6S (1b genotype) were obtained from R. Purcell (N1H) and the sequences are published in Genbank (AAB67036, see Yanagi, M., Purcell, R. H., Emerson, S. U. and Bukh, J. Proc. Natl. Acad. Sci. U.S.A. 94 (16), 8738–8743 (1997); AF054247, see Yanagi, M., St Claire, M., Shapiro, M., Emerson, S. U., Purcell, R. H. and Bukh, J, Virology 244 (1), 161–172. (1998)).

The BMS, $H_{77}C$ and J4L6S strains were used for production of recombinant NS3/4A protease complexes. DNA encoding the recombinant HCV NS3/4A protease complex (amino'acids 1027 to 1711) for these strains were manipulated as described by P. Gallinari et al. (see Gallinari P, Paolini C, Brennan D, Nardi C, Steinkuhler C, De Francesco R. Biochemistry. 38 (17):5620–32, (1999)). Briefly, a three-lysine solubilizing tail was added at the 3'-end of the NS4A coding region. The cysteine in the P1 position of the NS4A–NS4B cleavage site (amino acid 1711) was changed to a glycine to avoid the proteolytic cleavage of the lysine tag. Furthermore, a cysteine to serine mutation was introduced by PCR at amino acid position 1454 to prevent the autolytic cleavage in the NS3 helicase domain. The variant DNA fragment was cloned in the pET21b bacterial expression vector (Novagen)and the NS3/4A complex was expressed in *Escherichia. coli* strain BL21 (DE3) (Invitrogen) following the protocol described by P. Gallinari et al. (see Gallinari P, Brennan D, Nardi C, Brunetti M, Tomei L, Steinkuhler C, De Francesco R., J. Virol. 72 (8):6758–69 (1998)) with modifications. Briefly, NS3/4A expression was induced with 0.5 mM Isopropyl β-D-1-thiogalactopyranoside (IPTG) for 22 hr at 20° C. A typical fermentation (10L) yielded approximately 80 g of wet cell paste. The cells were resuspended in lysis buffer (10 mL/g) consisting of 25 mM N-(2-Hydroxyethyl)Piperazine-N'-(2-Ethane Sulfonic acid) (HEPES), pH 7.5, 20% glycerol, 500 mM Sodium Chloride (NaCl), 0.5% Triton-X100, 1 ug/ml lysozyme, 5 mM Magnesium Chloride ($MgCl_2$), 1 ug/ml Dnase1, 5 mM β-Mercaptoethanol (OME), Protease inhibitor-Ethylenediamine Tetraacetic acid (EDTA) free (Roche), homogenized and incubated for 20 mins at 4° C. The homogenate was sonicated and clarified by ultra-centrifugation at 235000 g for 1 hr at 4° C. Imidazole was added to the supernatant to a final concentration of 15 mM and the pH adjusted to 8.0. The crude protein extract was loaded on a Nickel-Nitrilotriacetic acid (Ni-NTA) column pre-equilibrated with buffer B (25 mM HEPES, pH 8.0, 20% glycerol, 500 mM NaCl, 0.5% Triton-X100, 15 mM imidazole, 5 mM βME). The sample was loaded at a flow rate of 1 mL/min. The column was washed with 15 column volumes of buffer C (same as buffer B except with 0.2% Triton-X100). The protein was eluted with 5 column volumes of buffer D (same as buffer C except with 200 mM Imidazole).

NS3/4A protease complex-containing fractions were pooled and loaded on a desalting column Superdex-S200 pre-equilibrated with buffer D (25 mM HEPES, pH 7.5, 20% glycerol, 300 mM NaCl, 0.2% Triton-X100, 10 mM PME). Sample was loaded at a flow rate of 1 mL/min. NS3/4A protease complex-containing fractions were pooled and concentrated to approximately 0.5 mg/ml. The purity of the NS3/4A protease complexes, derived from the BMS, $H_{77}C$ and J4L6S strains, were judged to be greater than 90% by SDS-PAGE and mass spectrometry analyses.

The enzyme was stored at −80° C., thawed on ice and diluted prior to use in assay buffer. The substrate used for the NS3/4A protease assay was RET S1 (Resonance Energy Transfer Depsipeptide Substrate; AnaSpec, Inc. cat #22991) (FRET peptide), described by Taliani et al. in Anal. Biochem. 240 (2):60–67 (1996). The sequence of this peptide is loosely based on the NS4A/NS4B natural cleavage site except there is an ester linkage rather than an amide bond at the cleavage site. The peptide substrate was incubated with one of the three recombinant NS3/4A complexes, in the absence or presence of a compound of the present invention, and the formation of fluorescent reaction product was followed in real time using a Cytofluor Series 4000.

The reagents were as follow: HEPES and Glycerol (Ultrapure) were obtained from GIBCO-BRL. Dimethyl Sulfoxide (DMSO) and bovine serum albumin (BSA) were obtained from Sigma. β-Mercaptoethanol was obtained from Bio Rad: Assay buffer: 50 mM HEPES, pH 7.5; 0.15M NaCl; 0.1% Triton; 15% Glycerol; 10 mM βME. Substrate: 2 µM final concentration (from a 2 mM stock solution in DMSO stored at −20° C.). HCV NS3/4A type 1a (1b), 2–3 nM final concentration (from a 5 µM stock solution in 25 mM HEPES, pH 7.5, 20% glycerol, 300 mM NaCl, 0.2% Triton-X100, 10 mM βME). For compounds with potencies approaching the assay limit, the assay was made more sensitive by adding 50 µg/ml BSA to the assay buffer and reducing the end protease concentration to 300 pM.

The assay was performed in a 96-well polystyrene black plate from Falcon. Each well contained 25 µl NS3/4A protease complex in assay buffer, 50 µl of a compound of the present invention in 10% DMSO/assay buffer and 25 µl substrate in assay buffer. A control (no compound) was also prepared on the same assay plate. The enzyme complex was mixed with compound or control solution for 1 min before initiating the enzymatic reaction by the addition of substrate. The assay plate was read immediately using the Cytofluor Series 4000 (Perspective Biosystems). The instrument was set to read an emission of 340 nm and excitation of 490 nm at 25° C. Reactions were generally followed for approximately 15 minutes.

The percent inhibition was calculated with the following equation:

$$100-[(\delta F_{inh}/\delta F_{con})\times 100]$$

where δF is the change in fluorescence over the linear range of the curve. A non-linear curve fit was applied to the inhibition-concentration data, and the 50% effective concentration ($IC_{50}$) was calculated by the use of Excel Xl-fit software using the equation, $y=A+((B-A)/(1+((C/x)^\wedge D)))$.

All of the compounds tested were found to have IC50s of 9 µM or less. Further, compounds of the present invention, which were tested against more than one type of NS3/4A complex, were found to have similar inhibitory properties though the compounds uniformly demonstrated greater potency against the 1b strains as compared to the 1a strains.

Specificity Assays

The specificity assays were performed to demonstrate the selectivity of the compounds of the present invention in inhibiting HCV NS3/4A protease as compared to other serine or cysteine proteases.

The specificities of compounds of the present invention were determined against a variety of serine proteases: human neutrophil elastase (HNE), porcine pancreatic elastase (PPE) and human pancreatic chymotrypsin and one cysteine protease: human liver cathepsin B. In all cases a 96-well plate format protocol using colorimetric p-nitroaniline (pNA) substrate specific for each enzyme was used as described previously (U.S. Pat. No. 6,323,180) with some modifications to the serine protease assays. All enzymes were purchased from Sigma while the substrates were from Bachem.

Each assay included a 2 hr enzyme-inhibitor pre-incubation at RT followed by addition of substrate and hydrolysis to ~30% conversion as measured on a Spectramax Pro microplate reader. Compound concentrations varied from 100 to 0.4 μM depending on their potency.

The final conditions for each assay were as follows:

50 mM Tris(hydroxymethyl)aminomethane hydrochloride (Tris-HCl) pH 8, 0.5M Sodium Sulfate (Na$_2$SO$_4$), 50 mM NaCl, 0.1 mM EDTA, 3% DMSO, 0.01% Tween-20 with: 133 μM succ-AAA-pNA and 20 nM HNE or 8 nM PPE; 100 μM succ-AAPF-pNA and 250 pM Chymotrypsin.

100 mM NaHPO$_4$ (Sodium Hydrogen Phosphate) pH 6, 0.1 mM EDTA, 3% DMSO, 1 mM TCEP (Tris(2-carboxyethyl)phosphine hydrochloride), 0.01% Tween-20, 30 μM Z-FR-pNA and 5 nM Cathepsin B (enzyme stock activated in buffer containing 20 mM TCEP before use).

The percentage of inhibition was calculated using the formula:

$$[1-((UV_{inh}-UV_{blank})/(UV_{ctl}-UV_{blank}))] \times 100$$

A non-linear curve fit was applied to the inhibition-concentration data, and the 50% effective concentration (IC$_{50}$) was calculated by the use of Excel Xl-fit software.

HCV Replicon Cell-based Assay

An HCV replicon whole cell system was established as described by Lohmann V, Korner F, Koch J, Herian U, Theilmann L, Bartenschlager R., Science 285 (5424):110–3 (1999). This system enabled us to evaluate the effects of our HCV Protease compounds on HCV RNA replication. Briefly, using the HCV strain 1B sequence described in the Lohmann paper (Assession number:AJ238799), an HCV cDNA was generated encoding the 5' internal ribosome entry site (IRES), the neomycin resistance gene, the EMCV (encephalomyocarditis viurs)-IRES and the HCV nonstructural proteins, NS3-NS5B, and 3' non-translated region (NTR). In vitro transcripts of the cDNA were transfected into the human hepatoma cell line, Huh7. Selection for cells constitutively expressing the HCV replicon was achieved in the presence of the selectable marker, neomycin (G418). Resulting cell lines were characterized for positive and negative strand RNA production and protein production over time.

Huh7 cells, constitutively expressing the HCV replicon, were grown in Dulbecco's Modified Eagle Media (DMEM) containing 10% Fetal calf serum (FCS) and 1 mg/ml G418 (Gibco-BRL). Cells were seeded the night before (1.5×10$^4$ cells/well) in 96-well tissue-culture sterile plates. Compound and no compound controls were prepared in DMEM containing 4% FCS, 1:100 Penicillin/Streptomysin, 1:100 L-glutamine and 5% DMSO in the dilution plate (0.5% DMSO final concentration in the assay). Compound/DMSO mixes were added to the cells and incubated for 4 days at 37° C. After 4 days, plates were rinsed thoroughly with Phosphate-Buffered Saline (PBS) (3 times 150 μl). The cells were lysed with 25 μl of a lysis assay reagent containing the FRET peptide (RET S1, as described for the in vitro enzyme assay). The lysis assay reagent was made from 5× cell Luciferase cell culture lysis reagent(Promega #E153A) diluted to 1× with distilled water, NaCl added to 150 mM final, the FRET peptide diluted to 10 μM final from a 2 mM stock in 100% DMSO. The plate was then placed into the Cytofluor 4000 instrument which had been set to 340 nm excitation/490 emission, automatic mode for 21 cycles and the plate read in a kinetic mode. EC$_{50}$ determinations were carried out as described for the IC$_{50}$ determinations.

Two different secondary assays were used to confirm EC$_{50}$ determinations from the replicon FRET assay. These included a quantitative RNA assay and a transient luciferase cell reporter assay. For the quantitative RNA assay, compound/no compound controls were incubated with the cells as described for the replicon FRET assay. After 4 days, cells were lyzed using the Rneasy kit (Qiagen). Purified total RNA was normalized using RiboGreen (Jones L J, Yue S T, Cheung C Y, Singer V L, Anal. Chem., 265 (2):368–74 (1998)) and relative quantitation of HCV RNA expression assessed using the Taqmann procedure (Kolykhalov A A, Mihalik K, Feinstone S M, Rice C M, Journal of Virology 74, 2046–2051 (2000)) and the Platinum Quantitative RT-PCR Thermoscript One-Step kit (Invitrogen cat #11731–015). Briefly, RNA made to a volume of 5 μl ($\leq$1 ng) was added to a 20 μl Ready-Mix containing the following: 1.25× Thermoscript reaction mix (containing Magnesium Sulfate and 2-deoxynucleoside 5'-triphosphates (dNTPs)), 3 mM dNTPs, 200 nM forward primer (sequence: 5'-gggagagccatagtggtctgc-3'), 600 nM reverse primer (5'-cccaaatctccaggcattga-3'), 100 nM probe (5'-6-FAM-cggaattgccaggacgaccgg-BHQ-1-3')(FAM: Fluorescein-aminohexyl amidite; BHQ: Black Hole Quencher), 1 μM Rox reference dye (Invitrogen cat #12223-012) and Thermoscript Plus Platinum Taq polymerase mixture. All primers were designed with ABI Prism 7700 software and obtained from Biosearch Technologies, Novato, Calif. Samples containing known concentrations of HCV RNA transcript were run as standards. Using the following cycling protocol (50° C., 30 min; 95° C., 5 min; 40 cycles of 95° C., 15 sec, 60° C., 1 min), HCV RNA expression was quantitated as described in the Perkin Elmer manual using the ABI Prism 7700 Sequence Detector.

The luciferase reporter assay was also used to confirm compound potency in the replicon. Utilization of a replicon luciferase reporter assay was first described by Krieger et al (Krieger N, Lohmann V, and Bartenschlager R, J. Virol. 75 (10):4614–4624 (2001)). The replicon construct described for our FRET assay was modified by replacing the resistance gene neomycin with the Blasticidin-resistance gene fused to the N-terminus of the humanized form of Renilla luciferase (restriction sites Ascl/Pmel used for the subcdoning). The adaptive mutation at position 1179 (serine to isoleucine) was also introduced (Blight K J, Kolykhalov, A A, Rice, C M, Science 290 (5498):1972–1974). The luciferase reporter assay was set up by seeding huh7 cells the night before at a density of 2×10$^6$ cells per T75 flask. Cells were washed the next day with 7.5 ml Opti-MEM. Following the Invitrogen protocol, 40 μl DMRIE-C was vortexed with 5 ml Opti-MEM before adding 5 μg HCV reporter replicon RNA. The mix was added to the washed huh7 cells and left for 4 hours at 37° C. In the mean time, serial compound dilutions and no compound controls were prepared in DMEM containing 10% FCS and 5% DMSO in the dilution plate (0.5% DMSO final concentration in the assay). Compound/DMSO mixes were added to each well of a 24-well plate. After 4 hours, the transfection mix was aspirated, and cells washed with 5 ml of Opti-MEM before trypsinization. Trypsinized cells were resuspended in 10% DMEM and seeded at 2×10$^4$ cells/well in the 24-well plates containing compound or no compound controls. Plates were incubated for 4 days. After 4 days, media was removed and cells washed with PBS. 100 μl 1×

Renilla Luciferase Lysis Buffer (Promega) was immediately added to each well and the plates either frozen at −80° C. for later analysis, or assayed after 15 mins of lysis. Lysate (40 μl) from each well was transferred to a 96-well black plate (clear bottom) followed by 200 μl 1× Renilla Luciferase assay substrate. Plates were read immediately on a Packard TopCount NXT using a luminescence program.

The percentage inhibition was calculated using the formula below:

% control=average luciferase signal in experimental wells (+compound) average luciferase signal in DMSO control wells (−compound)

The values were graphed and analyzed using XLFit to obtain the $EC_{50}$ value.

Biological Examples

The following Table lists compounds of the present invention which were assayed in vitro according to the method previously described. These $IC_{50}$ ranges used in this table are: A is <50 μM; B is <5 μM; C is <0.5 μM; D is <0.05 μM. All of the compounds of the present invention that were tested were found to have $IC_{50}$s of 9 μM or less against the BMS HCV NS3/4A complex. Preferred compounds had $IC_{50}$s of 0.021 μM, as was found for Compound 6, or less. Further, compounds of the present invention, which were tested against more than one type of NS3/4A complex, were found to have similar inhibitory properties; somewhat better inhibitory properties were exhibited against strain J4L6S. Representative compounds of the present invention were also assessed in the HCV replicon cell assay the results of which are provided in the Table. These $EC_{50}$ ranges used in this table are: A is <50 μM; B is <5 μM; C is <0.5 μM; D is <0.05 μM. Compounds of the present invention were found to have EC50s of about 13.3 μM or less. Preferred compounds have EC50s of about 0.124 μM, as found for Compound 6, or less. More preferred compounds of the present invention were found to have EC50s of 0.01 μM or less.

In the specificity assays, the same compound was found to have the following activity: HLE=30 μM; PPE>100 μM; Chymotrypsin>100 μM; Cathepsin B>100 μM. These results indicate this family of compounds are highly specific for the NS3 protease and many of these members inhibit HCV replicon replication.

| Compound | IC50 | EC50 | Compound | IC50 | EC50 |
|---|---|---|---|---|---|
| 1 | B | A | 2 | B | |
| 3 | B | A | 4 | A | |
| 5 | D | D | 6 | D | C |
| 7 | D | D | 8 | D | C |
| 9 | D | D | 10 | D | D |
| 11 | D | D | 12 | C | C |
| 13 | D | D | 14 | D | D |
| 15 | D | D | 16 | D | D |
| 17 | D | C | 18 | D | D |
| 19 | D | D | 20 | D | D |
| 21 | D | D | 22 | D | D |
| 23 | D | D | 24 | D | D |
| 25 | D | D | 26 | D | D |
| 27 | D | D | 28 | D | D |
| 29 | D | D | 30 | D | B |
| 31 | D | D | 32 | D | D |
| 33 | D | D | 34 | D | D |

What is claimed is:

1. A compound of formula I, including pharmaceutically acceptable salts thereof,

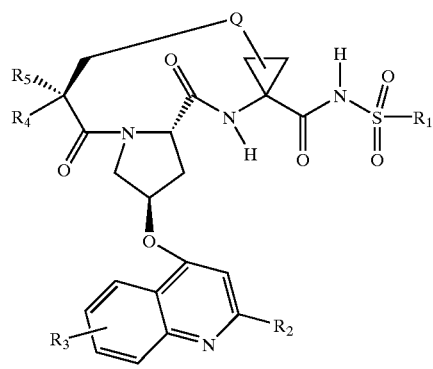

wherein:
(a) $R_1$ is $C_{1-6}$ alkyl or unsubstituted $C_{3-7}$ cycloalkyl;
(b) $R_2$ is H, halo, $C_{1-6}$ alkyl, $C_{1-6}$ alkoxy, $C_{3-6}$ cycloalkoxy, $C_6$ or 10 aryl or heterocycle; wherein heterocycle is a five-, six-, or seven-membered saturated or unsaturated heterocycle containing from one to four heteroatoms selected from nitrogen, oxygen and sulfur; said aryl or heterocycle being substituted with $R_{24}$;
wherein $R_{24}$ is H, halo, $C_{1-6}$ alkyl, —N($R_a$)($R_b$), —N($R_a$)C(O)(O$R_d$), —N($R_a$)C(O)($R_b$), —NHC(O)($R_a$)($R_c$) or —N($R_a$)$SO_2R_b$; wherein $R_a$ and $R_b$ are independently H, $C_{1-6}$ alkyl or $C_{3-6}$ cycloalkyl; $R_c$ is H, $C_{1-6}$ alkyl, $C_{3-6}$ cycloalkyl or $C_{1-6}$ alkoxy; $R_d$ is $C_{1-6}$ alkyl or $C_{3-6}$ cycloalkyl;
(c) $R_3$ is H, halo, $CF_3$, $C_{1-6}$ alkoxy or $C_{3-6}$ cycloalkoxy;
(d) $R_4$ is $NH_2$, or —NH—$R_{31}$; wherein $R_{31}$ is —C(O)—$R_{32}$, C(O)—$NHR_{32}$ or C(O)—$OR_{32}$; wherein $R_{32}$ is $C_1$–$C_6$ alkyl optionally substituted with halo, —$(CH_2)_p$—$C_{3-7}$ cycloalkyl or a tetrahydrofuran ring linked through the C3 or C4 position of the ring;
wherein p is 0–6;
(e) $R_5$ is H; and
(f) Q is a three to nine atom saturated or unsaturated alkylene chain optionally containing one to three heteroatoms independently selected from O or $S(O)_m$; wherein m is 0, 1 or 2.

2. A compound of claim 1 having the formula

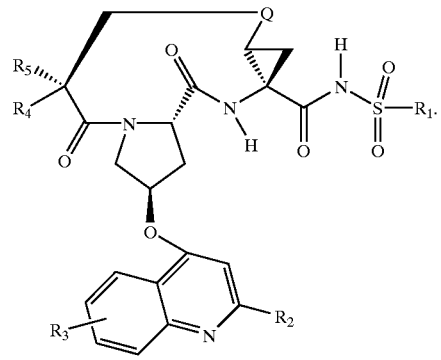

3. A compound of claim 2 wherein $R_1$ is cyclopropyl.
4. A compound of claim 2 wherein $R_2$ is phenyl.
5. A compound of claim 2 wherein $R_3$ is methoxy.

6. A compound of claim 2 wherein $R_4$ is $NH_2$ or tert-butoxycarbonylNH—.

7. A compound of claim 2 wherein Q is —$(CH_2)_n$CH=C— and n is 1–5.

8. A compound of claim 7 wherein n is 3 or 4.

9. A compound of claim 1 having the formula

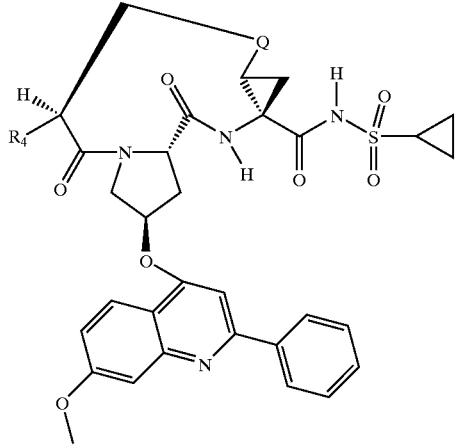

wherein:
(a) $R_4$ is $NH_2$ or tert-butoxycarbonylNH—;
(b) Q is —$(CH_2)_n$CH=C—; and
(c) n is 1–5.

10. A compound of claim 9 wherein n is 3 or 4.

11. A compound of claim 2 wherein:

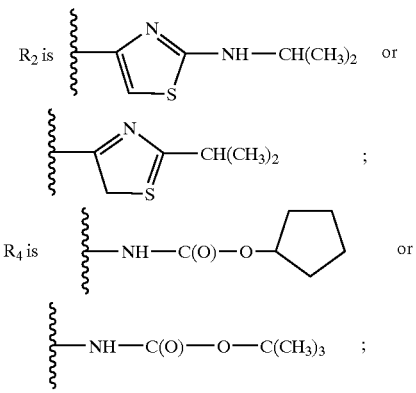

and $R_1$ is cyclopropyl.

12. A pharmaceutical composition, comprising a compound of any one of claims 1–11, and a pharmaceutically acceptable carrier.

13. A method of inhibiting HCV NS3 protease which comprises administering to a mammal in need of such treatment a therapeutically effective amount of a compound of any one of claims 1–11.

14. A method of treating an HCV infection, in a mammal in need thereof, comprising the administration to said mammal of a therapeutically effective amount of a compound of any one of claims 1–11.

* * * * *

UNITED STATES PATENT AND TRADEMARK OFFICE
CERTIFICATE OF CORRECTION

PATENT NO.   : 6,867,185 B2
DATED        : March 15, 2005
INVENTOR(S)  : Jeffrey Allen Campbell and Andrew Charles Good It is certified that error appears in the above-identified patent and that said Letters Patent is hereby corrected as shown below:

<u>Column 384,</u>
Line 10, the chemical structure should be changed:

From " 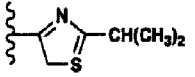 "

To: -- 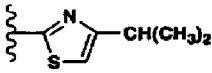 --

Signed and Sealed this

Twenty-fourth Day of May, 2005

JON W. DUDAS
*Director of the United States Patent and Trademark Office*